United States Patent
Laine et al.

(10) Patent No.: US 11,931,266 B2
(45) Date of Patent: *Mar. 19, 2024

(54) IMPLANT WITH INDEPENDENT ENDPLATES

(71) Applicant: NANOHIVE MEDICAL LLC, Woburn, MA (US)

(72) Inventors: Christopher Laine, Bellingham, MA (US); Ian Helmar, Beverly, MA (US); Lucas Diehl, Beverly, MA (US); Jason Tinley, Fort Worth, TX (US); Kevin D. Chappuis, Malden, MA (US); John F. Sullivan, Pelham, NH (US)

(73) Assignee: NANOHIVE MEDICAL LLC, Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/964,814

(22) Filed: Oct. 12, 2022

(65) Prior Publication Data

US 2023/0049783 A1 Feb. 16, 2023

Related U.S. Application Data

(63) Continuation of application No. 16/565,321, filed on Sep. 9, 2019, now abandoned, which is a
(Continued)

(51) Int. Cl.
*A61F 2/30* (2006.01)
*A61F 2/44* (2006.01)
(Continued)

(52) U.S. Cl.
CPC .............. *A61F 2/4455* (2013.01); *A61F 2/30* (2013.01); *A61F 2/446* (2013.01); *B22F 10/38* (2021.01);
(Continued)

(58) Field of Classification Search
CPC .......... A61F 2/4455; A61F 2/65; A61F 2/447; A61F 2002/30014; A61F 2002/30546;
(Continued)

(56) References Cited

U.S. PATENT DOCUMENTS 5,059,193 A 12/1991 Kuslich
5,615,528 A 4/1997 Owens
(Continued)

FOREIGN PATENT DOCUMENTS

CN 204971711 U 1/2016
EP 1506753 A1 2/2005
(Continued)

OTHER PUBLICATIONS

Ahmadi, S. et al., "Additively Manufactured Open-Cell Porous Biomaterials Made from Six Different Space-Filling Unit Cells: The Mechanical and Morphological Properties," Materials, vol. 8:1871-1896 (2015).
(Continued)

*Primary Examiner* — Christopher D. Prone
(74) *Attorney, Agent, or Firm* — McDermott Will & Emery LLP

(57) ABSTRACT

The biocompatible lattice structures and implants disclosed herein have an increased or optimized lucency, even when constructed from a metallic material. The lattice structures can also provide an increased or optimized lucency in a material that is not generally considered to be radiolucent. Lucency can include disparity, maximum variation in lucency properties across a structure, or dispersion, minimum variation in lucency properties across a structure. The implants and lattice structures disclosed herein may be optimized for disparity or dispersion in any desired direction. A desired direction with respect to lucency can include the anticipated x-ray viewing direction of an implant in the expected implantation orientation.

30 Claims, 68 Drawing Sheets

Related U.S. Application Data continuation-in-part of application No. 15/942,846, filed on Apr. 2, 2018, now Pat. No. 10,405,983, and a continuation-in-part of application No. 15/895,201, filed on Feb. 13, 2018, now abandoned, which is a continuation-in-part of application No. 15/615,227, filed on Jun. 6, 2017, now Pat. No. 9,962,269.

(60) Provisional application No. 62/619,260, filed on Jan. 19, 2018, provisional application No. 62/480,385, filed on Apr. 1, 2017, provisional application No. 62/480,383, filed on Apr. 1, 2017, provisional application No. 62/458,714, filed on Feb. 14, 2017, provisional application No. 62/346,720, filed on Jun. 7, 2016.

(51) Int. Cl.
  *B22F 10/38* (2021.01)
  *A61F 2/46* (2006.01)
  *B22F 10/28* (2021.01)
  *B22F 10/39* (2021.01)
  *B22F 10/50* (2021.01)
  *B22F 10/66* (2021.01)

(52) U.S. Cl.
  CPC .... *B22F 10/385* (2021.01); *A61F 2002/3008* (2013.01); *A61F 2002/30131* (2013.01); *A61F 2002/30141* (2013.01); *A61F 2002/30146* (2013.01); *A61F 2002/30148* (2013.01); *A61F 2002/30151* (2013.01); *A61F 2002/30154* (2013.01); *A61F 2002/30166* (2013.01); *A61F 2002/30322* (2013.01); *A61F 2002/30593* (2013.01); *A61F 2002/30784* (2013.01); *A61F 2002/3092* (2013.01); *A61F 2002/4632* (2013.01); *B22F 10/28* (2021.01); *B22F 10/39* (2021.01); *B22F 10/50* (2021.01); *B22F 10/66* (2021.01)

(58) Field of Classification Search
  CPC .. A61F 2002/30141; A61F 2310/00017; A61F 2/30; A61F 2002/30151; A61F 2002/30322; A61F 2002/30593; A61F 2002/30784; A61F 2/3092
  See application file for complete search history.

(56) References Cited

U.S. PATENT DOCUMENTS

| | | | |
|---|---|---|---|
| 5,674,294 A | 10/1997 | Bainville et al. |
| 6,149,688 A | 11/2000 | Brosnahan et al. |
| 6,159,244 A | 11/2000 | Brosnahan et al. |
| 6,193,757 B1 | 2/2001 | Foley et al. |
| 6,206,924 B1 | 3/2001 | Timm |
| 6,723,126 B1 | 4/2004 | Berry |
| 6,767,594 B1 | 7/2004 | Miroshin et al. |
| 6,902,579 B2 | 6/2005 | Harms et al. |
| 6,984,234 B2 | 1/2006 | Bray |
| 6,993,406 B1 | 1/2006 | Cesarano et al. |
| 7,128,760 B2 | 10/2006 | Michelson |
| 7,172,627 B2 | 2/2007 | Fiere et al. |
| 7,217,293 B2 | 5/2007 | Branch, Jr. |
| 7,637,950 B2 | 12/2009 | Baccelli et al. |
| D619,255 S | 7/2010 | Richter et al. |
| 7,799,079 B2 | 9/2010 | Hestad et al. |
| D626,233 S | 10/2010 | Cipoletti et al. |
| 7,846,207 B2 | 12/2010 | Lechmann et al. |
| 7,850,731 B2 | 12/2010 | Brittan et al. |
| 8,043,381 B2 | 10/2011 | Hestad et al. |
| D653,757 S | 2/2012 | Binder |
| 8,236,058 B2 | 8/2012 | Fabian et al. |
| 8,425,576 B2 | 4/2013 | Anderson et al. |
| D682,427 S | 5/2013 | Farris et al. |
| D692,136 S | 10/2013 | Tyber |
| 8,663,332 B1 | 3/2014 | To et al. |
| 8,697,231 B2 | 4/2014 | Longepied et al. |
| 8,740,983 B1 | 6/2014 | Arnold et al. |
| D708,747 S | 7/2014 | Curran et al. |
| D711,537 S | 8/2014 | Pimenta et al. |
| 8,900,307 B2 | 12/2014 | Hawkins et al. |
| 8,945,227 B2 | 2/2015 | Kirschman |
| 9,005,291 B2 | 4/2015 | Loebl et al. |
| D737,446 S | 8/2015 | Butler et al. |
| 9,155,819 B2 | 10/2015 | Fonte et al. |
| 9,186,257 B2 | 11/2015 | Geisler et al. |
| D750,249 S | 2/2016 | Grimberg, Jr. et al. |
| 9,271,836 B2 | 3/2016 | Pavento et al. |
| 9,271,843 B2 | 3/2016 | Fabian et al. |
| 9,308,076 B2 | 4/2016 | Ringeisen et al. |
| 9,421,108 B2 | 8/2016 | Hunt |
| 9,427,330 B2 | 8/2016 | Petersheim et al. |
| 9,456,901 B2 | 10/2016 | Jones et al. |
| 9,492,285 B2 | 11/2016 | Saidha et al. |
| 9,566,163 B2 | 2/2017 | Suddaby et al. |
| 9,649,200 B2 | 5/2017 | Wickham et al. |
| 9,662,225 B2 | 5/2017 | Pavento et al. |
| 9,662,226 B2 | 5/2017 | Wickham |
| D789,539 S | 6/2017 | Kleiner et al. |
| 9,668,877 B2 | 6/2017 | Pavento et al. |
| 9,713,537 B2 | 7/2017 | Bray |
| 9,782,270 B2 | 10/2017 | Wickham |
| 9,872,781 B2 | 1/2018 | Pavento et al. |
| D816,844 S | 5/2018 | Ricca et al. |
| 9,962,269 B2 * | 5/2018 | Jones .................... A61F 2/4425 |
| 10,045,797 B1 | 8/2018 | Walkenhorst et al. |
| 10,052,212 B2 | 8/2018 | Flechter et al. |
| D833,012 S | 11/2018 | Jones et al. |
| D833,611 S | 11/2018 | Jones et al. |
| D833,612 S | 11/2018 | Jones et al. |
| 10,130,488 B2 | 11/2018 | Saidha et al. |
| D835,279 S | 12/2018 | Jones et al. |
| D835,788 S | 12/2018 | Jones et al. |
| D840,036 S | 2/2019 | Jones et al. |
| 10,368,997 B2 | 8/2019 | Jones et al. |
| 10,405,983 B2 * | 9/2019 | Jones ..................... A61F 2/447 |
| 10,507,118 B2 | 12/2019 | Afzal |
| 10,588,749 B2 | 3/2020 | Sharp et al. |
| 10,624,746 B2 | 4/2020 | Jones et al. |
| 10,675,158 B2 | 6/2020 | Unger et al. |
| 10,695,184 B2 | 6/2020 | Jones et al. |
| 10,716,673 B2 | 7/2020 | Jones et al. |
| 10,744,001 B2 | 8/2020 | Sack |
| 10,842,634 B2 | 11/2020 | Pasini et al. |
| 10,884,429 B2 | 1/2021 | Jones et al. |
| 11,026,802 B2 | 6/2021 | Bray |
| 11,174,911 B2 | 11/2021 | Kang |
| 11,278,421 B2 | 3/2022 | Hunt |
| 11,369,419 B2 | 9/2022 | Mesiwala |
| 11,452,611 B2 | 9/2022 | Mcshane, III |
| 2002/0099376 A1 | 7/2002 | Michelson |
| 2002/0161444 A1 | 10/2002 | Choi |
| 2003/0114936 A1 | 6/2003 | Sherwood et al. |
| 2004/0162618 A1 | 8/2004 | Mujwid |
| 2004/0243241 A1 | 12/2004 | Istephanous |
| 2004/0258732 A1 | 12/2004 | Shikinami |
| 2005/0049706 A1 | 3/2005 | Brodke et al. |
| 2005/0059972 A1 | 3/2005 | Biscup |
| 2005/0101960 A1 | 5/2005 | Fiere et al. |
| 2005/0113916 A1 | 5/2005 | Branch |
| 2005/0129726 A1 | 6/2005 | Liebschner |
| 2005/0159813 A1 | 7/2005 | Molz |
| 2005/0251083 A1 | 11/2005 | Carr-Brendel et al. |
| 2006/0147332 A1 | 7/2006 | Jones et al. |
| 2006/0257817 A1 | 11/2006 | Shelton |
| 2006/0259144 A1 | 11/2006 | Trieu |
| 2006/0276925 A1 | 12/2006 | Lin et al. |
| 2007/0073398 A1 | 3/2007 | Fabian et al. |
| 2007/0123987 A1 | 5/2007 | Bernstein |
| 2007/0142914 A1 | 6/2007 | Jones et al. |
| 2007/0150068 A1 | 6/2007 | Dong et al. |
| 2007/0233247 A1 | 10/2007 | Schwab |

(56) References Cited

U.S. PATENT DOCUMENTS

| | | |
|---|---|---|
| 2007/0270858 A1 | 11/2007 | Trieu |
| 2008/0161925 A1 | 7/2008 | Brittan et al. |
| 2008/0161927 A1 | 7/2008 | Savage et al. |
| 2008/0169585 A1 | 7/2008 | Zinniel |
| 2008/0269903 A1 | 10/2008 | Francis et al. |
| 2008/0294262 A1 | 11/2008 | Levieux |
| 2008/0300634 A1 | 12/2008 | Gray |
| 2008/0306596 A1 | 12/2008 | Jones et al. |
| 2008/0306609 A1 | 12/2008 | Lee et al. |
| 2009/0012529 A1 | 1/2009 | Blain et al. |
| 2009/0037148 A1 | 2/2009 | Lin et al. |
| 2009/0105831 A1 | 4/2009 | Jones et al. |
| 2009/0182429 A1 | 7/2009 | Humphreys et al. |
| 2009/0287214 A1 | 11/2009 | Yu |
| 2009/0317278 A1 | 12/2009 | Kokubo |
| 2009/0326580 A1 | 12/2009 | Anderson et al. |
| 2010/0087925 A1 | 4/2010 | Kostuik et al. |
| 2010/0100185 A1 | 4/2010 | Trieu et al. |
| 2010/0145459 A1 | 6/2010 | McDonough et al. |
| 2010/0234948 A1 | 9/2010 | Khoury et al. |
| 2010/0286783 A1 | 11/2010 | Lechmann et al. |
| 2011/0004307 A1 | 1/2011 | Ahn et al. |
| 2011/0012280 A1 | 1/2011 | Deslauriers et al. |
| 2011/0029084 A1 | 2/2011 | Milbocker et al. |
| 2011/0029087 A1 | 2/2011 | Haider et al. |
| 2011/0144764 A1 | 6/2011 | Bagga et al. |
| 2011/0190892 A1 | 8/2011 | Kirschman |
| 2011/0224796 A1 | 9/2011 | Weiland et al. |
| 2011/0282392 A1 | 11/2011 | Murphy et al. |
| 2012/0022653 A1 | 1/2012 | Kirschman |
| 2012/0123546 A1 | 5/2012 | Medina |
| 2012/0150299 A1 | 6/2012 | Ergun et al. |
| 2012/0177939 A1 | 7/2012 | Longepied et al. |
| 2012/0179258 A1* | 7/2012 | Glazer ............... A61F 2/4611 623/17.16 |
| 2012/0185047 A1 | 7/2012 | Wooley |
| 2012/0215310 A1 | 8/2012 | Sharp et al. |
| 2012/0215313 A1 | 8/2012 | Saidha et al. |
| 2012/0303128 A1 | 11/2012 | Ullrich, Jr. et al. |
| 2012/0312779 A1 | 12/2012 | Patterson et al. |
| 2012/0321878 A1 | 12/2012 | Landon et al. |
| 2013/0026492 A1 | 1/2013 | Khan |
| 2013/0039094 A1 | 2/2013 | Kolb et al. |
| 2013/0060337 A1 | 3/2013 | Petersheim et al. |
| 2013/0073044 A1 | 3/2013 | Gamache |
| 2013/0211533 A1 | 8/2013 | Fonte et al. |
| 2013/0218276 A1 | 8/2013 | Fiechter et al. |
| 2013/0238095 A1 | 9/2013 | Pavento et al. |
| 2013/0282126 A1 | 10/2013 | Saidha et al. |
| 2013/0310939 A1 | 11/2013 | Fabian et al. |
| 2013/0325129 A1 | 12/2013 | Huang |
| 2014/0012382 A1 | 1/2014 | Doty |
| 2014/0012384 A1 | 1/2014 | Kana et al. |
| 2014/0037873 A1 | 2/2014 | Cheung et al. |
| 2014/0046447 A1 | 2/2014 | Dunworth et al. |
| 2014/0046448 A1 | 2/2014 | Kana et al. |
| 2014/0107786 A1 | 4/2014 | Geisler et al. |
| 2014/0121776 A1 | 5/2014 | Hunt |
| 2014/0277482 A1 | 9/2014 | Gfeller et al. |
| 2015/0005885 A1 | 1/2015 | Zhang et al. |
| 2015/0025635 A1 | 1/2015 | Laubert |
| 2015/0093283 A1 | 4/2015 | Miller et al. |
| 2015/0100126 A1 | 4/2015 | Melkent et al. |
| 2015/0360421 A1 | 12/2015 | Burhop et al. |
| 2016/0000574 A9 | 1/2016 | Fabian et al. |
| 2016/0022431 A1 | 1/2016 | Wickham |
| 2016/0027425 A1 | 1/2016 | Cook et al. |
| 2016/0038301 A1 | 2/2016 | Wickham |
| 2016/0058480 A1 | 3/2016 | Laubert et al. |
| 2016/0085882 A1 | 3/2016 | Li et al. |
| 2016/0113775 A1 | 4/2016 | Willis et al. |
| 2016/0166284 A1 | 6/2016 | Hacking et al. |
| 2016/0184103 A1 | 6/2016 | Fonte et al. |
| 2016/0199193 A1 | 7/2016 | Willis et al. |
| 2016/0206440 A1 | 7/2016 | DeRidder et al. |
| 2016/0235546 A1 | 8/2016 | Cheng et al. |
| 2016/0270931 A1 | 9/2016 | Trieu |
| 2017/0014235 A1 | 1/2017 | Jones et al. |
| 2017/0020685 A1 | 1/2017 | Geisler et al. |
| 2017/0042698 A1 | 2/2017 | Saidha et al. |
| 2017/0095337 A1 | 4/2017 | Pasini et al. |
| 2017/0119538 A1 | 5/2017 | Baynham |
| 2017/0312096 A1 | 11/2017 | Liu et al. |
| 2017/0325966 A1 | 11/2017 | Capote et al. |
| 2017/0348114 A1 | 12/2017 | Jones et al. |
| 2017/0367845 A1 | 12/2017 | Eisen et al. |
| 2018/0092752 A1 | 4/2018 | Williams |
| 2018/0140427 A1 | 5/2018 | Conway et al. |
| 2018/0221156 A1 | 8/2018 | Jones et al. |
| 2018/0228570 A1 | 8/2018 | Jones et al. |
| 2018/0228612 A1 | 8/2018 | Jones et al. |
| 2018/0228613 A1 | 8/2018 | Jones et al. |
| 2018/0243094 A1 | 8/2018 | Jones et al. |
| 2018/0243097 A1 | 8/2018 | Jones et al. |
| 2018/0280139 A1 | 10/2018 | Jones et al. |
| 2018/0280140 A1 | 10/2018 | Jones et al. |
| 2018/0280141 A1 | 10/2018 | Jones et al. |
| 2018/0280144 A1 | 10/2018 | Jones et al. |
| 2018/0280145 A1 | 10/2018 | Jones et al. |
| 2018/0296350 A1 | 10/2018 | Hamzey et al. |
| 2018/0318099 A1 | 11/2018 | Altarac et al. |
| 2018/0318100 A1 | 11/2018 | Altarac et al. |
| 2018/0368990 A1 | 12/2018 | Saidha et al. |
| 2018/0368992 A1 | 12/2018 | Zink et al. |
| 2019/0133778 A1 | 5/2019 | Johnston |
| 2019/0133783 A1 | 5/2019 | Unger et al. |
| 2019/0150910 A1 | 5/2019 | Jones et al. |
| 2019/0209215 A1 | 7/2019 | Baynham et al. |
| 2019/0250438 A1 | 8/2019 | Oton et al. |
| 2019/0343638 A1 | 11/2019 | Jones et al. |
| 2019/0343644 A1 | 11/2019 | Ryan |
| 2020/0000595 A1 | 1/2020 | Jones et al. |
| 2020/0038069 A1 | 2/2020 | Jones et al. |
| 2020/0138595 A1 | 5/2020 | Shoshtaev et al. |
| 2020/0155326 A1 | 5/2020 | Hunt |
| 2020/0261243 A1 | 8/2020 | Unger et al. |
| 2020/0281736 A1 | 9/2020 | Milz et al. |
| 2020/0337856 A1 | 10/2020 | Moore |
| 2020/0375726 A1 | 12/2020 | Limem et al. |
| 2021/0330473 A1 | 10/2021 | Hunt |
| 2022/0168108 A1 | 6/2022 | Laine |
| 2023/0022520 A1 | 1/2023 | Laine et al. |

FOREIGN PATENT DOCUMENTS

| | | |
|---|---|---|
| EP | 2647453 A2 | 10/2013 |
| EP | 1887954 B1 | 9/2014 |
| EP | 2992846 | 3/2016 |
| KR | 200188509 Y | 7/2000 |
| KR | 101398889 | 5/2014 |
| KR | 101830547 B1 | 4/2018 |
| WO | WO-1999033641 A1 | 7/1999 |
| WO | WO-0217823 A1 | 3/2002 |
| WO | WO-2009091627 A1 | 7/2009 |
| WO | WO2011022550 | 2/2011 |
| WO | WO-2014160389 A1 | 10/2014 |
| WO | WO-2014172495 A2 | 10/2014 |
| WO | WO2015053890 | 4/2015 |
| WO | WO-2015164982 A1 | 11/2015 |
| WO | WO-2016061148 A1 | 4/2016 |
| WO | WO-2016130878 A1 | 8/2016 |
| WO | WO-2017214114 A1 | 12/2017 |
| WO | WO-2018152077 A1 | 8/2018 |
| WO | WO-2018156905 A1 | 8/2018 |
| WO | WO-2018182834 A1 | 10/2018 |
| WO | WO-2018183809 A1 | 10/2018 |
| WO | WO-2020023938 A1 | 1/2020 |

OTHER PUBLICATIONS

Babaee S., et al., "Mechanical properties of open-cell rhombic dodecahedron cellular structures," Acta Materialia, vol. 60:2873-2885 (2012).

(56) References Cited

OTHER PUBLICATIONS

Chandran R.; "Optimization of Support Structures in Additive Manufacturing Process", Dissertation, University of Miami, 2016 (Year:2016).
European Search Report, 17810838.7, dated Dec. 19, 2019, 8 pages.
Hoffmann, W. et al., "Rapid prototyped porous nickel-titanium scaffolds as bone substitutes," Journal of Tissue Engineering, vol. 5:1-14 (2014).
International Preliminary Report on Patentability, PCT/US2017/36111, dated Jun. 27, 2018, 26 pages.
International Search Report and Written Opinion, PCT/US2017/36111, dated Nov. 6, 2017, 10 pages.
International Search Report and Written Opinion, PCT/US2018/017919, dated Jun. 6, 2018, 14 pages.
International Preliminary Report on Patentability, PCT/US2018/017919, dated Aug. 20, 2019, 11 pages.
International Preliminary Report on Patentability, PCT/US2018/019437, dated Aug. 27, 2019, 16 pages.
International Search Report and Written Opinion, PCT/US2018/019437, dated Jun. 28, 2018, 19 pages.
International Search Report and Written Opinion, PCT/US2018/014720, dated Jun. 1, 2018, 13 pages.
International Search Report and Written Opinion, PCT/US2018/025351, dated Jun. 8, 2018, 14 pages.
International Search Report and Written Opinion, PCT/US2019/043803, dated Nov. 7, 2019, 11 pages.
Leary M., et al. "Optimal topology for additive manufacture: A method for enabling additive manufacture of support-free optimal structures", Materials and Design, 2014, vol. 63, p. 678-690 (Year: 2014).
Nouri, A., "Titanium foam scaffolds for dental applications," Metallic Foam Bone, Chapter 5: 130-160 (2017) http://dx.doi.org/10.1016/B978-0-08-101289-5.00005-6.
Strano G., et al.; "A new approach to the design and optimization of support structures in additive manufacturing", Int. J. Adv Manufacturing Technology, 2013, 66, p. 1247-1254 (Year: 2013).
Stryker, "Tritanium PI Cage", Technical Data Sheet, https://www.stryker.com/builttofuse/; retrieved from wayback machine on Apr. 23, 2021; date Jun. 21, 2016.
Zhang,X., et al., "Additively Manufactured Scaffolds for Bone Tissue Engineering and the Prediction of their Mechanical Behavior: A Review," Materials, 10(10): 1-28 (2017).
Supplementary EP Search Report (EP 19 84 0280), dated Apr. 14, 2022.

\* cited by examiner

SECTION A-A

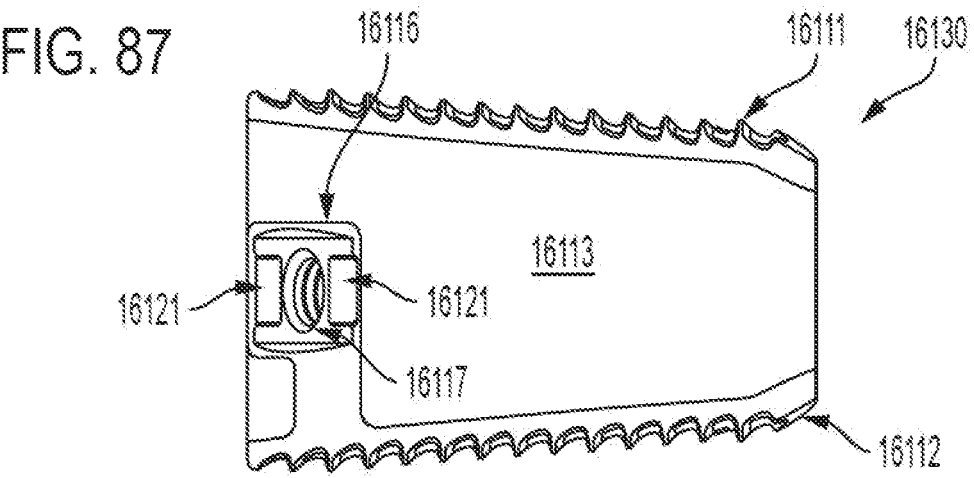
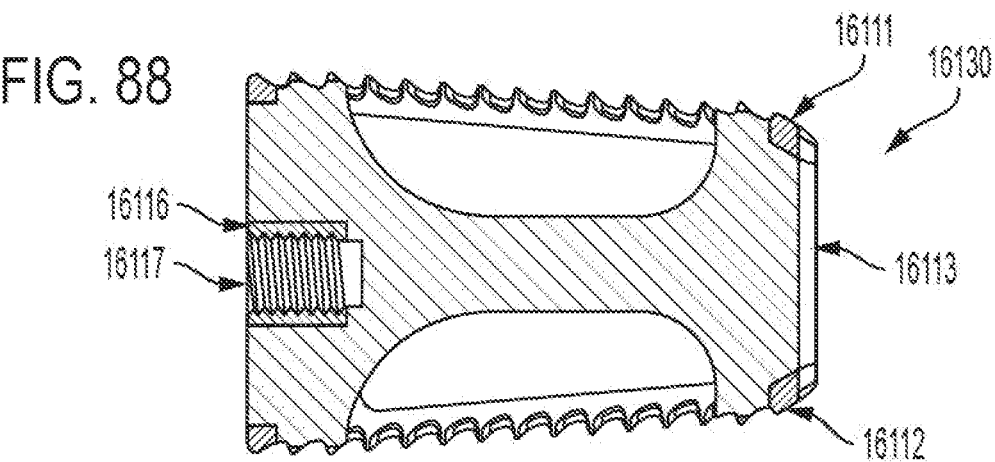
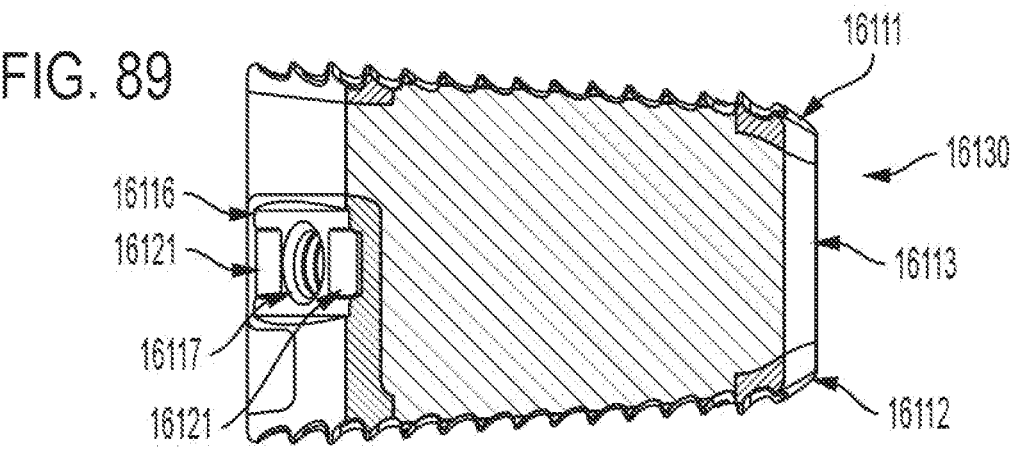

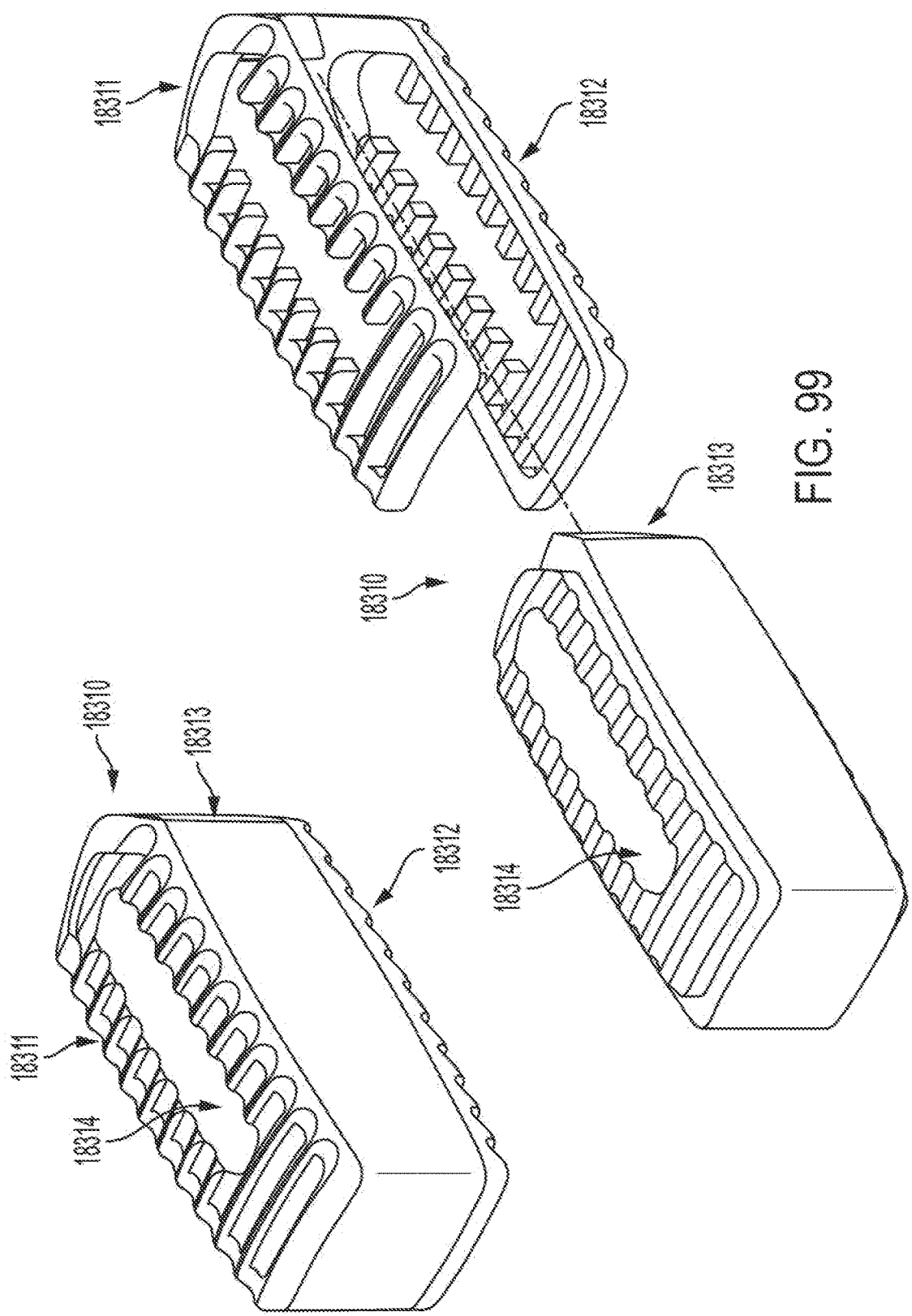

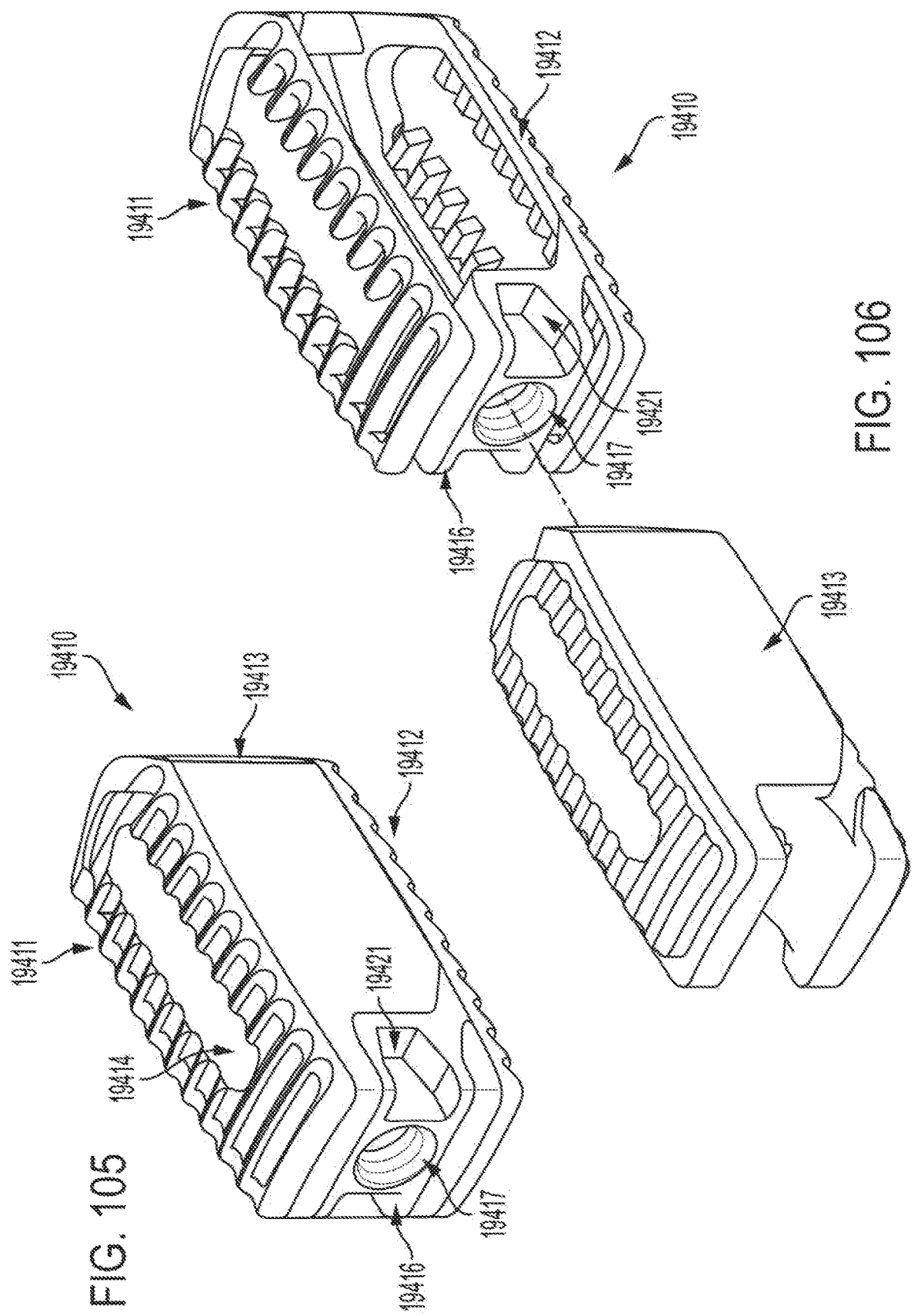

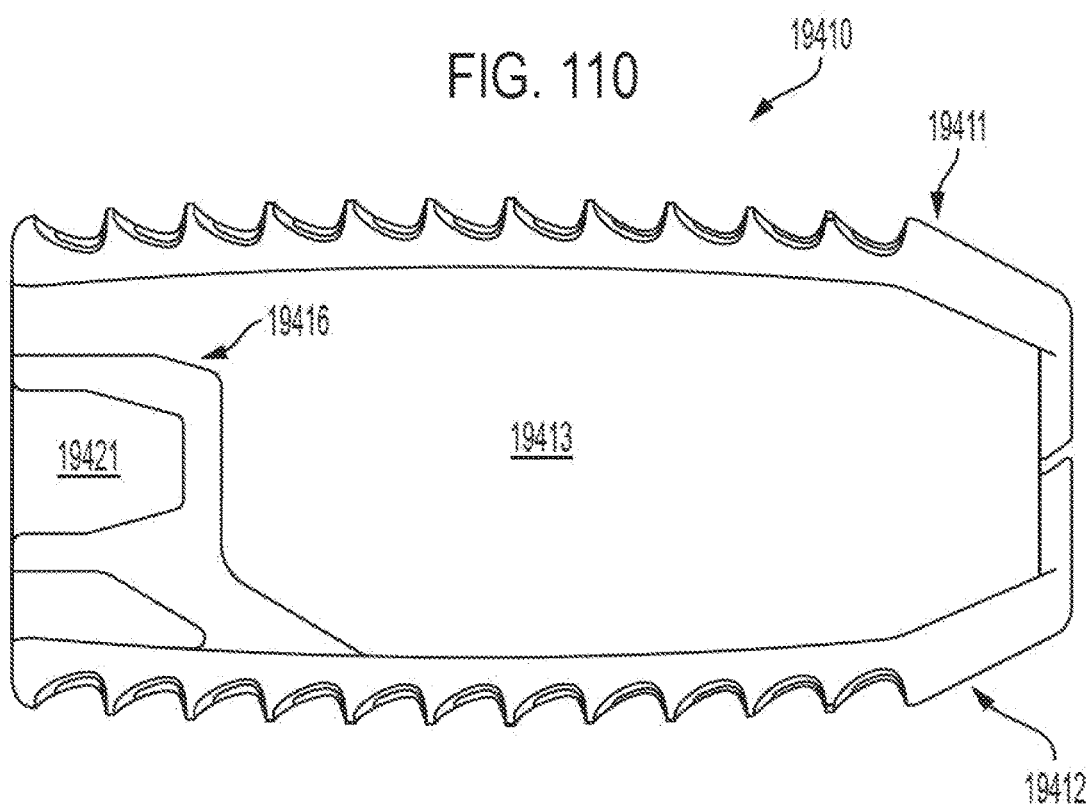
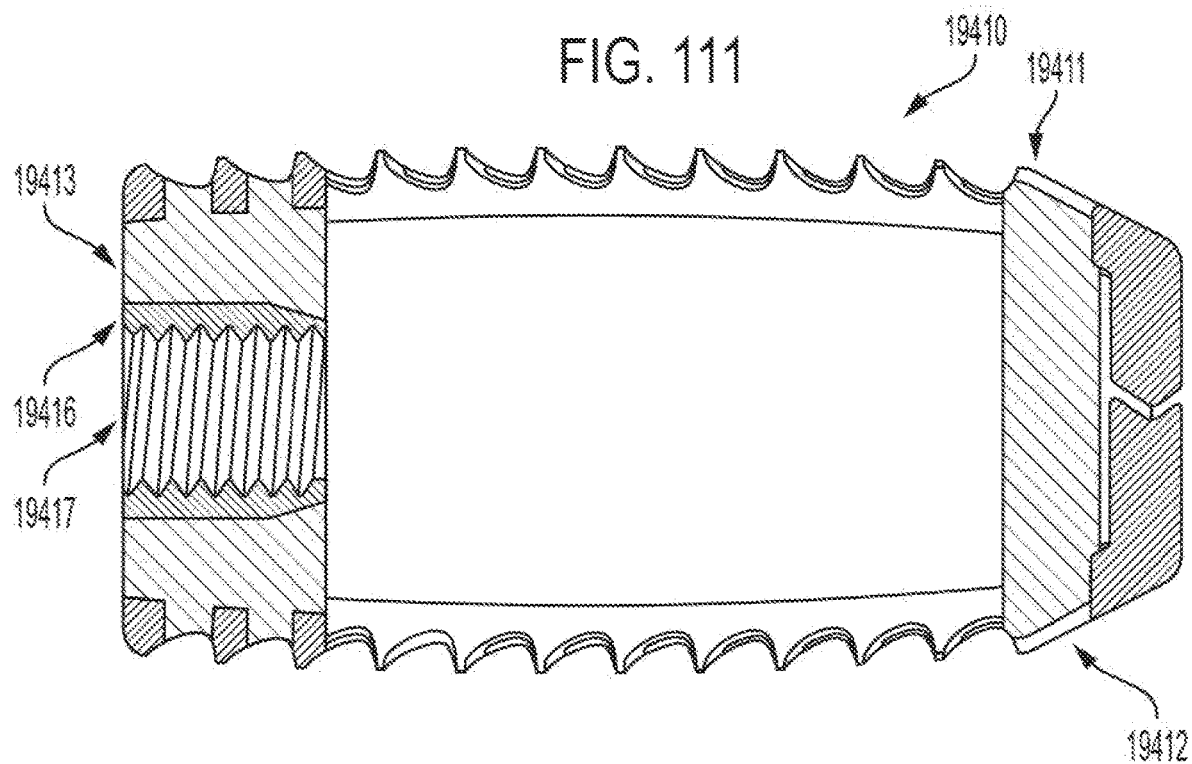

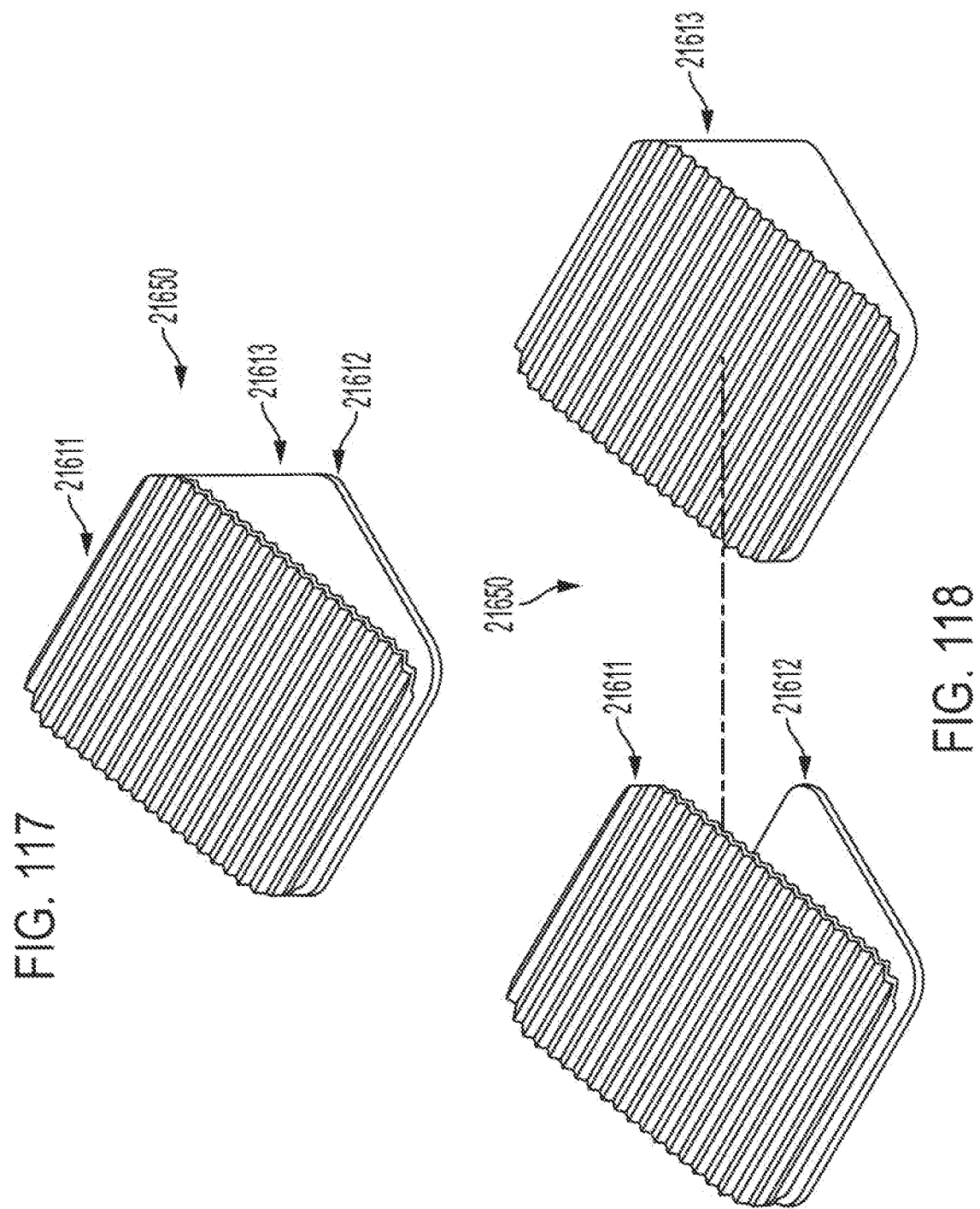

IMPLANT WITH INDEPENDENT ENDPLATES

CROSS REFERENCE TO RELATED APPLICATIONS

This application is a continuation of Ser. No. 16/565,321 filed Sep. 9, 2019, which is a continuation-in-part application of U.S. Nonprovisional patent application Ser. No. 15/895,201, filed Feb. 13, 2018, which claims priority to and the benefit of U.S. Provisional Patent Application No. 62/458,714, filed Feb. 14, 2017, U.S. Provisional Patent Application No. 62/480,383, filed Apr. 1, 2017, U.S. Provisional Patent Application No. 62/480,385, filed Apr. 1, 2017, and U.S. Provisional Patent Application No. 62/619,260, filed Jan. 19, 2018, and a continuation-in-part application of U.S. Nonprovisional patent application Ser. No. 15/942,846, filed Apr. 2, 2018 (U.S. Pat. No. 10,405,983), which is a continuation-in-part application of U.S. Nonprovisional patent application Ser. No. 15/615,227, filed Jun. 6, 2017 (U.S. Pat. No. 9,962,269), which claims the benefit of and priority to U.S. Provisional Patent Application No. 62/346,720, filed Jun. 7, 2016, which are hereby incorporated by reference in their entirety.

FIELD

The present disclosure relates to biocompatible lattice structures and, in particular, to lattice structures with increased lucency in a desired direction with respect to x-ray imaging and to markers with a variable radiolucency or radiopacity.

BACKGROUND

Medical implants can be constructed using a wide range of materials, including metallic materials, Polyether ether ketone (hereinafter "PEEK"), ceramic materials and various other materials or composites thereof. There are competing priorities when selecting a material for an implant in order for the implant to pass regulatory testing. Some priorities when designing an implant could include strength, stiffness, fatigue resistance, radiolucency, and bioactivity. Therefore, when designing an implant to meet regulatory standards, oftentimes, some compromises have to be made to meet all testing requirements.

BRIEF SUMMARY

The biocompatible lattice structures disclosed herein provide an increased lucency. Also disclosed herein is a method of designing and fabricating lattice structure with an increased lucency. In some aspects, markers with a varied radiolucency based on the viewing angle are disclosed.

The lattice structures disclosed herein can have increased lucency over other structures comprising similar materials, porosities, densities and/or volumetric densities. While described in the context of medical implants, it should be understood that the structures disclosed can also be beneficial when used, outside of the body, in medical devices that require a level of lucency or in devices outside of the medical field.

When implants comprise lattice structures or scaffolds for tissue growth, it is desirable to be able to monitor the healing process within the implant. In many cases, it is beneficial to be able to monitor the level of bone ingrowth at certain time intervals after implantation. Generally, imaging of the surgical site is completed using x-ray imaging, however, other types of imaging may also be used.

Many biocompatible structures, including lattice or porous structures, comprise a material generally considered to have radiopaque properties. Materials that are generally considered to be radiopaque also often can only become fully radiopaque when a certain bulk thickness is reached (The term "bulk thickness" refers to the actual thickness of a structure in a certain direction when any voids are removed). For instance, a structure with a uniform 50% volumetric density and a thickness of two inches can have a bulk thickness of one inch in that direction and a lattice with a 25% volumetric density and a thickness of two inches can have a bulk thickness of a half inch in that direction.

The elastic modulus of lattice structures may be modified by changing the volumetric density of the structure such that increasing the volumetric density generally increases the bulk elastic modulus and vice versa. Depending on the particular elastic modulus needed in an application, the need for radiolucency can be at odds with the need for an increased elastic modulus. Therefore, the lattice structures and methods of design and fabrication disclosed herein can be particularly useful in implants where there is a need for a lattice structure with increased lucency at all volumetric density levels.

The present invention provides systems and methods of providing medical implants with two or more independent surfaces. Some embodiments disclosed herein can be used to provide structural support or mechanical spacing. In other embodiments, the structures disclosed herein can provide a scaffold for bone growth. In some aspects, the present invention provides an interbody fusion device that can be implanted between adjacent bones or bone fragments to provide mechanical spacing and a level of mechanical stabilization above the amount required for bone growth but without causing unnecessary stress shielding.

Implants which aid in bone growth can be used in many types of joints, including the bones of the hands and feet or even in the fracture of a single bone. Some examples shown in this application have been adapted for use between adjacent vertebrae. Although some examples presented in this application are optimized for use between adjacent vertebrae, it is appreciated that the invention could be used in other types of adjacent bones or bone fragments within the inventive concept expressed herein. The present invention can be useful in many types of implants, including but not limited to, cervical, lumbar, and thoracic interbody fusion implants, vertebral body replacements, osteotomy wedges, dental implants, bone stems, acetabular cups, cranio-facial plating, bone replacement and fracture plating. Interbody fusion-type devices include implants for the spine and can be designated based on their location (e.g. cervical, thoracic, lumbar) or their intended surgical procedure (e.g. anterior lumbar interbody fusion, posterior lumbar interbody fusion, transforaminal lumbar interbody fusion).

Interbody fusion devices are commonly used in surgical procedures to alleviate chronic joint pain and neurological symptoms by increasing vertebral spacing and allowing the two adjacent bones to fuse together. For instance, in cases where back pain is caused by diseased or degenerated disc material between adjacent vertebrae, spinal fusion surgery can provide a patient with relief from chronic pain. Spinal fusion surgery normally includes the removal of the damaged disc material between adjacent vertebrae and the insertion of an interbody fusion device to provide the mechanical spacing previously provided by the removed disc and to provide mechanical stabilization between the adjacent vertebrae to allow them to fuse together over time. According to Wolff's Law, bone will adapt to stresses placed on it so that bone under stress will grow stronger and bone that isn't stressed will become weaker. In some embodiments, the present invention provides an interbody fusion device with a construct elastic modulus similar to that of the surrounding bone when implanted. By providing independent endplates, the body of the device can be optimized to provide a specific elastic modulus without interference from a rigidly connected endplate structure. Even without a rigidly connected endplate structure, some embodiments expressed herein can provide adequate mechanical spacing between the endplates of adjacent vertebrae. By having an implant body with an optimized elastic modulus and independent endplates, in some aspects, the present invention can stimulate new bone growth and increase the strength of new bone growth through the implant.

In some embodiments, the present invention is comprised of a substantially rigid upper endplate and a substantially rigid lower endplate attached to opposite ends of a body. For clarity and ease of understanding, directions within the figures are described as front, back, right side, left side, top and bottom. The top and bottom of the implants can correspond to the superior and inferior directions, respectively, when implanted in a human spine. The term front refers to the leading edge of the implant when being inserted during implantation. The term back refers to the end opposite the front. The term right side refers to the right side of the implant when viewed from above and the term left side refers to the side opposite the right side. These specific directional references are exemplary and used to the example orientations described herein.

In some examples, the upper and lower endplates are comprised of a substantially rigid biocompatible material, such as titanium or any alloys thereof, and capable of distributing the load asserted by the endplates of the adjacent vertebrae across the body of the device. In some examples, the body is comprised of a material with a lower elastic modulus in the superior to inferior direction than the endplates to provide an adequate amount of stabilization for bone growth between the adjacent vertebrae, but also enough flexibility to prevent undue stress shielding. In some examples, the body is comprised of a material that provides a scaffold for new bone growth, such as a metallic lattice or scaffold structure.

The inventive independent endplate and lattice construction disclosed herein can increase the volume of space available for bone or tissue ingrowth, increase the surface area for bone or tissue attachment and increase radiolucency. Providing an implant with endplates having a higher elastic modulus than the body provides the implant with resistance from surface deformations that can compromise the structural properties of a lattice while allowing the use of a body with a lower modulus of elasticity, increasing the loading of new bone growth. The increased loading on the new bone growth tends to stimulate bone growth and results in higher strength bone growth. It has been found that specific ratios of elastic moduli between the endplates and the body optimize the benefits of reduced surface deformation and increased bone loading.

The independent endplate implant construction disclosed herein is shown in exemplary embodiments, including embodiments than can be spinal interbody devices, a vertebral body replacement implant and an osteotomy wedge. While only a limited number of exemplary embodiments are shown, the independent endplate configuration can be used into other type of implants, especially other implants configured to attach to bone. Specifically, the independent endplate configuration would also be beneficial in dental applications to load new bone growth.

BRIEF DESCRIPTION OF THE SEVERAL VIEWS OF THE DRAWINGS

FIG. 87 is a side view of a second implant also showing the position of the endplates relative to one another.

FIG. 88 is a side sectioned view of a second implant, sectioned through line CC in FIG. 84.

FIG. 89 is an alternative side sectioned view of a second implant, sectioned through line DD in FIG. 84.

FIG. 98 is an isometric view of a fourth implant showing the inventive configuration of the endplates relative to the body on the exterior of the device.

FIG. 99 is an exploded isometric view of a fourth implant showing the endplates separated from the body.

FIG. 105 is an isometric view of a fifth implant showing the inventive configuration of the endplates relative to the body on the exterior of the device.

FIG. 106 is an exploded isometric view of a fifth implant showing the endplates separated from the body.

FIG. 110 is a side view of the fifth implant also showing the position of the endplates relative to one another.

FIG. 111 is a side sectioned view of the fifth implant, sectioned through line HH in FIG. 107.

FIG. 117 is an isometric view of a seventh implant showing the inventive configuration of the endplates relative to the body on the exterior of the device.

FIG. 118 is an exploded isometric view of the seventh implant showing the endplates separated from the body.

FIG. 120 is a rear view of the seventh implant configured without a tool engagement area.

FIG. 121 is a front view of the seventh implant showing the position of the endplates relative to one another.

FIG. 122 is a side view of the seventh implant also showing the position of the endplates relative to one another.

FIG. 123 is a side sectioned view of the seventh implant, sectioned through line JJ in FIG. 119.

FIG. 124 is a perspective view of an eighth implant showing the inventive configuration of the endplates relative to the body on the exterior of the device.

FIG. 125 is an exploded perspective view of the eighth implant showing the endplates separated from the body.

FIG. 126 is a side view of the eighth implant also showing the position of the endplates relative to one another.

FIG. 127 is a top view of the eighth implant showing a possible configuration of an endplate top surface and the location of a later presented section view.

FIG. 128 is a front view of the eighth implant showing the position of the endplates relative to one another.

FIG. 129 is a rear view of the eighth implant configured without a tool engagement area.

FIG. 130 is a side sectioned view of the eighth implant, sectioned through line KK in FIG. 127.

DETAILED DESCRIPTION

Figure 1:
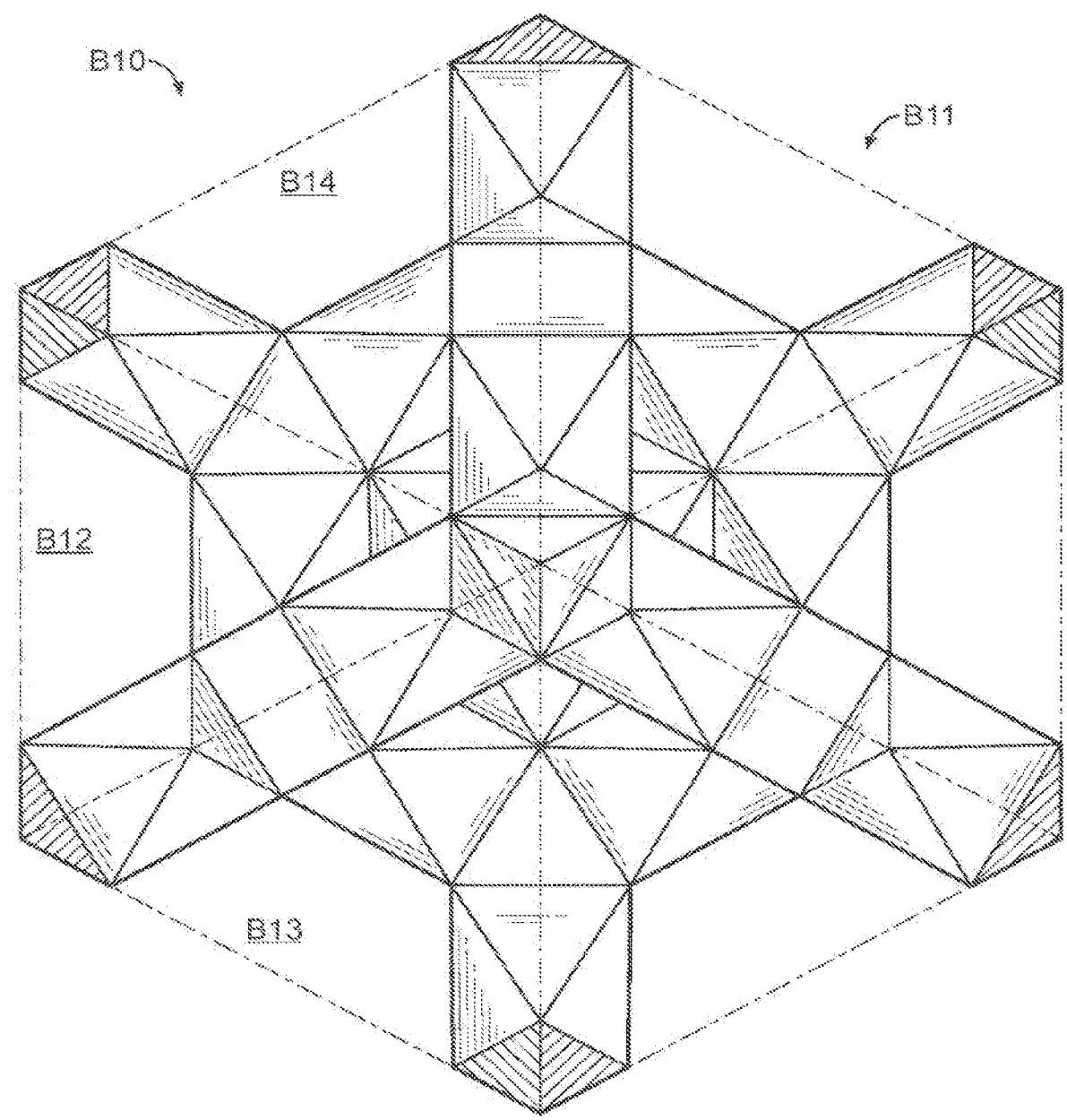
FIG. 1 is an isometric view of a single modified rhombic dodecahedron unit cell containing a full modified rhombic dodecahedron structure along with radial struts that comprise portions of adjacent unit cells.

In many situations, it is desirable to use an implant that is capable of bone attachment or osteointegration over time. It is also desirable in many situations to use an implant that is capable of attachment or integration with living tissue. Examples of implants where attachment to bone or osteointegration is beneficial include, but are not limited to, cervical, lumbar, and thoracic interbody fusion implants, vertebral body replacements, osteotomy wedges, dental implants, bone stems, acetabular cups, cranio-facial plating, bone replacement and fracture plating. In many applications, it is also desirable to stress new bone growth to increase its strength. According to Wolff s law, bone will adapt to stresses placed on it so that bone under stress will grow stronger and bone that isn't stressed will become weaker.

In some aspects, the systems and methods described herein can be directed toward implants that are configured for osteointegration and stimulating adequately stressed new bone growth. Many of the example implants of the present disclosure are particularly useful for use in situations where it is desirable to have strong bone attachment and/or bone growth throughout the body of an implant. Whether bone growth is desired only for attachment or throughout an implant, the present disclosure incorporates a unique lattice structure that can provide mechanical spacing, a scaffold to support new bone growth and a modulus of elasticity that allows new bone growth to be loaded with physiological forces. As a result, the present disclosure provides implants that grow stronger and healthier bone for more secure attachment and/or for a stronger bone after the implant osteointegrates.

The example embodiments of the disclosure presented can be comprised, in whole or in part, of a lattice. A lattice, as used herein, refers to a three-dimensional material with one or more interconnected openings that allow a fluid to communicate from one location to another location through an opening. A three-dimensional material refers to a material that fills a three-dimensional space (i.e., has height, width and length). Lattices can be constructed by many means, including repeating various geometric shapes or repeating random shapes to accomplish a material with interconnected openings. A lattice can alternatively be constructed by drilling holes in two directions of a material. For example, a square lattice can be constructed by generating square holes in one direction, such as a lateral direction, and by generating round holes in another direction, such as the caudal-rostral direction. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two locations together. Interconnections may be configured to allow a fluid to pass from one location to another location.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can comprise of the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 10% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprising repeating geometric patterns can be described using the characteristics of a repeating unit cell. A unit cell in a repeating geometric lattice is a three-dimensional shape capable of being repeated to form a lattice. A repeating unit cell can refer to multiple identical unit cells that are repeated over a lattice structure or a pattern through all or a portion of a lattice structure. Each unit cell is comprised of a certain volume of primary material and a certain void volume, or in other words, a spot volumetric density. The spot volumetric density may cover as few as a partial unit cell or a plurality of unit cells. In many situations, the spot volumetric density will be consistent with the material's volumetric density, but there are situations where it could be desirable to locally increase or decrease the spot volumetric density.

Unit cells can be constructed in numerous volumetric shapes containing various types of structures. Unit cells can be bound by a defined volume of space to constrict the size of the lattice structure or other type of structure within the unit cell. In some embodiments, unit cells can be bound by volumetric shapes, including but not limited to, a cubic volume, a cuboid volume, a hexahedron volume or an amorphous volume. The unit cell volume of space can be defined based on a number of faces that meet at corners. In examples where the unit cell volume is a cubic, cuboid or hexahedron volume, the unit cell volume can have six faces and eight corners, where the corners are defined by the location where three faces meet. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node.

While the present application uses volumetric density to describe example embodiments, it is also possible to describe them using other metrics, including but not limited to cell size, strut size or stiffness. Cell size may be defined using multiple methods, including but not limited to cell diameter, cell width, cell height and cell volume. Strut size may be defined using multiple methods, including but not limited to strut length and strut diameter.

Repeating geometric patterns are beneficial for use in lattice structures contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications may be referred to herein as structural lattices, load-bearing lattices or stressed lattices. In some instances, structural lattices, load-bearing lattices or stressed lattices may be simply referred to as a lattice. Repeating geometric shaped unit cells, particularly the rhombic dodecahedron, are well suited, in theory, for use in structural lattices because of their strength to weight ratio. To increase the actual strength and fatigue resistance of a rhombic dodecahedron lattice, in some embodiments, a modified strut comprised of triangular segments, rather than using a strut with a rectangular or circular cross section is disclosed. Some embodiments herein also modify the angles defining the rhombic faces of a rhombic dodecahedron to change the lattice's elastic modulus and fatigue resistance. The use of triangular segments provides a lattice with highly predictable printed properties that approach the theoretical strength values for a rhombic dodecahedron lattice.

In structural lattice applications, the strength and elastic modulus of the lattice can be approximated by the volumetric density. When the volumetric density increases, the strength and the elastic modulus increases. Compared to other porous structures, the lattice of the present disclosure has a higher strength and elastic modulus for a given volumetric density because of its ability to use the high strength to weight benefits of a rhombic dodecahedron, modified rhombic dodecahedron or radial dodeca-rhombus unit cell.

When configured to provide support for bone or tissue growth, a lattice may be referred to as a scaffold. Lattices can be configured to support bone or tissue growth by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support in-growth beyond mere surface attachment are referred to herein as bulk scaffolds. Scaffolds may also be included in implants as a structural component or a nonstructural component. Scaffolds used in structural applications may be referred to herein as structural scaffolds, load-bearing scaffolds or stressed scaffolds. In some instances, structural scaffolds, load-bearing scaffolds or stressed scaffolds may be simply referred to as a scaffold. In some instances, the use of the term scaffold may refer to a material configured to provide support for bone or tissue growth, where the material is not a lattice.

The scaffolds described herein can be used to promote the attachment or ingrowth of various types of tissue found in living beings. As noted earlier, some embodiments of the scaffold are configured to promote bone attachment and in-growth. The scaffolds can also be configured to promote attachment of in-growth of other areas of tissue, such as fibrous tissue. In some embodiments, the scaffold can be configured to promote the attachment or in-growth of multiple types of tissue. Some embodiments of the scaffolds are configured to be implanted near or abutting living tissue. Near living tissue includes situations where other layers, materials or coatings are located between a scaffold and any living tissue.

In some embodiments, bulk scaffolds with openings and interconnections that are larger than those known in the art are employed. Osteons can range in diameter from about 100 μm and it is theorized that a bundle of osteons would provide the strongest form of new bone growth. Bone is considered fully solid when it has a diameter of greater than 3 mm so it is theorized that a bundle of osteons with a diameter equaling approximately half of that value would provide significant strength when grown within a scaffold. Osteons can grow in irregular shapes so that the cross-sectional area of an osteon could predict its strength. A cylindrical osteon growth with a 3 mm diameter has a cross-sectional area of approximately 7 square mm and a cylindrical osteon with a 1.5 mm diameter has a cross-sectional area of 1.8 square mm. It is theorized that an osteon of an irregular shape with a cross-sectional area of at least 1.8 square millimeters could provide a significant strength advantage when grown in a scaffold.

Most skilled in the art would indicate that pores or openings with a diameter or width between 300 μm to 900 μm, with a pore side of 600 μm being ideal, provide the best scaffold for bone growth. Instead, some embodiments of the present disclosure include openings and interconnections with a diameter or width on the order of 1.0 to 15.0 times the known range, with the known range being 300 μm to 900 μm, resulting in openings from 0.07 mm$^2$ up to 145 mm$^2$ cross sectional area for bone growth. In some examples, pores or openings with a diameter or width between and including 100 μm to 300 μm could be beneficial. Some examples include openings and interconnections with a diameter on the order of 1.0 to 5.0 times the known range. It has been at least theorized that the use of much larger openings and interconnections than those known in the art will allow full osteons and solid bone tissue to form throughout the bulk scaffold, allowing the vascularization of new, loadable bone growth. In some examples, these pores may be 3 mm in diameter or approximately 7 mm² in cross sectional area. In other examples, the pores are approximately 1.5 mm in diameter or approximately 1.75 mm² in cross sectional area. The use of only the smaller diameter openings and interconnections known in the art are theorized to limit the penetration of new bone growth into a bulk scaffold because the smaller diameter openings restrict the ability of vascularization throughout the bulk scaffold.

A related structure to a lattice is a closed cell material. A closed cell material is similar to a lattice, in that it has openings contained within the bounds of a three-dimensional material, however, closed cell materials generally lack interconnections between locations through openings or other pores. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present disclosure can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, bulk metallic glass, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing, infiltrated binder jetting, print-to-cast, print-to-plating, bulk metallic glass extrusion, nano-laser printing and directed energy deposition.

In another example, the lattice of the present disclosure is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6Al4V ELI wrought (American Society for Testing and Materials ("ASTM") F136) is a particularly well-suited titanium alloy for scaffolds. While Ti6Al4V ELI wrought is the industry standard titanium alloy used for medical purposes, other titanium alloys, including but not limited to, unalloyed titanium (ASTM F67), Ti6Al4V standard grade (ASTM F1472), Ti6Al7Nb wrought (ASTM 1295), Ti5Al2.5Fe wrought (British Standards Association/International Standard Organization Part 10), CP and Ti6Al4V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be used.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), bone marrow aspirate (BMA), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating modified rhombic dodecahedron (hereinafter "MRDD") unit cell can present a preferable combination of stiffness, strength, fatigue resistance, and conditions for bone ingrowth. In some embodiments, the repeating MRDD lattice comprises titanium or a titanium alloy. A generic rhombic dodecahedron (hereinafter "RDD"), by definition, has twelve sides in the shape of rhombuses. When repeated in a lattice, an RDD unit cell is comprised of twenty-four struts that meet at fourteen vertices. The twenty-four struts define the twelve planar faces of the structure. An opening or interconnection is disposed at the center of each planar face, allowing communication from inside the unit cell to outside the unit cell.

Figure 2:
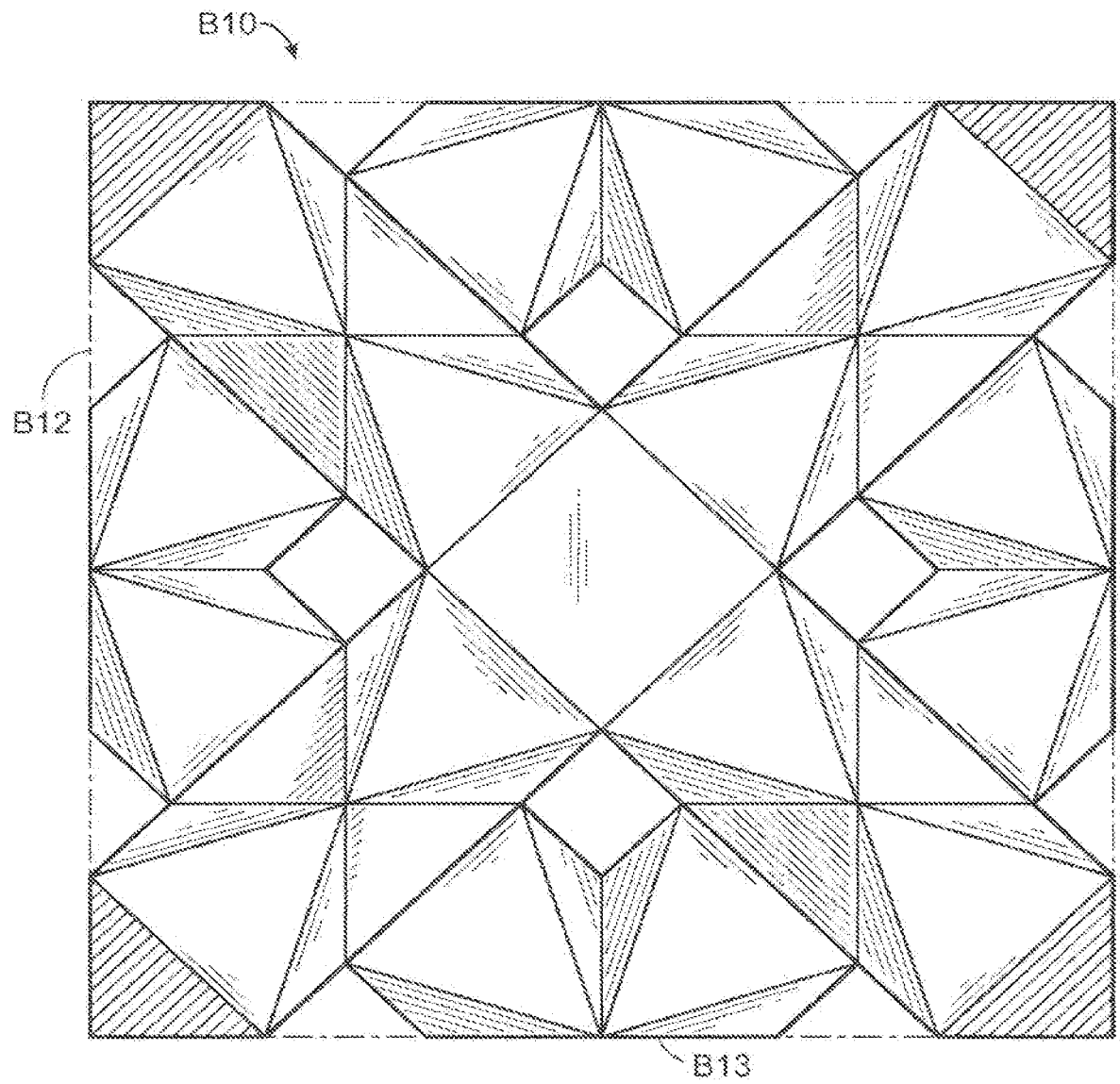
FIG. 2 is a side view of a single modified rhombic dodecahedron unit cell showing the configuration of interconnections when viewed from a lateral direction.

An example of the MRDD unit cell 10 is shown in FIGS. 1-5. FIG. 1 illustrates an isometric view of a single MRDD unit cell 10 containing a full MRDD structure along with radial struts 31 that comprise portions of adjacent unit cells. In FIG. 2 is a side view of a single MRDD unit cell 10 showing the configuration of interconnections when viewed from a lateral direction. A top or bottom view of the MRDD unit cell 10 would be substantially the same as the side view depicted in FIG. 2. The MRDD unit cell 10 differs in both structural characteristics and method of design from generic RDD shapes. A generic RDD is comprised of twelve faces, where each face is an identical rhombus with an acute angle of 70.5 degrees and an obtuse angle of 109.5 degrees. The shape of the rhombus faces in a generic RDD do not change if the size of the unit cell or the diameter of the struts are changed because the struts are indexed based on their axis and each strut axis passes through the center of the fourteen nodes or vertices.

In some embodiments of the MRDD, each node 30 is contained within a fixed volume that defines its bounds and provides a fixed point in space for the distal ends of the struts 31. The fixed volume containing the MRDD or a sub-unit cell of the MRDD can comprise of various shapes, including but not limited to, a cubic, cuboid, hexahedron or amorphous volume. Some examples use a fixed volume with six faces and eight corners defined by locations where three faces meet. The orientation of the struts 31 can be based on the center of a node face at its proximate end and the nearest corner of the volume to that node face on its distal end. Each node 30 is preferably an octahedron, more specifically a square bipyramid (i.e., a pyramid and inverted pyramid joined on a horizontal plane). Each node 30, when centrally located in a cuboid volume, more preferably comprises a square plane parallel to a face of the cuboid volume and six vertices. Each node 30 is oriented so that each of the six vertices are positioned at their closest possible location to each of the six faces of the cuboid volume. As used herein, the term "centrally located," with regards to the node's location within a volume refers to positioning the node at a location substantially equidistant from opposing walls of the volume. In some embodiments, the node 30 can have a volumetric density of 100% and in other embodiments, the node can have a volumetric density of less than 100%. Each face of the square bipyramid node 30 can be triangular and each face can provide a connection point for a strut 31.

The struts 31 can also be octahedrons, comprising an elongate portion of six substantially similar elongate faces and two end faces. The elongate faces can be isosceles triangles with a first internal angle, angle A, and a second internal angle, angle B, where angle B is greater than angle A. The end faces can be substantially similar isosceles triangles to one another with a first internal angle, angle C, and a second internal angle, angle D, where angle D is greater than angle C. Preferably, angle C is greater than angle A.

The strut direction of each strut is a line or vector defining the orientation of a strut and it can be orthogonal or non-orthogonal relative to the planar surface of each node face. In the MRDD and radial dodeca-rhombus structures disclosed herein, the strut direction can be determined using a line extending between the center of the strut end faces, the center of mass along the strut or an external edge or face of the elongate portion of the strut. When defining a strut direction using a line extending between the center of the strut end faces, the line is generally parallel to the bottom face or edge of the strut. When defining a strut direction using a line extending along the center of mass of the strut, the line can be nonparallel to the bottom face or edge of the strut. The octahedron nodes of the MRDD can be scaled to increase or decrease volumetric density by changing the origin point and size of the struts. The distal ends of the struts, however, are locked at the fixed volume corners formed about each node so that their angle relative to each node face changes as the volumetric density changes. Even as the volumetric density of an MRDD unit cell changes, the dimensions of the fixed volume formed about each node does not change. In FIG. 1, dashed lines are drawn between the corners of the MRDD unit cell 10 to show the cube 11 that defines its bounds. In the MRDD unit cell in FIG. 1, the height 12, width 13 and depth 14 of the unit cell are substantially the same, making the area defined by the cube 11.

In some embodiments, the strut direction of a strut 31 can intersect the center of the node and the corner of the cuboid volume nearest to the node face where the strut 31 is fixed. In some embodiments, the strut direction of a strut 31 can intersect just the corner of the cuboid volume nearest to the node face where the strut is fixed. In some embodiments, a reference plane defined by a cuboid or hexahedron face is used to describe the strut direction of a strut. When the strut direction of a strut is defined based on a reference plane, it can be between 0 degrees and 90 degrees from the reference plane. When the strut direction of a strut is defined based on a reference plane, it is preferably eight degrees to 30 degrees from the reference plane.

By indexing the strut orientation to a variable node face on one end and a fixed point on its distal end, the resulting MRDD unit cell can allow rhombus shaped faces with a smaller acute angle and larger obtuse angle than a generic RDD. The rhombus shaped faces of the MRDD can have two substantially similar opposing acute angles and two substantially similar opposing obtuse angles. In some embodiments, the acute angles are less than 70.5 degrees and the obtuse angles are greater than 109.5 degrees. In some embodiments, the acute angles are between 0 degrees and 55 degrees and the obtuse angles are between 125 degrees and 180 degrees. In some embodiments, the acute angles are between 8 degrees and 60 degrees and the obtuse angles are between 120 degrees and 172 degrees. The reduction in the acute angles increases fatigue resistance for loads oriented across the obtuse angle corner to far obtuse angle corner. The reduction in the acute angles and increase in obtuse angles also orients the struts to increase the MRDD's strength in shear and increases the fatigue resistance. By changing the rhombus corner angles from a generic RDD, shear loads pass substantially in the axial direction of some struts, increasing the shear strength. Changing the rhombus corner angles from a generic RDD also reduces overall deflection caused by compressive loads, increasing the fatigue strength by resisting deflection under load.

Figure 3:
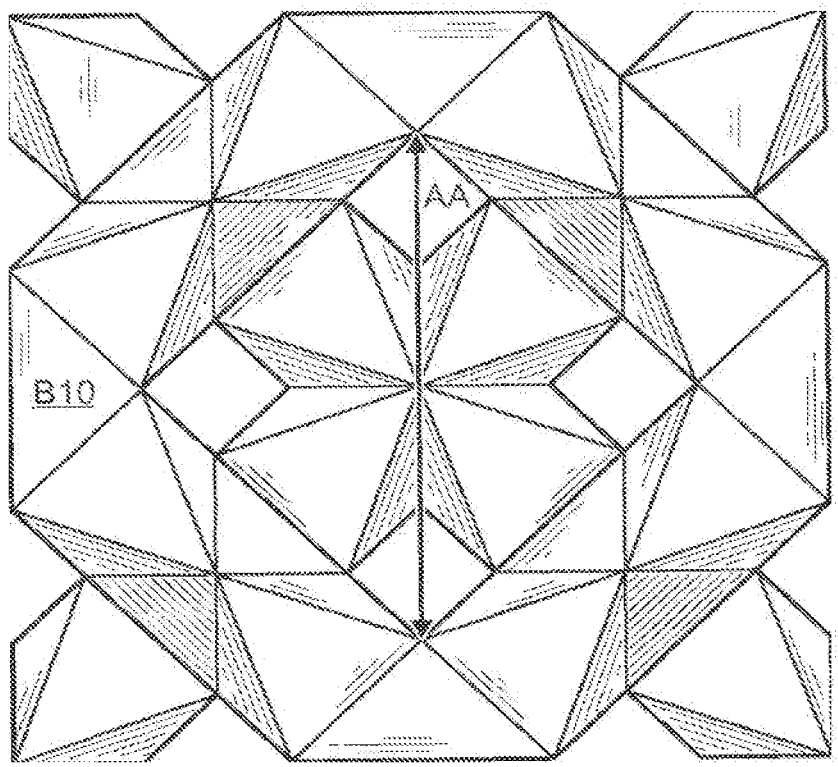
FIG. 3 is a side view of a single modified rhombic dodecahedron unit cell where the central void is being measured using the longest dimension method.
Figure 4:
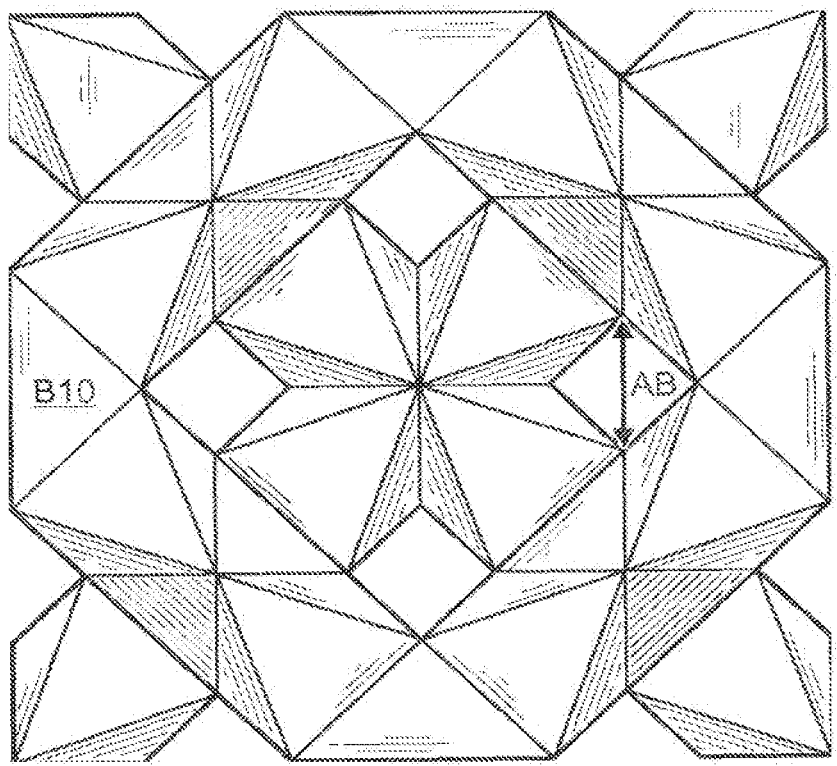
FIG. 4 is a side view of a single modified rhombic dodecahedron unit cell where an interconnection is being measured using the longest dimension method.

When placed towards the center of a lattice structure, the twelve interconnections of a unit cell 30 connect to twelve different adjacent unit cells, providing continuous paths through the lattice. The size of the central void and interconnections in the MRDD may be defined using the longest dimension method as described herein. Using the longest dimension method, the central void can be defined by taking a measurement of the longest dimension as demonstrated in FIG. 3. In FIG. 3, the longest dimension is labeled as distance AA. The distance AA can be taken in the vertical or horizontal directions (where the directions reference the directions on the page) and would be substantially the same in this example. The interconnections may be defined by their longest measurement when viewed from a side, top or bottom of a unit cell. In FIG. 4, the longest dimension is labeled as distance AB. The distance AB can be taken in the vertical or horizontal directions (where the directions reference the directions on the page). The view in FIG. 4 is a lateral view, however, in this example the unit cell will appear substantially the same when viewed from the top or bottom.

Figure 5:
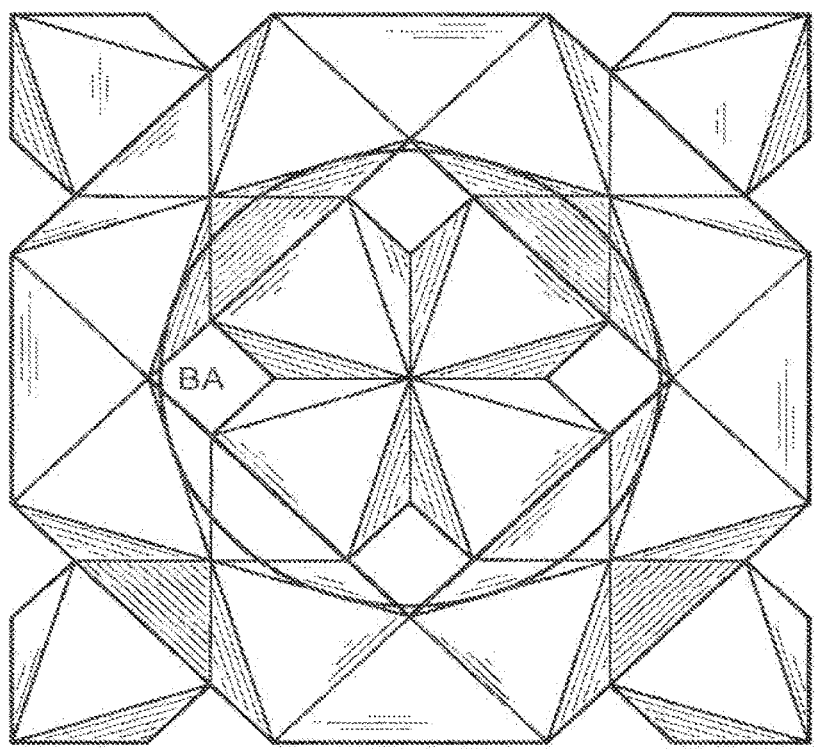
FIG. 5 is a side view of the central void of a modified rhombic dodecahedron unit cell being measured with the largest sphere method.
Figure 6:
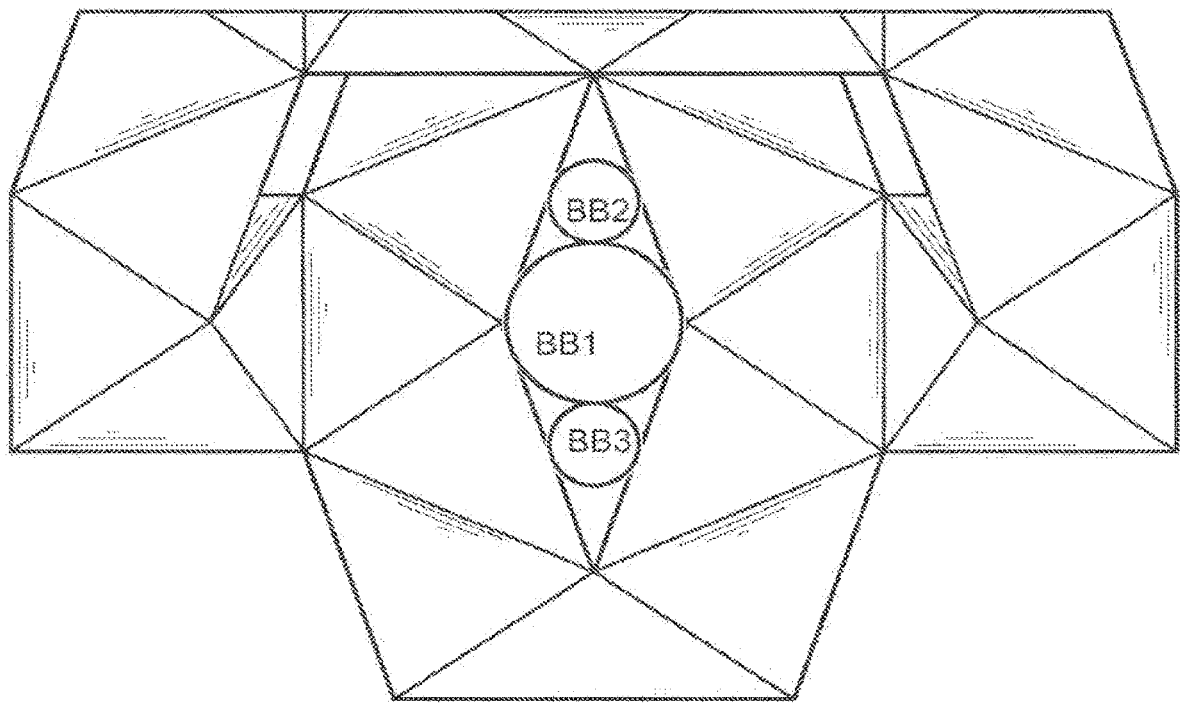
FIG. 6 is a view from a direction normal to the planar direction of an interconnection being measured with the largest sphere method.

The size of the central void and interconnections can alternatively be defined by the largest sphere method as described herein. Using the largest sphere method, the central void can be defined by the diameter of the largest sphere that can fit within the central void without intersecting the struts. FIG. 5 depicts an example of the largest sphere method being used to define the size of a central void with a sphere with a diameter of BA. FIG. 6 is a view from a direction normal to the planar direction of an interconnection being measured with the largest sphere method. The interconnections are generally rhombus shaped and their size can alternatively be defined by the size of the length and width of three circles drawn within the opening. As shown in FIG. 6, within the plane defining a side, a first circle BB1 is drawn at the center of the opening so that it is the largest diameter circle that can fit without intersecting the struts. A second circle BB2 and third circle BB3 is then drawn so that they are tangential to the first circle BB1 and the largest diameter circles that can fit without intersecting the struts. The diameter of the first circle BB1 is the width of the interconnection and the sum of the diameters of all three circles BB1, BB2 & BB3 represents the length of the interconnection. Using this method of measurement removes the acute corners of the rhombus shaped opening from the size determination. In some instances, it is beneficial to remove the acute corners of the rhombus shaped opening from the calculated size of the interconnections because of the limitations of additive manufacturing processes. For example, if an SLS machine has a resolution of 12 μm where the accuracy is within 5 μm, it is possible that the acute corner could be rounded by the SLS machine, making it unavailable for bone ingrowth. When designing lattices for manufacture on less precise additive process equipment, it can be helpful to use this measuring system to better approximate the size of the interconnections.

Using the alternative measuring method, in some examples, the width of the interconnections is approximately 600 μm and the length of the interconnections is approximately 300 μm. The use of a 600 μm length and 300 μm width provides an opening within the known pore sizes for bone growth and provides a surface area of roughly 1.8 square millimeters, allowing high strength bone growth to form. Alternative embodiments may contain interconnections with a cross sectional area of 1.0 to 15.0 times the cross-sectional area of a pore with a diameter of 300 μm. Other embodiments may contain interconnections with a cross sectional area of 1.0 to 15.0 times the cross-sectional area of a pore with a diameter of 900 μm.

The MRDD unit cell also has the advantage of providing at least two sets of substantially homogenous pore or opening sizes in a lattice structure. In some embodiments, a first set of pores have a width of about 200 μm to 900 μm and a second set of pores have a width of about 1 to 15 times the width of the first set of pores. In some embodiments, a first set of pores can be configured to promote the growth of osteoblasts and a second set of pores can be configured to promote the growth of osteons. Pores sized to promote osteoblast growth can have a width of between and including about 100 μm to 900 μm. In some embodiments, pores sized to promote osteoblast growth can have a width that exceeds 900 pm. Pores sized to promote the growth of osteons can have a width of between and including about 100 μm to 13.5 mm. In some embodiments, pores sized to promote osteon growth can have a width that exceeds 13.5 mm.

In some embodiments, it is beneficial to include a number of substantially homogenous larger pores and a number of substantially homogenous smaller pores, where the number of larger pores is selected based on a ratio relative to the number of smaller pores. For example, some embodiments have one large pore for every one to twenty-five small pores in the lattice structure. Some embodiments preferably have one large pore for every eight to twelve smaller pores. In some embodiments, the number of larger and smaller pores can be selected based on a percentage of the total number of pores in a lattice structure. For example, some embodiments can include larger pores for 4% to 50% of the total number of pores and smaller pores for 50% to 96% of the total number of pores. More preferably, some embodiments can include larger pores for about 8% to 13% of the total number of pores and smaller pores for about 87% to 92% of the total number of pores. It is believed that a lattice constructed with sets of substantially homogenous pores of the disclosed two sizes provides a lattice structure that simultaneously promotes osteoblast and osteon growth.

The MRDD unit cell may also be defined by the size of the interconnections when viewed from a side, top or bottom of a unit cell. The MRDD unit cell has the same appearance when viewed from a side, top or bottom, making the measurement in a side view representative of the others. When viewed from the side, as in FIG. 4, an MRDD unit cell displays four distinct diamond shaped interconnections with substantially right angles. The area of each interconnection is smaller when viewed in the lateral direction than from a direction normal to the planar direction of each interconnection, but the area when viewed in the lateral direction can represent the area available for bone to grow in that direction. In some embodiments, it may be desirable to index the properties of the unit cell and lattice based on the area of the interconnections when viewed from the top, bottom or lateral directions.

In some embodiments of the lattice structures disclosed herein, the central void is larger than the length or width of the interconnections. Because the size of each interconnection can be substantially the same in a repeating MRDD structure, the resulting lattice can be comprised of openings of at least two discrete sizes. In some embodiments, it is preferable for the diameter of the central void to be approximately two times the length of the interconnections. In some embodiments, it is preferable for the diameter of the central void to be approximately four times the width of the interconnections.

In some embodiments, the ratio between the diameter of the central void and the length or width of the interconnections can be changed to create a structural lattice of a particular strength. In these embodiments, there is a correlation where the ratio between the central void diameter and the length or width of the interconnections increases as the strength of the structural lattice increases.

Figure 7:
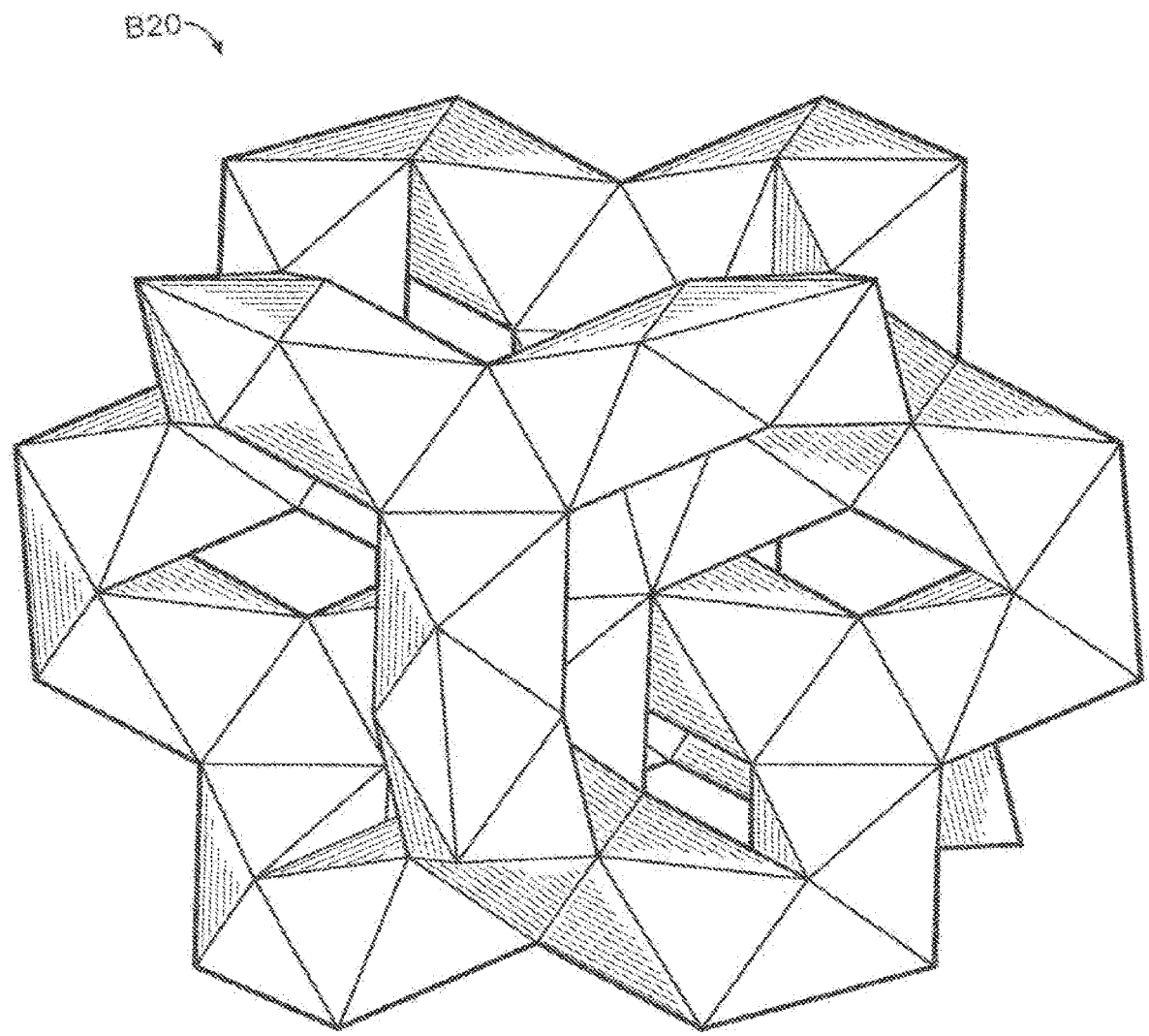
FIG. 7 is an isometric view of a single radial dodeca-rhombus unit cell.
Figure 8:
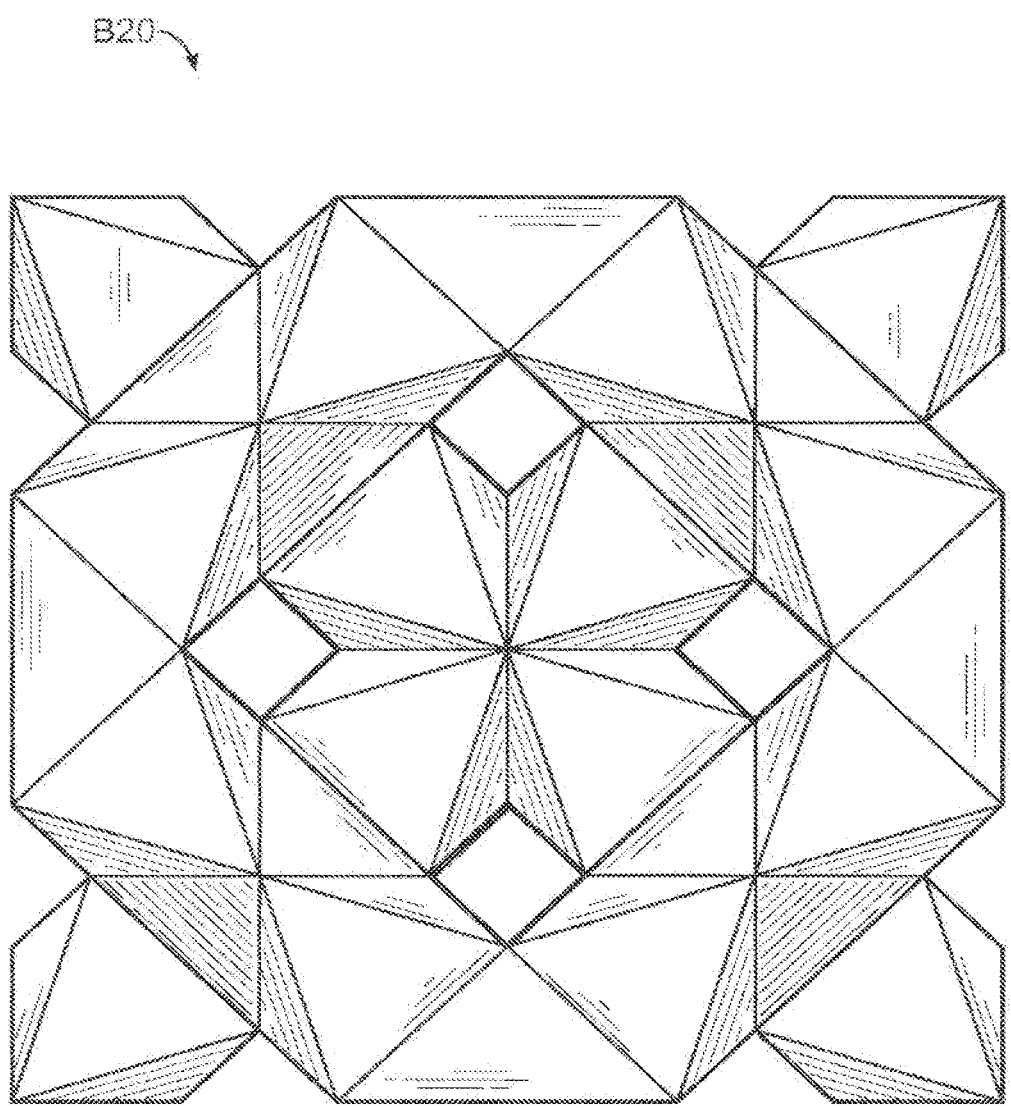
FIG. 8 is a side view of a single radial dodeca-rhombus unit cell.

It is also believed that a lattice using a repeating radial dodeca-rhombus (hereinafter "RDDR") unit cell can present a preferable combination of stiffness, strength, fatigue resistance, and conditions for bone ingrowth. In some embodiments, the repeating RDDR lattice comprises titanium or a titanium alloy. In FIG. 7 is an isometric view of a single RDDR unit cell 20 containing a full RDDR structure. In FIG. 8 is a side view of a single RDDR unit cell 20 showing the configuration of interconnections when viewed from a lateral direction. A top or bottom view of the RDDR unit cell 20 would be substantially the same as the side view depicted in FIG. 8.

As used herein, an RDDR unit cell 20 is a three-dimensional shape comprising a central node with radial struts and mirrored struts thereof forming twelve rhombus shaped structures. The node is preferably an octahedron, more specifically a square bipyramid (i.e., a pyramid and inverted pyramid joined on a horizontal plane). Each face of the node is preferably triangular and fixed to each face is a strut comprised of six triangular facets and two end faces. The central axis of each strut can be orthogonal or non-orthogonal relative to the planar surface of each node face. The central axis may follow the centroid of the strut. The RDDR is also characterized by a central node with one strut attached to each face, resulting in a square bipyramid node with eight struts attached.

Figure 9:
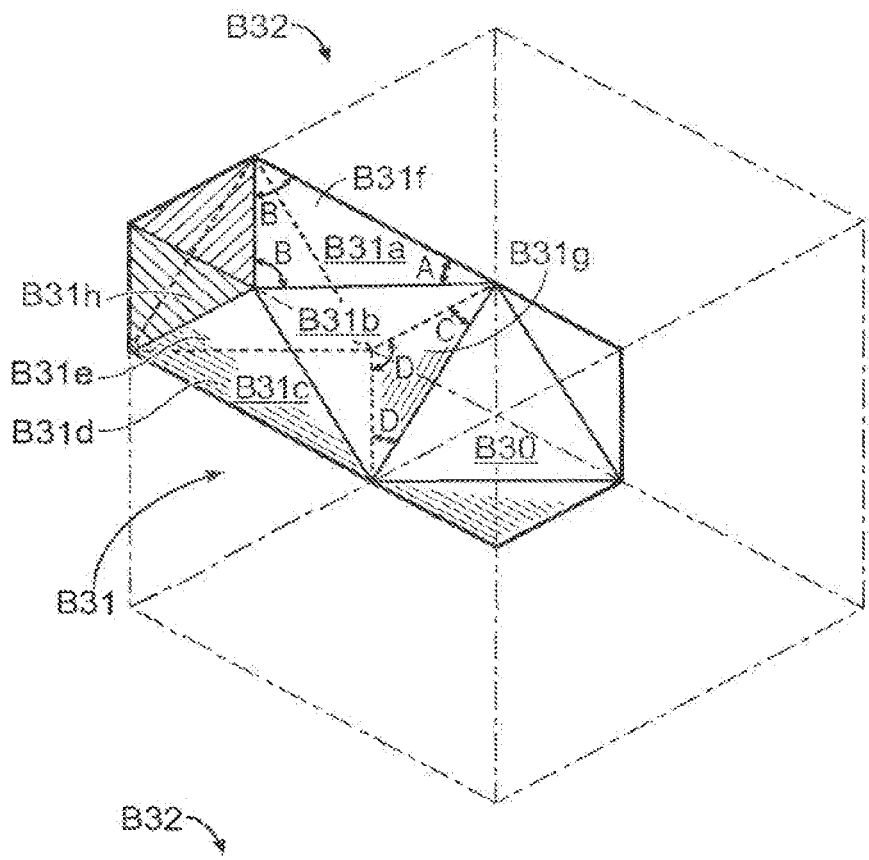
FIG. 9 is an isometric view of an example of a single node and single strut combination that could be used in a radial dodeca-rhombus unit cell.

Examples of node and strut combinations are shown in FIGS. 9-13. FIG. 9 depicts an isometric view of a single node 30 with a single strut 31 attached. The node 30 is a square bipyramid oriented so that two peaks face the top and bottom of a volume 32 defining the bounds of the node 30 and any attached strut(s) 31. The node 30 is oriented so that the horizontal corners are positioned at their closest point to the lateral sides of the volume 32. The strut 31 extends from a node 30 face to the corner of the volume 32 defining the bounds of the node and attached struts. In FIG. 9, the central axis of the strut 31 is 45 degrees above the horizontal plane where the node's planar face is 45 degrees above a horizontal plane.

FIG. 9 also details an octahedron strut 31, where dashed lines show hidden edges of the strut. The strut 31 is an octahedron with an elongate portion of six substantially similar elongate faces and two end faces. The elongate faces 31a, 31b, 31c, 31d, 31e and 31f of the strut 31 define the outer surface of the strut's elongate and somewhat cylindrical surface. Each of the elongate faces 31a, 31b, 31c, 31d, 31e and 31f is an isosceles triangle with a first internal angle, angle A, and a second internal angle, angle B, where angle B is greater than angle A. The strut 31 also has two end faces 31f, 31g, which are isosceles triangles that are substantially similar to one another, having a first internal angle, angle C, and a second internal angle, angle D, and where angle D is greater than angle C. When comparing the internal angles of the elongate faces 31a, 31b, 31c, 31d, 31e and 31f to the end faces 31f and 31g, angle C is greater than angle A.

Figure 10:
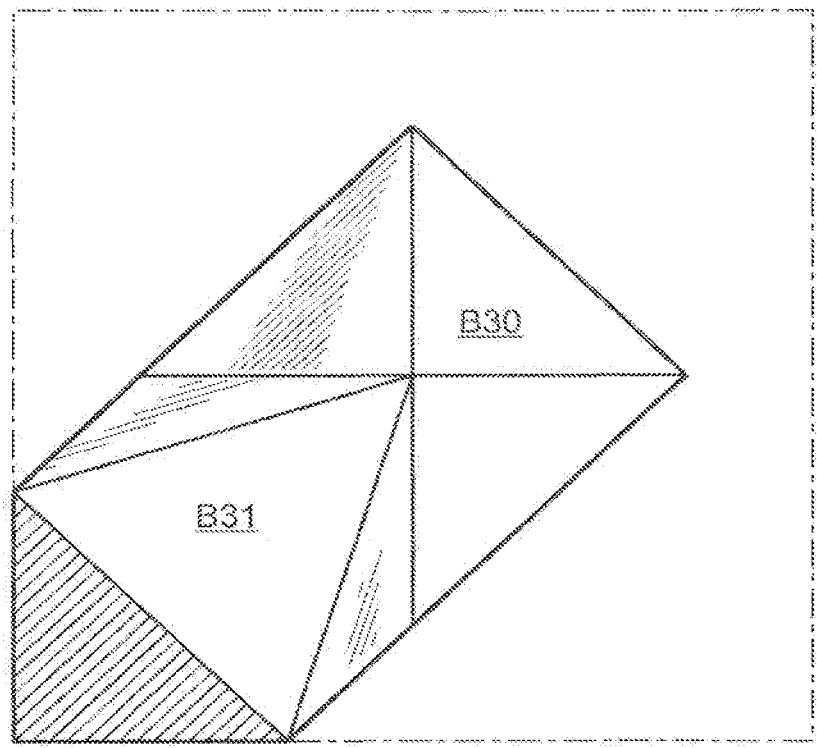
FIG. 10 is a side view of an example of a single node and single strut combination that could be used in a radial dodeca-rhombus unit cell.
Figure 11:
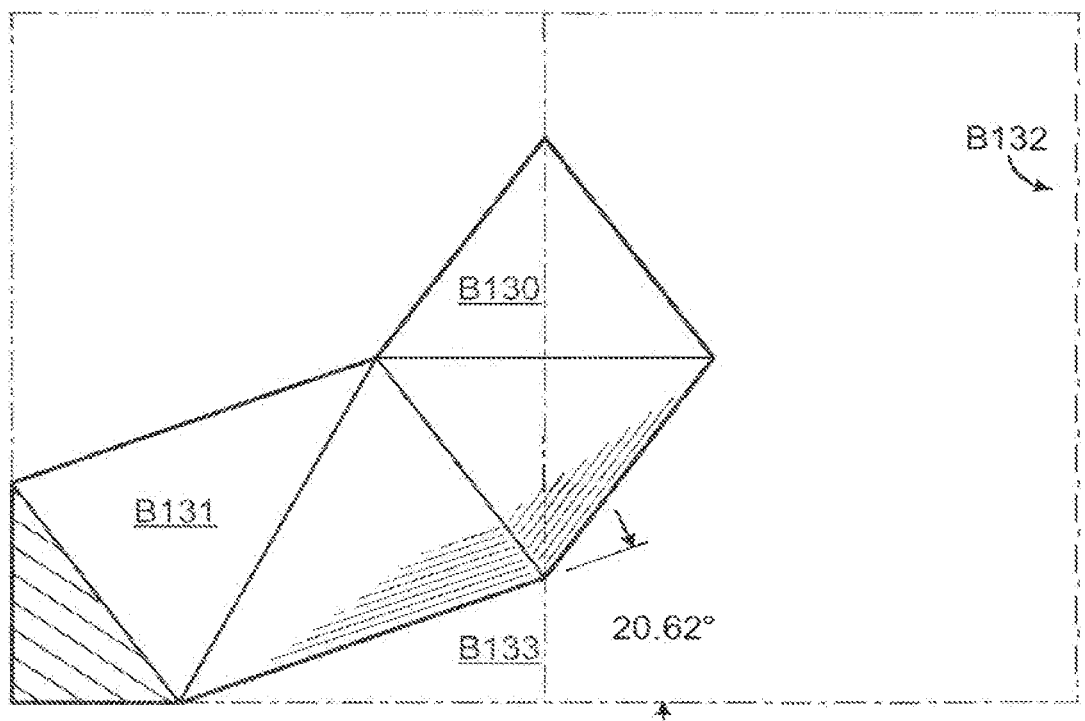
FIG. 11 is a side view of a single node and single strut combination configured for use in a lattice with an elastic modulus of approximately 3 GPa, viewed from the corner of the volume defining the bounds of the combination.
Figure 12:
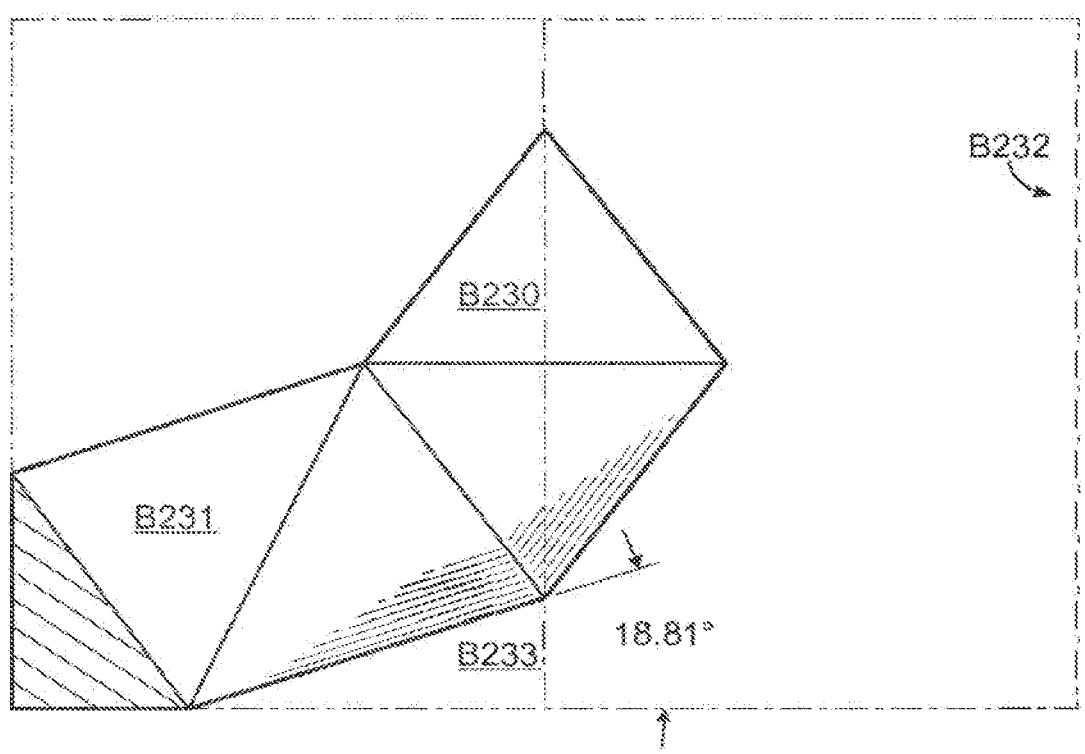
FIG. 12 is a side view of a single node and single strut combination configured for use in a lattice with an elastic modulus of approximately 4 GPa, viewed from the corner of the volume defining the bounds of the combination.
Figure 13:
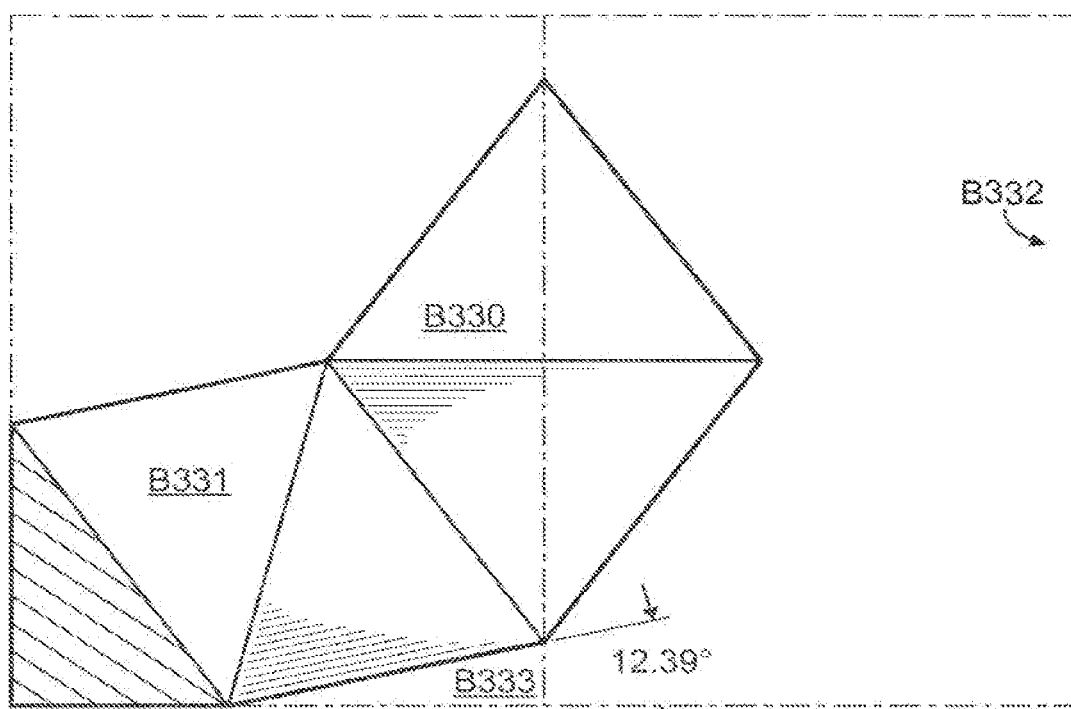
FIG. 13 is a side view of a single node and single strut combination configured for use in a lattice with an elastic modulus of approximately 10 GPa, viewed from the corner of the volume defining the bounds of the combination.

In FIG. 10 is a side view of the node 30 and strut 31 combination bounded by volume 32. In the side view, the height of the node 30 compared to the height of the cube 32 can be compared easily. FIGS. 11-13 depict side views of node and strut combinations, viewed from a corner of the volume rather than a wall or face, and where the combinations have been modified from FIGS. 9-10 to change the volumetric density of the resulting unit cell. In FIG. 11, the height of the node 130 has increased relative to the height of the volume 132. Since the distal end of the strut 131 is fixed by the location of a corner of the volume 132, the strut 131 must change its angle relative to its attached node face so that it becomes non-orthogonal. The node 130 and strut 131 combination, where the angle of the strut 131 from a horizontal plane is about 20.6 degrees, would be appropriate for a lattice structure with an elastic modulus of approximately 3 GPa, for a lattice structure comprising, for example, Ti4Al6V and a 2 mm×2 mm×2 mm unit cell.

In FIG. 12, the height of the node 230 relative to the height of the cube 232 has been increased over the ratio of FIG. 11 to create a node 230 and strut 231 combination that would be appropriate for a lattice structure with an elastic modulus of approximately 4 GPa, for a lattice structure comprising, for example, Ti4Al6V and a 2 mm×2 mm×2 mm unit cell. As the height of the node 230 increases, the angle between the strut 231 and a horizontal plane decreases to about 18.8 degrees. As the height of the node 230 increases, the size of the node faces also increase so that the size of the strut 231 increases. While the distal end of the strut 231 is fixed to the corner of the volume 232, the size of the distal end increases to match the increased size of the node face to maintain a substantially even strut diameter along its length. As the node and strut increase in volume, the volumetric density increases, as does the elastic modulus. In FIG. 13, the height of the node 330 relative to the height of the volume 332 has been increased over the ratio of FIG. 13 to create a node 330 and strut 331 combination that would be appropriate for a lattice structure with an elastic modulus of approximately 10 GPa, for a lattice structure comprising, for example, Ti4Al6V and a 2 mm×2 mm×2 mm unit cell. In this configuration, the angle 333 between the strut 331 and a horizontal plane decreases to about 12.4 degrees and the volumetric density increases over the previous examples. The single node and strut examples can be copied and/or mirrored to create unit cells of appropriate sizes and characteristics. For instance, the angle between the strut and a horizontal plane could be increased to 25.8 degrees to render a lattice with a 12.3% volumetric density and an elastic modulus of about 300 MPa. While a single node and single strut were shown in the examples for clarity, multiple struts may be attached to each node to create an appropriate unit cell or sub-unit cell.

Adjacent struts extending from adjacent node faces on either the upper half or lower half of the node have an angle from the horizontal plane and a lateral separation angle defined by an angle between the strut directions of adjacent struts. In the MRDD and RDDR structures, adjacent struts have an external edge or face of the elongate portion extending closest to the relevant adjacent strut. The lateral separation angle, as used herein, generally refers to the angle between an external edge or face of the elongate portion of a strut extending closest to the relevant adjacent strut. In some embodiments, a lateral separation angle defined by a line extending between the center of the strut end faces or a line defined by the center of mass of the struts can be used in reference to a similar calculation for an adjacent strut.

Figure 14:
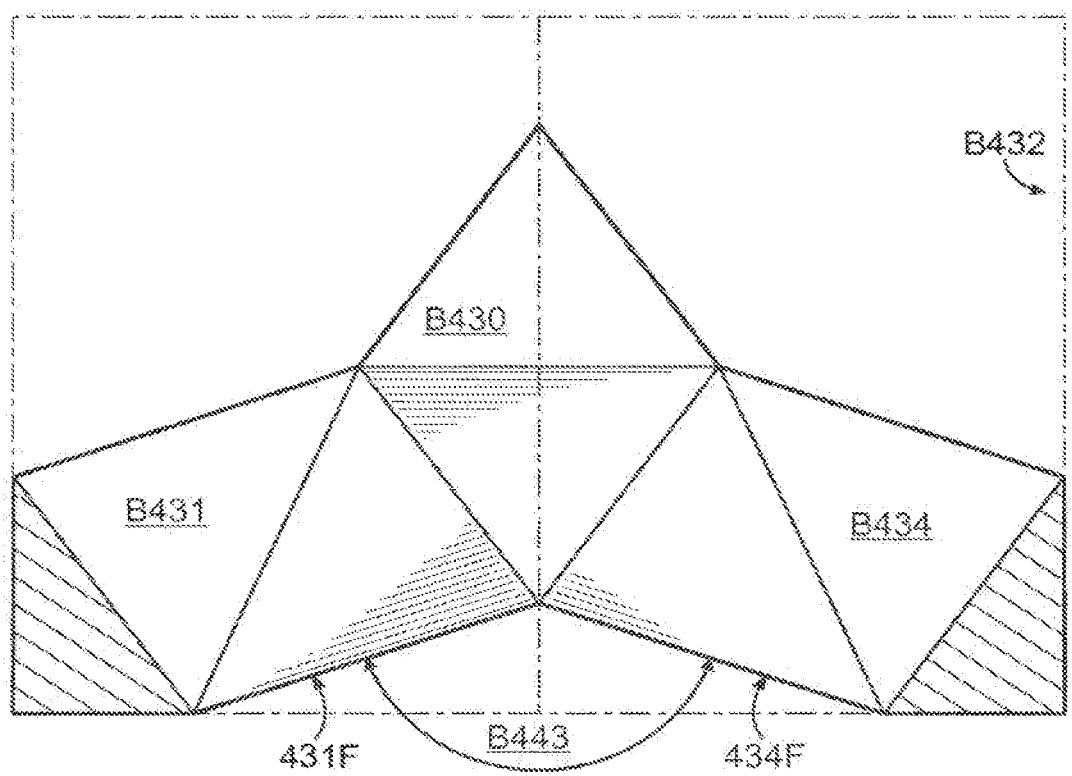
FIG. 14 is a side view of a single node and two adjacent struts viewed from the corner of the volume defining the bounds of the combination and the lateral separation angle.

The lateral separation angle is the angle between the nearest face or edge of a strut to an adjacent strut. The lateral separation angle can be measured as the smallest angle between the nearest edge of a strut to the nearest edge of an adjacent strut, in a plane containing both strut edges. The lateral separation angle can also be measured as the angle between the nearest face of a strut to the nearest face of an adjacent strut in a plane normal to the two strut faces. In embodiments without defined strut edges or strut faces, the lateral separation angle can be measured as an angle between the nearest portion of one strut to the nearest portion of an adjacent strut. For a unit cell in a cubic volume, as the strut angle from the horizontal plane decreases, the lateral separation angle approaches 90 degrees. For a unit cell in a cubic volume, as the strut angle from the horizontal plane increases, the lateral separation angle approaches 180 degrees. In some embodiments, it is preferable to have a lateral separation angle greater than 109.5 degrees. In some embodiments, it is preferable to have a lateral separation angle of less than 109.5 degrees. In some embodiments, it is preferable to have a lateral separation angle of between and including about 108 degrees to about 156 degrees. In some embodiments, it is more preferable to have a lateral separation angle of between and including 111 degrees to 156 degrees. In some embodiments, it is more preferable to have a lateral separation angle of between and including 108 degrees to 120 degrees. In some embodiments, it is most preferable to have a lateral separation angle of between and including about 111 degrees to 120 degrees. In some embodiments, it is more preferable to have a lateral separation angle of between and including 128 degrees to 156 degrees. FIG. 14 depicts a side view, viewed from a corner of the cube 432, of a single node 430 with two adjacent struts 431, 434 attached, and where the lateral separation angle 443 is identified. When measured from the nearest edge of a strut to the nearest edge of an adjacent strut, the lateral separation angle 443 is about 116 degrees.

Figure 16:
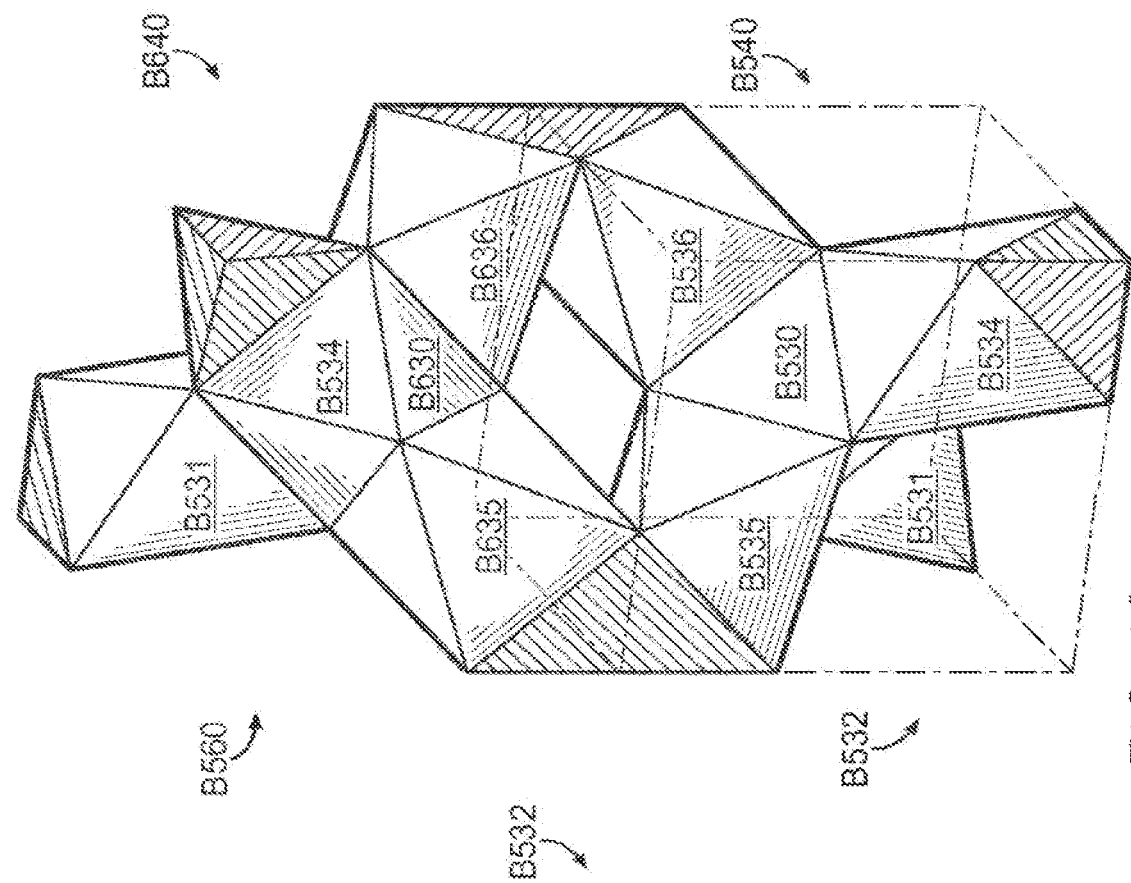
FIG. 16 is an isometric view of two sub-unit cells in a stacked formation where the upper sub-unit cell is inverted and fixed to the top of the lower sub-unit cell.
Figure 15:
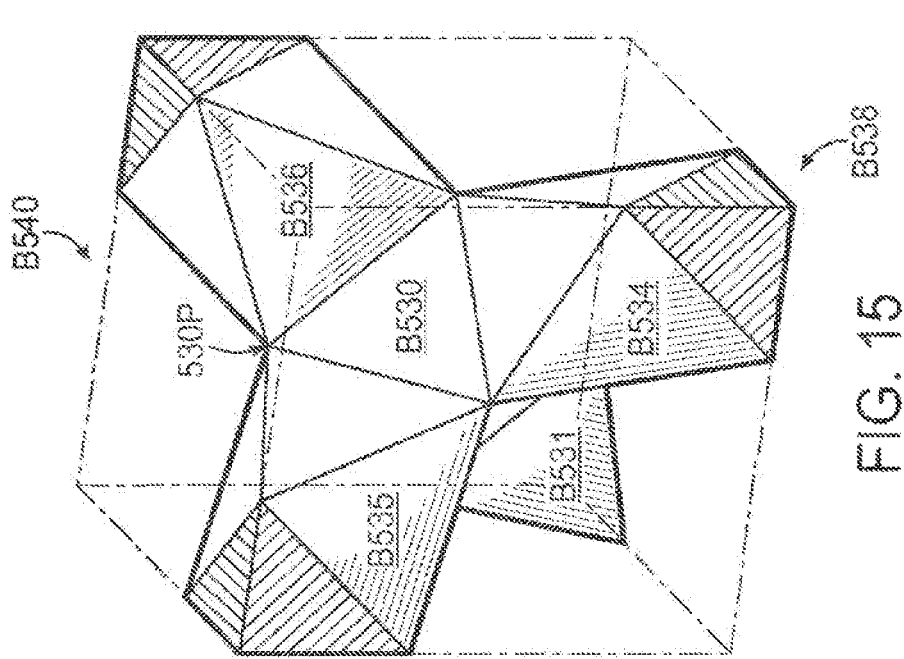
FIG. 15 is an isometric view of a sub-unit cell comprised of a single node and four struts.
Figure 17:
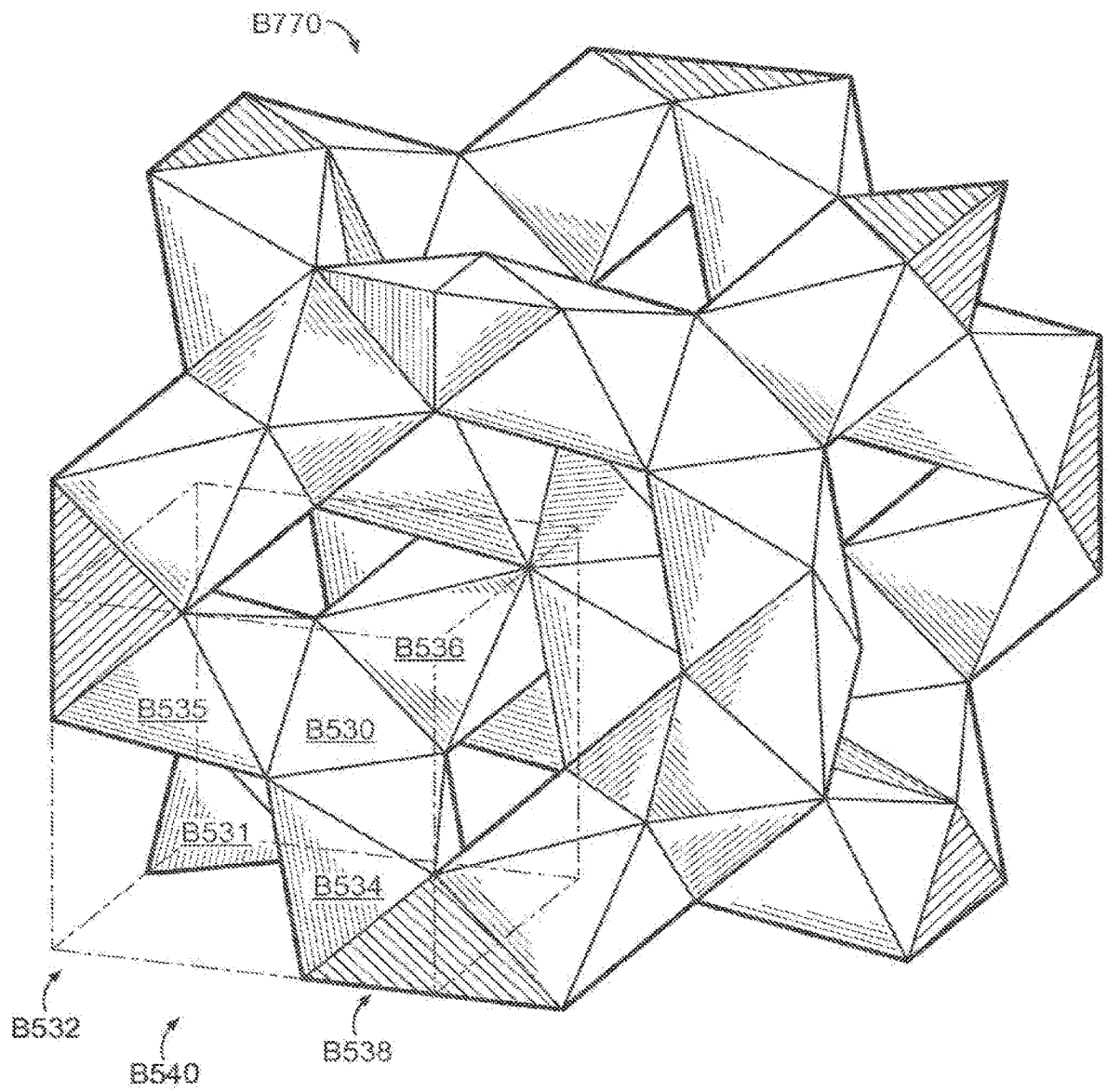
FIG. 17 is an isometric view of eight sub-unit cells stacked together to form a single unit cell.

In some embodiments, a unit cell is built up from multiple sub-unit cells fixed together. FIG. 15 depicts an isometric view of an example sub-unit cell comprising a single node and four struts. FIG. 16 depicts an isometric view of two sub-unit cells in a stacked formation where the upper sub-unit cell is inverted and fixed to the top of the lower sub-unit cell. FIG. 17 depicts an isometric view of eight sub-unit cells stacked together to form a single RDDR unit cell.

In FIG. 15, the node 530 is a square bipyramid, oriented so that the two peaks face the top and bottom of a cubic volume 532. In some embodiments, the volume 532 can be a cuboid volume, a hexahedron volume, an amorphous volume or of a volume with one or more non-orthogonal sides. The peaks refer to the point where four upper faces meet and the point where four lower faces meet. The node 530 is oriented so that the horizontal vertices face the lateral sides of the cubic volume 532. The strut 531 is fixed to a lower face of the node 530 face on its proximate end, and it extends to the nearest corner of the cubic volume 532 at its distal end. The distal end of the strut 531 can remain fixed to the cubic volume 532 even if the node 530 changes in size to adjust the sub-unit cell properties.

On the lower face of the node 530 that is opposite the face which strut 531 is fixed, the proximate end of strut 534 is fixed to the node 530. The strut 534 extends to the nearest corner of cubic volume 532 at its distal end. The strut 535 is fixed on its proximate end to an upper node 530 face directed about 90 degrees laterally from the node 530 face fixed to strut 531. The strut 535 extends to the nearest corner of the cubic volume 532 at its distal end. On the upper face of the node 530 that is opposite the face which strut 535 is fixed, the proximate end of strut 536 is fixed to the node 530. The strut 536 extends to the nearest corner of the cubic volume 532 at its distal end.

In some embodiments, the struts 531, 534-536 are octahedrons with triangular faces. The strut face fixed to a node 530 face can be substantially the same size and orientation of the node 530 face. The strut face fixed to the nearest corner of the cube 532 can be substantially the same size as the strut face fixed to the node 530 and oriented on a substantially parallel plane. The remaining six faces can be six substantially similar isosceles triangles with a first internal angle and a second internal angle larger than said first internal angle. The six substantially similar isosceles triangles can be fixed along their long edges to an adjacent and inverted substantially similar isosceles triangle to form a generally cylindrical shape with triangular ends.

When forming a sub-unit cell 540, it can be beneficial to add a one-eighth node 538 to each corner of the cube 532 fixed to a strut 531, 534-536. When replicating the sub-unit cell 540, the one-eighth node 538 attached to each strut end is combined with one-eighth nodes from adjacent sub-unit cells to form nodes located between the struts of adjacent sub-unit cells.

In FIG. 16 is a first sub-unit cell 540 fixed to a second sub-unit cell 640 to form a quarter unit cell 560 used in some embodiments. The second sub-unit cell 640 comprises a square bipyramid node 630, oriented so that the two peaks face the top and bottom of a cubic volume. The node 630 is oriented so that the horizontal vertices face the lateral sides of the cubic volume. The strut 635 is fixed to a lower face of the node 630 face on its proximate end and extends to the nearest corner of the cubic volume at its distal end. On the lower face of the node 630 opposite the face which strut 635 is fixed, the proximate end of strut 636 is fixed to the node 630. The strut 636 extends to the nearest corner of cubic volume at its distal end. The strut 634 is fixed on its proximate end to an upper node 630 face directed about 90 degrees laterally from the node 630 face fixed to strut 635. The strut 634 extends to the nearest corner of the cubic volume at its distal end. On the upper face of the node 630 opposite the face which strut 634 is fixed, the proximate end of strut 631 is fixed to the node 630. The strut 631 extends to the nearest corner of the cubic volume at its distal end.

The first sub-unit 540 is used as the datum point in the embodiment of FIG. 16, however, it is appreciated that the second sub-unit cell 640 or another point could also be used as the datum point. Once the first sub-unit cell 540 is fixed in position, it is replicated so that the second sub-unit cell 640 is substantially similar to the first. The second sub-unit cell 640 is rotated about its central axis prior to being fixed on the top of the first unit-cell 540. In FIG. 16, the second sub-unit cell 640 is inverted to achieve the proper rotation, however, other rotations about the central axis can achieve the same result. The first sub-unit cell 540 fixed to the second sub-unit cell 640 forms a quarter unit cell 560 that can be replicated and attached laterally to other quarter unit cells to form a full unit cell.

Alternatively, a full unit cell can be built up by fixing a first group of four substantially similar sub-unit cells together laterally to form a square, rectangle or quadrilateral when viewed from above. A second group of four substantially similar subunit cells rotated about their central axis can be fixed together laterally to also form a square, rectangle or quadrilateral when viewed from above. The second group of subunit ells can be rotated about their central axis prior to being fixed together laterally or inverted after being fixed together to achieve the same result. The second group is then fixed to the top of the first group to form a full unit cell.

In FIG. 17 is an example of a full unit cell 770 formed by replicating the sub-unit cell 540 of FIG. 15. The cube 532 defining the bounds of the sub-unit cell 540 is identified as well as the node 530 and struts 531, 534-536 for clarity. The full unit cell 770 of FIG. 17 can be formed using the methods described above or using variations within the inventive concept.

Each strut extending from the node, for a given unit cell, can be substantially the same length and angle from the horizontal plane, extending radially from the node. At the end of each strut, the strut is mirrored so that struts extending from adjacent node faces form a rhombus shaped opening. Because the struts can be non-orthogonal to the node faces, rhombuses of two shapes emerge. In this configuration, a first group of four rhombuses extend radially from the node oriented in vertical planes. The acute angles of the first group of rhombuses equal twice the strut angle from the horizontal plane and the obtuse angles equal 180 less the acute angles. Also in this configuration is a second group of eight rhombuses extending radially so that a portion of the second group of eight rhombuses fall within the lateral separation angle between adjacent struts defining the first group of four rhombuses. The acute angles of the second group of rhombuses can be about the same as the lateral separation angle between adjacent struts that define the first group of four rhombuses and the obtuse angles equal 180 less the acute angles.

The characteristics of a scaffold may also be described by its surface area per volume. For a 1.0 mm×1.0 mm×1.0 mm solid cube, its surface area is 6.0 square mm. When a 1.0 cubic mm structure is comprised of a lattice structure rather than a 100% volumetric density material, the surface area per volume can increase significantly. In low volumetric density scaffolds, the surface area per volume increases as the volumetric density increases. In some embodiments, a scaffold with a volumetric density of 30.1% would have a surface area of 27.4 square mm per cubic mm. In some embodiments, if the volumetric density was decreased to 27.0%, the lattice would have a surface area of 26.0 square mm per cubic mm and if the volumetric density were decreased to 24.0%, the lattice would have a surface area of 24.6 square mm per cubic mm.

The MRDD and RDDR structures disclosed herein also have the advantage of an especially high modulus of elasticity for a given volumetric density. When used as a lattice or scaffold, an implant with an adequate modulus of elasticity and a low volumetric density can be achieved. A low volumetric density increases the volume of the implant available for bone ingrowth.

In Table 1, below, are a number of example lattice configurations of various lattice design elastic moduli. The lattice configurations shown in Table 1 can comprise, for example, Ti4Al6V and a 2 mm×2 mm×2 mm unit cell. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in other embodiments. One advantage of the presently disclosed lattice structures is that the approximate actual elastic modulus is much closer to the design elastic modulus than has been previously achieved. During testing, one embodiment of a lattice was designed for a 4.0 GPa design elastic modulus. Under testing, the lattice had an actual elastic modulus of 3.1 GPa, achieving an actual elastic modulus within 77% of the design elastic modulus.

For each lattice design elastic modulus, a volumetric density, ratio of design elastic modulus to volumetric density, surface area in mm$^2$, ratio of surface area to volumetric density and ratio of surface area to lattice design elastic modulus is given.

properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

In some embodiments, the sub-unit cells can be designed by controlling the height of the node relative to the height of the volume that defines the sub-unit cell. Controlling the height of the node can impact the final characteristics and appearance of the lattice structure. In general, increasing the height of the node increases the strut thickness, increases the volumetric density, increases the strength and increases the elastic modulus of the resulting lattice. When increasing the height of the node, the width of the node can be held constant in some embodiments or varied in other embodiments.

In some embodiments, the sub-unit cells can be designed by controlling the volume of the node relative to the volume that defines the sub-unit cell. Controlling the volume of the node can impact the final characteristics and appearance of the lattice structure. In general, increasing the volume of the node increases the strut thickness, increases the volumetric density, increases the strength and increases the elastic modulus of the resulting lattice. When increasing the volume

TABLE 1

Table of example lattice structures based on lattice design elastic modulus in GPa

| Lattice Design Elastic Modulus (GPa) | Approx. Actual Elastic Modulus (GPa) | Volumetric Density (percent) | Ratio of Design Elastic Modulus to Volumetric Density | Surface Area (mm$^2$) | Ratio of Surface Area to Volumetric Density | Ratio of Surface Area to Lattice Design Elastic Modulus |
|---|---|---|---|---|---|---|
| 0.3 | 0.233 | 18.5 | 1.6 | 22.5 | 121.5 | 74.9 |
| 3 | 2.33 | 29.9 | 10.0 | 27.5 | 92.2 | 9.2 |
| 4 | 3.10 | 33.4 | 12.0 | 28.8 | 86.4 | 7.2 |
| 5 | 3.88 | 36.4 | 13.8 | 29.9 | 82.2 | 6.0 |
| 6 | 4.65 | 38.8 | 15.5 | 30.7 | 79.1 | 5.1 |
| 7 | 5.43 | 40.8 | 17.2 | 31.3 | 76.9 | 4.5 |
| 8 | 6.20 | 42.1 | 19.0 | 31.8 | 75.4 | 4.0 |
| 9 | 6.98 | 43.2 | 20.8 | 32.1 | 74.3 | 4.0 |

In some of the embodiments disclosed herein, the required strut thickness can be calculated from the desired modulus of elasticity. Using the following equation, the strut thickness required to achieve a particular elastic modulus can be calculated for some MRDD and RDDR structures:

Strut Thickness = $(-0.0035*(EA2)) + (0.0696*E) + 0.4603$

In the above equation, "E" is the modulus of elasticity. The modulus of elasticity can be selected to determine the required strut thickness required to achieve that value or it can be calculated using a preselected strut thickness. The strut thickness is expressed in mm and represents the diameter of the strut. The strut thickness may be calculated using a preselected modulus of elasticity or selected to determine the modulus of elasticity for a preselected strut thickness.

In some embodiments, the unit cell can be elongated in one or more directions to provide a lattice with anisotropic of the node, the width or height of the node could be held constant in some embodiments.

In Table 2, below, are a number of example lattice configurations of various lattice design elastic moduli. The lattice configurations shown in Table 2 can comprise, for example, Ti4Al6V and a 2 mm×2 mm×2 mm unit cell. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in some embodiments. For each lattice design elastic modulus, a lattice approximate elastic modulus, a node height, a volumetric density, a node volume, a ratio of node height to volumetric density, a ratio of node height to lattice design elastic modulus and a ratio of volumetric density to node volume is given.

TABLE 2

Table of example lattice structures based on lattice design elastic modulus in GPa

| Lattice Design Elastic Modulus (GPa) | Lattice Approx. Actual Elastic Modulus (GPa) | Node Height (mm) | Volumetric Density (percent) | Node Volume (mm3) | Ratio of Node Height to Vol. Density | Ratio of Node Height to Lattice Design Elastic Modulus | Ratio of Vol. Density to Node Volume |
|---|---|---|---|---|---|---|---|
| 0.30 | 0.23 | 0.481 | 18.5 | 0.0185 | 2.60 | 1.60 | 9.98 |
| 3.00 | 2.33 | 0.638 | 29.9 | 0.0432 | 2.14 | 0.21 | 6.91 |
| 4.00 | 3.10 | 0.683 | 33.4 | 0.0530 | 2.05 | 0.17 | 6.29 |
| 5.00 | 3.88 | 0.721 | 36.4 | 0.0624 | 1.98 | 0.14 | 5.82 |
| 6.00 | 4.65 | 0.752 | 38.8 | 0.0709 | 1.94 | 0.13 | 5.48 |
| 7.00 | 5.43 | 0.776 | 40.8 | 0.0779 | 1.90 | 0.11 | 5.23 |
| 8.00 | 6.20 | 0.793 | 42.1 | 0.0831 | 1.88 | 0.10 | 5.07 |
| 9.00 | 6.98 | 0.807 | 43.2 | 0.0877 | 1.87 | 0.09 | 4.93 |

Some embodiments of the disclosed lattice structures are particularly useful when provided within an elastic modulus range between an including 0.375 GPa to 4 GPa. Some embodiments, more preferably, include a lattice structure with an elastic modulus between and including 2.5 GPa to 4 GPa. Some embodiments include a lattice structure with a volumetric density between and including 5% to 40%. Some embodiments, more preferably, include a lattice structure with a volumetric density between and including 30% to 38%.

The lattice structures disclosed herein have particularly robust loading and fatigue characteristics for low volumetric density ranges and low elastic moduli ranges. Some embodiments of the lattice structures have a shear yield load and a compressive yield load between and including 300 to 15000N in static and dynamic loading up to 5,000,000 cycles at 5 Hz. Some embodiments have a compressive shear strength and an axial load between and including 300 to 15000N in static and dynamic loading up to 5,000,000 cycles at 5 Hz. Some embodiments have a shear strength and an axial load between and including 300 to 15000N in static and dynamic loading up to 5,000,000 cycles at 5 Hz. Some embodiments have a torsional yield load up to 15 Nm.

In one example, the inventive lattice structure has a volumetric density of between and including 32% to 38%, an elastic modulus between and including 2.5 GPa to 4 GPa and a shear strength and an axial load between and including 300 to 15000N in static and dynamic loading up to 5,000,000 cycles at 5 Hz. Some examples include a first set of substantially homogeneous openings with a width of about 200 μm to 900 μm and a second set of substantially homogenous openings with a width of about 1 to 15 times the width of the first set of openings, where the number of openings in the second set are provided at a ratio of about 1:8 to 1:12 relative to the number of openings in the first set.

The disclosed structures can also have benefits when used in applications where osteointegration is not sought or undesirable. By including a growth inhibiting coating or skin on a structure, the lattice disclosed herein can be used to provide structural support without providing a scaffold for bone growth. This may be desirable when used in temporary implants or medical devices that are intended to be removed after a period of time.

Some embodiments presented herein relate to a biocompatible lattice with increased lucency, a method of designing a lattice with increased lucency, variable markers for use in medical implants with at least a degree of radiolucency, a method of designing variable markers for use in medical implants with at least a degree of radiolucency and a method of using variable markers in medical implants with a degree of radiolucency. Variable markers, as used herein, refers to any area of an implant that has a different lucency, radiolucency, radiopacity or radiodensity in at least two different viewing directions. A viewing direction, as used herein, refers to a direction that an implant is viewed from or towards. A viewing direction can refer to various types of views including, for example, visual sight and the direction from an x-ray generator to an x-ray receiver in an x-ray machine (hereinafter, the "x-ray direction"). A viewing direction can refer to an x-ray direction for an implant after it has been implanted. The implants disclosed herein can be designed to be implanted in a predetermined orientation where the x-ray direction for in situ imaging post-surgery can be predicted during the design stage of the implant.

Variable markers can have one or more aligned directions, meaning a direction where the variable markers are designed to produce a specific lucency, radiolucency, radiopacity or radiodensity property. Variable markers can have one or more misaligned directions, meaning directions where the variable markers are designed to produce a different lucency, radiolucency, radiopacity or radiodensity in comparison to an aligned direction. In some embodiments, the variable markers can have an aligned direction and misaligned direction with overlapping viewing directions so that a variable marker from a particular viewing direction could result in an aligned viewing property and a misaligned viewing property. The variable markers can be configured to provide either increased lucency or decreased lucency when viewed in an aligned direction in comparison to when viewed in a misaligned direction. In some embodiments, the lattice structures with increased lucency include variable markers. Only example embodiments are shown herein and it is understood that the use of other unit cell structures, other lattice structures and other porous structures would be within the inventive concept expressed herein. The directions described herein are in relation to the three-dimensional Cartesian Coordinate System where the x axis and y axes are horizontal and the z axis is vertical (also described herein as the x, y and z "direction"). These specific directional references are example and used to the example orientations described herein.

Biocompatible lattices can be comprised of a material that has radiopaque properties when a certain bulk thickness is reached. In this case, bulk thickness means the actual thickness of the primary material in a lattice in a certain direction when the voids are removed. For instance, a lattice with a 50% volumetric density and a thickness of two inches would have a bulk thickness of one inch in that direction and a lattice with a 25% volumetric density and a thickness of two inches would have a bulk thickness of a half inch in that direction.

As used herein, radiodensity refers to the opacity or lucency of a material when viewed in in an x-ray or similar process. The radiodensity of a material may range from radiopaque to radiolucent. Radiopaque means that the material completely blocks the transmission of x-rays. A radiopaque material would show up as white in most x-rays. Radiolucent means that the material does not block the transmission of x-rays or blocks less than all of the x-rays. A fully radiolucent material would show up as black on most x-rays. A partially radiolucent material would show up as gray on most x-rays. As a material becomes more radiolucent, it shows up progressively darker on most x-rays.

Figure 18:
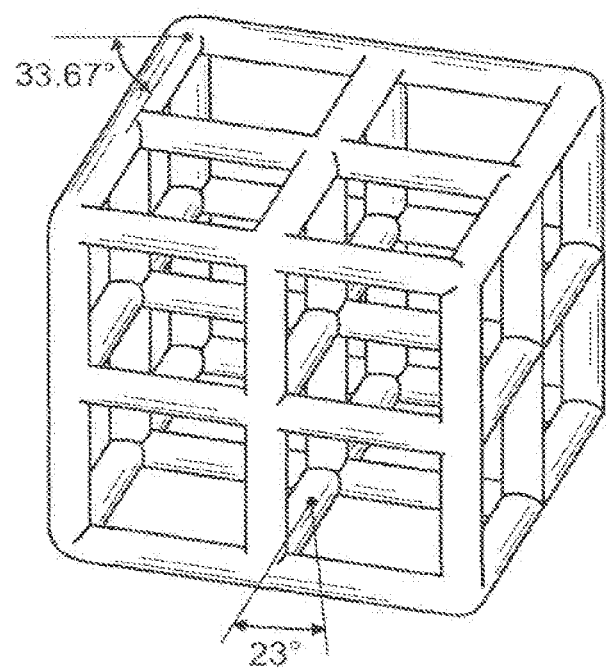
FIG. 18 is a perspective view of an example of a cubic unit cell and rotated 23 degrees about the z axis and 33.67 degrees about the x axis from a normal face.

FIG. 18 depicts an example embodiment of the inventive lattice that uses a repeating cubic unit cell structure. The viewing direction or x-ray direction in FIG. 18 and the example embodiments disclosed in FIGS. 18-38 can be a direction normal to the page. The example in FIG. 18 has been rotated 23 degrees about the z axis and 33.67 degrees about the x axis from a normal face to provide increased dispersion. The angles of rotation about the x, y and z axes are relative to an origin orientation for a single unit cell or a structure comprised of a plurality of unit cells. In the cubic cell example, the origin orientation is where one cell face is within the plane defined by the x and z axes, another cell face is within the plane defined by the y and z axes and another cell face is within the plane defined by the x and y axes. When a cubic cell is positioned in this particular origin orientation, the rotation of the cubic cell may also be described as an angle of rotation from a normal face. Because the origin orientation is used as a reference point for the rotations taught herein, the example rotations disclosed would change accordingly if a different origin orientation were used as a reference.

When using a repeating geometric unit cell in a lattice, depending on the orientation of the unit cells, the degree of lucency and the type of lucency (e.g. dispersion or disparity) through the material can be modified. While many types of lucency may be targeted using the methods described herein, only the maximum relative disparity and maximum relative dispersion angles will be discussed in detail. The maximum relative disparity angles are the rotations in degrees about the x, y and z axes for a certain repeating geometric unit cell that provides the maximum difference in lucency across the bulk volume. The maximum disparity angles result in an open cell structure with the highest possible difference between the maximum bulk thickness and minimum bulk thickness in the desired direction, in other words, a minimum uniformity of bulk thickness. The maximum relative dispersion angles are the rotations in degrees about the x, y and z axes for a certain repeating geometric unit cell that provides the minimum difference in lucency across the bulk volume. The maximum dispersion angles result in an open cell structure with the lowest possible difference between the maximum bulk thickness and minimum bulk thickness in the desired direction, in other words, a maximum uniformity of bulk thickness.

The average bulk thickness is an average taken of the bulk thickness across the bulk volume in the desired direction. For increased lucency, it is desirable to have a lower average bulk thickness in the desired direction. When orienting a structure for the maximum dispersion angle, it can be beneficial to optimize the rotation angles to create a structure with a minimum average bulk thickness and maximum uniformity of the bulk thickness in the desired direction. While a minimum average bulk thickness is desirable for lucency, the average bulk thickness in a desired direction is largely a function of the strut and unit cell characteristics. However, there can be a measurable reduction in average bulk thickness when certain types of unit cell structures with struts of certain dimensions are rotated. The reduction in average bulk thickness resulting from a rotation is more pronounced in simpler unit cell structures, such as a triangular unit cell.

The desired direction, when used to describe the embodiments, is the direction from which a lucency property is desired. Most of the time, the desired direction for a lucency property will be the direction from which an x-ray image will be taken. For example, in a spinal interbody implant, x-ray imaging is usually taken from the lateral or anterior-posterior directions. In this case, the desired direction could be from the lateral or anterior-posterior direction as the implant sits in vivo. In the drawings disclosed herein, the desired direction can be a direction normal to the sheet or screen upon which the drawings are depicted.

The repeating geometric pattern in FIG. 18 has been rotated to increase dispersion in the desired direction. For a repeating cubic unit cell, maximum relative dispersion is best achieved through the use of at least two rotations, in this case about the z and x axes. When oriented in accordance with FIG. 18, there is a minimal amount of overlap between the struts and the nodes in the sample do not overlap at all. This is an example of the maximization of uniformity of bulk thickness achievable in dispersion. Partial dispersion can be achieved with either rotation individually, but would result in either horizontal or vertical lines of disparity.

As the overall thickness of the open cell scaffold increases, more cells may be added and nodes and struts will begin to overlap, increasing the bulk thickness of the structure. The optimal angles for maximum dispersion and minimal bulk thickness will vary with the overall number of cells in the structure.

Additionally, the actual maximum dispersion depends on the ratio between the diameter of the struts compared to the size of the unit cell. As strut diameter approaches the overall size of the unit cell, effectively closing off the cells, there is no rotation that would substantially minimize bulk thickness. However, as the aspect ratio decreases, a rotation can again achieve the offsetting of struts to minimize bulk thickness. The aspect ratio is the ratio between the strut thickness and strut length. The aspect ratio can be decreased by, for example, increasing the strut length in the case of thick struts.

As an example, in a 2.0 mm cubic unit cell (where the dimensions in the x, y and z axes are 2.0 mm) with struts of 0.5 mm diameter, the central void is approximately 1.0 mm in width and height. By rotating this unit cell and aligning each strut with a central void, the bulk thickness can be approximately halved. As the struts in this example are increased in diameter, the impact of the rotation is reduced.

Figure 19:
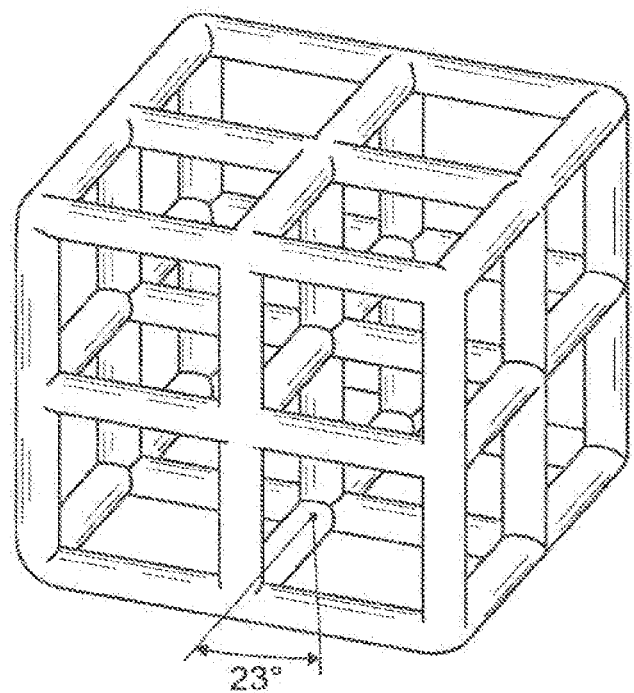
FIG. 19 is a perspective view of an example of a cubic unit cell and rotated 22 degrees about the z axis and 30 degrees about the x axis from a normal face.

FIG. 19 depicts an example embodiment of the inventive lattice using a cubic unit cell and rotated to a different orientation. In FIG. 19, the lattice has been rotated 22 degrees about the z axis and 30 degrees about the x axis from an origin orientation normal to a cubic unit cell face. Even with less of a rotation about the x and z axis than in FIG. 18, the embodiment of FIG. 19 still maintains a similar dispersion effect with minimal overlap of nodes and struts.

Figure 20:
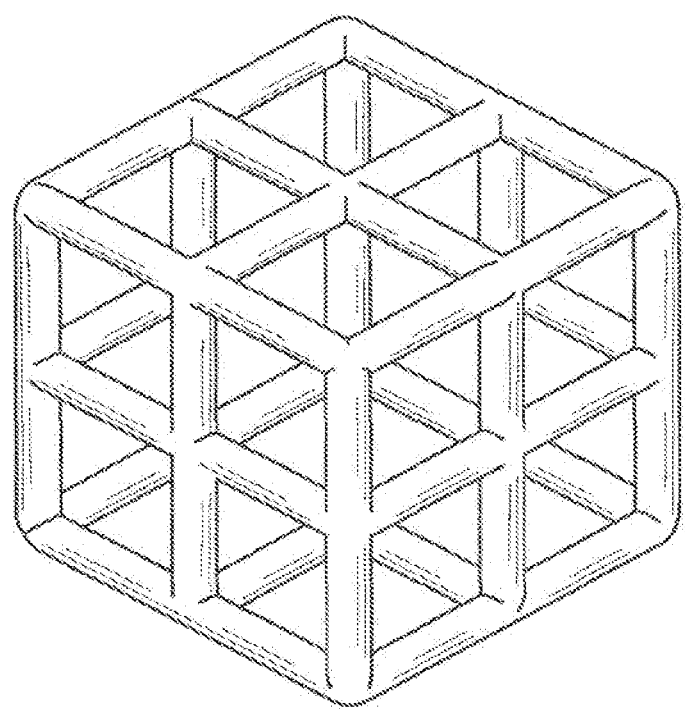
FIG. 20 is a perspective view of an example of a cubic unit cell and rotated 45 degrees about the z and x axes from a normal face.
Figure 21:
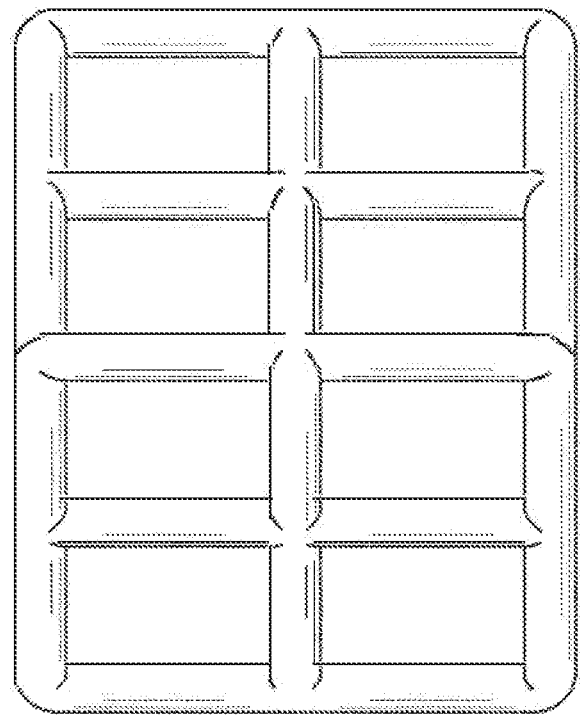
FIG. 21 is a perspective view of an example of u a cubic unit cell and rotated 45 degrees along x axis from a normal face.
Figure 22:
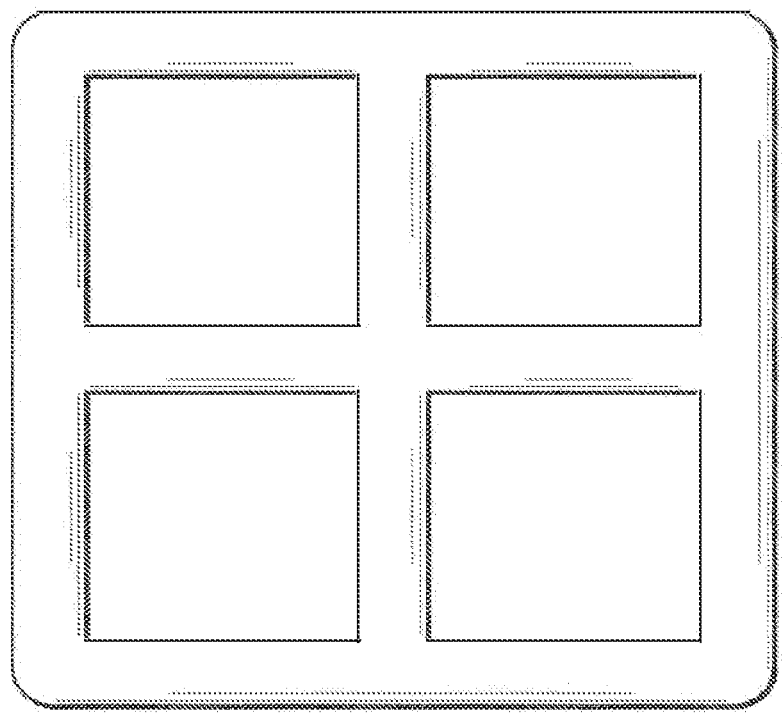
FIG. 22 is a perspective view of an example of a cubic unit cell with no rotation from a normal face.
Figure 25:
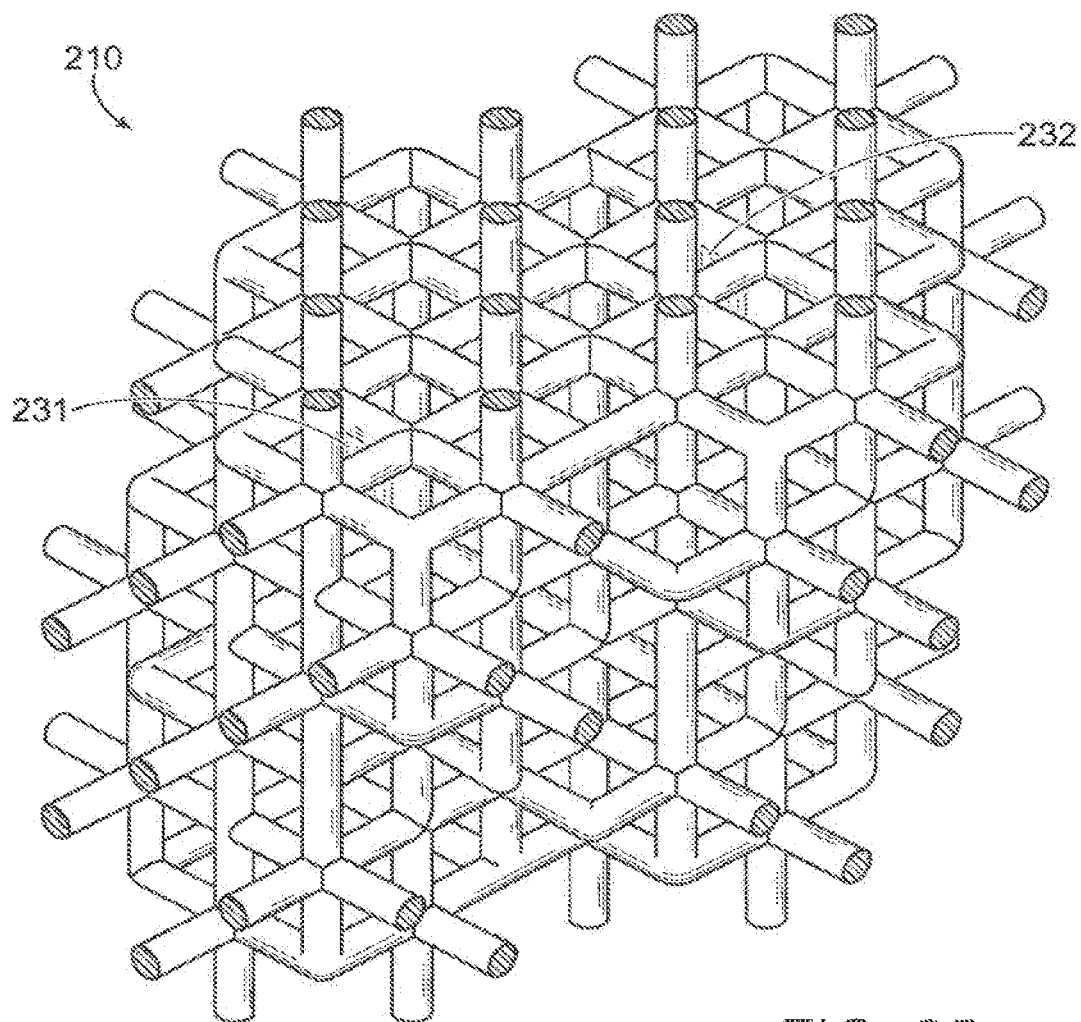
FIG. 25 is an isometric view of a second example embodiment of the variable markers comprised of partially filled unit cells and shown in a misaligned direction.

High disparity embodiments can be achieved through a variety of rotation combinations. FIG. 20 depicts an example embodiment of a lattice of cubic unit cells where the lattice has been rotated 45 degrees about the z axis and 45 degrees about the x axis from an origin orientation normal to a cubic unit cell face. FIG. 21 depicts an example embodiment of a lattice of cubic unit cells, where the lattice has been rotated 45 degrees about the x axis from an origin orientation normal to a cubic unit cell face. FIG. 25 depicts an example embodiment of a lattice of cubic unit cells where the lattice has not been rotated from an origin orientation normal to a cubic unit cell face. All of the high relative disparity embodiments are characterized by significant overlap between the nodes and struts of the unit cells. The significant overlap increases the bulk thickness of the structure at certain points in the desired direction, increasing radiopacity in those areas. The high relative disparity embodiments also have areas where no struts or nodes obscure visibility through the structure, increasing the radiolucency in those areas.

A diamond cubic cell has two interpenetrating face centered Bravais lattices within a cubic cell, wherein the Bravais lattices are shifted along a diagonal of the cubic cell by one quarter of the diagonal length. For a single diamond cubic unit cell in an origin orientation where three cubic faces are aligned with the x, y and z axes, respectively, the maximum relative disparity in the desired direction can be achieved when the unit cell is rotated approximately 45 degrees about the z axis from the origin orientation. In some embodiments of a single diamond cubic unit cell in an origin orientation where three cubic faces are aligned with the x, y and z axes, respectively, the maximum relative disparity in the desired direction can be achieved when the unit cell is rotated approximately 45 degrees about the x axis or y axis from the origin orientation. For the same single diamond cubic unit cell, relative maximum dispersion can be achieved at approximately 0 and 90° rotations from the origin orientation. The origin orientation can also be measured relative to a planar face of the cubic cell.

For a single lattice unit cell comprising a repeating generic RDD, MRDD or RDDR structure in an origin orientation where three cubic faces are aligned with the x, y and z axes, respectively, the maximum relative dispersion in the desired direction can occur when the structure is rotated approximately 45 degrees about the z axis from the origin orientation. In some embodiments of a single lattice unit cell comprising a repeating generic RDD, MRDD or RDDR structure in an origin orientation where three cubic faces are aligned with the x, y and z axes, respectively, the maximum relative dispersion in the desired direction can occur when the structure is rotated approximately 45 degrees about the x axis or y axis from the origin orientation. The maximum relative disparity in the desired direction can occur when the single unit cell structure is not rotated at all (0°). While only some types of unit cell structures have been disclosed, there are many types of repeating unit cell structures that can be used to achieve similar results. Possible scaffold geometries that are appropriate include, but are not limited to, rhombic dodecahedron, diamond, dodecahedron, square, pentagonal, hexagonal, octagonal, sctet struts, trunic octa, diagonal struts, other known geometric structures, and rounded or reinforced versions of each geometry. The rotation along the x, y or z axes may be different for different unit cell shapes and materials and can be determined based on the disclosure herein. The amount of rotation about the x, y or z axes will also depend on the aspect ratio of the unit cells and the number of unit cells comprising the structure. As the number of unit cells increases, the nodes and struts will overlap, but through rotating the structure, the overlap of the nodes and struts may be optimized. The use of rounded or reinforced nodes would increase the amount of material present near the nodes, increasing the bulk thickness over areas where the nodes are present. The origin orientation can also be measured relative to a planar face of the cubic cell.

Rotations of structures may be represented relative to a base reference frame or as Euler angles in a reference frame, preferably in a right-hand reference frame about the x, y, and z axes and composed in a rotation matrix. Additional translation of the lattice structure may be achieved in the same step by expanding the matrix. While a Cartesian coordinate system is used as an example reference frame or coordinate system, other reference frames could be appropriate and could be more efficient, depending on the structure being analyzed.

These angles are determined based on the aspect ratios and geometries of the particular lattice structure. Specifically, the strut diameter, cell height, cell width, cell depth, and overall thickness, length, and height of the device are key parameters for solving rotation angles in x, y, and z axes, according to the following:

$$R(x,y,z,a,\beta,y)=F(h,w,d,T,H,L)$$

Where:
d=Strut diameter
h=Cell height
w=Cell width
d=Cell depth
T=Device Thickness
H=Device Height
L=Device Length In some embodiments, the rotation of a structure can be referred to based on a rotation in degrees about an axis. The high x-ray lucency structures disclosed herein, in some embodiments, are achieved by rotating the structure from an origin orientation between and including zero degrees to 180 degrees in either direction about an axis. In some embodiments, the high x-ray lucency structures are achieved by rotating the structure from an origin orientation between and including zero degrees to 360 degrees about an axis. In some embodiments, a lattice structure in its origin orientation could provide the desired lucency property in the desired viewing direction so that it could be beneficial not to rotate the lattice structure at all. In some embodiments, the high x-ray lucency structures are achieved by rotating the structure from an origin orientation between and including 35 degrees to 55 degrees in either direction about an axis.

Some examples of lattices comprising repeating geometric unit cells that have been optimized for lucency were disclosed above, but the method used to design the example embodiments can be applied to unit cells of other specifications using a manual or computer aided method disclosed herein. The method of optimizing a structure for lucency is described herein as a method of design and manufacture. The method of optimizing a structure for lucency disclosed herein can be applied to many types of structures, including but not limited to, lattice structures with repeating geometric patterns and porous structures with either repeating structures or random structures. While the methods disclosed generally design the orientation of the lattice first and then produce the lattice in a method of manufacture, the steps could just as easily be reversed. A lattice may be first manufactured and then oriented using the method of design. For instance, a lattice may be first manufactured and then, by using the characteristics of the manufactured structure, a user may use the method of design to orient the structure for a lucency quality. The lattice could then be rotated to that orientation and cut, machined or formed into its final shape.

The method of design can be performed through a manual process either by manufacturing a structure and performing evaluations on a physical model or performed in a software that generates the structure within a specified volume of the implant at a user-defined unit cell orientation and then displays the result for visualization. In a first example method of design, the user iterates the process, changing the orientation parameters for the unit cell, regenerating the structure, assessing the achieved bulk thickness of the device, and the uniformity of that thickness across the implant. Once the user is satisfied with the minimally achieved bulk thickness and its uniformity, the parameters and final structure is accepted. Computer aided design (hereinafter "CAD") or other three-dimensional (hereinafter "3D") models of the unit cell structure can also be used as a starting point to identify optimal rotations or starting points.

The method of design can also be performed using a process aided with algorithms and visualizations tools. In a second example method of design, a user would:

1. Generate or import a bulk volume repeating structure in a form capable of analysis by an analysis tool. An analysis tool, as used herein, refers to any application or process used to analyze data. An analysis tool could be an application or program capable of analyzing multiple variables, such as MATLAB®, FreeMat, Octave, Mathematica®, or any comparable or custom software. The analysis tool may comprise a different program, comprise a user generated program or comprise any other program, device, person or persons capable of analyzing multiple variables. The analysis tool can also be one or more people visually analyzing a repeating structure. The form capable of analysis is different for each type of analysis tool available. For example, in an application or program, the repeating structure would likely need to be imported or a facsimile created within the capabilities of the application or program. If the analysis tool is a person, one form capable of analysis would be a manufactured repeating unit cell structure.

2. Propagate the bulk volume at some orientation throughout the specific device volume or perform on a raw structure independent of specific device constraints. The bulk volume can alternatively be sectioned to the appropriate dimensions of a selected implant type.

3. Determine the uniformity of the bulk thickness from a desired direction. The uniformity of bulk thickness can be determined through multiple methods, including by measuring the bulk thicknesses across the bulk volume in the desired direction(s) for viewing and then calculating the uniformity of bulk thickness. In some methods, the bulk thicknesses may be visualized as a 2D heat map of the structure in the desired direction(s). In some methods, the coefficient of determination ($R^2$) would be a good indicator of the uniformity of bulk thickness.

4. Iterate across rotations of the bulk volume to identify the desired uniformity.

5. The parameters are captured, and a final structure is generated. This method of design does not need to be performed in the precise order described above and may also be automated. A first possibility is simply by performing all possible combinations of angle rotations in a Monte Carlo simulation. A second, by applying artificial intelligence and machine learning algorithms (k-means, regression, Support Vector Machines, neural networks, or other such techniques) to achieve the optimal angle of rotation for a specific structure.

The methods of increasing lucency of implants can also include the step of selecting a focal length to determine a region of interest on an implant. The focal length, as used herein, refers to the expected distance between an imaging device and the implant during imaging during or after implantation. Many x-rays are taken from a focal length of about 2-2.5 feet, but this distance could be adjusted to accommodate a particular x-ray machine that deviates from the usual distance. In many x-ray machines, a distance of about 5 feet is used between an x-ray emitter and receiver, with a patient located about an equal distance from the emitter and receiver. The x-ray emitter is commonly moved relative to a patient to chance the field of view or amount of detail in the x-ray image. The focal length helps identify a specific area of interest in the implant for imaging. When imaging is taken with an emitter about 2-2.5 feet away from a patient, the area of interest can be more lucent than the remainder of the implant due to the viewing angle of the x-ray machine.

In some methods, an infinite focal length can be used to determine the optimal lucency property angle for an entire side of an implant. In some methods, where a focal length of some value is used, the implant can have a rotation gradient to provide an even lucency effect, even with a focal length of less than infinite. A rotation gradient could be provided in a lattice so that the unit cells are rotated relative to an orientation around a focal point. The rotation gradient could compensate for x-ray machines with a particularly short focal length or to maximize the imaging area. A maximized imaging area could be useful to provide a broader image of the implant during and after implantation. A maximized imaging area could also be useful to display internal serialization, numerals, letters, or identification patterns (e.g., a barcode or a matrix barcode) over a broad area of an implant.

These algorithms can be expanded further to include variations of the unit cell size and strut thickness within specified constraints to further optimize the structure. Such constraints may include bounded ranges on each parameter, overall device volumetric density, construct stiffness, or other relational conditions between or external to these parameters.

In a third example method of design, a user would:

1. Choose a repeating geometric structure and material that meets the structural requirements.

2. Pick an origin orientation for a bulk volume comprising the selected repeating geometric structure and material.

3. Run a multivariable analysis for uniformity of bulk volume from the desired direction(s) where the structure is rotated from its origin orientation by at least 90 degrees along the x, y and z axes. In cases of asymmetry, it may be necessary to rotate in the positive and negative directions about each axis (e.g. a rotation of 90 degrees and −90 degrees about an axis). In unit cells where a reduction in average bulk thickness can be achieved through a rotation, it can be beneficial to run a multivariable analysis for average bulk thickness as well.

4. Use the multivariable analysis to determine the rotation from the origin orientation that produces desirable lucency characteristics in the desired direction(s) (i.e. dispersion).

This method of design represents a series of steps that may be taken to optimize a preselected repeating geometric lattice structure for lucency in a desired direction. These steps do not need to be taken in order and additional variables may be considered before, after or during the method of design to optimize a repeating geometric lattice for a particular application. For example, the method of design could include the cell size or strut thickness as variables rather than an input value in the first step, or account for structures with variable cell size or strut thickness. Other variables or constraints may also be considered within this method of design.

In some embodiments, voids may be included within the implant to reduce the bulk thickness in the desired direction. Generally, a lower bulk thickness is better for lucency and the inclusion of voids in the desired direction can reduce the bulk thickness in that direction.

The use of the above disclosed lattice and method of design can also be used to design variable markers in some embodiments. Variable markers in implants can be useful during implantation to assist the surgeon in positioning. The structures of can be rotated locally to increase the bulk density in certain locations to provide one or more areas of radiopacity, increased radiodensity, radiolucency, increased radiolucency, lucency or increased lucency. As used herein, in reference to markers, increased radiodensity indicates that an area has a higher radiodensity than the immediately surrounding area. The example embodiments disclosed herein may also include radiopaque or increased radiodensity variable markers constructed using various techniques, including but not limited to, filling in certain cells, providing thicker struts on certain cells, or providing thicker or reinforced nodes where certain struts meet. In some embodiments, the variable markers are a configured as a particular shape, such as a circle, rectangle, cross or "X" mark to assist in the location or alignment of the implant. In some embodiments, variable markers in the shape of one or more characters (letters, numerals, etc.), a name or a logo may be included in the implant. When a variable marker includes characters, a name or a logo oriented to face in the desired direction, they can be visible on an x-ray as a lighter region. In the alternative, a void, area of lower density, or area of lower bulk thickness may be provided to create a darker area on an x-ray representing a character, a name or a logo. When including a variable marker in the shape of one or more characters, they can be added through the addition of a block of material or a void of material in the open cell structure in the shape of the desired character(s). In some embodiments, the variable markers may represent a barcode, QR (matrix) barcode, or other data encoding method such as filling of specific cells within the lattice as a method of device serialization.

The variable markers disclosed herein can be used with the aforementioned lattice structures with high x-ray lucency to improve the visibility of the variable markers in metallic materials. The variable markers can also be used in a lattice structure with a rotation gradient angled towards an x-ray focal point to provide a larger area on an implant with high x-ray lucency.

In some embodiments, the variable markers may be configured so that the variable markers become more lucent during misalignment and more opaque when properly aligned (or vice versa). It would be useful to provide variable markers that increase or decrease in lucency when rotated to provide a surgeon a clear indication of when an implant is aligned or misaligned. In some embodiments, the variable markers may comprise a biocompatible lattice where the variable markers comprise orientation features relative to other variable markers.

Figure 23:
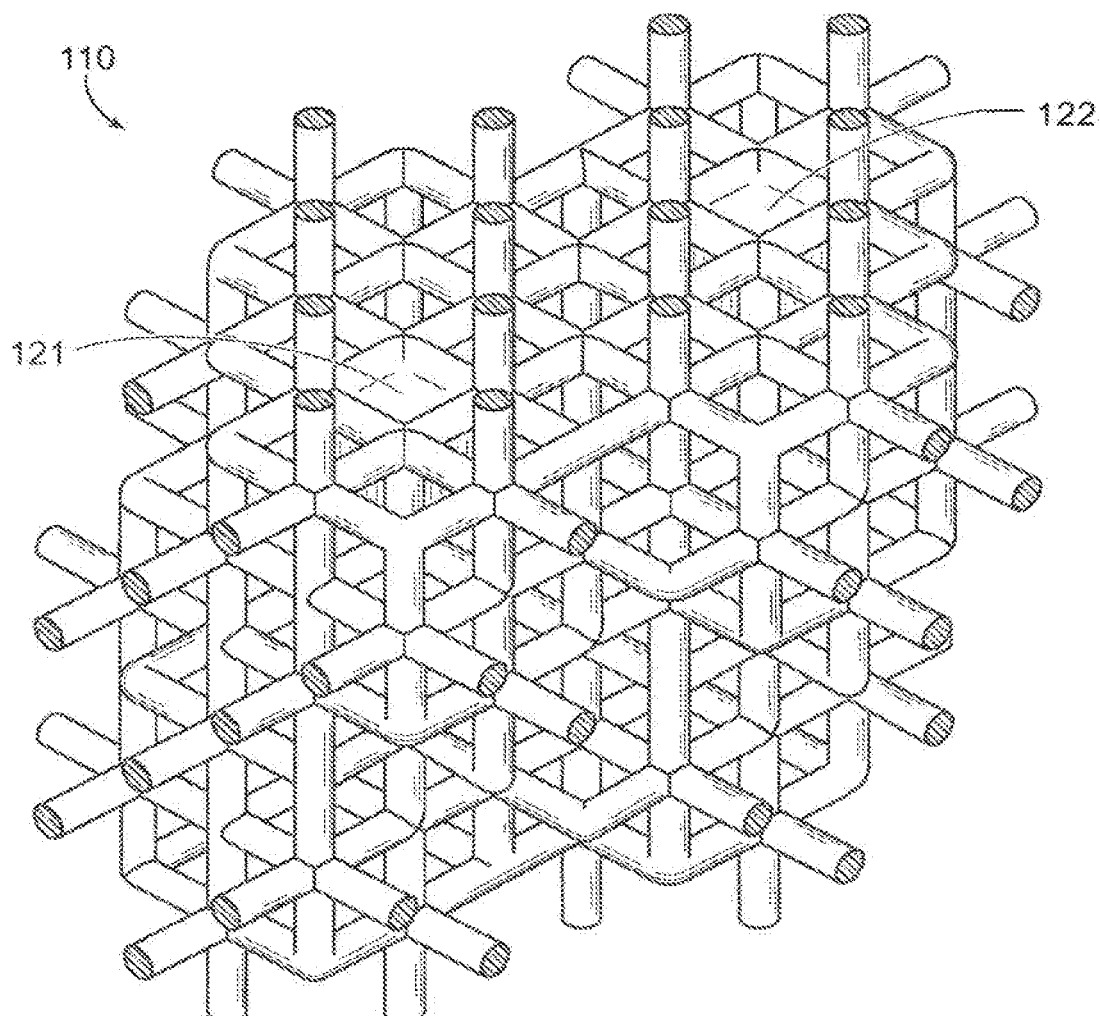
FIG. 23 is an isometric view of a first example embodiment of the variable lucent markers (hereinafter "variable markers") comprised of filled unit cells and shown in a misaligned direction.
Figure 24:
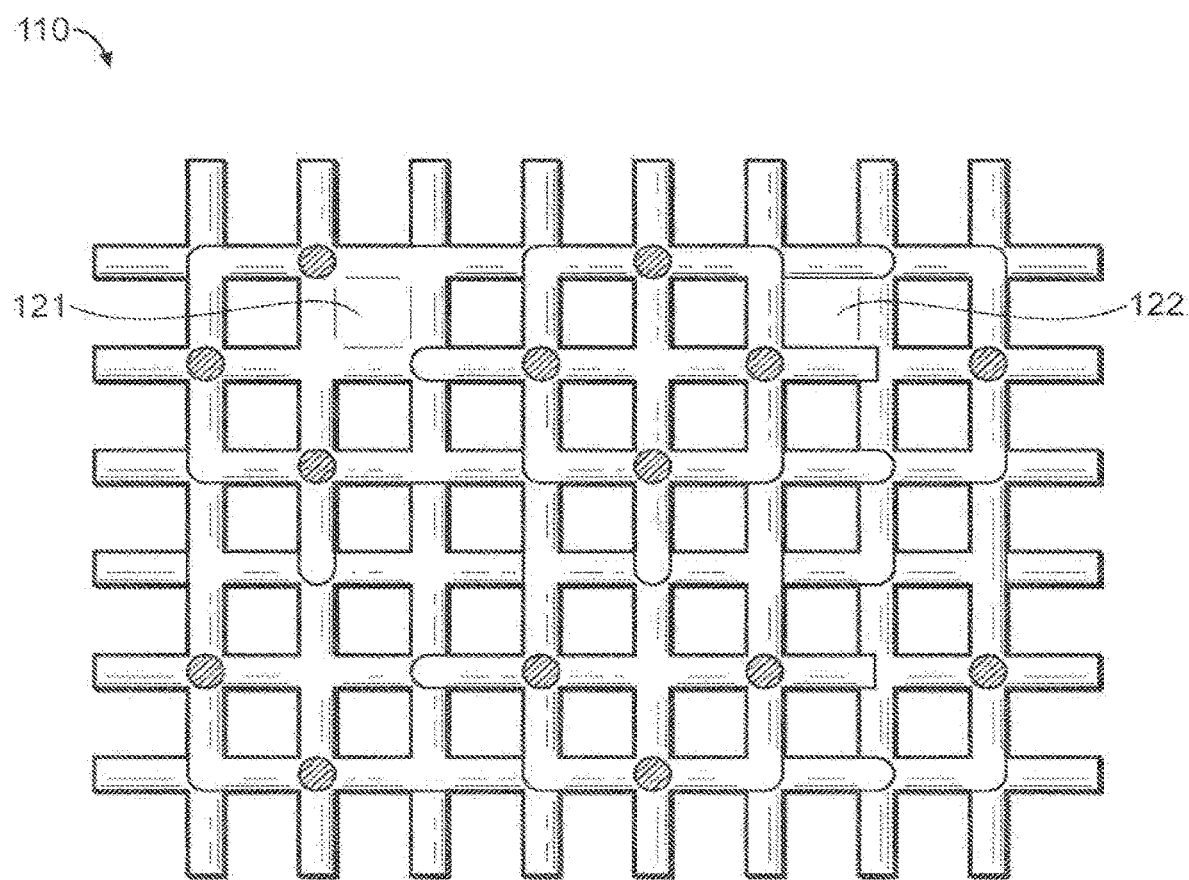
FIG. 24 is a side view of a first example embodiment of the variable markers comprised of filled unit cells and shown in a misaligned direction.

FIGS. 23-24 illustrate a first example embodiment of the variable markers that uses selectively filled unit cells. Variable radiodensity as used in reference to the variable markers means that the markers have at least a first radiodensity when viewed from a first direction and a second radiodensity when viewed from a second direction. The variable markers may optionally have additional radiodensities when viewed from additional directions.

FIG. 23 illustrates an isometric view of the first example embodiment of the variable markers shown in a lattice 110. The lattice 110 uses a repeating square unit cell, however other types of unit cells, as noted earlier, can be substituted. Within the lattice 110, two filled unit cells 121 and 122 have been added. The filled unit cells 121 and 122 can be solidly filled so that there are no voids within the planes that define the cell walls, having a volumetric density of about 100%. They may optionally contain a central void, be filled with a material with a volumetric density of less than 100%, only partially filled or filled with a material with a volumetric density of between and including 0% to 30%, 30% to 45% or 45% to 50%. In the isometric view of FIG. 23, the filled unit cells 121 and 122 are at a misalignment viewing direction, meaning that the filled unit cells 121 and 122 will show up as more radiolucent than in an aligned viewing direction.

Lattice structures with variable markers can have a pre-inclusion density, referring to the volumetric density of the lattice structure without markers or inclusions that do not significantly impact the lattice structure's overall elastic modulus. Lattice structures with variable markers can also have a post-inclusion density referring to the volumetric density of the lattice structure with markers or inclusions that do not significantly impact the lattice structure's overall elastic modulus. In some embodiments an impact of less than about 10 MPa to a lattice structure's overall elastic modulus is not a significant impact. In some embodiments, an impact of less than about 100 MPa to a lattice structure's overall elastic modulus is not a significant impact.

FIG. 24 depicts a side view of the first example embodiment of the variable markers. The side view of the lattice 110 is shown from a second misalignment direction where the location of the filled unit cells 121 and 122 do not overlay one another in this view. As a misalignment viewing direction, the filled unit cells 121 and 122 will show up as more radiolucent than in an aligned viewing direction. In the first example embodiment, the aligned direction is 90 degrees in either direction about a vertical axis from the side view in FIG. 24. If the lattice 110 is rotated by 90 degrees in either direction about a vertical axis from the side view in FIG. 24, the filled unit cells 121 and 122 will overlay one another. With the volume of filled unit cells 121 and 122 overlapping, the area of the overlapped area will appear much more radiopaque than in a misalignment direction. Overlay, as used herein, refers to when a marker is at least partially in the same location relative to a viewing direction. For instance, in an aligned direction, a marker closer to the viewer in a viewing direction could overlay a marker further from the viewer, creating a localized area with higher or lower lucency. If the markers have a higher volumetric density that the surrounding structure, any marker overlay over another will create a localized are of lower lucency. If the markers have a lower volumetric density that the surrounding structure, any marker overlay over another will create a localized area of higher lucency. An aligned direction can be characterized by one marker only partially overlaying another marker. A misaligned direction could be characterized by one marker partially overlaying another marker, but not completely overlaying the other marker.

Figure 26:
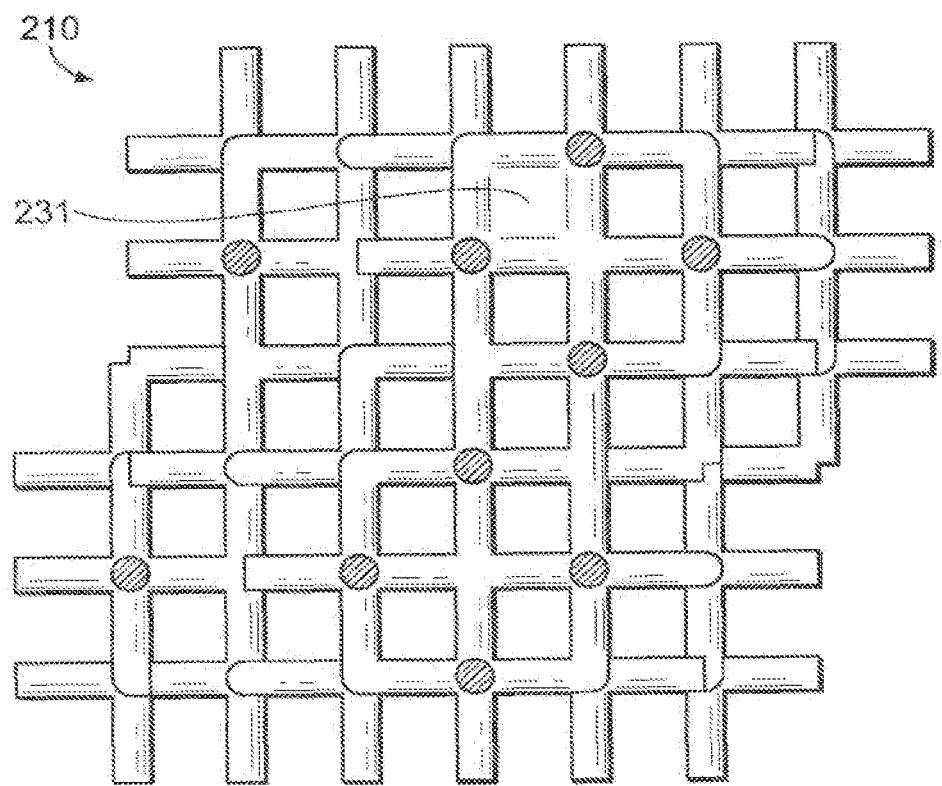
FIG. 26 is a side view of a second example embodiment of the variable markers comprised of partially filled unit cells and shown in an aligned direction.
Figure 27:
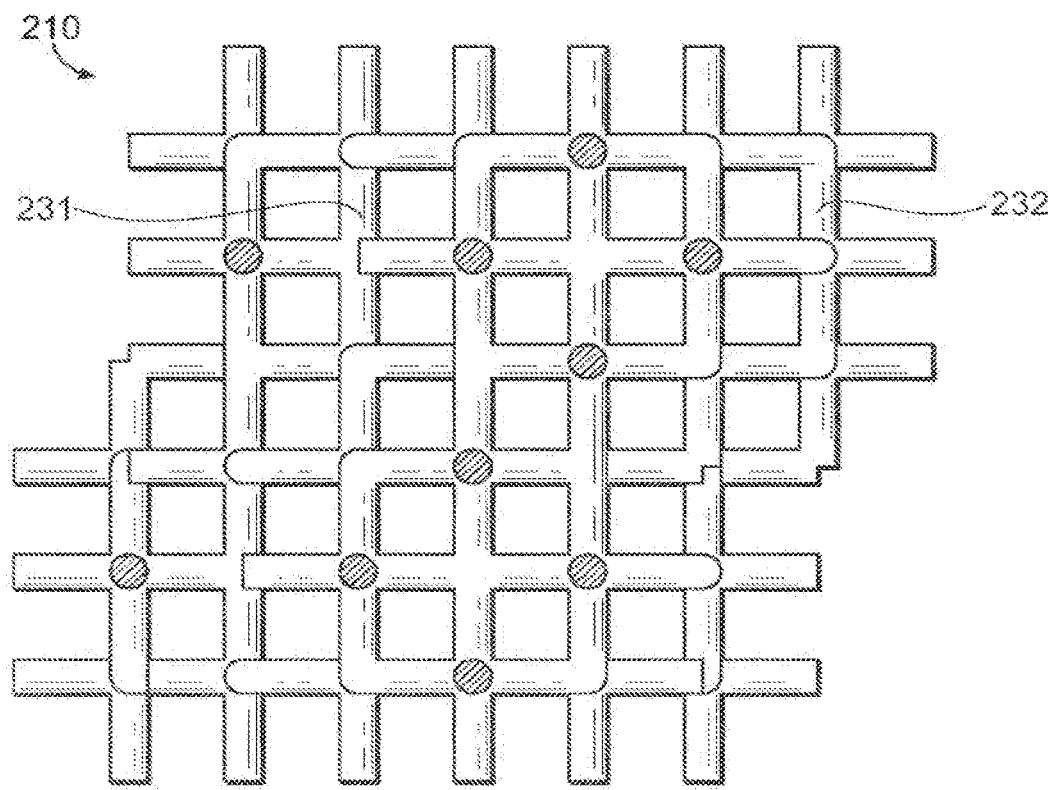
FIG. 27 is an alternative side view of a second example embodiment of the variable markers comprised of partially filled unit cells and shown in a second aligned direction.

FIGS. 25-27 illustrate a second example embodiment of the variable markers that employs partially filled unit cells.

FIG. 25 illustrates an isometric view of the second example embodiment of the variable markers shown in a lattice 25210. The lattice 25210 used is a repeating square unit cell, however other types of unit cells, as noted earlier, can be substituted. Within the lattice 25210, two partially filled unit cells 25231 and 25232 have been added. The partially filled unit cells 25231 and 25232 can be solidly filled so that there is are no voids within the filled area. The filled area may optionally contain one or more voids, be filled with a material with a volumetric density of less than 100% or only partially filled. In the isometric view of FIG. 25, the partially filled unit cells 25231 and 25232 are at a misalignment viewing direction, meaning that the partially filled unit cells 25231 and 25232 will show up as more radiolucent than in an aligned viewing direction.

In FIG. 26 is a side view of the second example embodiment of the variable markers. The side view of the lattice 25210 is shown from an aligned direction where the location of partially filled unit cells 25231 and 25232 overlap in this view. The partially filled unit cell 25232 is located behind partially filled unit cell 25231 in this view so that when viewing the variable markers in the aligned direction, the x-ray would need to travel through both partially filled unit cells 25231 and 25231, decreasing their radiolucency.

FIG. 27 illustrates an alternative side view of the second example embodiment of the variable markers. The alternative side view of the lattice 25210 is shown from a second alignment direction that can be used to highlight or identify a second direction to a user. The partially filled unit cells 25231 and 25232, in this example, are comprised of a filled unit cell wall, with substantially square faces in the aligned direction and narrow edges in the second alignment direction. The filled unit cell walls have a greater radiodensity from the narrow edge (their planar direction) than from the substantially square faces because of the increased amount of bulk thickness in the planar direction. The filled unit cell walls also have an elongated shape when viewed in the planar direction rather than a substantially square shape when viewed in a direction normal to the planar direction. Therefore, when viewing a single filled wall from a narrow edge or planar direction, it will be elongated and be less radiolucent than the same filled wall viewed from the direction of the square faces. The difference in radiodensity and appearance when viewed in the aligned direction or second aligned direction can be amplified by adding additional overlapping filled unit cell walls to increase the bulk thickness of the material in the aligned or second aligned directions.

Figure 28:
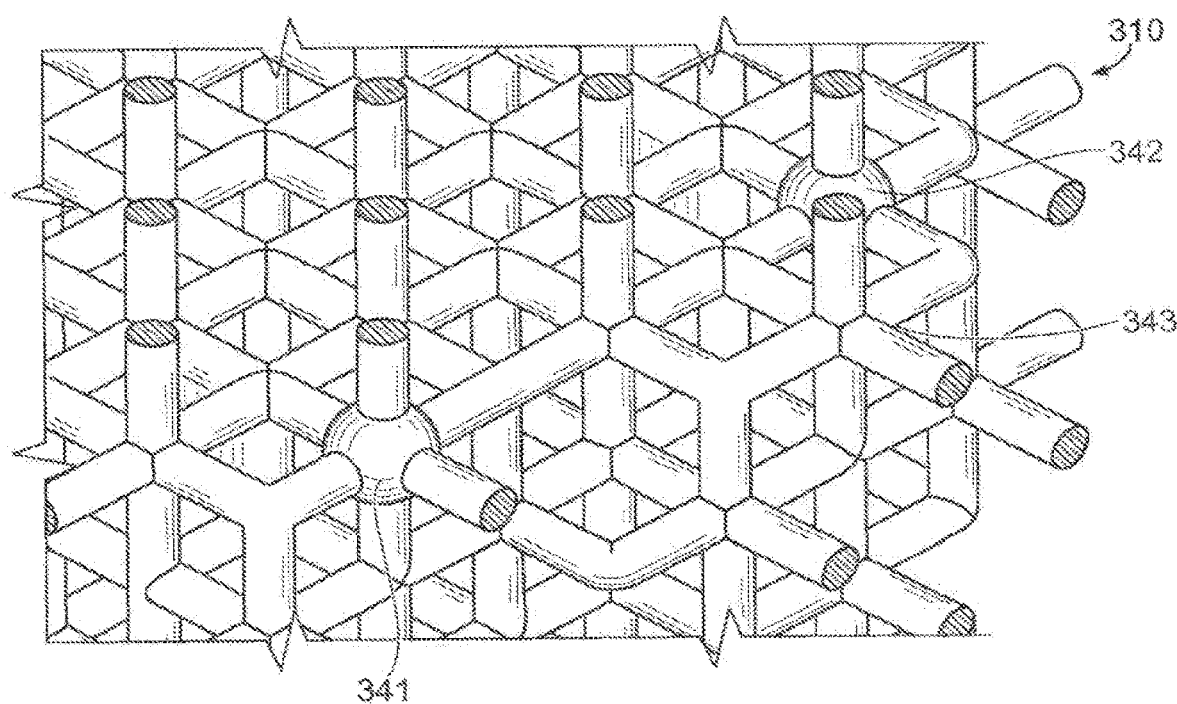
FIG. 28 is an isometric view of a third example embodiment of the variable markers comprised of enlarged nodes and shown in a misaligned direction.

FIGS. 28-31 illustrate a third example embodiment of the variable markers that uses selectively enlarged nodes. FIG. 28 illustrates an isometric view of the third example embodiment of the variable markers shown in a lattice 28310. The lattice 28310 comprises a repeating square unit cell, however other types of unit cells, as noted earlier, can be substituted. Within the lattice 28310, three enlarged nodes 28341-28343 have been added. The enlarged nodes 28341-28343 can be solidly filled so that there are no voids within the filled area and a volumetric density of about 100%. The filled area may optionally contain one or more voids, be filled with a material with a volumetric density of less than 100%, only partially filled, or filled with a material with a volumetric density of between and including 0% to 30%. In the isometric view of FIG. 28, the enlarged nodes 28341-28343 are at a misalignment viewing direction, meaning that the enlarged nodes 28341-28343 will show up as more radiolucent than in an aligned viewing direction.

Figure 29:
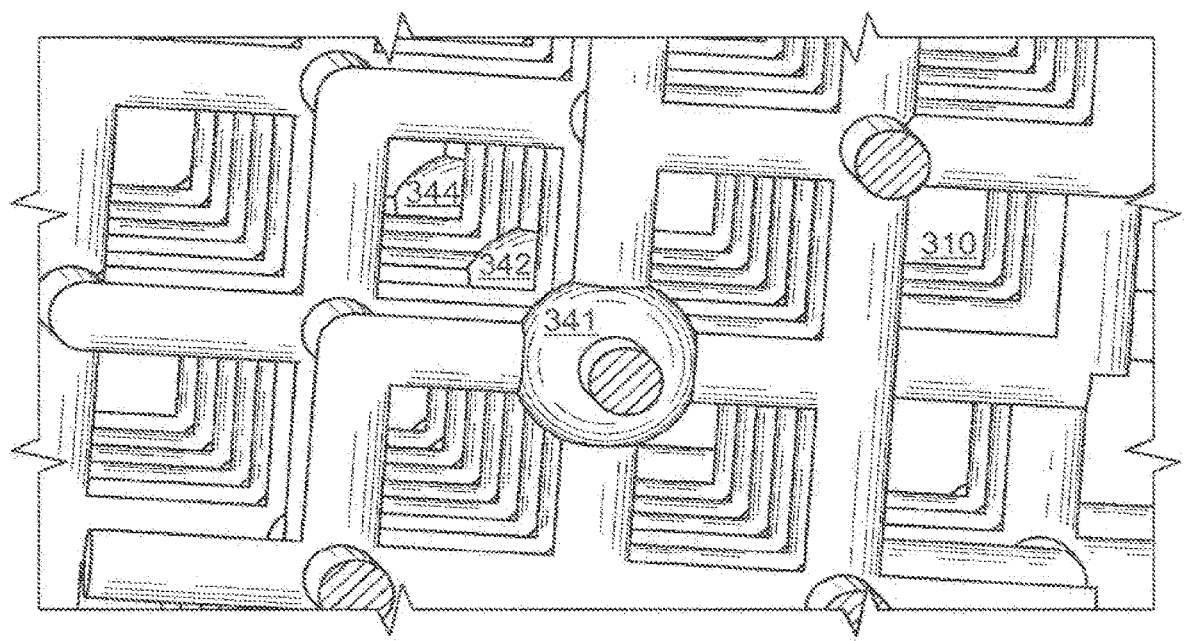
FIG. 29 is an offset side view of a third example embodiment of the variable markers comprised of enlarged nodes and shown in a misaligned direction that is approaching an aligned direction.

FIG. 29 depicts an offset side view of a third example embodiment of the variable markers. In FIG. 29, the offset side view is a misalignment direction that is approaching a side aligned direction. In the third example embodiment, the aligned direction occurs when the lattice 28310 is rotated so that one or more enlarged nodes 28341-28344 are overlapping. In FIG. 29, the enlarged nodes, 28341, 28342 and 28344 partially overlay one another, but do not fully overlay one another.

Figure 30:
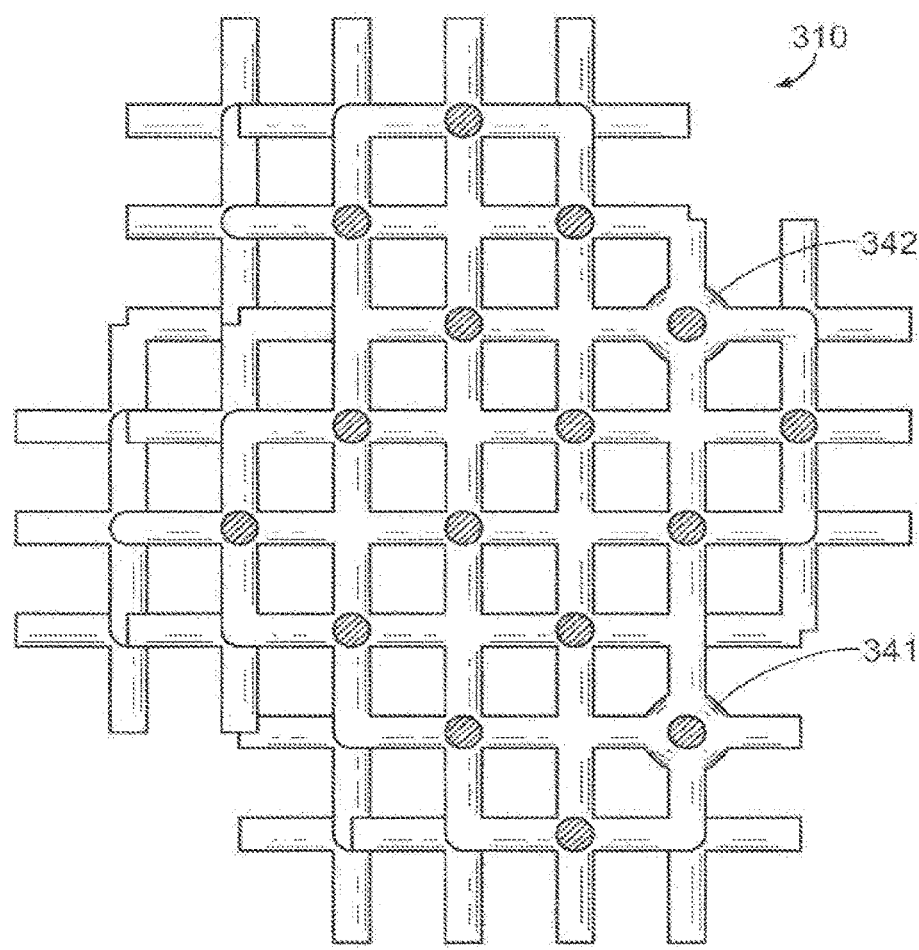
FIG. 30 is a top view of a third example embodiment of the variable markers comprised of enlarged nodes and shown in an aligned direction.

FIG. 30 depicts a top view of the third example embodiment of the variable markers. The top view can be an alternative aligned direction if further enlarged nodes are located directly below enlarged nodes 28341 and 28342. If no additional enlarged nodes are located below enlarged nodes 28341 and 28342, the top view would be an additional misalignment view.

Figure 31:
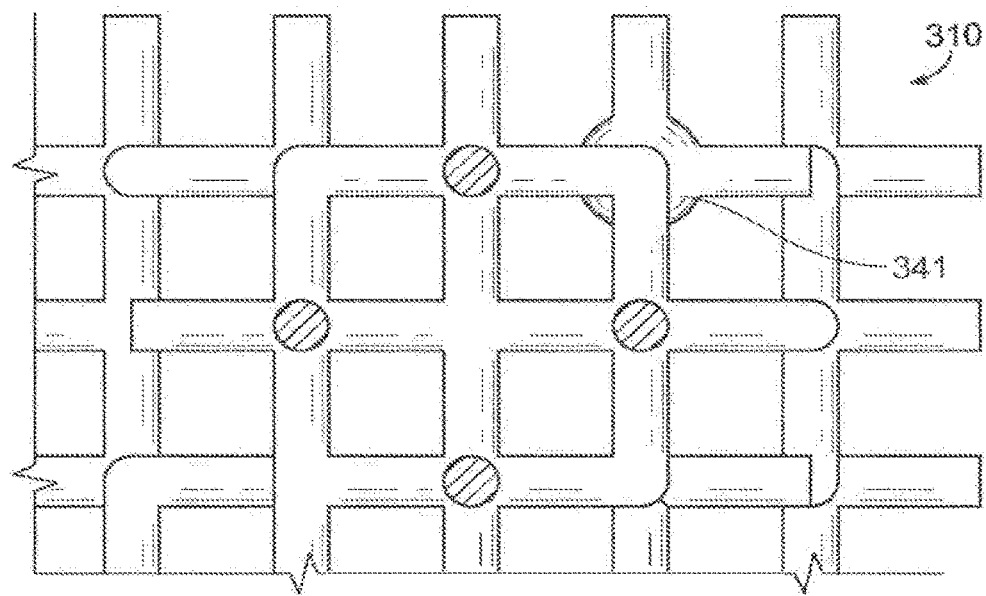
FIG. 31 is a side view of a third example embodiment of the variable markers comprised of enlarged nodes and shown in an aligned direction.

FIG. 31 depicts a side view of the third example embodiment of the variable markers. The side view of the lattice 28310 is shown from an aligned direction where the location of enlarged nodes 28341 and 28342 overlap in this view. Enlarged node 28342 is located behind enlarged node 28341 in this view so that when viewing the variable markers in the aligned direction, the x-ray would need to travel through both enlarged nodes 28341 and 28342, decreasing their radiolucency.

Figure 32:
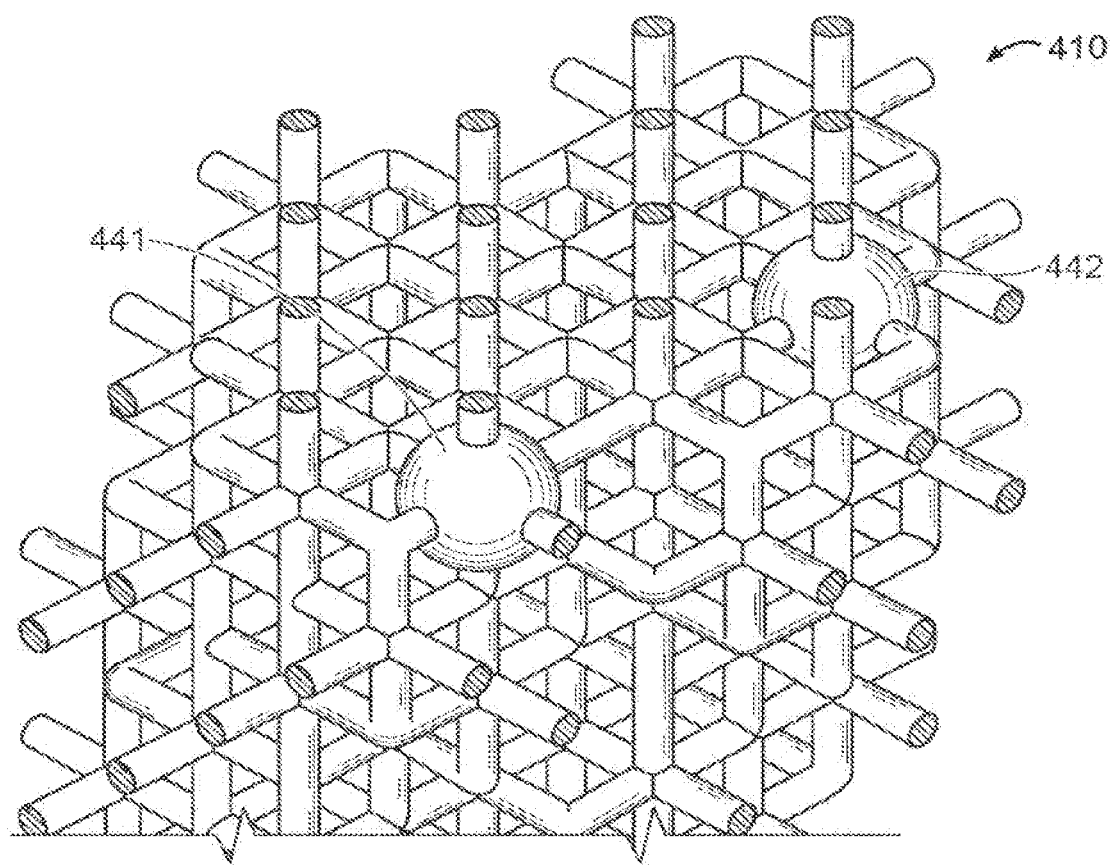
FIG. 32 is an isometric view of a fourth example embodiment of the variable markers also comprised of enlarged nodes and shown in a misaligned direction.

FIG. 32 depicts a fourth example embodiment of the variable markers that uses selectively enlarged nodes. FIG. 32 depicts an isometric view of the fourth example embodiment of the variable markers shown in a lattice 32410. The lattice 32410 used is comprised of a repeating square unit cell, however other types of unit cells, as noted earlier, can be substituted. Within the lattice 32410, two enlarged nodes 32441 and 32442 have been added. The enlarged nodes 32441 and 32442 can be solidly filled so that there is are no voids within the filled area, having a volumetric density of about 100%. The filled area may optionally contain one or more voids, be filled with a material with a volumetric density of less than 100%, only partially filled or filled with a material with a volumetric density of between and including 0% to 30%. In the isometric view of FIG. 32, the enlarged nodes 32441 and 32442 are at a misalignment viewing direction, meaning that the enlarged nodes 32441 and 32442 will show up as more radiolucent than in an aligned viewing direction.

For the fourth example embodiment, the aligned directions would fall in a lateral direction. One aligned direction could be viewed by rotating the lattice 32410 from the orientation in FIG. 32 by about 45 degrees about the x axis and about 45 degrees about the z axis. A second aligned direction could be viewed by rotating the lattice 32410 from the orientation in FIG. 32 by about 45 degrees about the x axis and about 135 degrees about the z axis.

Figure 33:
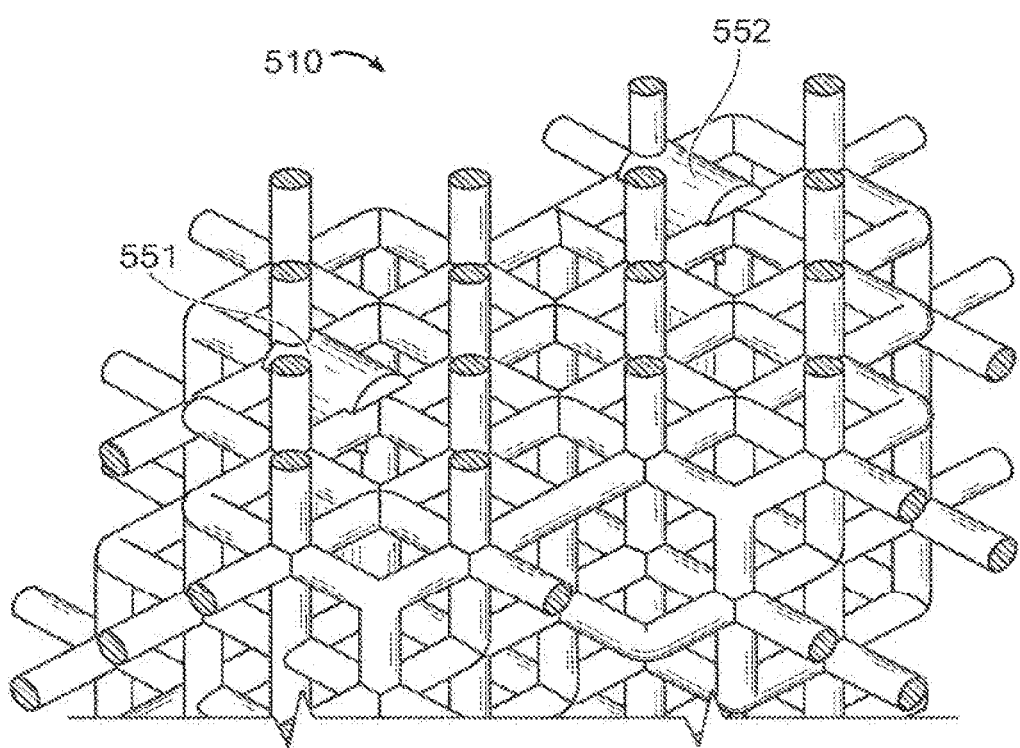
FIG. 33 is an isometric view of a fifth example embodiment of the variable markers comprised of enlarged struts and shown in a misaligned direction.
Figure 34:
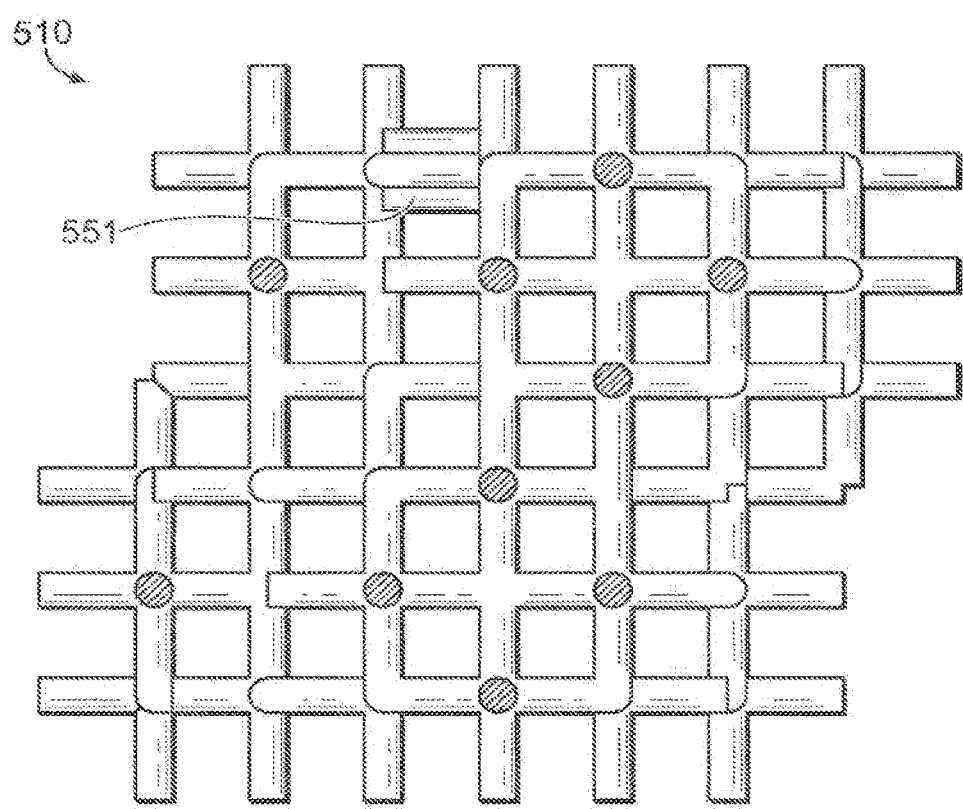
FIG. 34 is a side view of a fifth example embodiment of the variable markers comprised of enlarged struts and shown in an aligned direction.

FIGS. 33-34 illustrate a fifth example embodiment of the variable markers that uses selectively enlarged struts. FIG. 33 illustrates an isometric view of the fifth example embodiment of the variable markers shown in a lattice 33510. The lattice 33510 used is comprised of a repeating square unit cell, however other types of unit cells, as noted earlier, can be substituted. Within the lattice 33510, two enlarged struts 33551 and 33552 have been added. The enlarged struts 33551 and 33552 can be solidly filled so that there is are no voids within the filled area, having a volumetric density of about 100%. The enlarged struts may also be employed using other characteristics, including but not limited to, partially enlarged struts, enlarged struts between adjacent nodes, enlarged struts on an area centered over a node, struts smoothly integrated into the surrounding structure and/or struts sharply integrated into the surrounding structure. The filled area may optionally contain one or more voids, be filled with a material with a volumetric density of less than 100%, only partially filled or filled with a material with a volumetric density of between and including 0% to 30%. In the isometric view of FIG. 33, the enlarged struts 33551 and 33552 are at a misalignment viewing direction, meaning that the enlarged struts 33551 and 33552 will show up as more radiolucent than in an aligned viewing direction.

In FIG. 34 is a side view of the fifth example embodiment, showing the lattice 33510 in an aligned direction. In the aligned direction, the enlarged strut 33551 fully overlays the enlarged strut 33552 so that only enlarged strut 33551 is visible. The opposite side would also be an aligned direction in this embodiment.

The variable markers disclosed herein can be implemented in various types of implants, including the high x-ray lucency lattice structures disclosed herein, other porous structures and substantially solid structures. The variable markers could be used in some solid metallic structures and in some solid polymer structures, particularly PEEK structures.

The variable markers can be designed relative to the lucency of the bulk volume they are connected to, fixed to or contained within. The relative lucency of the bulk volume is best determined as an average baseline lucency representing the average lucency of the bulk volume in a given direction without the inclusion of any variable markers. Therefore, the average baseline lucency can be the lucency of a lattice prior to the inclusion of any markers or inclusions and quantifiable by the volumetric density and luminosity in imaging. The average baseline lucency can be taken across the entire side of a bulk volume if using an infinite focal length, or across a focal area when using a finite focal length. Once the variable markers are included with the bulk volume, a second average lucency may be taken of the bulk volume and the variable marker. The second average lucency can be called a post-inclusion lucency in some embodiments, where the lucency of the lattice in a misaligned direction including any markers or inclusions is quantifiable by the volumetric density and luminosity in imaging. It is preferable for the inclusion of a variable marker to change the average baseline lucency of the bulk volume by 35% or less when viewed in a misaligned direction. It is more preferable for the inclusion of a variable marker to change the average baseline lucency of the bulk volume by 15% or less when viewed in a misaligned direction. In some embodiments, it is preferable for the inclusion of a variable marker to change the average baseline lucency of the bulk volume by an amount between and including 4% and 12% when viewed in a misaligned direction.

The variable markers can cause a change from the average baseline lucency that can be quantified in an aligned direction. When the variable markers are in an aligned direction, they can cause a localized change in lucency compared to the average baseline lucency. It is preferably for the variable markers to cause a localized change in lucency of at least 1% compared to the average baseline lucency. In some embodiments, it is preferable for the variable markers to cause a localized change in lucency of at least 4% compared to the average baseline lucency. In some embodiments, it is preferable for the variable markers to cause a localized change in lucency of at least 15 percent compared to the average baseline lucency. The localized change in lucency refers to a measure of lucency taken at an area local to the variable marker and used in comparison with the average baseline lucency. The area local to the variable marker can be measured as the visible area of a variable marker when viewed in an aligned direction. In some embodiments, the area local to the variable marker can be measured as an area including a variable marker when viewed in an aligned direction and including an area near the variable marker of about one to ten times the visible area of the variable marker when viewed in an aligned direction.

The variable markers disclosed herein can comprise a marker with various volumetric density properties. In some embodiments, the variable markers have a volumetric density of about 100%. In some embodiments, the variable markers have a volumetric density of less than 100%. In some embodiments, the variable markers have a volumetric density of between and including 0% to 30%. In some embodiments, the variable markers have a volumetric density of between and including 0% to 25%.

Figure 35:
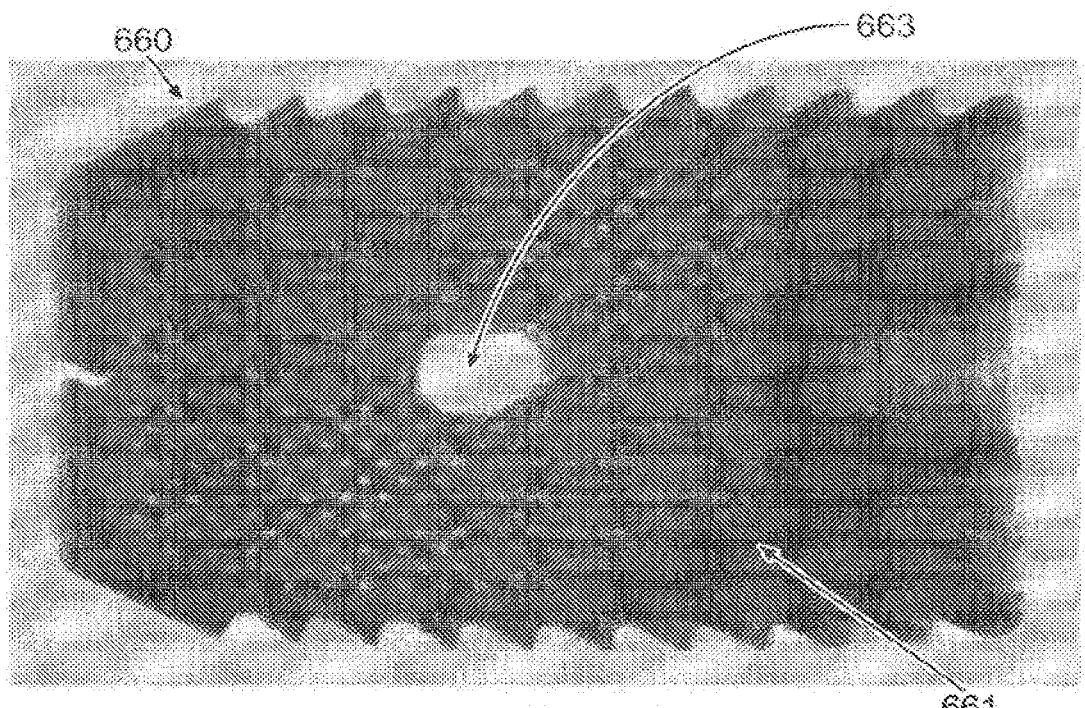
FIG. 35 is a side view of an example interbody fusion implant incorporating variable markers shown in an aligned direction.
Figure 36:
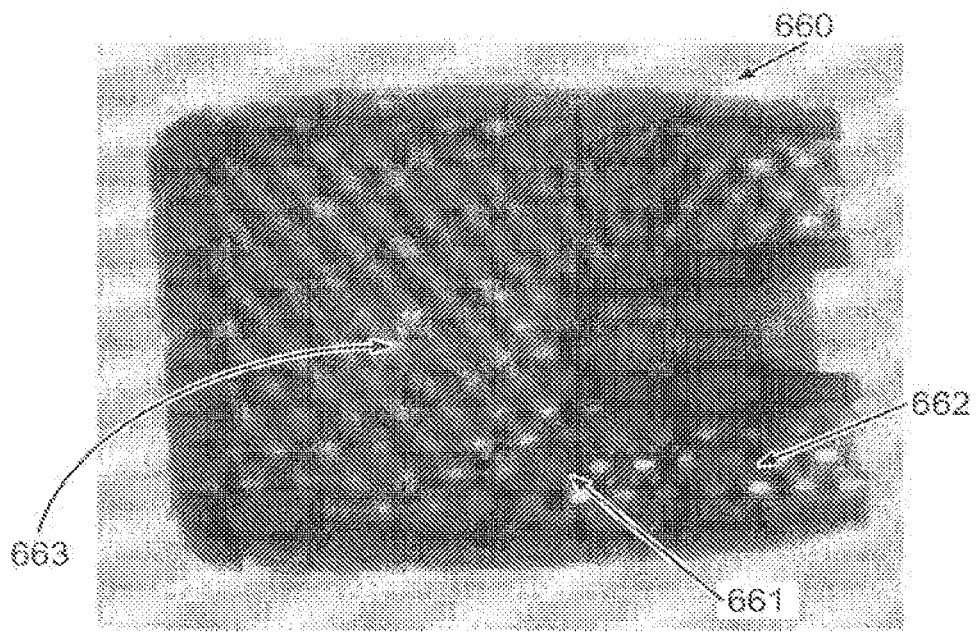
FIG. 36 is a perspective view of an example interbody fusion implant incorporating variable markers shown in a misaligned direction.

FIGS. 35-36 illustrate an example of an implant 35660 that includes diagonal variable markers 35661 and 35662. In FIG. 35 is a side view of the implant 35660 in an aligned direction. In the aligned direction, the diagonal variable marker 35661 fully overlays the diagonal variable marker 35662 so that the area is less radiolucent than the surrounding body of the implant. The diagonal variable markers 35661 and 35662 in the example embodiment comprise struts with a diameter of approximately one mm and configured to overlap at the aligned direction. In the side view of FIG. 35, the aligned direction, the diagonal variable marker 35661 is largely radiopaque due to a significant overlap with the diagonal variable marker 35662. When the diagonal variable markers 35661 and 35662 are viewed in the aligned direction, the closer marker to the viewer partially or fully overlays the more distant marker from the viewer. FIG. 36, where the implant 35660 is rotated approximately 45 degrees about the z axis from its position in FIG. 35 to a misaligned direction, the diagonal variable markers 35661 and 35662 become more radiolucent than when viewed from the FIG. 35 orientation as the amount of overlap between the struts decreases.

The implant 35660 also includes another variable marker 35663 configured for providing a measure of alignment. In the aligned view of FIG. 35, the variable marker 35663 is fully radiolucent. The variable marker 35663 is provided as an elongate lateral opening in the implant, however, other structures are possible. In some embodiments, the variable marker 35663 can be multiple discrete openings or voids that appear in a line away from the viewer in the aligned view and appear individually in a misaligned view. In some embodiments, the variable marker 35663 can be multiple omitted struts, omitted nodes, smaller struts than the surrounding structure or smaller nodes than the surrounding structure that appear in a line away from the viewer in the aligned view and appear individually in a misaligned view. In the misaligned view of FIG. 36, the variable implant marker 35663 is hidden by the more radiodense surrounding structure.

Figure 38:
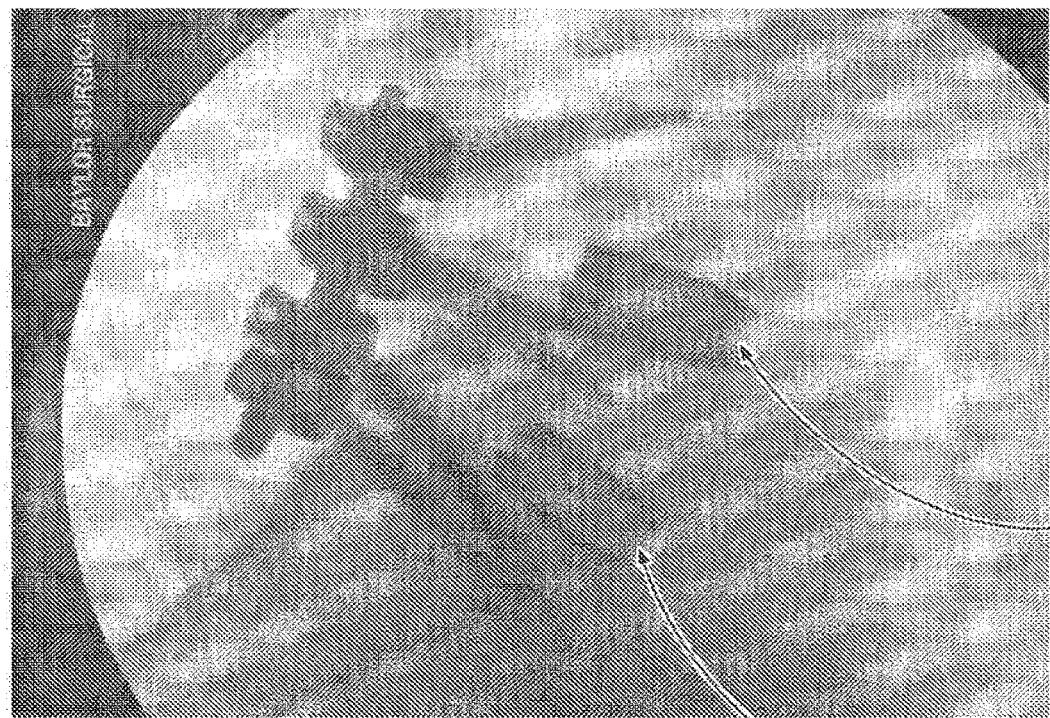
FIG. 38 is an example of an interbody fusion implant, designed using the high x-ray lucency lattice and methods of designing a high x-ray lucency lattice disclosed herein, and imaged on an x-ray machine in a lateral direction.
Figure 37:
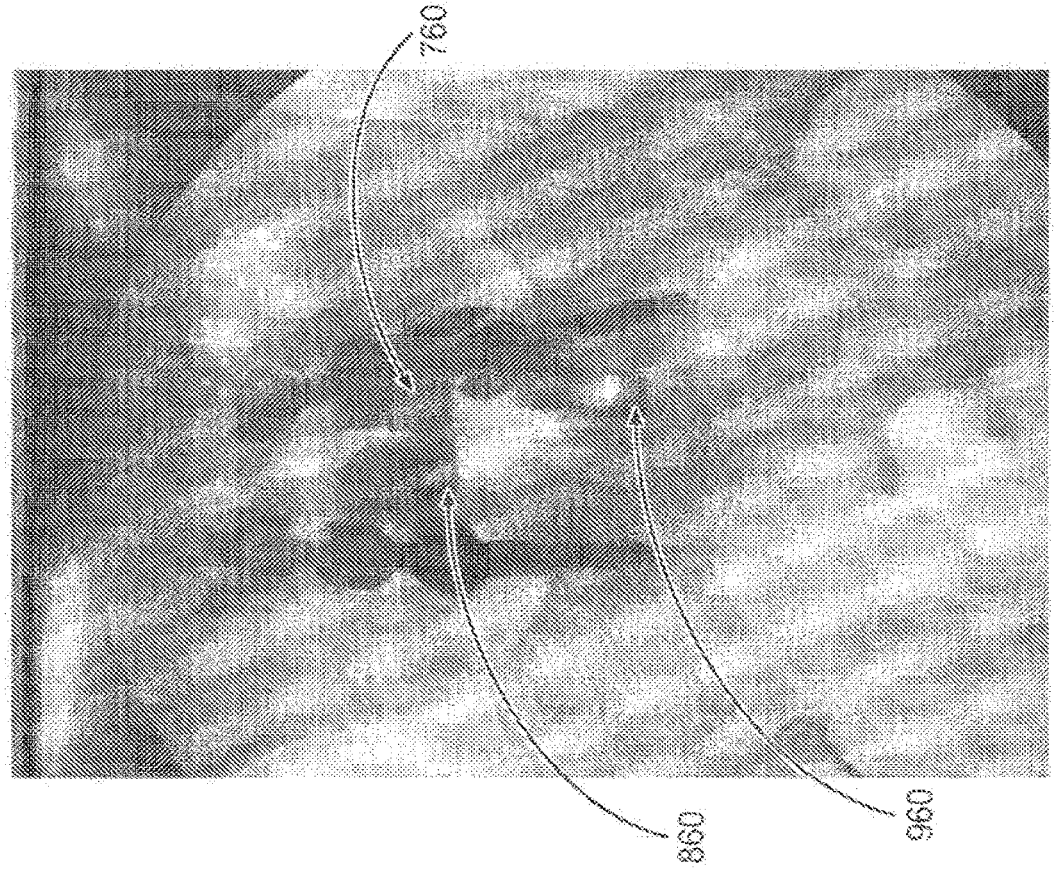
FIG. 37 is an example of an interbody fusion implant, designed using the high x-ray lucency lattice and methods of designing a high x-ray lucency lattice disclosed herein, and imaged on an x-ray machine in the anterior to posterior direction.

FIGS. 37-38 depict an example of an interbody fusion implant, designed using the high x-ray lucency lattice and methods of designing a high x-ray lucency lattice disclosed herein, and imaged on an x-ray machine. The image in FIG. 37 was taken from the anterior to posterior direction and the image in FIG. 38 was taken in a lateral direction. These x-ray images of a first implant 760, a second implant 860 and a third implant 960 were taken from predetermined desired directions, which are the anterior to posterior and lateral directions in this case. The example implants 760, 860 and 960 include endplates with a higher volumetric density than the lattice body, making the endplates appear darker in the x-ray image than the lattice body. The fixation rods and screws on either side of the implants 760, 860 and 960 were not constructed or designed according to the disclosure herein and are largely radiopaque. In comparison, the lattice body portion of the implants 760, 860 and 960 constructed and designed according to the disclosure herein are significantly more radiolucent than the fixation rods and screws despite the 8 mm depth of the implant being greater than that of ordinary 5.5 mm diameter rods or screws.

In some embodiments, the lattice structure can include closed cell structures or hollowed out structures to reduce the volumetric density and also increase lucency. Closed cell structures could include rods or nodes within the lattice structure with hollow centers. Hollowed out structures could include U-channels, I-beams, H-beams or any elongate structure with elongate portions removed.

In FIGS. 39 to 45 is an example implant 1060 including the inventive lucency optimized lattice structure. The implant 1060 can be inserted in or between bones, segments of bone or within an area carved out of a single bone to provide mechanical spacing and mechanical stability to promote bone growth. Alternatively, the implant 1060 can be inserted within or near tissue other than bone in some embodiments. The implant 1060 can be comprised substantially of three components—an upper endplate 1011, a lower endplate 1012 and a body 1013. The upper and lower endplates 1011 and 1012 can comprise a biocompatible material with a higher elastic modulus than the body 1013. The body 1013 can comprise a biocompatible material with a lower elastic modulus than the upper and lower endplates 1011 and 1012.

Figure 39:
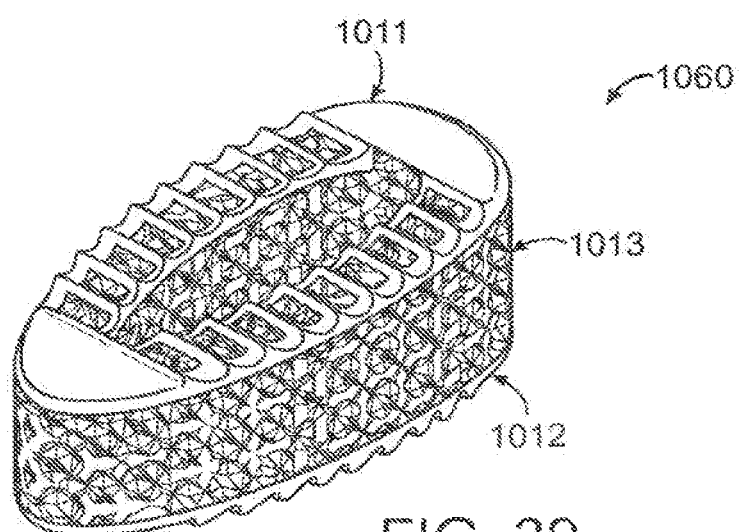
FIG. 39 is a perspective view of an example of a first implant 1060 designed using the high x-ray lucency lattice and methods of designing a high x-ray lucency lattice disclosed herein.

In FIG. 39 is a perspective view of the implant 1060, showing the independent configuration of the endplates 1011 and 1012 relative to the body 1013. The implant 1060 can be described as having an elongate direction and a lateral direction normal to the elongate direction. Implant 1060 includes a body 1013 comprising an MRDD lattice optimized for disparity in a lateral direction. The MRDD lattice used in the body 1013 uses an origin orientation similar to that of the MRDD unit cell in FIG. 8. In the case of implant 1060, the MRDD unit cell in FIG. 8 is oriented so that the direction normal to the page in FIG. 8 is oriented in a lateral direction on the implant 1060 to maximize disparity. Depending on the anticipated implant orientation, the direction of disparity or the direction of a desired lucency property can be adjusted and does not necessarily need to be in a lateral direction. The direction of disparity could be, for example, to the front of the implant, to the rear of the implant or at an oblique angle. In some embodiments, the direction of disparity is oriented towards the direction of expected x-ray imaging expected after the implant is fixed within a patient. For an implant 1060 comprising an MRDD lattice, some embodiments will have maximum disparity in a lateral direction when the MRDD lattice is rotated about any axis and fixed about 0-18 degrees from the origin orientation in FIG. 8. In some embodiments, an implant 1060 comprising an MRDD lattice will have maximum disparity in a lateral direction when the MRDD lattice is rotated about any axis and fixed about 0-5 degrees from the origin orientation in FIG. 8.

Figure 40:
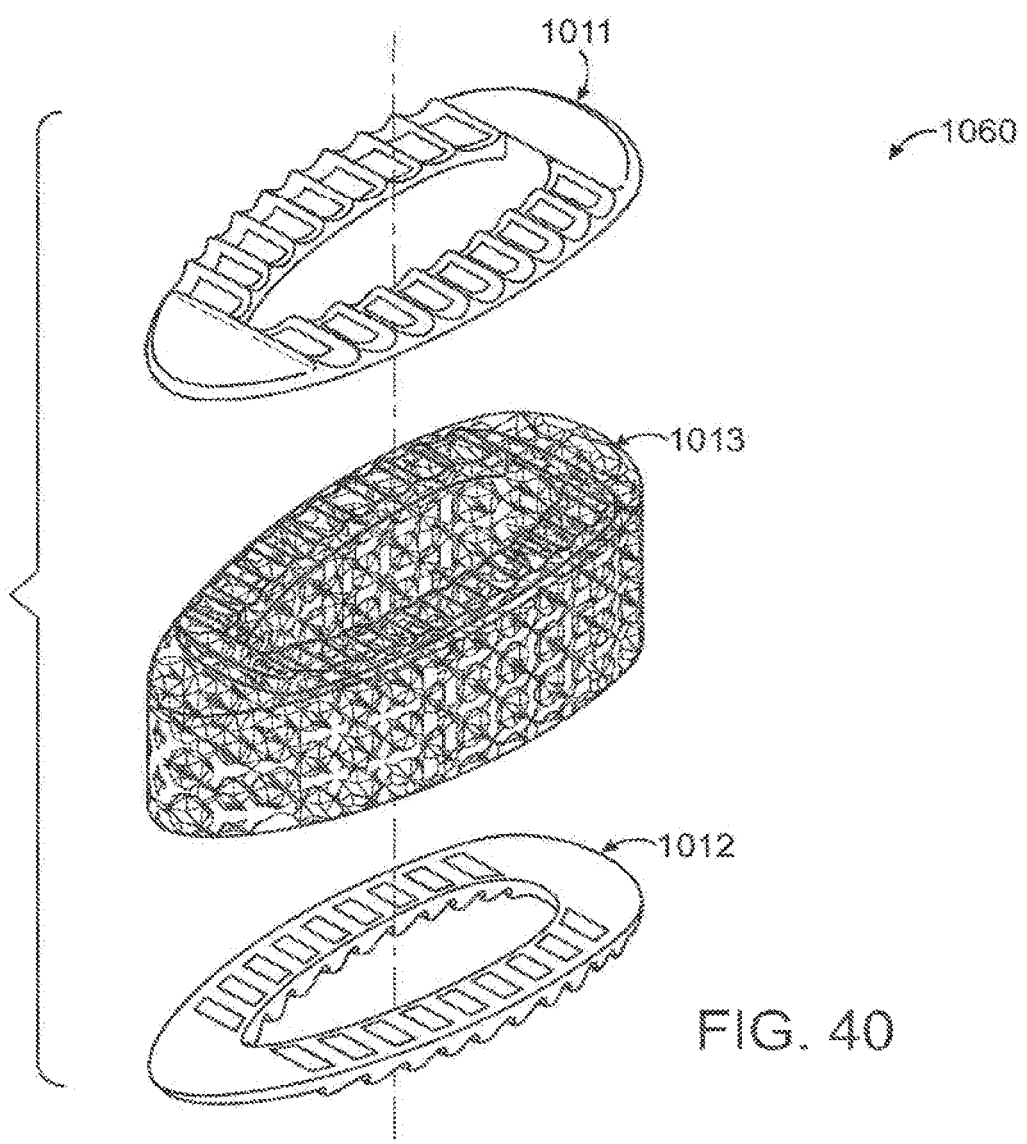
FIG. 40 is an exploded perspective view of the first example of an implant 1060 using high x-ray lucency lattice and methods of designing a high x-ray lucency lattice disclosed herein.
Figure 41:
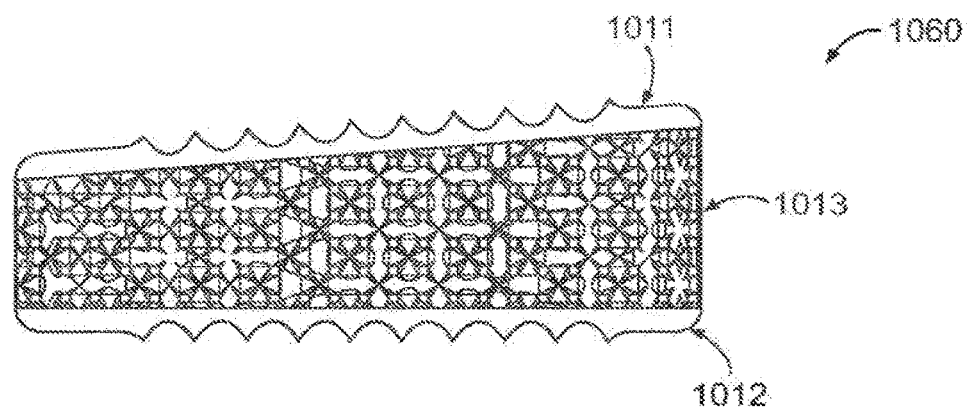
FIG. 41 is a side view of the first example of implant 1060 comprising a repeating modified rhombic dodecahedron unit cell and configured for disparity in a lateral or side direction.
Figure 42:
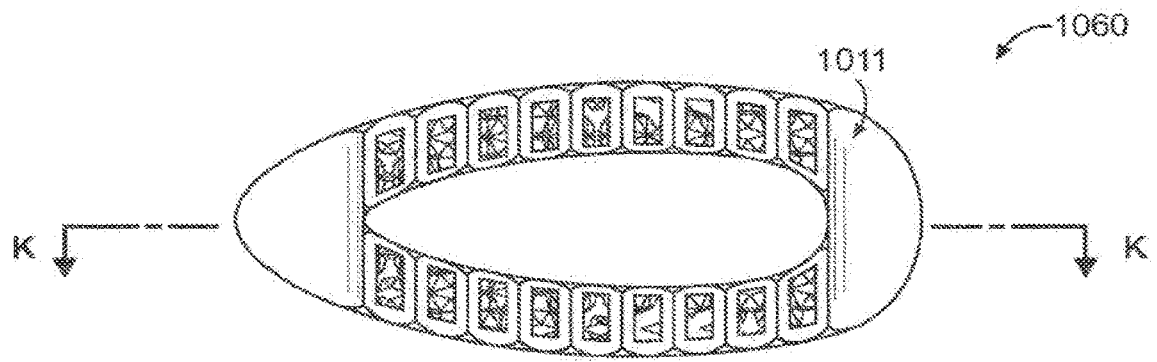
FIG. 42 is a top view of the first example of implant 1060 showing the section K-K used in FIG.
Figure 43:
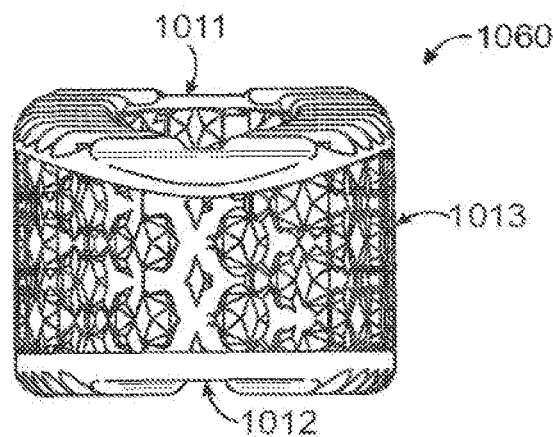
FIG. 43 is a front view of the first example of the implant 1060, showing the independent endplates 1011 and 1012.
Figure 44:
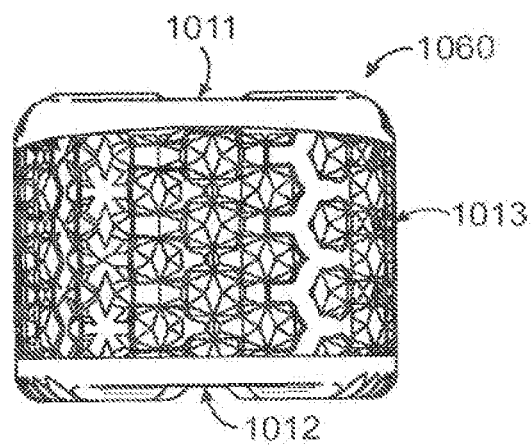
FIG. 44 is a rear view of the first example of the implant 1060 showing the independent endplates 1011 and 1012.

In FIG. 40 is an exploded perspective view of the implant 1060, showing the endplates 1011 and 1012 separated from the body 1013 and showing the lack of a direct and rigid connection between the endplates 1011 and 1012 in this embodiment. There may be direct connections between the endplates 1011 and 1012 to adjust the construct properties as long as the endplates 1011 and 1012 are capable of some movement relative to one another. In FIG. 41 is a side view of the implant 1060, showing the position of the endplates relative to one another and showing how body 1013 comprises an MRDD lattice configured for disparity in a lateral direction. In FIG. 42 is a top view of the implant 1060 showing an example endplate configuration and identifying line K-K. In FIG. 43 is a front view and in FIG. 44 is a rear view of the implant 1060.

Figure 45:
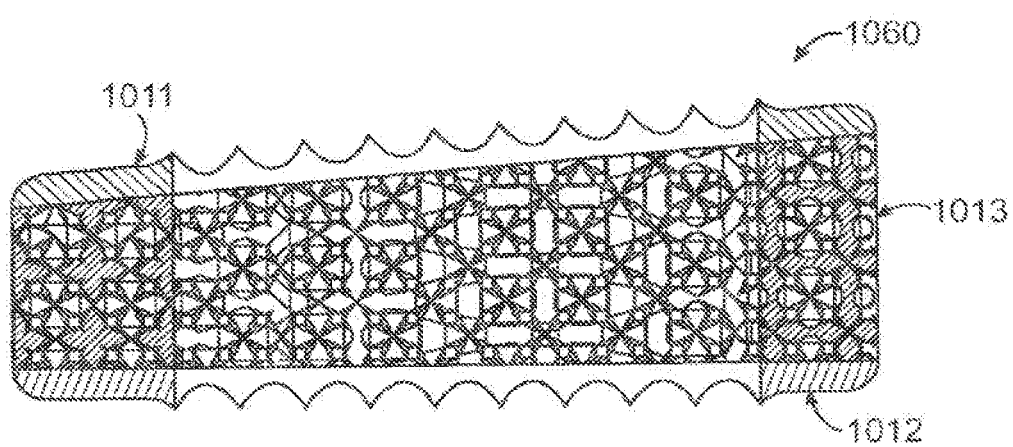
FIG. 45 is a side sectioned view of the first example of the implant 1060 sectioned along K-K shown in FIG. 43.

In FIG. 45 is a side sectioned view of the implant 1060, sectioned through line K-K in FIG. 42 and showing that the endplates 1011 and 1012 do not directly contact one another throughout the device in this example. FIG. 45 also shows that the body 1013 of this embodiment comprises an MRDD lattice configured for disparity in a lateral direction.

In FIGS. 46 to 52 is an example implant 1160 including the inventive lucency optimized lattice structure. The implant 1160 can be inserted in or between bones, segments of bone or within an area carved out of a single bone to provide mechanical spacing and mechanical stability to promote bone growth. Alternatively, the implant 1060 can be inserted within or near tissue other than bone in some embodiments. The implant 1160 can be comprised substantially of three components—an upper endplate 1111, a lower endplate 1112 and a body 1113. The upper and lower endplates 1111 and 1112 can comprise a biocompatible material with a higher elastic modulus than the body 1113. The body 1113 can comprise a biocompatible material with a lower elastic modulus than the upper and lower endplates 1111 and 1112.

Figure 46:
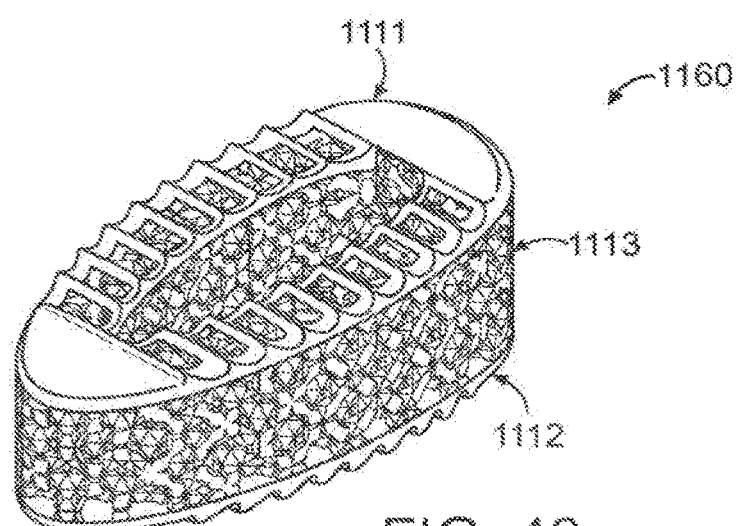
FIG. 46 is a perspective view of an example of a second implant 1160 designed using the high x-ray lucency lattice and methods of designing a high x-ray lucency lattice disclosed herein.

FIG. 46 is a perspective view of the implant 1160, showing the independent configuration of the endplates 1111 and 1112 relative to the body 1113. The implant 1160 can be described as having an elongate direction and a lateral direction normal to the elongate direction. Implant 1160 includes a body 1113 comprising an MRDD lattice optimized for disparity in a lateral direction. Compared to implant 1060, the MRDD lattice comprising the body 1113 of implant 1160 has been rotated about 45 degrees about a lateral axis of the implant 1160. Therefore, the MRDD lattice in implant 1160 has been rotated about 45 degrees from the origin position in FIG. 8 about an axis normal to the page. Depending on the anticipated implant orientation, the direction of disparity or the direction of a desired lucency property can be adjusted and does not necessarily need to be in a lateral direction. The direction of disparity could be, for example, to the front of the implant, to the rear of the implant or at an oblique angle. In some embodiments, the direction of disparity is oriented towards the direction of expected x-ray imaging expected after the implant is fixed within a patient. For an implant 1160 comprising an MRDD lattice, some embodiments will have maximum disparity in a lateral direction when the MRDD lattice is rotated about any axis and fixed about 0-60 degrees from the origin orientation in FIG. 8. In some embodiments, an implant 1160 comprising an MRDD lattice will have maximum disparity in a lateral direction when the MRDD lattice is rotated about any axis and fixed about 0-5 degrees from the origin orientation in FIG. 8.

Figure 47:
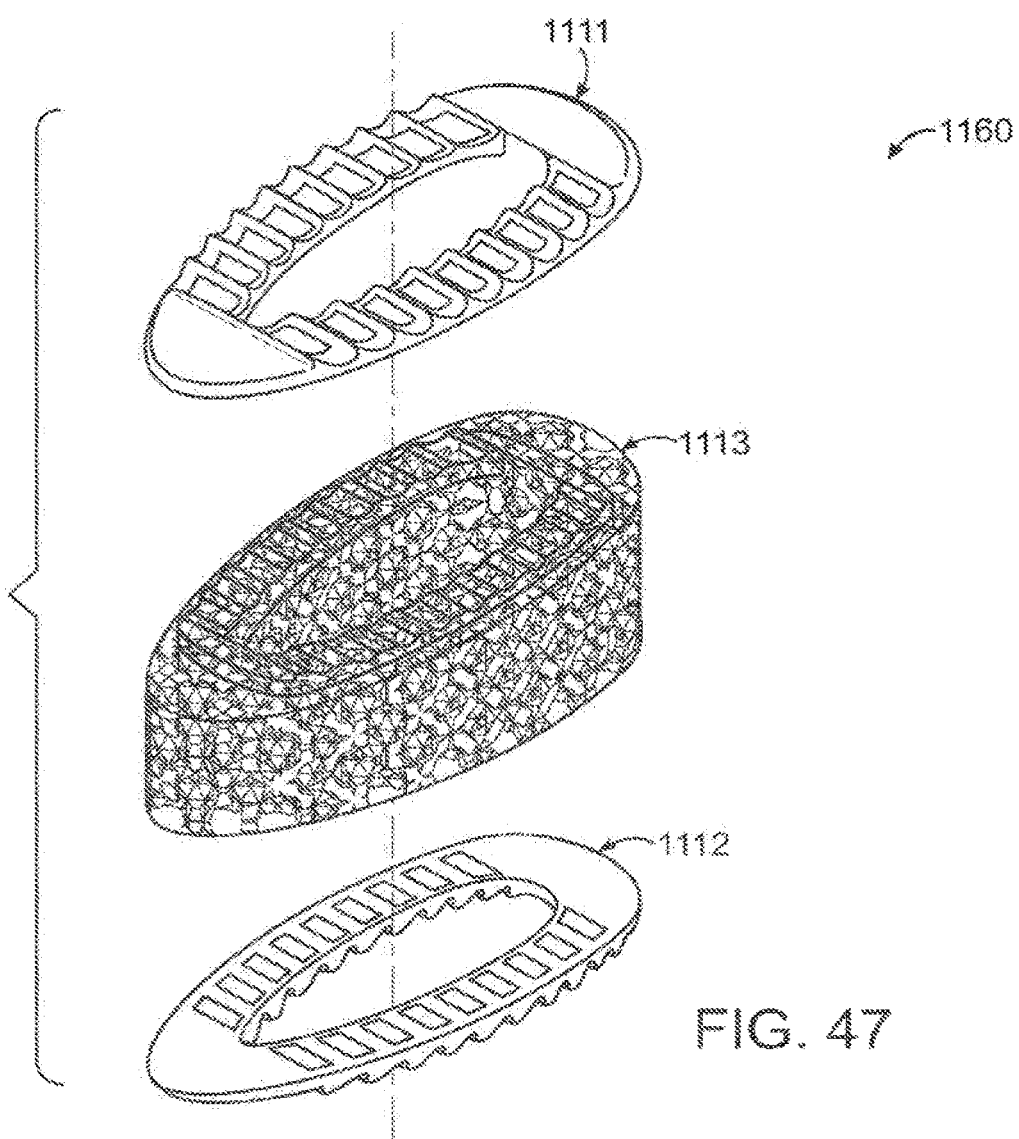
FIG. 47 is an exploded perspective view of the second example of an implant 1160 using high x-ray lucency lattice and methods of designing a high x-ray lucency lattice disclosed herein.
Figure 48:
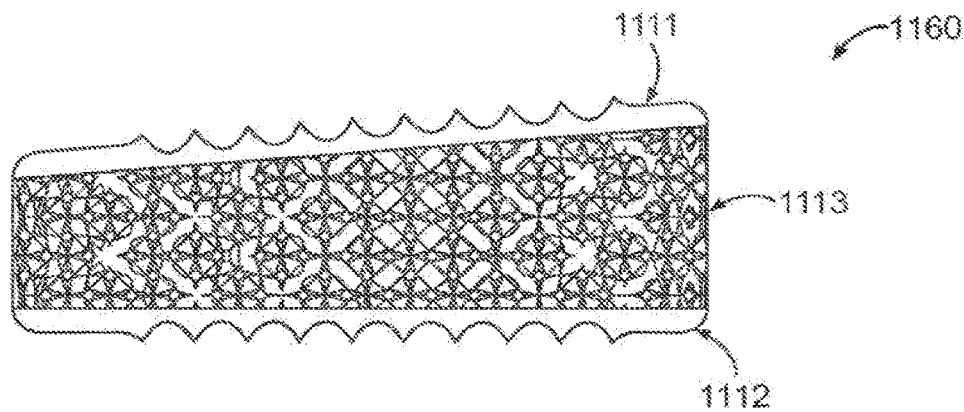
FIG. 48 is a side view of the second example of implant 1160 comprising a repeating modified rhombic dodecahedron unit cell and configured for disparity in a lateral or side direction.
Figure 49:
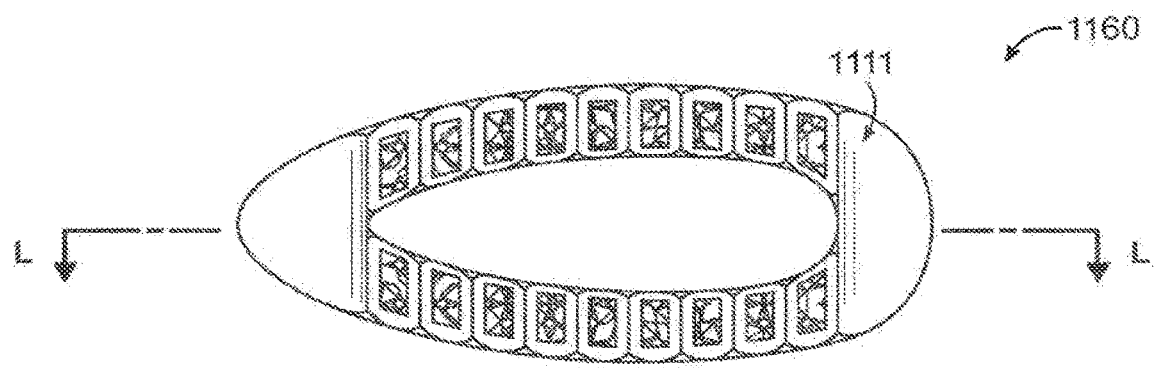
FIG. 49 is a top view of the second example of implant 1160 showing the section L-L used in FIG. 52.
Figure 50:
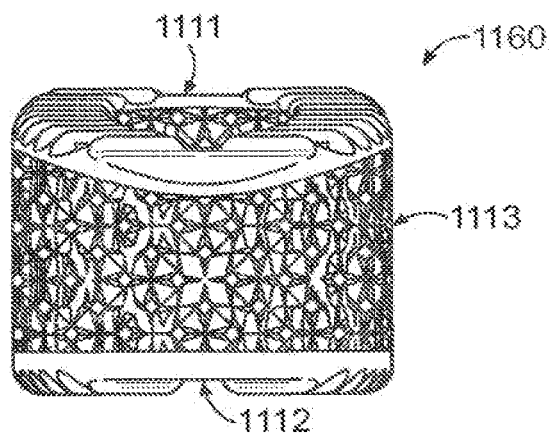
FIG. 50 is a front view of the second example of the implant 1160, showing the independent endplates 1111 and 1112.
Figure 51:
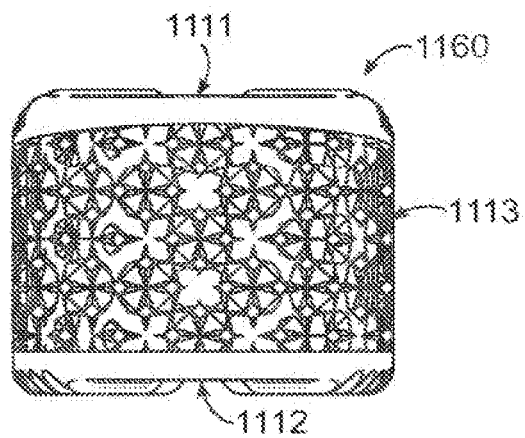
FIG. 51 is a rear view of the second example of the implant 1160 showing the independent endplates 1111 and 1112.

In FIG. 47 is an exploded perspective view of the implant 1060, showing the endplates 1111 and 1112 separated from the body 1113 and showing the lack of a direct and rigid connection between the endplates 1111 and 1112 in this embodiment. There may be direct connections between the endplates 1111 and 1112 to adjust the construct properties as long as the endplates 1111 and 1112 are capable of some movement relative to one another. In FIG. 48 is a side view of the implant 1160, showing the position of the endplates relative to one another and showing that body 1133 comprises an MRDD lattice configured for disparity in a lateral direction. In FIG. 49 is a top view of the implant 1160 showing an example endplate configuration and identifying line L-L. In FIG. 50 is a front view and in FIG. 51 is a rear view of the implant 1160.

Figure 52:
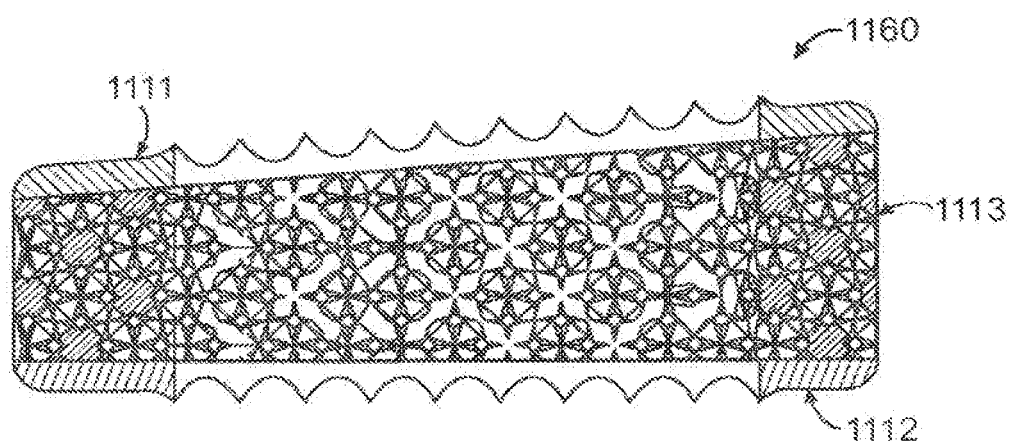
FIG. 52 is a side sectioned view of the first example of the implant 1160 sectioned along L-L shown in FIG. 49.

In FIG. 52 is a side sectioned view of the implant 1160, sectioned through line L-L in FIG. 49 and showing that the endplates 1111 and 1112 do not directly contact one another throughout the device in this example. FIG. 52 also shows that the body 1113 of this embodiment comprises an MRDD lattice configured for disparity in a lateral direction.

In FIGS. 53 to 59 is an example implant 1260 including the inventive lucency optimized lattice structure. The implant 1260 can be inserted in or between bones, segments of bone or within an area carved out of a single bone to provide mechanical spacing and mechanical stability to promote bone growth. Alternatively, the implant 1060 can be inserted within or near tissue other than bone in some embodiments. The implant 1260 can be comprised substantially of three components—an upper endplate 1211, a lower endplate 1212 and a body 1213. The upper and lower endplates 1211 and 1212 can comprise a biocompatible material with a higher elastic modulus than the body 1213. The body 1213 can comprise a biocompatible material with a lower elastic modulus than the upper and lower endplates 1211 and 1212.

Figure 53:
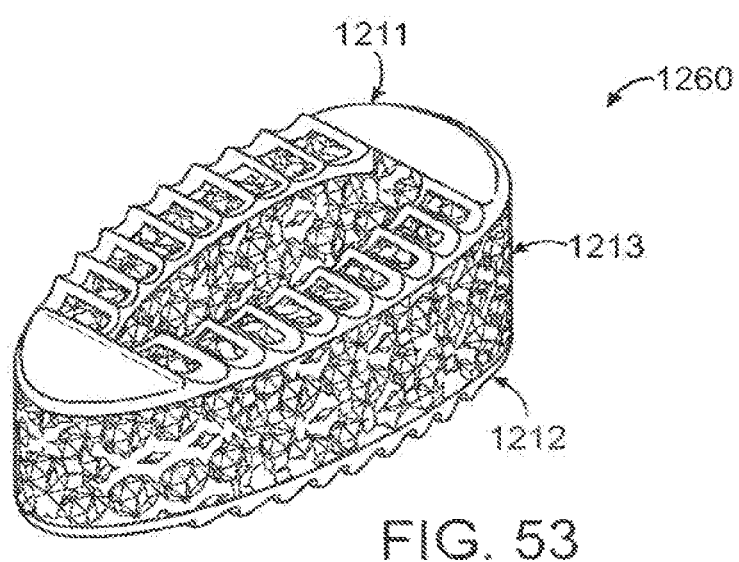
FIG. 53 is a perspective view of an example of a third implant 1260 designed using the high x-ray lucency lattice and methods of designing a high x-ray lucency lattice disclosed herein.

In FIG. 53 is a perspective view of the implant 1260, showing the independent configuration of the endplates 1211 and 1212 relative to the body 1213. The implant 1260 can be described as having an elongate direction and a lateral direction normal to the elongate direction. Implant 1260 includes a body 1213 comprising an MRDD lattice optimized for dispersion in the lateral direction. Compared to implant 1060, the MRDD lattice comprising the body 1113 of implant 1160 has been rotated about 22.5 degrees about the vertical axis of the implant 1260. Therefore, the MRDD lattice in implant 1260 has been rotated about 22.5 degrees from the datum position in FIG. 8 about a z-axis or an axis that is aligned with the vertical direction of the page. The 22.5 degree rotation in implant 1260 is example and the precise amount of rotation required to achieve maximum dispersion for a lattice of predetermined properties could be determined through the methods disclosed herein. The position of the lattice for maximum dispersion can depend factors, such as, the thickness of the lattice, the thickness of the struts and the size of the nodes. Depending on the anticipated implant orientation, the direction of dispersion or the direction of a desired lucency property can be adjusted and does not necessarily need to be in a lateral direction. The direction of dispersion could be, for example, to the front of the implant, to the rear of the implant or at an oblique angle. In some embodiments, the direction of dispersion is oriented towards the direction of expected x-ray imaging expected after the implant is fixed within a patient. For an implant 1260 comprising an MRDD lattice, some embodiments will have maximum dispersion in a lateral direction when the MRDD lattice is rotated about any axis and fixed about 5-40 degrees from the origin orientation in FIG. 8. In some embodiments, an implant 1260 comprising an MRDD lattice will have maximum dispersion in a lateral direction when the MRDD lattice is rotated about any axis and fixed about 15-30 degrees from the origin orientation in FIG. 8.

Figure 54:
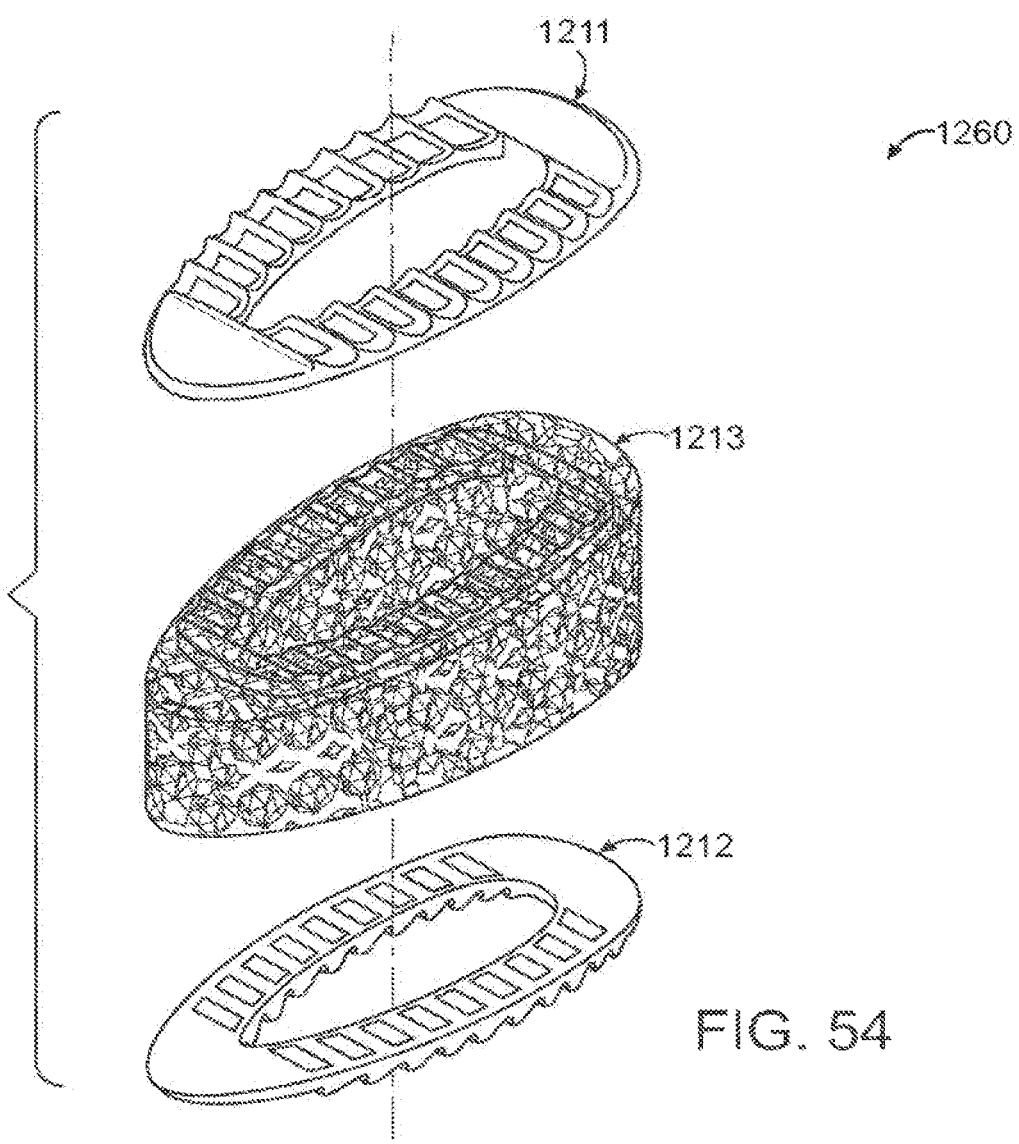
FIG. 54 is an exploded perspective view of the third example of an implant 1260 using high x-ray lucency lattice and methods of designing a high x-ray lucency lattice disclosed herein.
Figure 55:
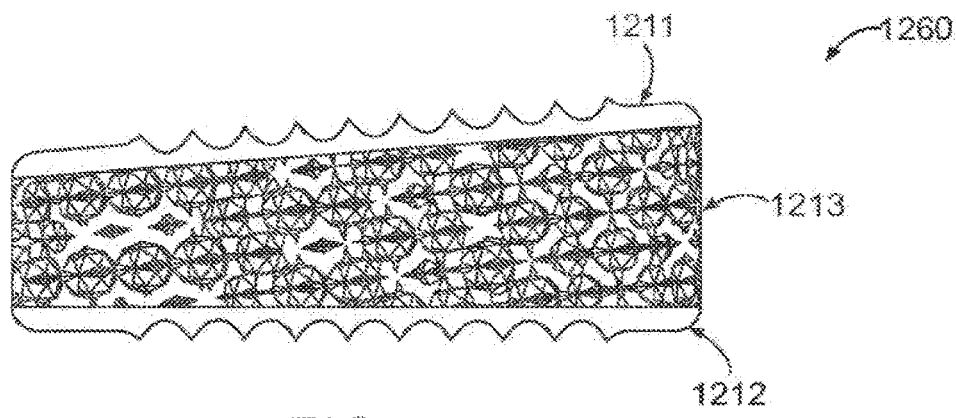
FIG. 55 is a side view of the third example of implant 1260 comprising a repeating modified rhombic dodecahedron unit cell and configured for dispersion in a lateral or side direction.
Figure 56:
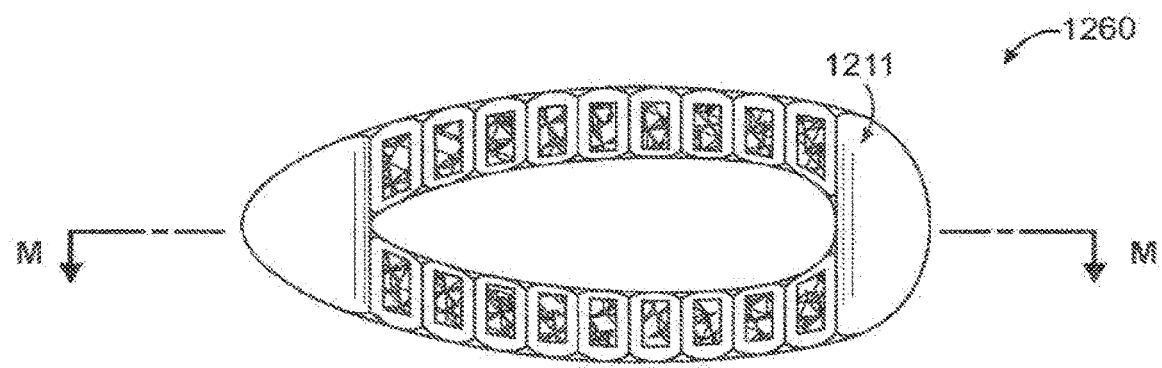
FIG. 56 is a top view of the first example of implant 1260 showing the section M-M used in FIG. 59.
Figure 57:
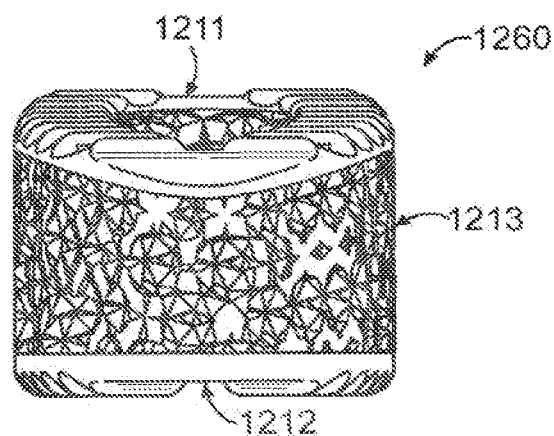
FIG. 57 is a front view of the third example of the implant 1260, showing the independent endplates 1211 and 1212.
Figure 58:
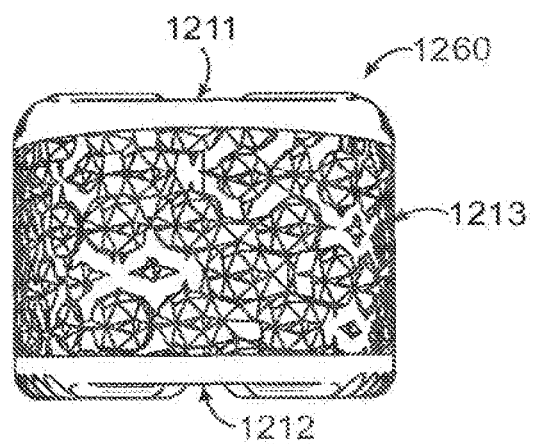
FIG. 58 is a rear view of the third example of the implant 1260 showing the independent endplates 1211 and 1212.

In FIG. 54 is an exploded perspective view of the implant 1260, showing the endplates 1211 and 1212 separated from the body 1213 and showing the lack of a direct and rigid connection between the endplates 1211 and 1212 in this embodiment. There may be direct connections between the endplates 1211 and 1212 to adjust the construct properties as long as the endplates 1211 and 1212 are capable of some movement relative to one another. In FIG. 55 is a side view of the implant 1260, showing the position of the endplates relative to one another and showing that body 1233 comprises an MRDD lattice configured for dispersion in a lateral direction. In FIG. 56 is a top view of the implant 1260 showing an example endplate configuration and identifying line M-M. In FIG. 57 is a front view and in FIG. 58 is a rear view of the implant 1260.

Figure 59:
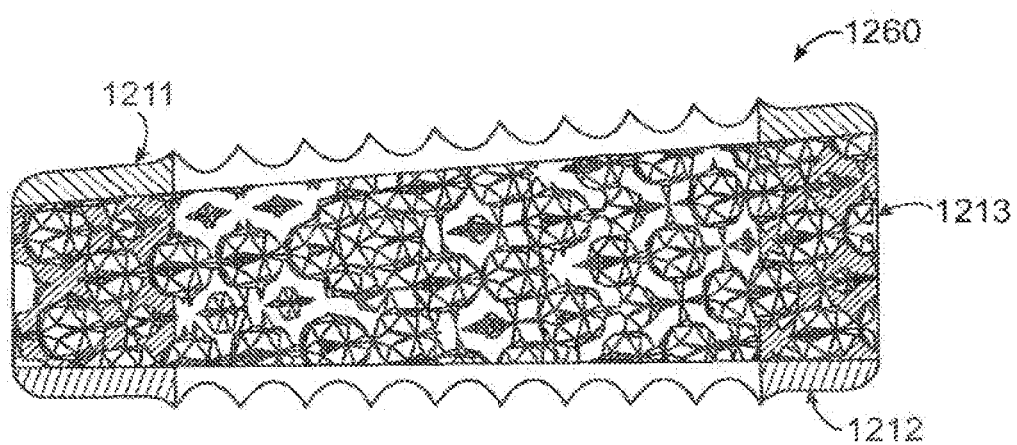
FIG. 59 is a side sectioned view of the third example of the implant 1260 sectioned along M-M shown in FIG. 56.

In FIG. 59 is a side sectioned view of the implant 1260, sectioned through line MM in FIG. 56 and showing that the endplates 1211 and 1212 do not directly contact one another throughout the device in this example. FIG. 59 also shows that the body 1213 of this embodiment comprises an MRDD lattice configured for dispersion in a lateral direction.

In FIGS. 60 to 66 is an example implant 1360 including the inventive lucency optimized lattice structure. The implant 1360 can be inserted in or between bones, segments of bone or within an area carved out of a single bone to provide mechanical spacing and mechanical stability to promote bone growth. Alternatively, the implant 1060 can be inserted within or near tissue other than bone in some embodiments. The implant 1360 can be comprised substantially of three components—an upper endplate 1311, a lower endplate 1312 and a body 1313. The upper and lower endplates 1311 and 1312 can comprise a biocompatible material with a higher elastic modulus than the body 1313. The body 1313 can comprise a biocompatible material with a lower elastic modulus than the upper and lower endplates 1311 and 1312.

Figure 60:
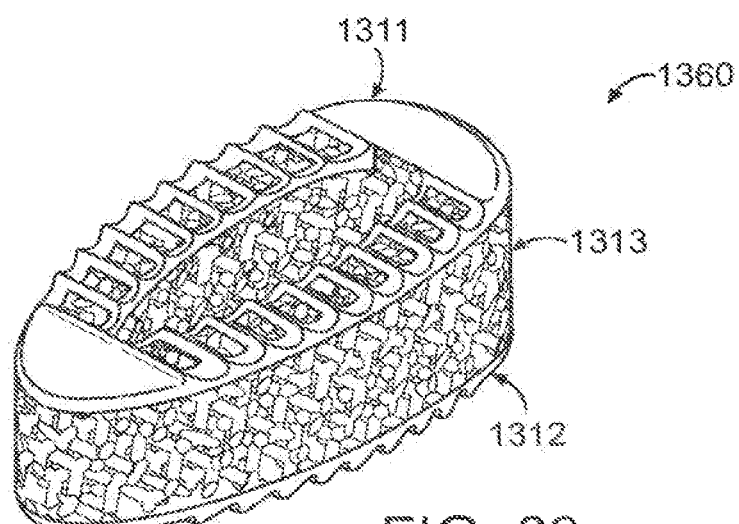
FIG. 60 is a perspective view of an example of a fourth implant 1360 designed using the high x-ray lucency lattice and methods of designing a high x-ray lucency lattice disclosed herein.

In FIG. 60 is a perspective view of the implant 1360, showing the independent configuration of the endplates 1311 and 1312 relative to the body 1313. The implant 1360 can be described as having an elongate direction and a lateral direction normal to the elongate direction. Implant 1360 includes a body 1313 comprising a square lattice optimized for dispersion in the lateral direction. In the example implant 1360, the body 1313 comprises a square lattice that that has been rotated relative to the origin position in FIG. 22. The square lattice in the body 1313 has been rotated about 45 degrees about a z-axis or an axis that is aligned with the vertical direction of the page in FIG. 22. The square lattice in the body 1313 has also been rotated about 45 degrees about an x or y-axis or an axis that is normal to the page in FIG. 22. The two about 45 degree rotations of the lattice from the origin position in implant 1360 is example and the precise amount of rotation(s) required to achieve maximum dispersion for a lattice of predetermined properties can be determined through the methods disclosed herein. The position of the lattice for maximum dispersion can depend factors, such as, the thickness of the lattice, the thickness of the struts and the size of the nodes. Depending on the anticipated implant orientation, the direction of dispersion or the direction of a desired lucency property can be adjusted and does not necessarily need to be in a lateral direction. The direction of dispersion could be, for example, to the front of the implant, to the rear of the implant or at an oblique angle. In some embodiments, the direction of dispersion is oriented towards the direction of expected x-ray imaging expected after the implant is fixed within a patient. For an implant 1360 comprising a square lattice, some embodiments will have maximum dispersion in a lateral direction when the square lattice is rotated about any two axes by about 20-70 degrees from the origin orientation in FIG. 22 and fixed in position. In some embodiments, an implant 1360 comprising a square lattice will have maximum dispersion in a lateral direction when the square lattice is rotated about any two axes by about 38-52 degrees from the origin orientation in FIG. 22 and fixed in position.

Figure 61:
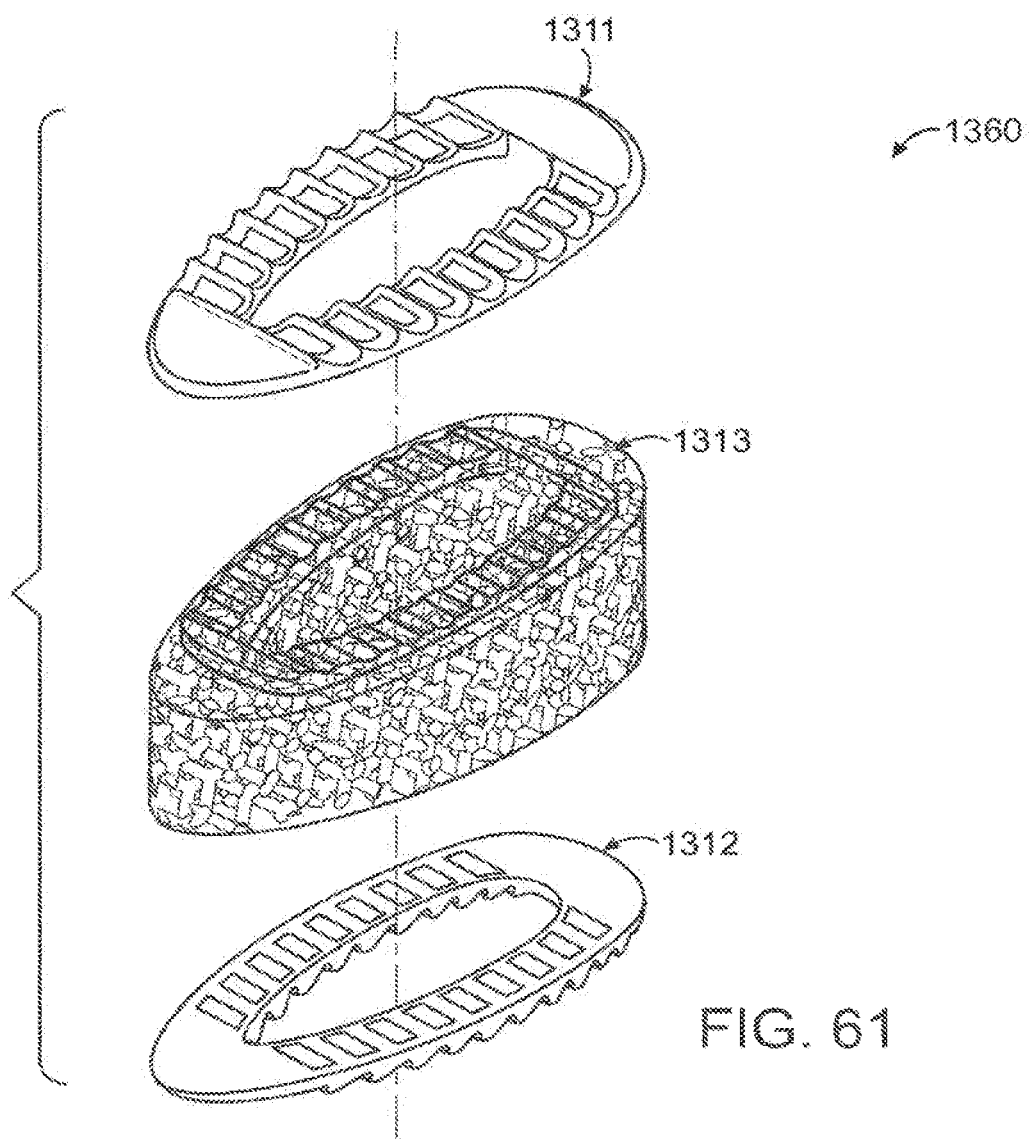
FIG. 61 is an exploded perspective view of the fourth example of an implant 1360 using high x-ray lucency lattice and methods of designing a high x-ray lucency lattice disclosed herein.
Figure 62:
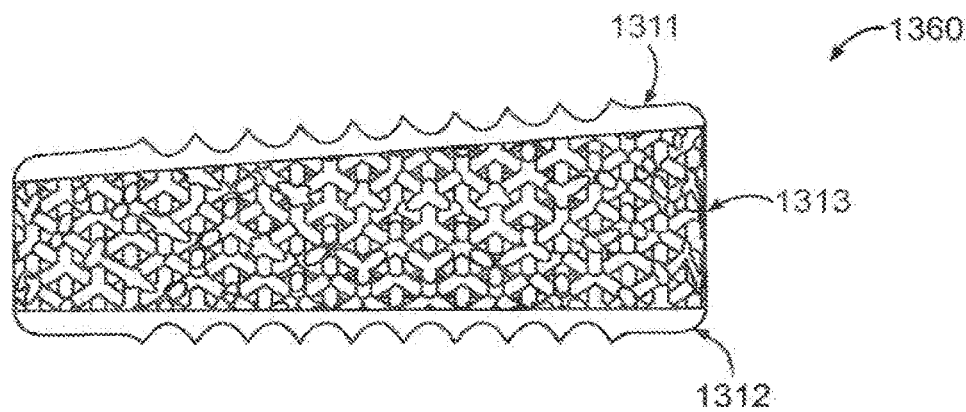
FIG. 62 is a side view of the fourth example of implant 1360 comprising a square lattice structure optimized for dispersion and configured for dispersion in a lateral or side direction.
Figure 63:
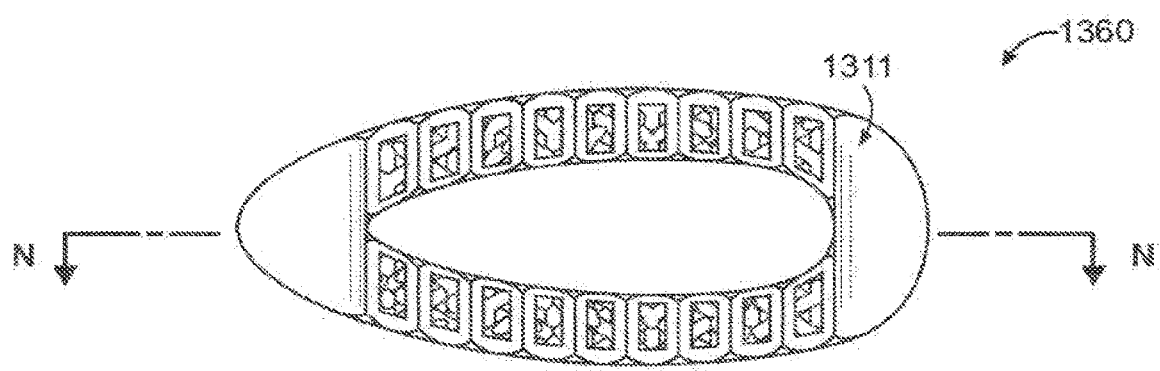
FIG. 63 is a top view of the fourth example of implant 1360 showing the section N-N used in FIG. 66.
Figure 64:
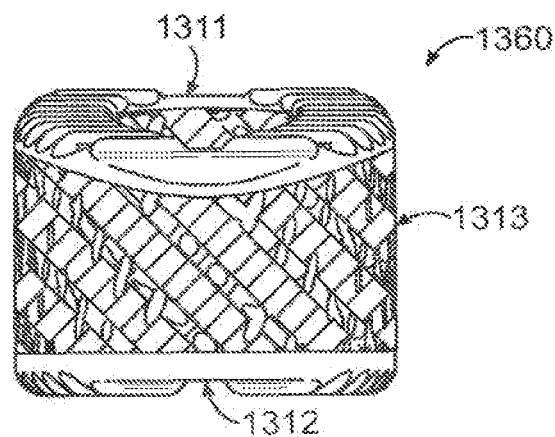
FIG. 64 is a front view of the fourth example of the implant 1360, showing the independent endplates 1311 and 1312.
Figure 65:
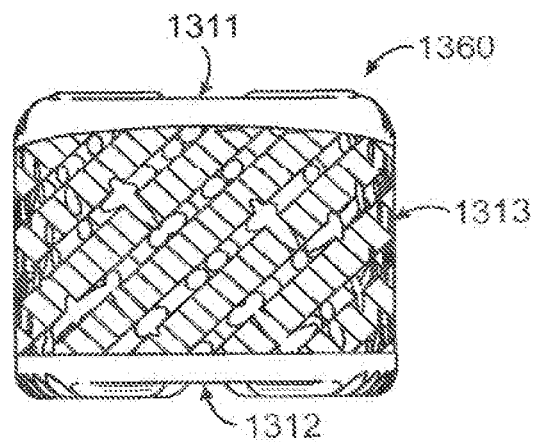
FIG. 65 is a rear view of the fourth example of the implant 1360 showing the independent endplates 1311 and 1312.

In FIG. 61 is an exploded perspective view of the implant 1360, showing the endplates 1311 and 1312 separated from the body 1313 and showing the lack of a direct and rigid connection between the endplates 1311 and 1312 in this embodiment. There may be direct connections between the endplates 1311 and 1312 to adjust the construct properties as long as the endplates 1311 and 1312 are capable of some movement relative to one another. In FIG. 62 is a side view of the implant 1360, showing the position of the endplates relative to one another and showing how body 1333 comprises a square lattice configured for dispersion in a lateral direction. In FIG. 63 is a top view of the implant 1360 showing an example endplate configuration and identifying line N-N. In FIG. 64 is a front view and in FIG. 65 is a rear view of the implant 1360.

Figure 66:
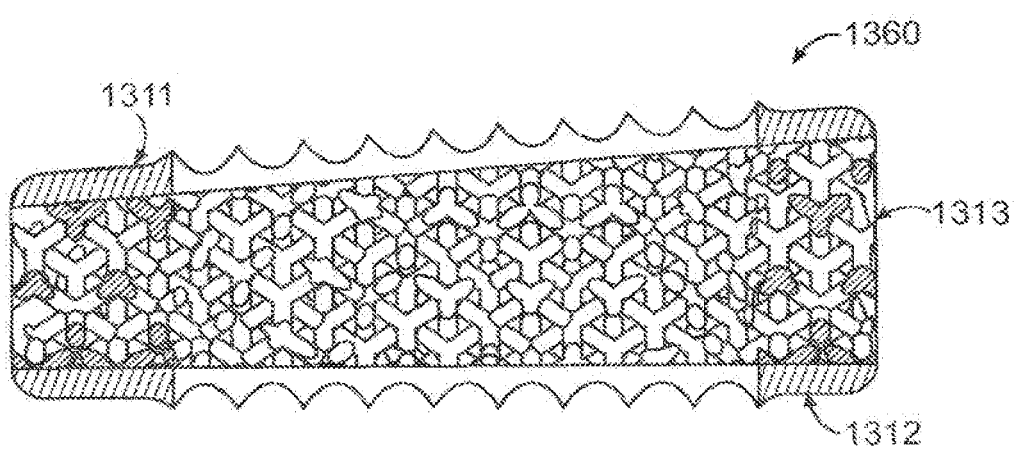
FIG. 66 is a side sectioned view of the fourth example of the implant 1360 sectioned along N-N shown in FIG. 63.

In FIG. 66 is a side sectioned view of the implant 1360, sectioned through line NN in FIG. 63 and showing that the endplates 1311 and 1312 do not directly contact one another throughout the device in this example. FIG. 66 also shows that the body 1313 of this embodiment comprises a square lattice configured for dispersion in a lateral direction.

Figure 67:
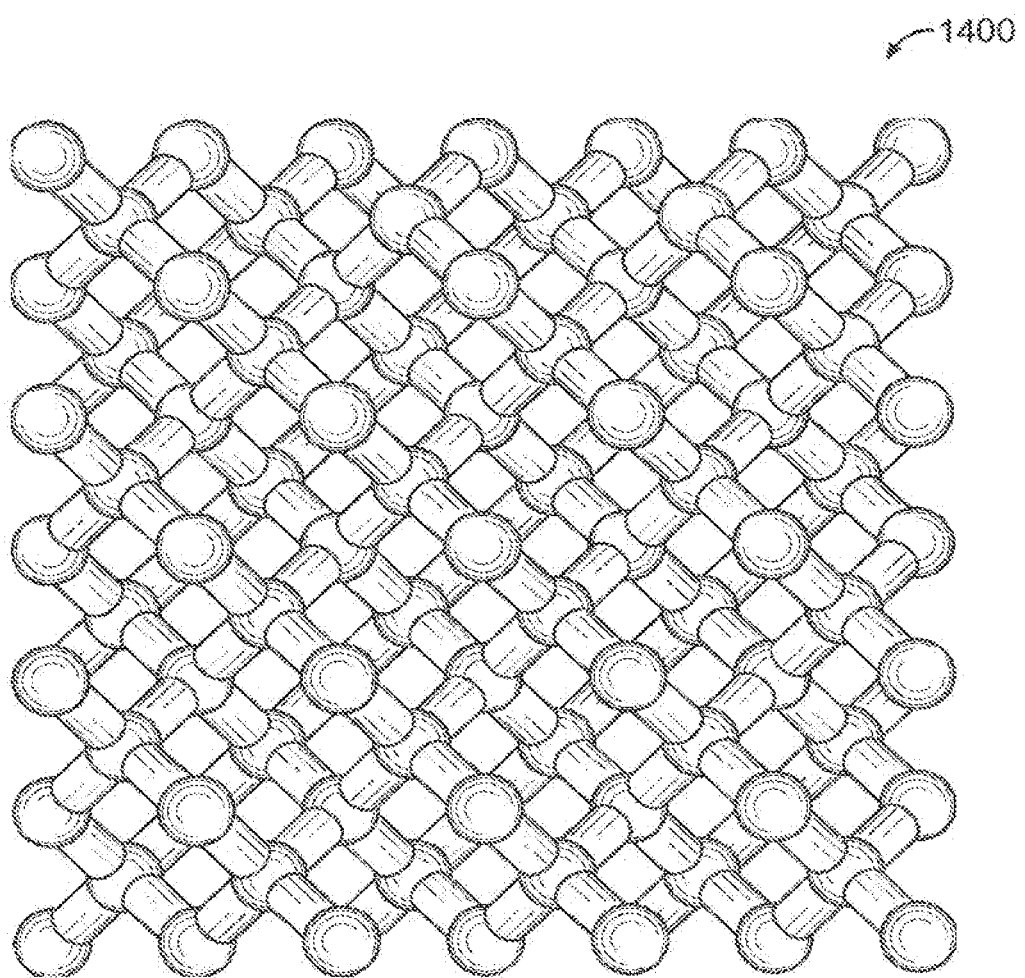
FIG. 67 is an example of a diamond lattice structure comprising struts meeting at nodes.

In FIG. 67 is a diamond lattice 1400 in a datum position used in FIGS. 68 to 74. In FIGS. 68 to 74 is an example implant 1460 including the inventive lucency optimized lattice structure. The implant 1460 can be inserted in or between bones, segments of bone or within an area carved out of a single bone to provide mechanical spacing and mechanical stability to promote bone growth. Alternatively, the implant 1060 can be inserted within or near tissue other than bone in some embodiments. The implant 1460 can be comprised substantially of three components—an upper endplate 1411, a lower endplate 1412 and a body 1413. The upper and lower endplates 1411 and 1412 can comprise a biocompatible material with a higher elastic modulus than the body 1413. The body 1413 can comprise a biocompatible material with a lower elastic modulus than the upper and lower endplates 1411 and 1412.

Figure 68:
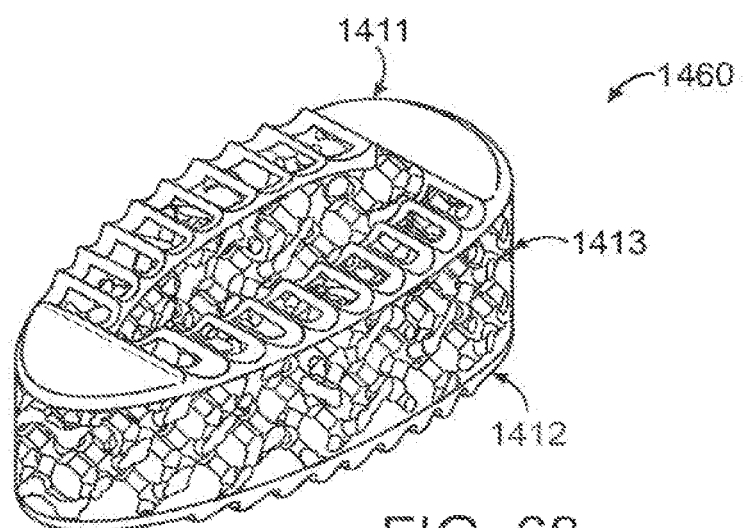
FIG. 68 is a perspective view of an example of a fifth implant 1460 designed using the high x-ray lucency lattice and methods of designing a high x-ray lucency lattice disclosed herein.

In FIG. 68 is a perspective view of the implant 1460, showing the independent configuration of the endplates 1411 and 1412 relative to the body 1413. The implant 1460 can be described as having an elongate direction and a lateral direction normal to the elongate direction. Example implant 1460 can include a body 1413 comprising a diamond lattice optimized for dispersion in the lateral direction. The diamond lattice used in the body 1413 is a diamond lattice that that has been rotated relative to the datum position in FIG. 67 by about 22.5 degrees about a z-axis or an axis that is aligned with the vertical direction of the page in FIG. 67, The 22.5 degree rotation in implant 1460 is example and the precise amount of rotation required to achieve maximum dispersion for a lattice of predetermined properties could be determined through the methods disclosed herein. The position of the lattice for maximum dispersion can depend factors, such as, the thickness of the lattice, the thickness of the struts and the size of the nodes. Depending on the anticipated implant orientation, the direction of dispersion or the direction of a desired lucency property can be adjusted and does not necessarily need to be in a lateral direction. The direction of dispersion could be, for example, to the front of the implant, to the rear of the implant or at an oblique angle. In some embodiments, the direction of dispersion is oriented towards the direction of expected x-ray imaging expected after the implant is fixed within a patient. For an implant 1460 comprising a diamond lattice 1400, some embodiments could have maximum dispersion in a lateral direction when the diamond lattice 1400 is rotated about a z-axis and fixed about 5-40 degrees from the origin orientation in FIG. 67. In some embodiments, an implant 1460 comprising a diamond lattice 1400 could have maximum dispersion in a lateral direction when the diamond lattice 1400 is rotated about a z-axis and fixed about 15-30 degrees from the origin orientation in FIG. 67.

Figure 69:
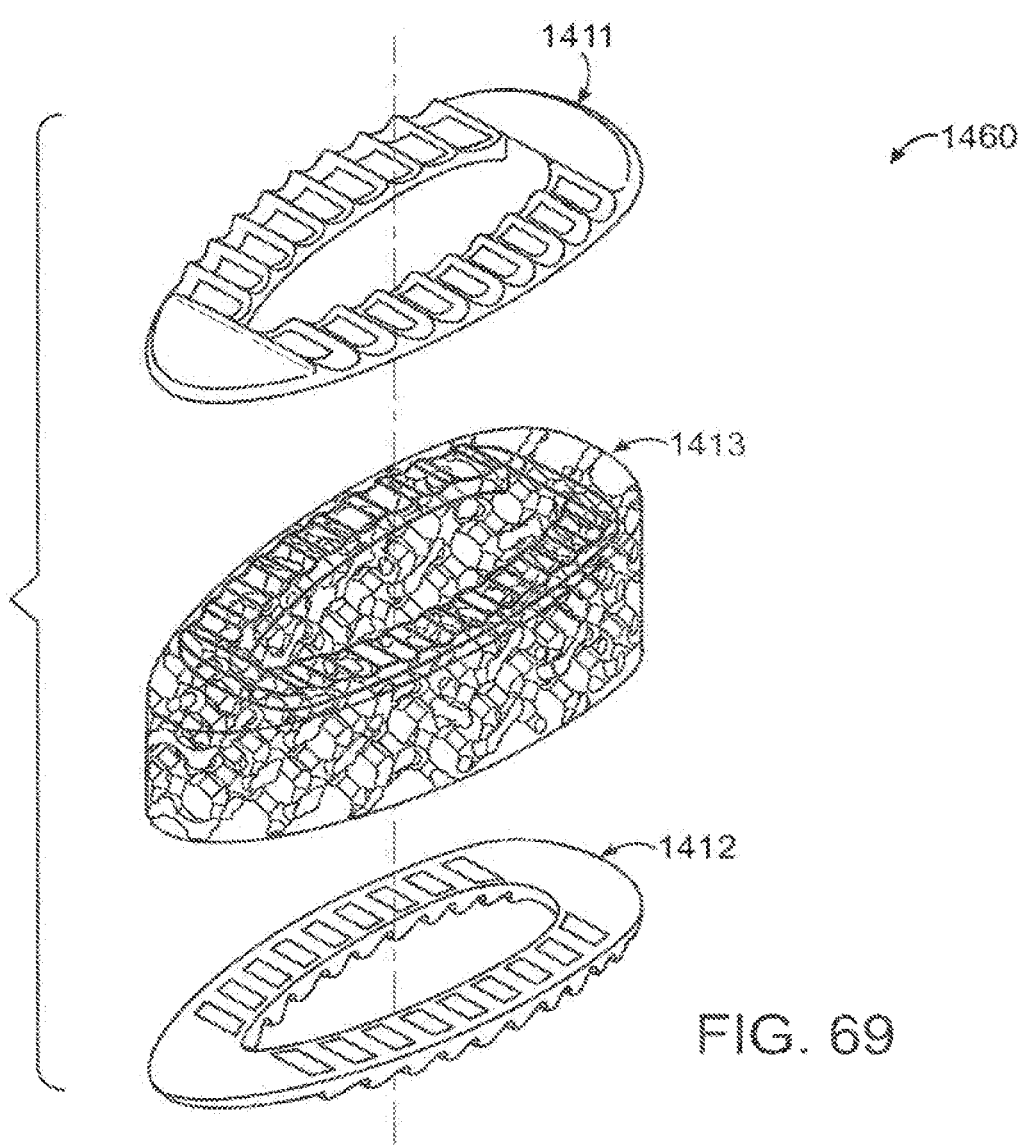
FIG. 69 is an exploded perspective view of the fifth example of an implant 1460 using high x-ray lucency lattice and methods of designing a high x-ray lucency lattice disclosed herein.
Figure 70:
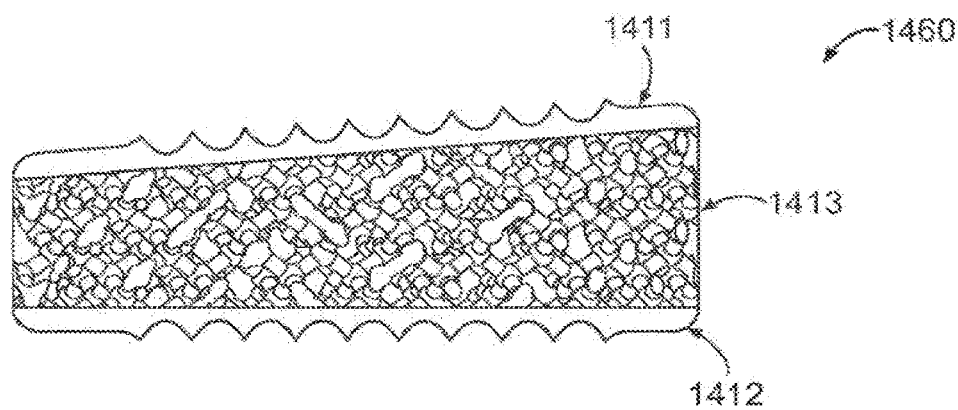
FIG. 70 is a side view of the fifth example of implant 1460 comprising a diamond lattice structure configured for dispersion in a lateral or side direction.
Figure 71:
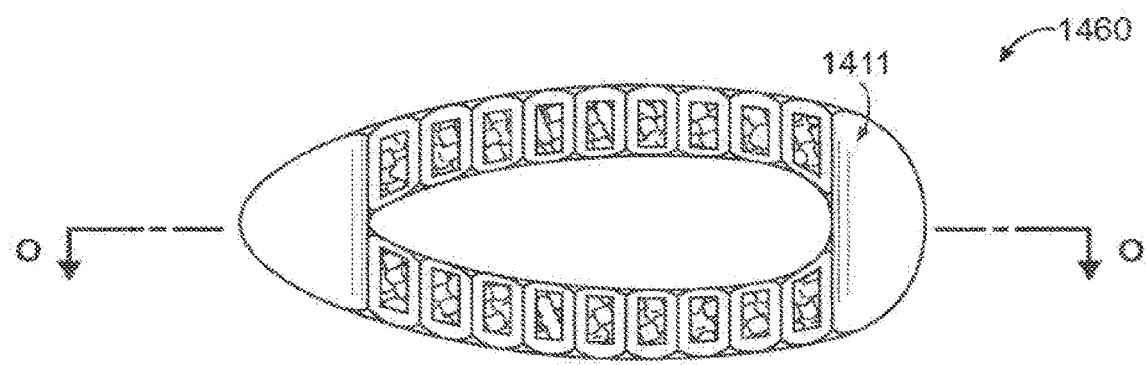
FIG. 71 is a top view of the first example of implant 1460 showing the section 0-0 used in FIG. 74.
Figure 72:
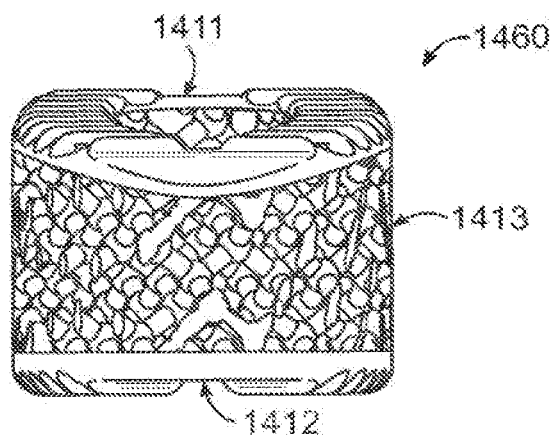
FIG. 72 is a front view of the fifth example of the implant 1460, showing the independent endplates 1411 and 1412.
Figure 73:
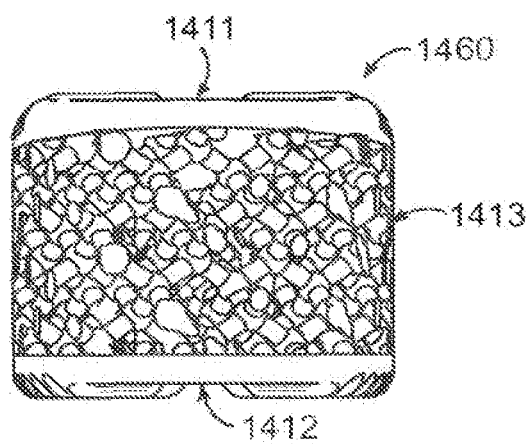
FIG. 73 is a rear view of the first example of the implant 1460 showing the independent endplates 1411 and 1412.

In FIG. 69 is an exploded perspective view of the implant 1460, showing the endplates 1411 and 1412 separated from the body 1413 and showing the lack of a direct and rigid connection between the endplates 1411 and 1412 in this embodiment. There may be direct connections between the endplates 1411 and 1412 to adjust the construct properties as long as the endplates 1411 and 1412 are capable of some movement relative to one another. In FIG. 70 is a side view of the implant 1460, showing the position of the endplates relative to one another and showing that the body 1433 comprises a diamond lattice configured for dispersion in a lateral direction. In FIG. 71 is a top view of the implant 1460 showing an example endplate configuration and identifying line 0-0. In FIG. 72 is a front view and in FIG. 73 is a rear view of the implant 1460.

Figure 74:
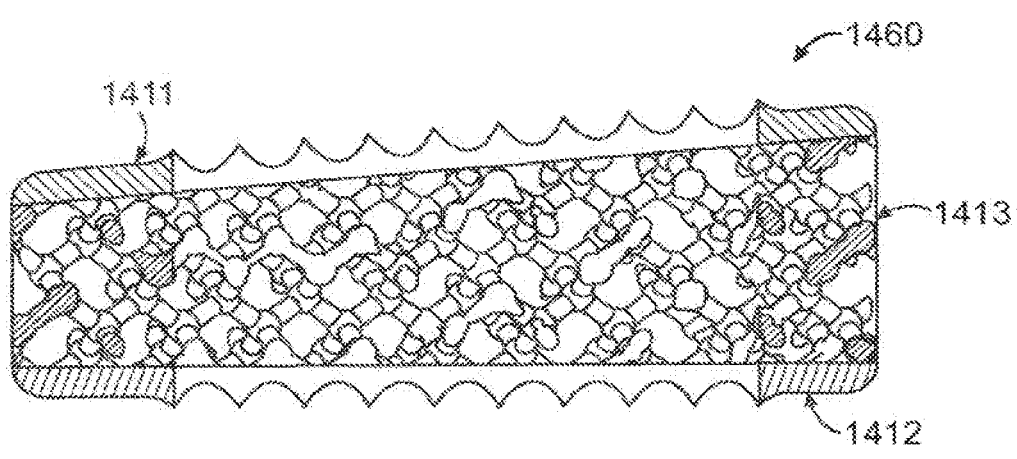
FIG. 74 is a side sectioned view of the first example of the implant 1460 sectioned along 0-0 shown in FIG. 71.

In FIG. 74 is a side sectioned view of the implant 1460, sectioned through line 00 in FIG. 71 and showing that the endplates 1411 and 1412 do not directly contact one another throughout the device in this example. FIG. 74 also shows that the body 1413 of this embodiment comprises a diamond lattice configured for dispersion in a lateral direction.

In any of the implants 1060, 1160, 1260, 1360 and 1460, the upper endplates 1011, 1111, 1211, 1311 and 1411 and respective lower endplate 1012, 1112, 1212, 1312 and 1412 are independent to one another with respect to their ability to move independently of one another. In some embodiments, the upper endplate 1011, 1111, 1211, 1311 and 1411 and respective lower endplate 1012, 1112, 1212, 1312 and 1412 are on opposite sides of their respective body 1013, 1113, 1213, 1313 and 1413 so that the endplates 1011, 1111, 1211, 1311, 1411, 1012, 1112, 1212, 1312 and 1412 can move independently of one another and where the amount of independent movement can be determined largely by the stiffness of the body 1013, 1113, 1213, 1313 and 1413. While a body is disclosed as a structure that can provide independence between endplates, other structures noted previously may provide a similar independence.

In any of the implants 1060, 1160, 1260, 1360 and 1460, the body 1013, 1113, 1213, 1313 and 1413 preferably provides mechanical spacing of the implant site and provides adequate rigidity to allow for bone or tissue ingrowth. In some examples, the endplates 1011, 1111, 1211, 1311, 1411, 1012, 1112, 1212, 1312 and 1412 use optional raised ridges or teeth to mechanically anchor the endplates 1011, 1111, 1211, 1311, 1411, 1012, 1112, 1212, 1312 and 1412 and prevent expulsion. The endplates 1011, 1111, 1211, 1311, 1411, 1012, 1112, 1212, 1312 and 1412 can allow for bone or tissue attachment or ingrowth, providing stability between the implant and the patient's bone or tissue.

In any of the implants 1060, 1160, 1260, 1360 and 1460, the upper and lower endplates 1011, 1111, 1211, 1311, 1411, 1012, 1112, 1212, 1312 and 1412 can comprise a material or lattice with a volumetric density between and including 60% and 100%. Embodiments of the device include examples where the endplates 1011, 1111, 1211, 1311, 1411, 1012, 1112, 1212, 1312 and 1412 comprise a lattice with a volumetric density between and including 80% and 100%, 60% and 90%, 70% and 90%, 60% and 64% and less than 60%. In some embodiments, the body 1013, 1113, 1213, 1313 and 1413 comprises a lattice with a volumetric density between and including 5% to 50%. Embodiments of the device include examples where the body 1013, 1113, 1213, 1313 and 1413 comprises a lattice with a volumetric density between and including 5% to 10%, 10% to 18%, 18% to 25%, 25% to 38% and 35% to 50%. In some examples, the lattice comprises a metallic scaffold. In some embodiments, the lattice comprises a scaffold comprising titanium or an alloy thereof.

In any of the implants 1060, 1160, 1260, 1360 and 1460, the upper and lower endplates 1011, 1111, 1211, 1311, 1411, 1012, 1112, 1212, 1312 and 1412 can comprise a material or lattice with an elastic modulus between and including 300 MPa to 130 GPa. Embodiments of the device include examples where the upper and lower endplates comprise a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 1013, 1113, 1213, 1313 and 1413 comprises a lattice with an elastic modulus between and including 10 MPa to 12 GPa. Embodiments of the devices include examples where the body 1013, 1113, 1213, 1313 and 1413 comprises a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 1013, 1113, 1213, 1313 and 1413 comprises a lattice with an elastic modulus that is substantially similar to the bulk elastic modulus of the adjacent bone. The body 1013, 1113, 1213, 1313 and 1413 may also have an elastic modulus gradient matching the slope to maintain constant stiffness across the length. In some examples, the lattice comprises a metallic scaffold. In others, the lattice is comprised of a scaffold comprised of titanium or an alloy thereof.

In any of the implants 1060, 1160, 1260, 1360 and 1460, the implant can be a posterior lumbar interbody fusion (hereinafter "PLIF") implant, a transforaminal lumbar interbody implant (hereinafter "TLIF"), a PLIF/TLIF implant, an anterior lumbar interbody fusion (hereinafter "ALIF") implant, a vertebral body replacement or corpectomy (hereinafter "VBR") implant, a cervical stand-alone implant, an interbody fusion implant, an osteotomy wedge, an ankle fusion spacer implant, and/or a bone fusion implant. In some embodiments, a single implant can be described as a PLIF or TLIF implant because PLIF and TLIF implants are often very similar and sometimes indistinguishable. Compared to PLIF implants, TLIF implants may be slightly longer (front to back) and may have a curve in a lateral direction. PLIF implants are generally implanted from a straight posterior approach, where TLIF implants are generally implanted from an angle between the posterior direction and a lateral direction. Both PLIF and TLIF implants may have lordosis. Therefore, an implant described primarily as a PLIF implant could also be used in a TLIF procedure without change or with common features in some TLIF implants added. In some embodiments, the implant 1060, 1160, 1260, 1360 and 1460 is configured for tissue attachment, tissue including but not limited to bony structures and connective tissue. In some embodiments, the implant 1060, 1160, 1260, 1360 and 1460 is configured to allow tissue in-growth, tissue including but not limited to bony structures and connective tissue.

In some embodiments of the implants with independent endplates disclosed herein, a first endplate is mechanically connected to a second endplate substantially via a body, where the body is disposed at least partially between the first and second endplates.

In some embodiments, substantially via the body refers to a connection where the body has an elastic modulus that is at least 50 percent of a construct elastic modulus. In some embodiments, substantially via the body refers to a connection where the body has an elastic modulus that is at least 90 percent of a construct elastic modulus. In some embodiments, the implant is configured to fuse multiple levels of the spine. In some embodiments, the implant is configured to fuse adjacent levels of the spine. In some embodiments, the implant is configured to fuse non-adjacent levels of the spine. In some embodiments, an endplate on the implant is configured to contact a bony structure. In some embodiments, an endplate on the implant is configured to contact tissue. In some embodiments, two endplates on the implant are configured to contact bony structures. In some embodiments, one endplate on the implant is configured to contact a bony structure and another endplate is configured to contact tissue. In some embodiments, two endplates on the implant are configured to contact tissue. In some embodiments, tissue is a connective tissue.

The variable markers disclosed herein would be beneficial if used in an image guided or robotic surgery. The variable markers disclosed herein can be configured so that the predetermined viewing direction comprises a direction of anticipated viewing during implantation. Image guided surgery includes surgical procedures where a surgeon uses a navigation system to monitor or track the location of a patient's anatomy, the implant and/or surgical tools. Robotic surgery includes surgical procedures where a surgeon uses a remotely controlled instrument to conduct a surgery. During image guided or robotic surgery, a surgeon's view can be augmented using additional real-time imaging.

The medical implants disclosed herein include a medical implant, comprising a porous structure disposed within an implant volume, the porous volume comprising a repeating unit cell defined by a plurality of struts and nodes, and wherein the porous volume is configured and fixed within the implant volume to minimize the overlap of struts and nodes in a predetermined viewing direction. The medical implants disclosed herein include a medical implant, comprising a porous structure disposed within an implant volume, the porous volume comprising a repeating unit cell defined by a plurality of struts and nodes, and wherein the porous volume is configured and fixed within the implant volume to maximize the overlap of struts and nodes in a predetermined viewing direction. The predetermined viewing direction can comprise a direction relative to the implant volume and/or a direction of anticipated x-ray viewing after implantation. The porous volume can comprise a lattice structure. The repeating unit cell that forms a lattice structure can comprise at least one of radial dodeca-rhombus, rhombic dodecahedron, modified rhombic dodecahedron, diamond, dodecahedron, square, pentagonal, hexagonal, octagonal, sctet struts, trunic octa, diagonal struts, reinforced and weakened versions of each of said geometries.

The repeating unit cell can be elongated in a direction normal to a direction comprising at least one of an anticipated direction of new bone growth and an expected direction of physiological loading. The medical implants can further comprise: a body comprising a metallic lattice structure; and a first endplate spaced apart from a second endplate, the first endplate being mechanically connected to the second endplate only via the body; wherein: said first endplate comprises an upper surface for contacting a first segment of bone and a lower surface fixed to said body; said second endplate comprises a lower surface for contacting a second segment of bone and an upper surface fixed to said body; wherein an elastic modulus of each of the first endplate and second endplate is higher than an elastic modulus of the body; wherein the body is disposed at least partially between the first and second endplates; and each of said first and second endplates comprises a metal. In some embodiments, the struts and/or nodes further comprise internal voids. In some embodiments, the struts further comprise a structure comprising at least one of a U-channel, an I-beam and an H-beam.

The medical implants disclosed herein can comprise: a first metallic volume and a second metallic volume, the first and second volume being coupled to the porous structure; a predetermined x-ray viewing direction; and wherein the first volume is positioned within the porous structure to at least partially overlay the second volume when the medical implant is viewed in the predetermined x-ray viewing direction. The first volume can comprise at least one of an enlarged strut, an enlarged node and a filled unit cell. The first marker can comprise a volumetric density of about 100 percent. The first volume can comprise a volumetric density of less than 100 percent. The first volume can comprise a volumetric density of between and including 0 percent to 30 percent.

The medical implants disclosed herein can comprise: a first void coupled to the porous structure; an average baseline lucency comprising the average lucency across the porous structure; wherein the first void provides a localized difference in lucency that deviates from the average baseline lucency by at least 4 percent when in an aligned direction. In some embodiments, the predetermined viewing direction further comprises a direction of anticipated viewing during implantation. In some embodiments, implantation is an image guided surgery and/or a robotic surgery.

What has been described is a biocompatible lattice with high x-ray lucency, a method of designing a lattice with high x-ray lucency, variable markers for use in medical implants with at least a degree of radiolucency, a method of designing variable markers for use in medical implants with at least a degree of radiolucency and a method of using variable markers in medical implants with a degree of radiolucency. In this disclosure, there are shown and described only example embodiments of the invention, but, as aforementioned, it is to be understood that the invention is capable of use in various other combinations and environments and is capable of changes or modifications within the scope of the inventive concept as expressed herein.

In some aspects, the systems and methods described herein can be directed toward implants that are configured for osteointegration and stimulating adequately stressed new bone growth. Many of the exemplary implants of the present invention are particularly useful for use in situations where it is desirable to have strong bone attachment and/or bone growth throughout the body of an implant. Whether bone growth is desired only for attachment or throughout an implant, the present invention incorporates a unique lattice structure that can provide mechanical spacing, a scaffold to support new bone growth and a modulus of elasticity that allows new bone growth to be loaded with physiological forces. As a result, the present invention provides implants that grow stronger and healthier bone for more secure attachment and for a stronger bone after the implant osteointegrates.

The exemplary embodiments of the invention presented can be comprised, in whole or in part, of a lattice. A lattice, as used herein, refers to a three-dimensional material with one or more interconnected openings that allow a fluid to communicate from one opening to another location. A three-dimensional material refers to a material that fills a three-dimensional space (i.e. has height, width and length). Lattices can be constructed by many means, including repeating various geometric shapes or repeating random shapes to accomplish a material with interconnected openings. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two openings together. Interconnections may be configured to allow a fluid to pass from one opening to another.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can be comprise the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 70% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprised of repeating geometric patterns can be described using the characteristics of a repeating unit cell. A unit cell in a repeating geometric lattice is a three-dimensional shape capable of being repeated to form a lattice. A repeating unit cell can refer to multiple identical unit cells that are repeated over a lattice structure or a pattern through all or a portion of a lattice structure. Each unit cell is comprised of a certain volume of primary material and a certain void volume, or in other words, a spot volumetric density. The spot volumetric density may cover as few as a partial unit cell or a plurality of unit cells. In many situations, the spot volumetric density will be consistent with the material's volumetric density, but there are situations where it could be desirable to locally increase or decrease the spot volumetric density. Unit cells can be constructed in numerous volumetric shapes containing various types of structures. Unit cells can be bound by a defined volume of space to constrict the size of the lattice structure or other type of structure within the unit cell. In some embodiments, unit cells can be bound by volumetric shapes, including but not limited to, a cubic volume, a cuboid volume, a hexahedron volume or an amorphous volume. The unit cell volume of space can be defined based on a number of faces that meet at corners. In examples where the unit cell volume is a cubic, cuboid or hexahedron volume, the unit cell volume can have six faces and eight corners, where the corners are defined by the location where three faces meet. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node. Such unit cells may be identical or substantially unique throughout a structure, and may be grouped into clusters, layers, or other configurations throughout a structure.

While the present application uses volumetric density to describe exemplary embodiments, it would also be possible to describe them using other metrics, including but not limited to cell size, strut size or stiffness. Cell size may be defined using multiple methods, including but not limited to cell diameter, cell width, cell height and cell volume. Strut size may be defined using multiple methods, including but not limited to strut length and strut diameter.

Repeating geometric patterns are beneficial for use in lattices contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications are referred to herein as structural lattices, load-bearing lattices or stressed lattices. In some instances, structural lattices, load-bearing lattices or stressed lattices may be simply referred to as a lattice. Repeating geometric shaped unit cells, particularly the rhombic dodecahedron, are well suited, in theory, for use in structural lattices because of their strength to weight ratio. To increase the actual strength and fatigue resistance of a rhombic dodecahedron lattice, the present invention, in some embodiments, includes a modified strut comprised of triangular segments, rather than using a strut with a rectangular or circular cross section. Some embodiments herein also modify the angles defining the rhombic faces of a rhombic dodecahedron to change the lattice's elastic modulus and fatigue resistance. The use of triangular segments provides a lattice with highly predictable printed properties that approach the theoretical strength values for a rhombic dodecahedron lattice. In structural lattice applications, the strength and elastic modulus of the lattice can be approximated by the volumetric density. When the volumetric density increases, the strength and the elastic modulus increases. Compared to other porous structures, the lattice of the present invention has a higher strength and elastic modulus for a given volumetric density because of its ability to use the high strength to weight benefits of a rhombic dodecahedron, modified rhombic dodecahedron or radial dodeca-rhombus unit cell.

The term "elastic modulus," as used herein, can refer to either the elastic modulus of a material or the effective elastic modulus of a volume of material. An elastic modulus quantifies a material or volume of material's resistance to elastic deformation in response to a stress. A volume of material can have an elastic modulus of the material itself and an effective elastic modulus of the entire volume of material. An effective elastic modulus can be determined by compressing the volume of material and treating it as a homogenous material for the purposes of calculating the effective elastic modulus. When the term "elastic modulus" is used herein, it can refer to both or either of the elastic modulus of a material or the effective elastic modulus of a volume of material.

When configured to provide support for bone or tissue growth, a lattice can be referred to as a scaffold. Lattices can be configured to support bone or tissue growth by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support ingrowth beyond mere surface attachment are referred to herein as bulk scaffolds. Scaffolds may also be included in implants as a structural component or a nonstructural component. Scaffolds used in structural applications may be referred to herein as structural scaffolds, load-bearing scaffolds or stressed scaffolds. In some instances, structural scaffolds, load-bearing scaffolds or stressed scaffolds may be simply referred to as a scaffold. In some instances, the use of the term scaffold may refer to a material configured to provide support for bone or tissue growth, where the material is not a lattice.

The scaffolds described herein can be used to promote the attachment or in-growth of various types of tissue found in living beings. As noted earlier, some embodiments of the scaffold are configured to promote bone attachment and in-growth. The scaffolds can also be configured to promote attachment of in-growth of other areas of tissue, such as fibrous tissue. In some embodiments, the scaffold can be configured to promote the attachment or in-growth of multiple types of tissue. Some embodiments of the scaffolds are configured to be implanted near or abutting living tissue. Near living tissue includes situations where other layers, materials or coatings are located between a scaffold and any living tissue.

In some embodiments, the present invention uses bulk scaffolds with openings and interconnections that are larger than those known in the art. Osteons can range in diameter from about 100 µm and it is theorized that a bundle of osteons would provide the strongest form of new bone growth. Bone is considered fully solid when it has a diameter of greater than 3 mm so it is theorized that a bundle of osteons with a diameter equaling approximately half of that value would provide significant strength when grown within a scaffold. It is also theorized that osteons may grow in irregular shapes so that the cross-sectional area of an osteon could predict its strength. A cylindrical osteon growth with a 3 mm diameter has a cross-sectional area of approximately 7 square mm and a cylindrical osteon with a 1.5 mm diameter has a cross-sectional area of 1.8 square mm. It is theorized that an osteon of an irregular shape with a cross-sectional area of at least 1.8 square millimeters could provide a significant strength advantage when grown in a scaffold.

Most skilled in the art would indicate that pores or openings with a diameter or width between 300 μm to 900 μm, with a pore side of 600 μm being ideal, provide the best scaffold for bone growth. Instead, some embodiments of the present invention include openings and interconnections with a diameter or width on the order of 1.0 to 15.0 times the known range, with the known range being 300 μm to 900 μm, resulting in openings from 0.07 mm² up to 145 mm² cross sectional area for bone growth. In some examples, pores or openings with a diameter or width between and including 100 μm to 300 μm could be beneficial. Some examples include openings and interconnections with a diameter on the order of 1.0 to 5.0 times the known range. It has been at least theorized that the use of much larger openings and interconnections than those known in the art will allow full osteons and solid bone tissue to form throughout the bulk scaffold, allowing the vascularization of new, loadable bone growth. In some examples, these pores may be 3 mm in diameter or approximately 7 mm² in cross sectional area. In other examples, the pores are approximately 1.5 mm in diameter or approximately 1.75 mm² in cross sectional area. The use of only the smaller diameter openings and interconnections known in the art are theorized to limit the penetration of new bone growth into a bulk scaffold because the smaller diameter openings restrict the ability of vascularization throughout the bulk scaffold.

A related structure to a lattice is a closed cell material. A closed cell material is similar to a lattice, in that it has openings contained within the bounds of a three-dimensional material, however, closed cell materials generally lack interconnections between locations through openings or other pores. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present invention can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing and directed energy deposition. The material used in the body of the device may be different from that which is used in the endplates.

In another example, the lattice of the present invention is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6Al4V ELI wrought (American Society for Testing and Materials ("ASTM") F136) is a particularly well-suited titanium alloy for scaffolds. While Ti6Al4V ELI wrought is the industry standard titanium alloy used for medical purposes, other titanium alloys, including but not limited to, unalloyed titanium (ASTM F67), Ti6Al4V standard grade (ASTM F1472), Ti6Al7Nb wrought (ASTM 1295), Ti5Al2.5Fe wrought (British Standards Association/International Standard Organization Part 10), CP and Ti6Al4V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be appropriate for various embodiments of the present invention.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, RBM texturing, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating rhombic dodecahedron (hereinafter "RDD") unit cell can present a preferable combination of stiffness, strength, fatigue resistance, and conditions for bone ingrowth. In some embodiments, the repeating RDD lattice is comprised of titanium or a titanium alloy. Some embodiments include a repeating RDD unit cell with comprised of 24 struts that meet in 14 vertices, where the 24 struts define the 12 planar faces of the structure, where each face is an identical rhombus with an acute angle of 70.5 degrees and an obtuse angle of 109.5 degrees and disposed at the center of each planar face is an opening, or interconnection, allowing communication from inside the unit cell to outside the unit cell. At the center of some RDD unit cells is a generally spherical opening, the central void. Therefore, each RDD unit cell can have a central void and 12 interconnections to an area outside of the unit cell. When placed towards the center of a lattice structure, the 12 interconnections of an RDD unit cell can connect to 12 different adjacent unit cells, providing a continuous path through the lattice.

In some embodiments, the unit cell can be elongated in one or more directions to provide a lattice with anisotropic properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

Figure 75:
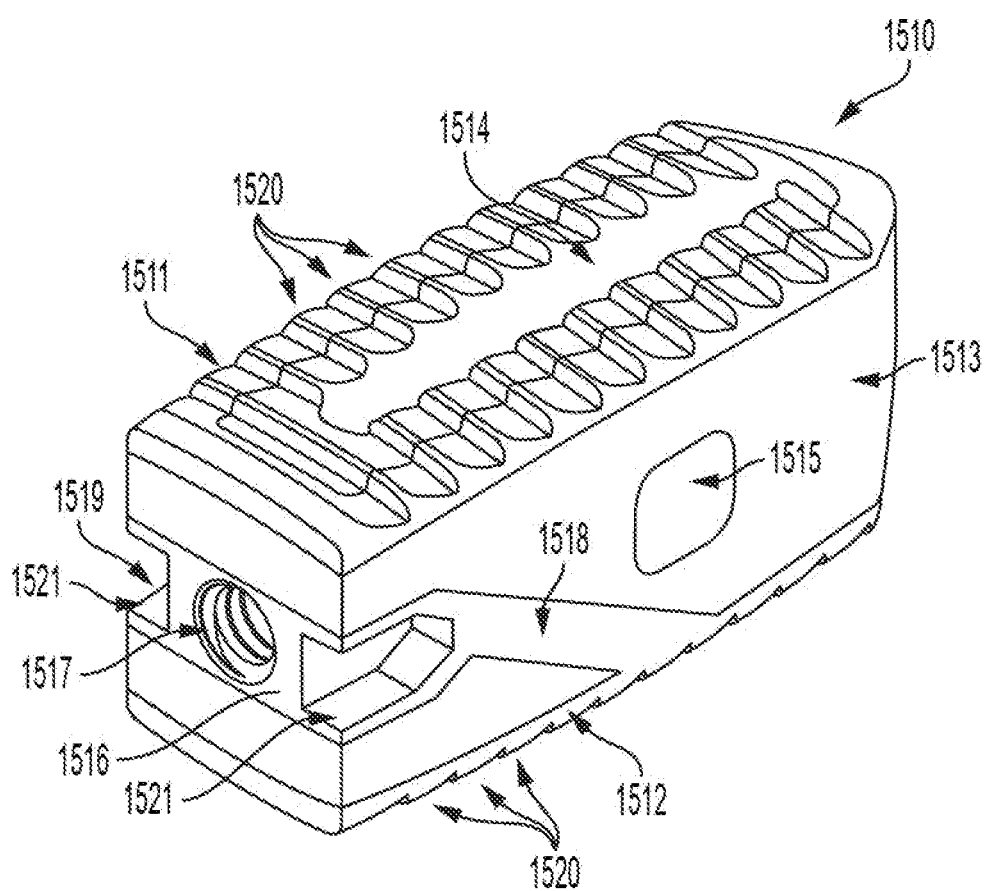
FIG. 75 is an isometric view of a first implant showing the inventive configuration of the endplates relative to the body on the exterior of the device.

In FIG. 75 is an isometric view of a first exemplary embodiment of a first implant 1510 with an independent endplate structure. In some embodiments, the implant 1510 can be inserted between the endplates of two adjacent vertebrae, providing mechanical spacing between the endplates of the adjacent vertebrae and mechanical stability to promote bone growth, allowing the vertebrae to fuse together over time.

In some embodiments, the implant 1510 can be a posterior lumbar interbody fusion (hereinafter "PLIF") implant or transforaminal lumbar interbody implant (hereinafter "TLIF"). A single implant can be described as a PLIF or TLIF implant because PLIF and TLIF implants are often very similar and sometimes indistinguishable. Compared to PLIF implants, TLIF implants may be slightly longer (front to back) and may have a curve in a lateral direction. PLIF implants are generally implanted from a straight posterior approach, where TLIF implants are generally implanted from an angle between the posterior direction and a lateral direction. Both PLIF and TLIF implants may have lordosis. Therefore, an implant described primarily as a PLIF implant could also be used in a TLIF procedure without change or with common features in some TLIF implants added.

The first implant 1510 can be comprised substantially of three components—an upper endplate 1511, a lower endplate 1512 and a body 1513. The upper and lower endplates 1511 and 1512 can be comprised of a biocompatible material with a higher elastic modulus in the superior to inferior direction than the body 1513. The body 1513 can be comprised of a biocompatible material with a lower elastic modulus in the superior to inferior direction than the upper and lower endplates 1511 and 1512.

The upper endplate 1511 and lower endplate 1512 are independent to one another with respect to their ability to move independently of one another. Independent, as used herein, refers to the ability of surfaces or volumes to move relative to another rather than refer to the lack of a physical connection. For instance, by attaching the upper endplate 1511 and lower endplate 1512 on opposite sides of a body 1513, the endplates 1511 & 1512 can move independently of one another where the amount of independent movement can be determined largely by the elastic modulus of the body 1513. While a body is disclosed as a structure that can provide independence between endplates, other structures may provide a similar independence. Other structures include, but are not limited to, a spring member between the endplates or any other mechanism that provides a different elastic modulus than the endplates themselves. In some embodiment, the endplates 1511 & 1512 are connected substantially only via the body 1513. In some embodiments, the endplates 1511 & 1512 are connected substantially only via a connecting structure taking the function of the body 1513. As used herein, a connection "substantially via" an element refers to a structure where the element providing the connection provides at least 50% of a construct elastic modulus in a direction from one endplate to another. In some embodiments, the endplates 1511 & 1512 are connected substantially only via the body 1513, where the body 1513 provides at least 50% of a construct elastic modulus in a direction from one endplate to another. In some embodiments, the endplates 1511 & 1512 are connected substantially only via the body 1513, where the body 1513 provides at least 75% of a construct elastic modulus in a direction from one endplate to another. In some embodiments, the endplates 1511 & 1512 are connected substantially only via the body 1513, where the body 1513 provides at least 90% of a construct elastic modulus in a direction from one endplate to another.

The body 1513 preferably provides mechanical spacing between the adjacent bony structures or vertebrae and provides adequate rigidity between them to allow for bone ingrowth. The use of a body 1513 with a lower elastic modulus than the endplates 1511 and 1512 can allow the new bone growth to be stressed while ingrowth occurs, resulting in a stronger fused bone. The relatively higher stiffness of the endplates 1511 and 1512 distributes the load across the surface of the less stiff body 1513 and reduces the occurrence of the bony structures or vertebral endplates from indenting the upper or lower surface of the body 1513. In some examples, the endplates 1511 and 1512 use optional raised ridges or teeth 1520 to mechanically anchor the endplates 1511 and 1512 to bony structures or the endplates of the adjacent vertebrae. The ridges 1520 extend from the endplates 1511 and 1512 to the surface of the body 1513 that extends to the superior and inferior surface of the device. In addition to distributing the load across the body 1513 and anchoring the interbody fusion device 1510 relative to the adjacent bony structures or vertebrae, the endplates 1511 and 1512 can allow for bone attachment, providing stability between the interbody fusion device and the endplates of the adjacent vertebrae.

The implant 1510 also provides an optional lumen 1514 as a vertical bone fusion window and an optional viewing window 1515 for radiolucency or bone fusion. The fusion or viewing windows can be used by clinicians to insert one or more compounds that promote bone growth or to assess fusion through the lumen 1514 during the healing process. Some compounds that would be appropriate for use in the fusion or viewing windows 1514 and 1515 are autograft, allograft synthetic graft, or a combination.

The lower endplate 1512 of the implant 1510 can include a tool engagement area 1516 to allow surgical tools to be fastened to the device 1510 during a surgical procedure. In some examples, the tool engagement area 1516 contains a threaded opening 1517 that is configured to accept a threaded rod to facilitate placement of the device 1510. On either side of the threaded opening 1517 can be a void 1521 designed to accommodate stabilizers on the threaded rod, if used. While the threaded opening 1517 can provide an adequate amount of leverage to locate the device 1510, the addition of two stabilizers on an installation instrument that contact the device 1510 in the voids 1521 can increase the ability of a surgeon to rotate the device during insertion. The tool engagement area 1516 can be connected to the lower endplate 1512 by a right connection arm 1518 and left connection arm 1519. In one example, the tool engagement area 1516, right connection arm 1518, left connection arm 1519 and lower endplate 1512 are comprised of a single piece of material. It is appreciated that various configurations could be used to accomplish the same ends. In some embodiments, the tool engagement area 1516 is not attached directly to either the upper endplate 1511 or lower endplate 1512. In some embodiments, the tool engagement area 1516 is attached to the upper endplate 1511.

The upper and lower endplates 1511 and 1512 can be made of a biocompatible material that allows for bone attachment, either to the material directly or through the application of a bioactive surface treatment. In one embodiment, the upper and lower endplates 1511 and 1512 are made of an implantable metal. In another example, the upper and lower endplates 1511 and 1512 are made from titanium or an alloy thereof, providing strength to the endplates, with an optional bioactive coating. In another example, the upper and lower endplates 1511 and 1512 are made from commercially pure titanium, providing strength to the endplates, with an optional bioactive coating.

It is also contemplated that the upper and lower endplates 1511 & 1512 may be comprised of a lattice or scaffold structure to allow for bone ingrowth, while maintaining the ability of the endplates to sustain high point loads. If the upper and/or lower endplates 1511 & 1512 are comprised of a lattice or scaffold structure, they may be defined by their volumetric density. The volumetric density of an upper or lower endplate 1511 & 1512 is based on the volume of the endplate itself, not including the volume of the lumen within the endplate. In some embodiments, the upper and lower endplates 1511 & 1512 area material or lattice comprising titanium or any alloys thereof with a volumetric density between and including 60% and 100%. In one example, the upper and lower endplates 1511 and 1512 are a material or lattice comprising titanium or any alloys thereof with a volumetric density between and including 80% and 100%. In another example, the endplates 1511 & 1512 area material or lattice comprising titanium or any alloys thereof with a volumetric density between and including 70% and 90%. In another example, the endplates 1511 & 1152 are a material or lattice comprising titanium or any alloys thereof with a volumetric density between and including 60% and 90%. In another example, the endplates 1511 & 1512 are a material or a lattice comprising titanium or any alloys thereof with a volumetric density between and including 60% and 64%. In some embodiments, the endplates 1511 & 1512 are a material or lattice comprising titanium or any alloys thereof with a volumetric density of less than 60%.

The volumetric density and/or material chosen for the endplates 1511 & 1512 can be varied to achieve an endplate with an elastic modulus that is indexed to the elastic modulus of the body. In some embodiments, the elastic modulus of the endplates is selected based on the stiffness of the adjacent bone. In most patients, cortical bone has an elastic modulus between and including 15.2 to 20.7 GPa. When selecting an elastic modulus for the endplates 1511 & 1512, a patient's actual cortical bone elastic modulus may be used or an approximation based on the patient's age and medical history may be used. In some embodiments, the elastic modulus of the endplates 1511 & 1512 can be less than the elastic modulus of the patient's cortical layer of bone. In certain surgical procedures, portions of a patient's cortical bone at the implant site may be removed, making it beneficial to reduce the elastic modulus of the endplates 1511 & 1512 below that of cancellous bone. In some embodiments, it may be desirable for the endplates to have an elastic modulus that is less than that of the patient's cancellous bone.

In some embodiments, the upper and lower endplates 1511 & 1512 are comprised of a material or a lattice with an elastic modulus between and including 10 MPa to 130 GPa. Embodiments of the device include examples where the upper and lower endplates are comprised of a material or lattice with an elastic modulus between and including 10 MPa to 5 GPa, 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some examples, the lattice is comprised of a metallic scaffold. In others, the lattice is comprised of a scaffold comprising titanium or any alloys thereof. In this embodiment and others, the use of endplates or a body with a lower modulus of elasticity, within the ranges given, could be beneficial for use in patients with poor bone quality or who are osteoperotic.

In some embodiments, the upper endplate 1511 and lower endplate 1512 are comprised of the same material and possess the same volumetric density and lattice structure (if any). In other embodiments, the upper endplate 1511 and lower endplate 1512 are comprised of different materials, volumetric density and/or lattice structure. It could be desirable for the upper endplate 1511 and lower endplate 1512 to have different physical properties when the strength and composition of the adjacent bone is different near their respective endplate.

In one example, the body 1513 is comprised of an implantable material that provides a scaffold for bone growth. In another example, the body 1513 is comprised of titanium or any alloys thereof, with an optional bioactive coating. In another example, the body 1513 is made from commercially pure titanium, with an optional bioactive coating. The body 1513 is preferably comprised of a structural lattice to provide mechanical separation between the endplates 1511 & 1512. The body 1513 is more preferably comprised of a repeating RDD structural scaffold comprised of titanium or any alloys thereof with a volumetric density between and including 5% to 50%. In some embodiments, the body 1513 is comprised of a repeating RDD structural scaffold comprised of titanium or any alloys thereof with a volumetric density between and including 5% to 10%. In some embodiments with a body with a lower modulus of elasticity, the body 1513 is comprised of a repeating RDD structural scaffold comprised of titanium or any alloys thereof with a volumetric density between and including 10% to 18%. In some embodiments, the body 1513 is comprised of a repeating RDD structural scaffold comprised of titanium or any alloys thereof with a volumetric density between and including 18% to 25%. In some embodiments, the body 1513 is comprised of a repeating RDD structural scaffold comprised of titanium or any alloys thereof with a volumetric density between and including 25% to 38%. In some embodiments, the body 1513 is comprised of a repeating RDD structural scaffold comprised of titanium or any alloys thereof with a volumetric density between and including 35% to 50%. In some embodiments, the body 1513 is comprised of a repeating RDD structural scaffold comprised of titanium or any alloys thereof with a volumetric density between and including 32% to 38%. The preferred volumetric density ranges disclosed are directed towards a body 1513 constructed from a repeating RDD structural scaffold comprised of titanium or any alloys thereof and can be adjusted within the scope of the inventive concept to suit a different material or different lattice structure.

In one example, the body 1513 is comprised of a lattice comprised of titanium or any alloys thereof with an elastic modulus in the superior to inferior direction of between and including 8 to 12 GPa. In another example, the body 1513 is comprised of a lattice comprising titanium or any alloys thereof with an elastic modulus in the superior to inferior direction of between and including 1 to 5 GPa. In another example, the body 1513 is comprised of a lattice comprising titanium or any alloys thereof with an elastic modulus in the superior to inferior direction of between and including 2 to 4 GPa. In another example, the body 1513 is comprised of a lattice comprising titanium or any alloys thereof with an elastic modulus in the superior to inferior direction of between and including 3 to 9 GPa. In another example, the body 1513 is comprised of a lattice comprising titanium or any alloys thereof with an elastic modulus in the superior to inferior direction of between and including 10 MPa to 300 MPa. In another example, the body 1513 is comprised of a lattice comprising titanium or any alloys thereof with an elastic modulus in the superior to inferior direction of between and including 300 MPa to 2 GPa. In another example, the body 1513 is comprised of a lattice comprising titanium or any alloys thereof with an elastic modulus in the superior to inferior direction of between and including 300 MPa to 4 GPa. In another example, the body 1513 is comprised of a lattice comprising titanium or any alloys thereof with an elastic modulus in the superior to inferior direction of between and including 300 MPa to 12 GPa. In another example, the body 1513 is comprised of a lattice comprising titanium or any alloys thereof with an elastic modulus in the superior to inferior direction that is substantially similar to the bulk elastic modulus in the superior to inferior direction of the adjacent bone.

To achieve a targeted elastic modulus in the superior to inferior direction, the shape of the lattice structure and/or the volumetric density of the body 1513 can be adjusted to suit a particular material and material's elastic modulus. While any implantable material could be used for the body 1513, the shape of the lattice structure and volumetric density of the material may need to be changed to create a body 1513 with the specific elastic modulus required. For instance, a material with a lower elastic modulus than a titanium alloy when both have a volumetric density of 100% would need to have a higher volumetric density or use a lattice repeating unit cell shape that increases the elastic modulus of the structure to achieve a body with a similar elastic modulus.

By adapting the lattice structure and volumetric density of the material, any implantable material could be appropriate for the body 1513. In one example, the body 1513 is comprised of an implantable lattice with an elastic modulus in the superior to inferior direction of between 8 to 12 GPa. In another example, the body 1513 is comprised of an implantable lattice with an elastic modulus in the superior to inferior direction of between 1 to 5 GPa. In another example, the body 1513 is comprised of an implantable lattice with an elastic modulus in the superior to inferior direction of between 2 to 4 GPa. In another example, the body 1513 is comprised of an implantable lattice with an elastic modulus in the superior to inferior direction of between 3 to 9 GPa. In another example, the body 1513 is comprised of an implantable lattice with an elastic modulus in the superior to inferior direction of between and including 10 MPa to 300 MPa. In another example, the body 1513 is comprised of an implantable lattice with an elastic modulus in the superior to inferior direction of between and including 300 MPa to 2 GPa. In another example, the body 1513 is comprised of an implantable lattice with an elastic modulus in the superior to inferior direction of between and including 300 MPa to 4 GPa. In another example, the body 1513 is comprised of an implantable lattice with an elastic modulus in the superior to inferior direction of between and including 300 MPa to 12 GPa. In another example, the body 1513 is comprised of an implantable lattice with an elastic modulus in the superior to inferior direction that is substantially similar to the bulk elastic modulus in the superior to inferior direction of the adjacent bone. While implantable metals are often an appropriate material for the body 1513, other materials with a similar elastic modulus and/or the capacity for bone ingrowth can also be used, including, but are not limited to, a glass ceramic composition with a porous structure.

The body 1513 may optionally be treated with one or more bioactive coatings in one or more areas to promote certain reactions. For instance, the body 1513 may optionally be treated with a bioactive coating, such as an HA coating, to promote bone growth.

The volumetric density of the body 1513 may also be varied to adjust the mechanical stability offered by the device 1510 in a particular direction. In one example, the body 1513 has a higher elastic modulus at the front and back of the device 1510. In one example, the area between the back of the device and the back wall of the lumen 1514 and the area between the front of the device and the front wall of the lumen 1514 have an elastic modulus between and including 8 to 12 GPa and the remainder of the body has an elastic modulus between and including 4 to 8 GPa. In some examples, it may be desirable for the body 1513 to have a higher elastic modulus at the center of the device than towards the front and back. A lower elastic modulus towards the edges of a device could reduce stress risers in the vertebral endplate, especially if the edges of the implant have a high risk of subsidence into the vertebral endplate or the implant is too small for the disc space. The use of a lower modulus of elasticity towards the center of a device would allow less pressure on the softer center of the vertebral endplate, which would be beneficial in patients with low bone quality so that the implant edges can rest on the stronger annulus of the vertebral body. The elastic modulus of the body may be adjusted by varying the parameters of the body 1513. When the body 1513 is a repeating geometric metallic lattice, the parameters of the unit cells may be locally modified to change the elastic modulus of that area. Some methods of increasing the strength and elastic modulus include, but are not limited to, increasing the diameter of the unit cell struts, increasing the size of the unit cell nodes, applying post-processing such as HIP treatment to unify material grains, modifying laser printing characteristics to control layer adhesion strength, or applying etching processes to reduce crack propagation sites. Performing the opposite modification would generally decrease the elastic modulus.

The lumen 1514 and window 1515 can optionally be filled with a lattice or scaffold of substantially the same material as the body 1513. The lumen 1514 and window 1515 could also be optionally be filled with a lattice or scaffold with a different volumetric density, primary material and/or unit cell structure than the body 1513 to affect the bone ingrowth process.

Figure 76:
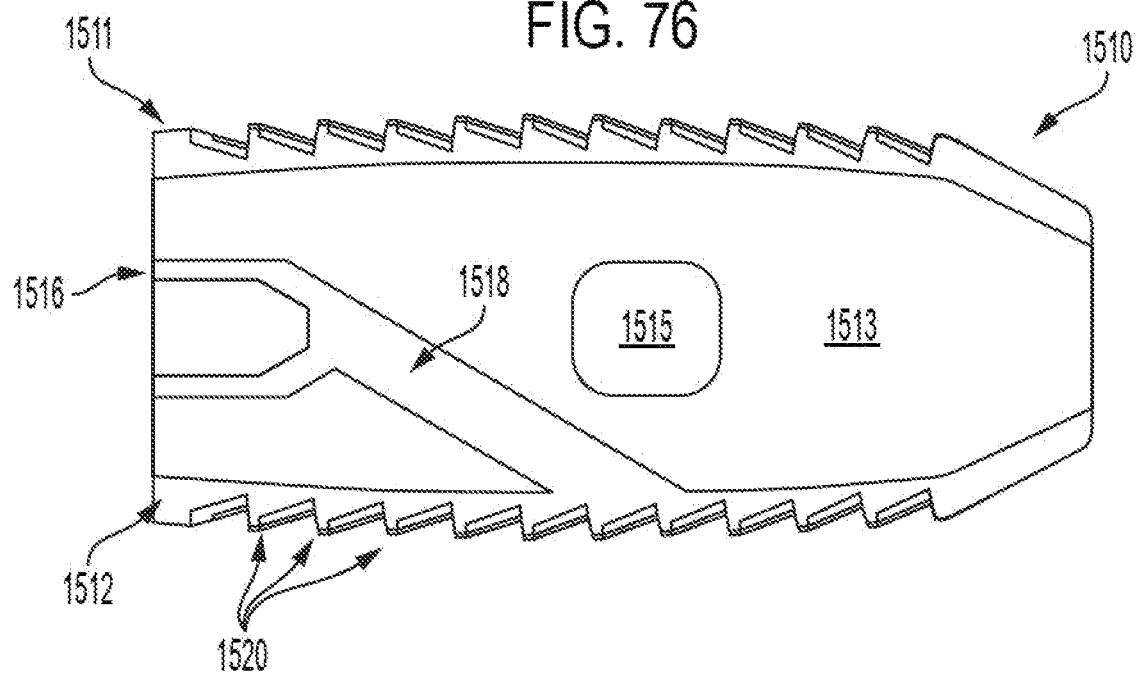
FIG. 76 is a right-side view of a first implant showing a separation between the endplates.

In FIG. 76 is a right-side view of the first implant 1510. In some versions, the left side view is a mirror image of the right-side view. In some versions, the left side and right-side may not be a mirror image. From the side, the upper endplate 1511, lower endplate 1512 and body 1513 are visible. The ridges 1520 are present on the superior and inferior surface of the device 1510 on the upper and lower endplates 1511 and 1512 and the portion of the body 1513 that extends to the superior and inferior surfaces. The ridges 1520 can be changed depending on the particular application and it is appreciated that many different types of ridges or surface patterns could be used to provide mechanical stabilization of the device 1510 relative to the endplates of the adjacent vertebrae.

The window 1515 is visible from the side and extends through the device in some examples. While this example shows a square opening with rounded corners and substantially the same shape through the device, other fusion window shapes could be used effectively. The tool engagement area 1516 can be formed as a single piece, including the right connection arm 1518, left connection arm 1519 (not visible in this view) and the lower endplate 1512. The left connection arm 1519 can be substantially the same shape as the right connection arm 1518.

Figure 77:
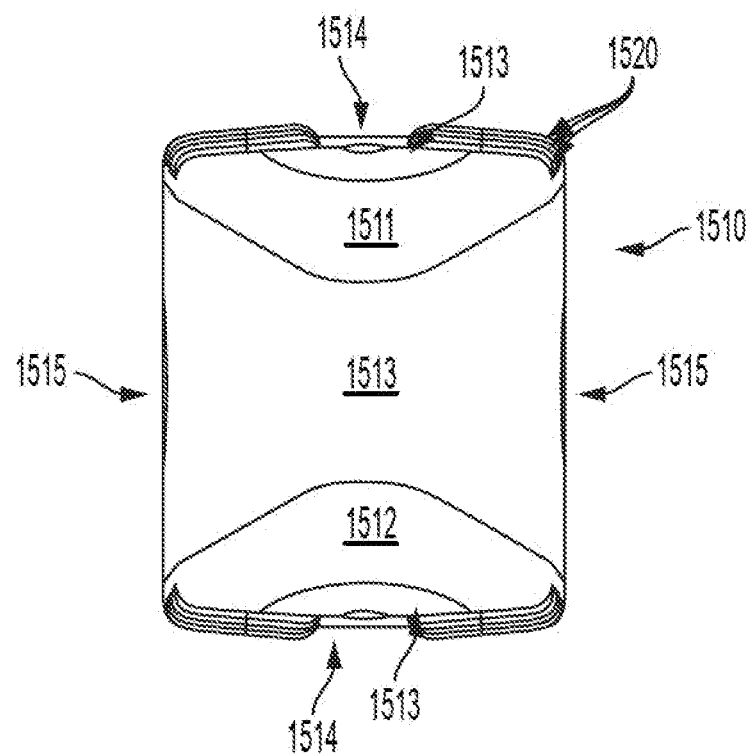
FIG. 77 is a front view of a first implant showing the leading edge of the implant and the separation between the endplates.

In FIG. 77 is a front view of the first implant 1510. From the front, the upper endplate 1511, lower endplate 1512 and body 1513 are visible. The upper and lower endplates 1511 and 1512 can taper together towards the front of the device. Because of the taper, the portions of the body that extends to the superior and inferior surfaces are visible in this view. The sides of the device 1510 also taper towards the front of the device so that the openings to window 1515 are visible from the front. The openings for the lumen 1514 are also visible from the front, adjacent to the ridges 1520.

Figure 78:
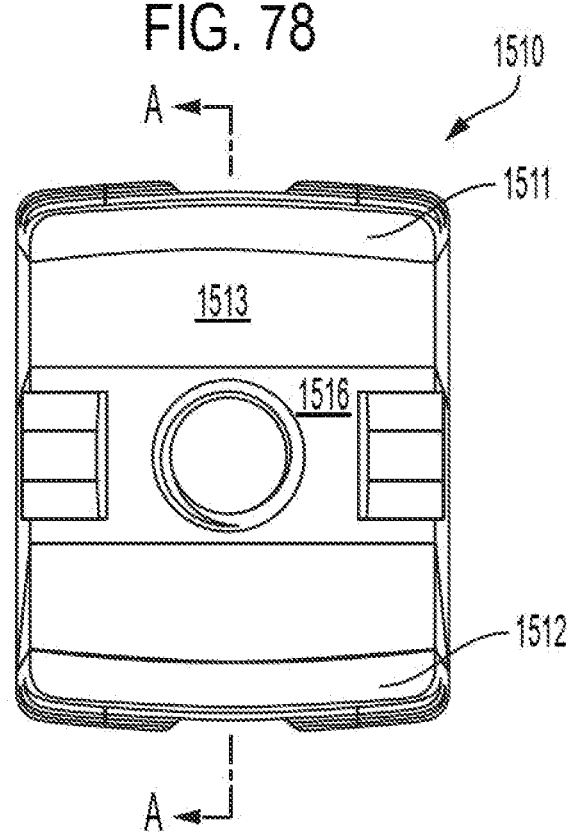
FIG. 78 is a rear view of a first implant showing an optional tool engagement area.

In FIG. 78 is a rear view of the implant 1510. From the rear, the upper endplate 1511, lower endplate 1512 and body 1513 are visible. Tool engagement area 1516 can face rearward to assist in placing the device in a patient. The location of the tool engagement area 1516 can vary based on the location where the device is to be inserted. In FIG. 78, the line between the points labeled "A" define the section view of FIG. 79.

Figure 79:
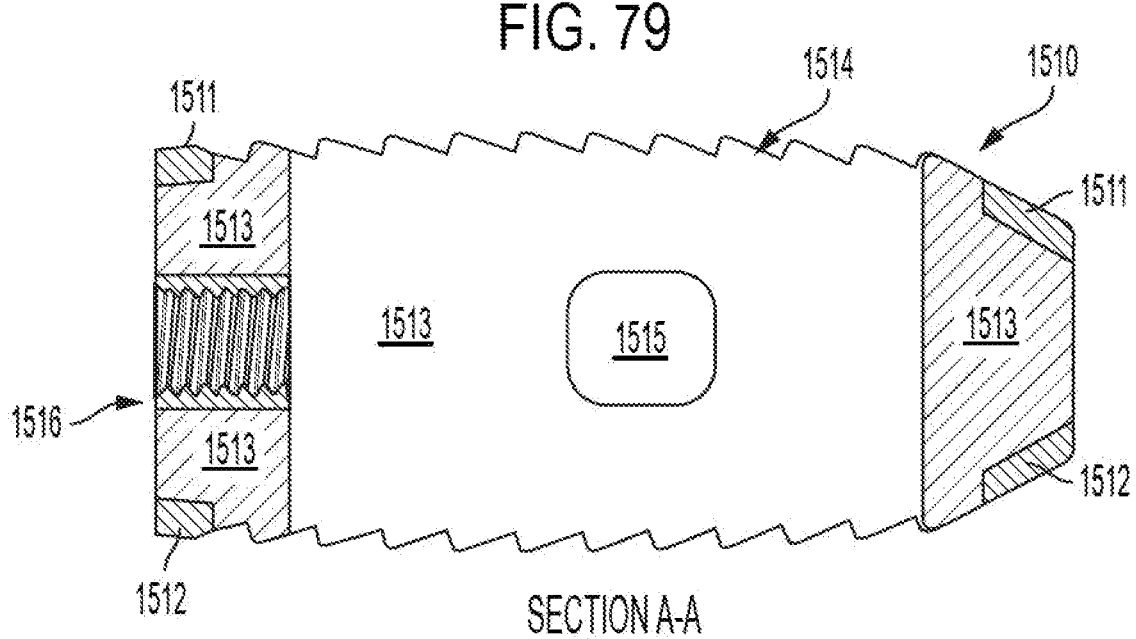
FIG. 79 is a side sectioned view, sectioned at plane defined by line AA in FIG. 78, of a first implant showing the separation between the endplates throughout the device.

In FIG. 79 is a side sectioned view of the first implant 1510. In the sectioned view of FIG. 79, the device is shown from the right side where the device was cut vertically along the centerline of the device (along line AA in FIG. 78) if viewed from the front or rear.

The sectioned view of FIG. 79 cuts through the upper endplate 1511, lower endplate 1512, the body 1513 and the tool engagement area 1516. In this example, the upper endplate 1511 is connected to the top of the body 1513 and the lower endplate is connected to the bottom of the body 1513, without a direct connection between the upper endplate 1511 and lower endplate 1513. The lack of a direct and rigid connection between the upper endplate 1511 and lower endplate 1512 allow them to move independently of one another, largely based on the physical properties of the body 1513. Without a rigid connection between the endplates 1511 & 1512, this example allows the physical properties of the body 1513 to largely dictate the level of mechanical stability afforded to the adjacent bony structures or vertebrae. There may be direct connections between the endplates 1511 & 1512 to adjust the construct properties as long as the endplates 1511 & 1512 are capable of some movement relative to one another.

As noted earlier, other structures can be employed to allow independence between the endplates 1511 & 1512, including but not limited to, springs or member(s) that allow the endplates 1511 & 1512 to move relative to one another. In some embodiments, the body can be substituted with a structure that allows independence between the endplates 1511 & 1512. In some embodiments, the volumetric density of the endplates is higher than that of the body, causing the body's properties to substantially dominate the properties of the implant.

In FIG. 79, the lumen 1514 is sectioned through its center in this view so that the left wall of the lumen 1514 is visible. In this example, the window 1515 passes through both sides of the body 1513 and the portion passing through the left side of the device 1510 is visible. The tool engagement area 1516 can be connected to the lower endplate 1512 by right and left connection arms 1518 and 1519 that are not visible in this view. The connection arms, in this example, run along the exterior sides of the device 1510, but do not extend to the vertical fusion window 1514.

Figure 80:
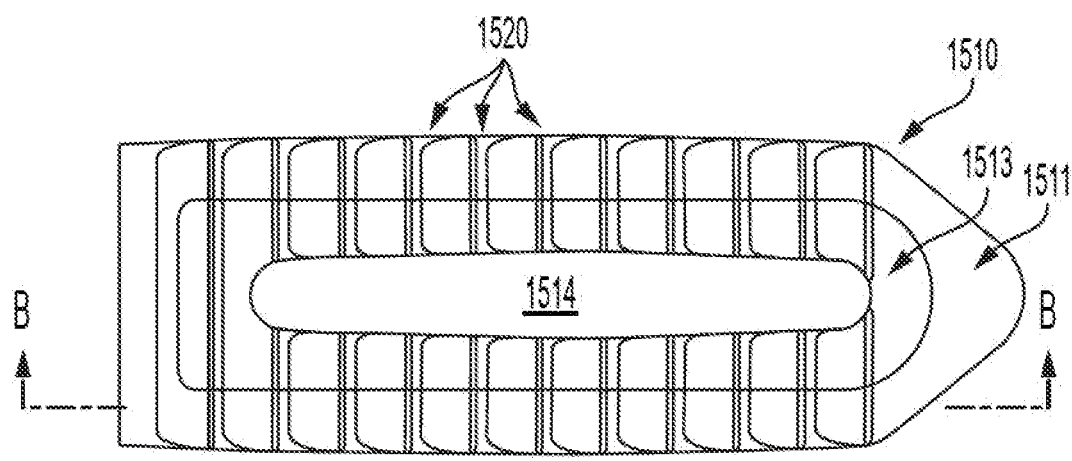
FIG. 80 is a top view of a first implant showing an exemplary configuration for an endplate surface.

In FIG. 80 is a top view of the first implant 1510. In some examples, the bottom view can be a mirror image of the top view, however in other examples, the top view and bottom view may not be a mirror image of one another. From the top, the upper endplate 1511 and body 1513 are visible. The orientation and shape of the lumen 1514 can be clearly seen in this view. While the lumen 1514 is shown as an oval shaped opening of the same size in the superior to inferior direction, other shapes could be appropriate for the lumen. In this example, the portion of the body 1513 that extends to the superior surface is flush with the superior surface of the upper endplate 1511 so that the ridges 1520 of the upper endplate 1511 extend to the surface of the body 1513. In FIG. 80, the line between the points labeled "B" define the section view of FIG. 81.

Figure 81:
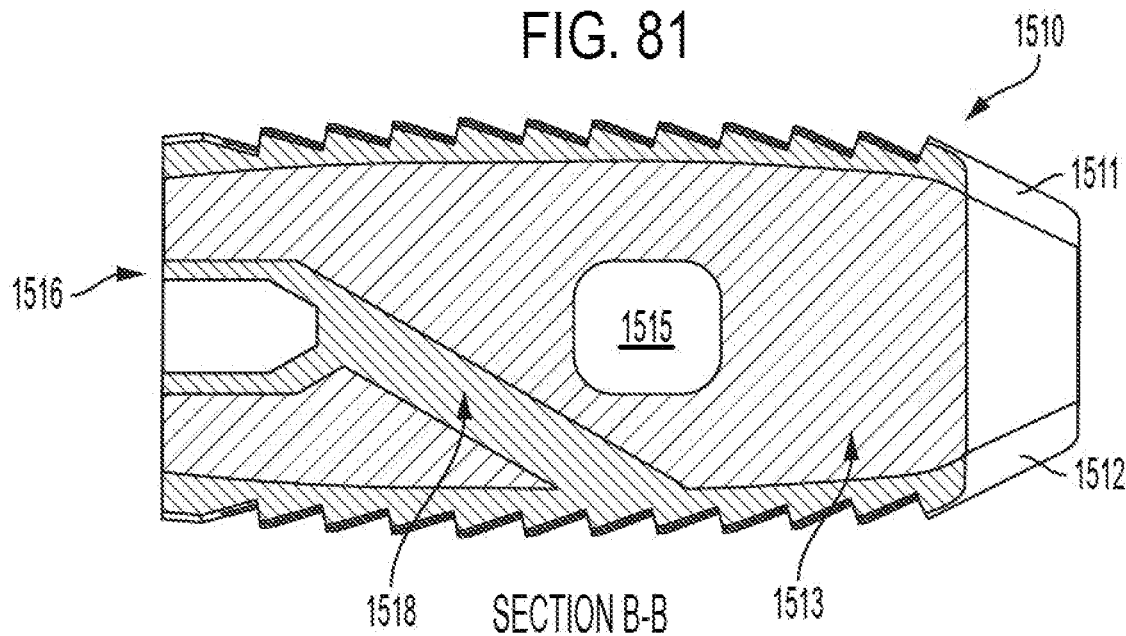
FIG. 81 is a side sectioned view, sectioned at a plane defined by line BB in FIG. 80, of a first implant also showing the separation between the endplates throughout the device.

In FIG. 81 is an alternative side sectioned view of the implant 1510. In the sectioned view of FIG. 81, the device is shown from the right side where the device was cut vertically to the right of the centerline of the device (along line BB in FIG. 80) if viewed from the top or rear.

The sectioned view of FIG. 81 cuts through the upper endplate 1511, lower endplate 1512, the body 1513, the rigid section 1516 and the right connection arm 1518. The section was taken to the right of centerline between the lumen 1514 (not visible in this view) and the right side of the device 1510. Also, clearly visible in this sectioned view is that the upper endplate 1511 and lower endplate 1512 are connected only to the body 1513, without a direct and rigid connection between the endplates 1511 & 1512. As there is no direct and rigid connection between the endplates 1511 & 1512, the physical properties of the body 1513 dictate the level of mechanical stability afforded to the adjacent vertebrae. There may be direct connections between the endplates 1511 & 1512 to adjust the construct properties as long as the endplates 1511 & 1512 are capable of some movement relative to one another. In this example, the window 1515 passes through both sides of the body 1513 and the portion passing through the right side of the device 1510 is visible. The right connection arm 1518 that connects the rigid section 1516 to the lower endplate 1512 is sectioned in this view.

Certain ranges of elastic moduli for the endplates 1511 & 1512 and the body 1513 were disclosed above, but the use of endplates with an elastic modulus indexed from that of the body can provide the benefits of increased bone loading without surface deformations to the implant that can compromise the strength characteristics of the material. The elastic moduli ranges for the endplates and body can be narrowed and selected based on the tables and equations later in this disclosure.

In some embodiments, the first implant 1510 is a PLIF implant. In some embodiments, the first implant 1510 is a TLIF implant. In some embodiments, the first implant 1510 is a PLIF/TLIF implant. In some embodiments, the first implant 1510 is an interbody fusion implant. In some embodiments, the first implant 1510 is a bone fusion implant. In some embodiments, the first implant 1510 is configured for tissue attachment, tissue including but not limited to bony structures and connective tissue. In some embodiments, the first implant 1510 is configured to allow tissue in-growth, tissue including but not limited to bony structures and connective tissue.

In FIGS. 82 to 89 is a second implant 16130 with an independent endplate structure. The second implant 16130 can be inserted between the endplates of two bony structures or adjacent vertebrae, providing mechanical spacing between them and mechanical stability to promote bone growth, allowing the bony structures or vertebrae to fuse together over time. The second implant 16130 can be comprised substantially of three components—an upper endplate 16111, a lower endplate 16112 and a body 16113. The upper and lower endplates 16111 & 16112 can be comprised of a biocompatible material with a higher elastic modulus in the superior to inferior direction than the body 16113. The body 16113 can be comprised of a biocompatible material with a lower elastic modulus in the superior to inferior direction than the upper and lower endplates 16111 & 16112.

Figure 82:
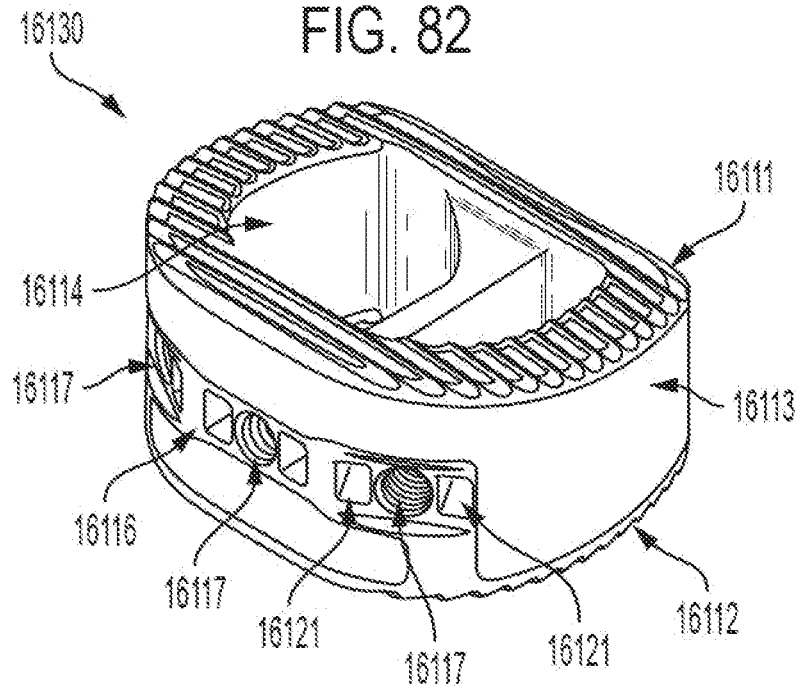
FIG. 82 is an isometric view of a second implant showing the inventive configuration of the endplates relative to the body on the exterior of the device.
Figure 83:
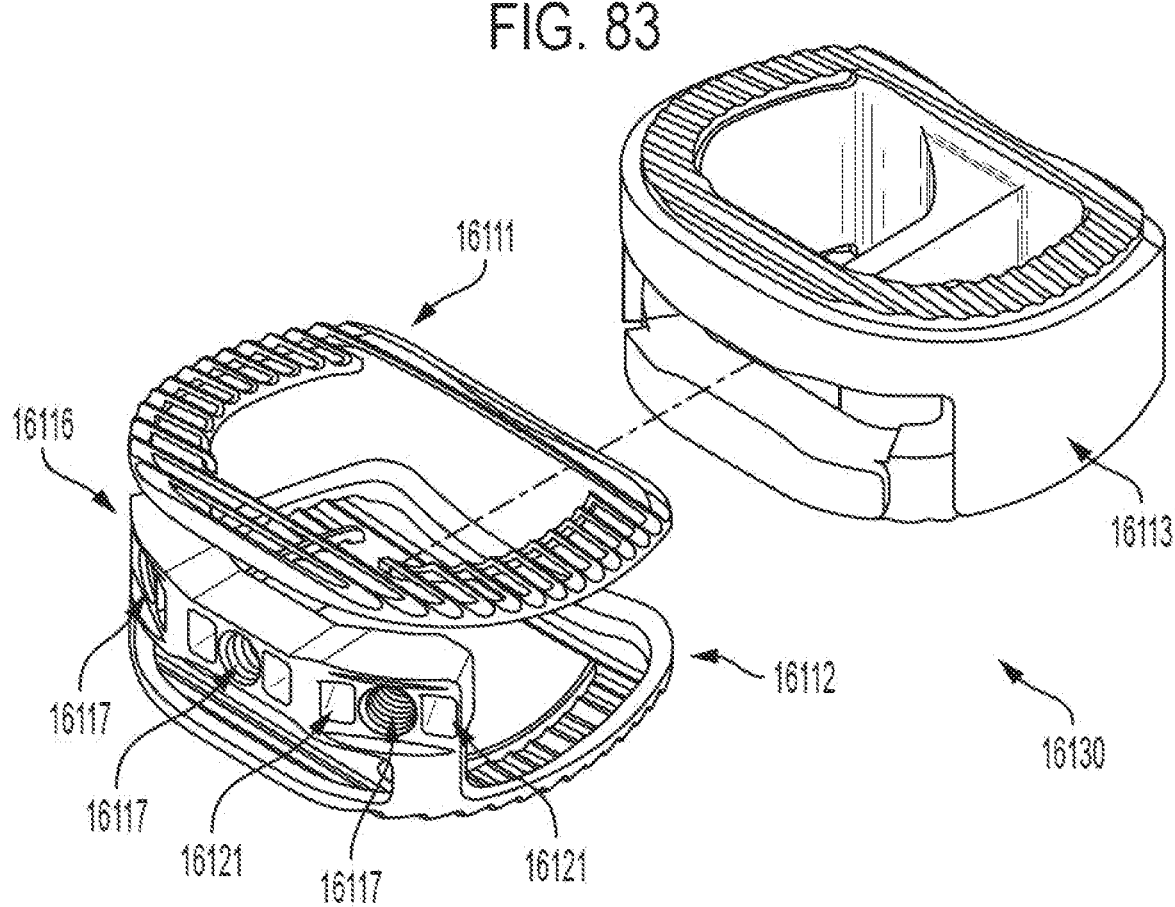
FIG. 83 is an exploded isometric view of a second implant showing the endplates separated from the body.
Figure 84:
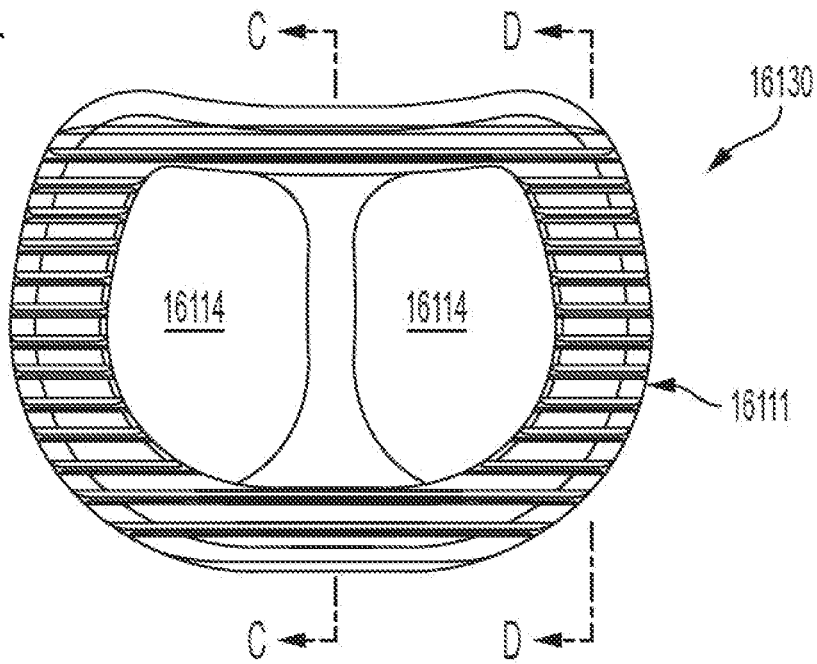
FIG. 84 is a top view of a second implant showing a possible configuration of an endplate top surface and the location of later presented section views.
Figure 85:
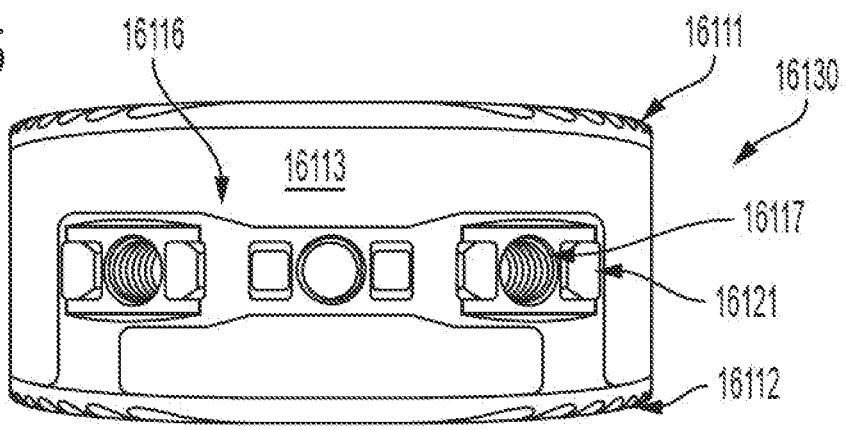
FIG. 85 is a rear view of a second implant showing the optional rear tool engagement area.
Figure 86:
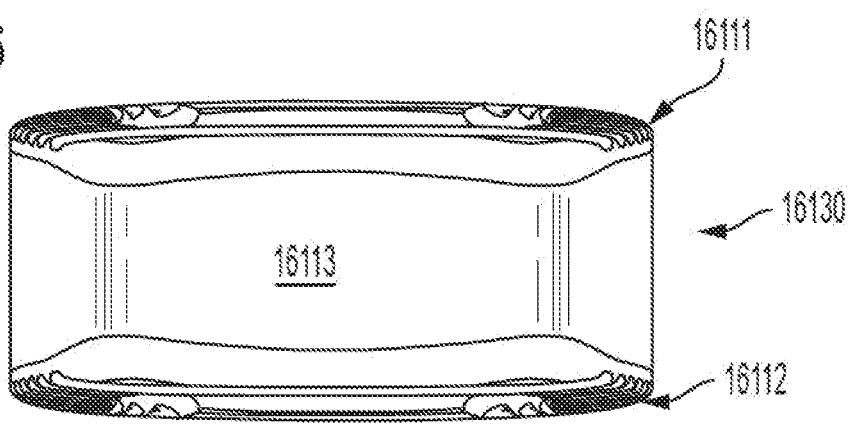
FIG. 86 is a front view of a second implant showing the position of the endplates relative to one another.

In FIG. 82 is an isometric view of the second implant 16130, showing the independent configuration of the endplates 16111 & 16112 relative to the body 16113. In FIG. 83 is an exploded isometric view of the second implant 16130, showing the endplates 16111 & 16112 separated from the body 16113, showing the lack of a direct and rigid connection between the endplates 16111 & 16112 in this embodiment. There may be direct connections between the endplates 16111 & 16112 to adjust the construct properties as long as the endplates 16111 & 16112 are capable of some movement relative to one another. In FIG. 84 is a top view of the implant 16130 showing an exemplary endplate configuration and identifying lines CC and DD. In FIG. 85 is a rear view of the implant 16130 showing the optional rear tool engagement area. In FIG. 86 is a front view of the implant 16130 showing the position of the endplates relative to one another. In FIG. 87 is a side view of the implant 16130, also showing the position of the endplates relative to one another. In FIG. 88 is a side sectioned view of the implant 16130, sectioned through line CC in FIG. 84 and in FIG. 88 is an alternative side sectioned view of the implant 16130, sectioned through line DD in FIG. 84. The side sectioned views show that the endplates 16111 & 16112 do not directly contact one another throughout the device in this example.

The upper endplate 16111 and lower endplate 16112 are independent to one another with respect to their ability to move independently of one another. In some embodiments, the upper endplate 16111 and lower endplate 16112 are on opposite sides of the body 16113 so that the endplates 16111 & 16112 can move independently of one another and where the amount of independent movement can be determined largely by the stiffness of the body 16113. While a body is disclosed as a structure that can provide independence between endplates, other structures noted previously may provide a similar independence.

The body 16113 preferably provides mechanical spacing between the adjacent bony structures or vertebrae and provides adequate rigidity between them to allow for bone ingrowth. The use of a body 16113 with a lower elastic modulus than the endplates 16111 & 16112 can allow the new bone growth to be stressed while ingrowth occurs, resulting in a stronger fused bone. The relatively higher modulus of elasticity of the endplates 16111 & 16112 distributes the load across the surface of the body 16113 and reduces the occurrence of the bony structures or vertebral endplates from indenting the upper or lower surface of the body 16113. In some examples, the endplates 16111 & 16112 use optional raised ridges or teeth 16120 to mechanically anchor the endplates 16111 & 16112 to the bony structures or the endplates of the adjacent vertebrae. The ridges 16120 can extend from the endplates 16111 & 16112 to the surface of the body 16113 that extends to the superior and inferior surface of the device. In addition to distributing the load across the body 16113 and anchoring the interbody fusion device 16130 relative to the adjacent vertebrae, the endplates 16111 & 16112 can allow for bone attachment or ingrowth, providing stability between the device and the bony structures or end plates of the adjacent vertebrae.

The implant 16130 also provides optional lumen 16114 as vertical bone fusion windows for radiolucency or bone fusion. The fusion windows can be used by clinicians to insert one or more compounds that promote bone growth or to assess fusion through the lumen 16114 during the healing process. Some compounds that would be appropriate for use in the fusion or viewing windows 16114 are autograft, allograft synthetic graft, or a combination.

The lower endplate 16112 of the implant 16130 can include a tool engagement area 16116 to allow surgical tools to be fastened to the device 16130 during a surgical procedure. In some examples, the tool engagement area 16116 contains one or more threaded openings 16117 that are configured to accept a threaded rod to facilitate placement of the device 16130. On either side of each threaded opening 16117 can be a void 16121 designed to accommodate stabilizers on the threaded rod, if used. While the threaded openings 16117 can provide an adequate amount of leverage to locate the device 16130, the addition of stabilizers on an installation instrument that contact the device 16130 in the voids 16121 can increase the ability of a surgeon to rotate the device during insertion. The tool engagement area 16116 can be connected to an endplate 16111 & 16112 and/or to the body 16113.

In some embodiments, the upper and lower endplates 16111 & 11612 are comprised of a material or lattice with a volumetric density between and including 60% and 100%. Embodiments of the device include examples where the endplates 16111 & 16112 are comprised of a material or lattice with a volumetric density between and including 80% and 100%, 60% and 90%, 70% and 90%, 60% and 64% and less than 60%. In some embodiments, the body 16113 is comprised of a lattice with a volumetric density between and including 5% to 50%. Embodiments of the device include examples where the body 16113 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium of an alloy thereof.

In some embodiments, the upper and lower endplates 16111 & 16112 are comprised of a material or lattice with an elastic modulus between and including 300 MPa to 130 GPa. Embodiments of the device include examples where the upper and lower endplates are comprised of a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 16113 is comprised of a lattice with an elastic modulus between and including 10 MPa to 12 GPa. Embodiments of the device include examples where the body 16113 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 16113 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In some embodiments, the second implant 16130 is an Anterior Lumbar Interbody Fusion (hereinafter "ALIF") implant. In some embodiments, the second implant 16130 is an interbody fusion implant. In some embodiments, the second implant 16130 is a cervical stand-alone implant. In some embodiments, the second implant 16130 is an ankle fusion spacer implant. In some embodiments, the second implant 16130 is a bone fusion implant. In some embodiments, the second implant 16130 is configured for tissue attachment, tissue including but not limited to bony structures and connective tissue. In some embodiments, the second implant 16130 is configured to allow tissue ingrowth, tissue including but not limited to bony structures and connective tissue.

In FIGS. 90 to 97 is a third implant 17230 with an independent endplate structure. The third implant 17230 can be inserted between bony structures or the endplates of two adjacent vertebrae, providing mechanical spacing between them and mechanical stability to promote bone growth, allowing the bony structures or vertebrae to fuse together over time. The third implant 17230 can be comprised substantially of three components—an upper endplate 17211, a lower endplate 17212 and a body 17213. The upper and lower endplates 17211 & 17212 can be comprised of a biocompatible material with a higher elastic modulus in the superior to inferior direction than the body 17213. The body 17213 can be comprised of a biocompatible material with a lower elastic modulus in the superior to inferior direction than the upper and lower endplates 17211 & 17212.

Figure 90:
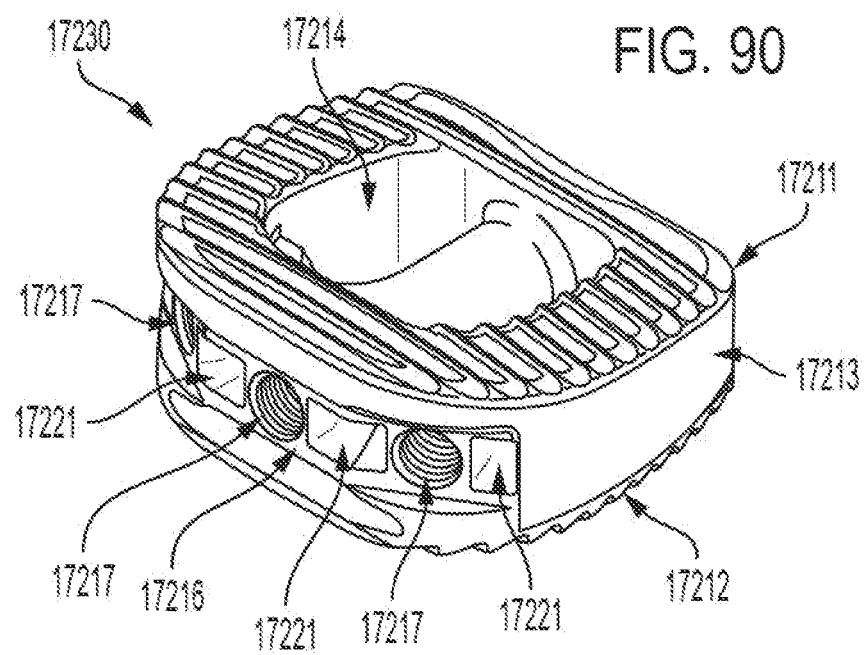
FIG. 90 is an isometric view of a third implant showing the inventive configuration of the endplates relative to the body on the exterior of the device.
Figure 91:
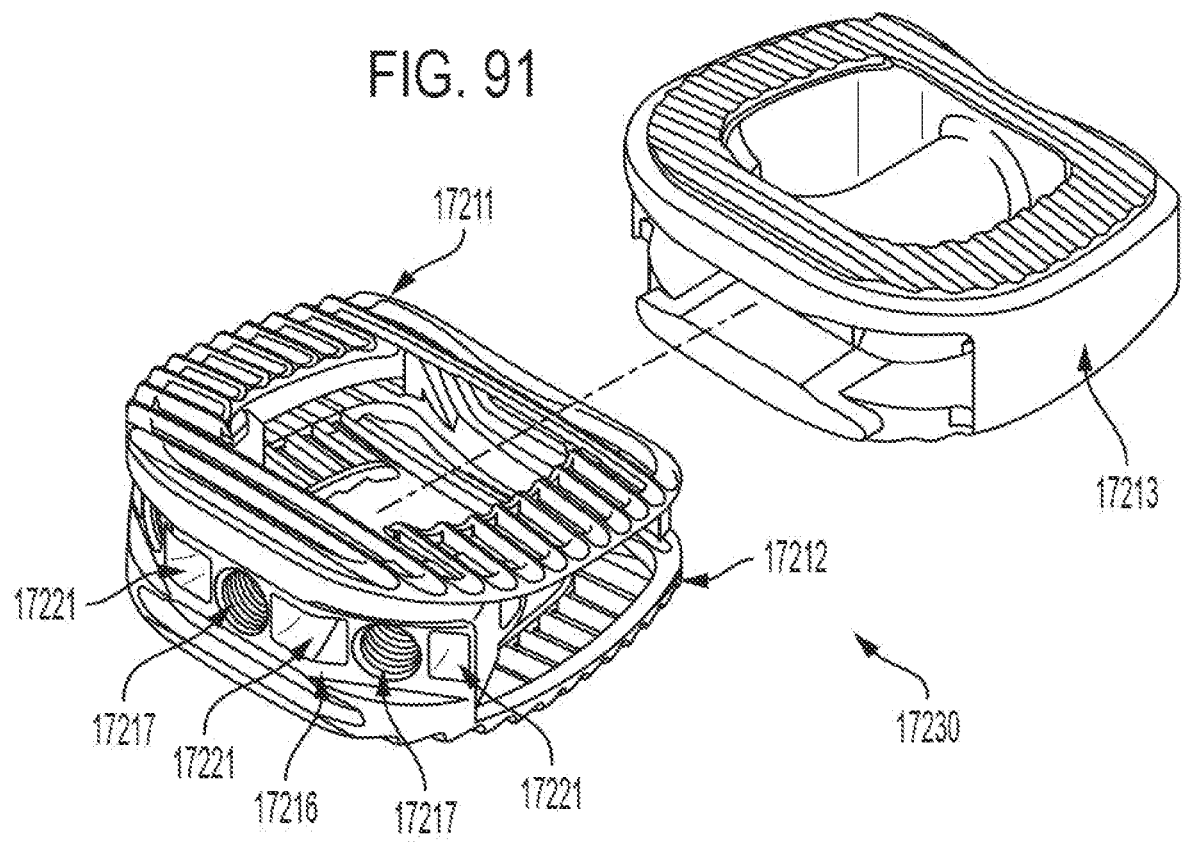
FIG. 91 is an exploded isometric view of the third implant showing the endplates separated from the body.
Figure 92:
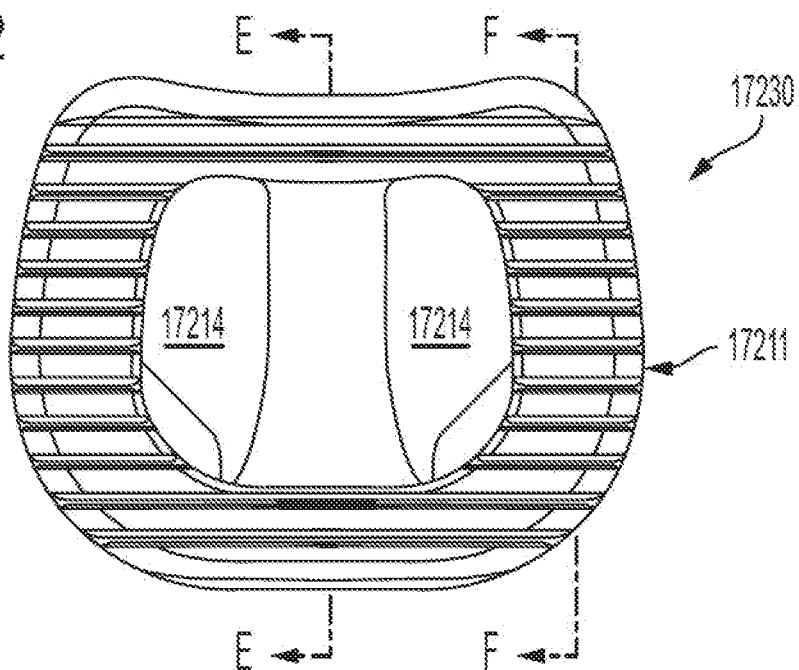
FIG. 92 is a top view of the third implant showing a possible configuration of an endplate top surface and the location of later presented section views.
Figure 93:
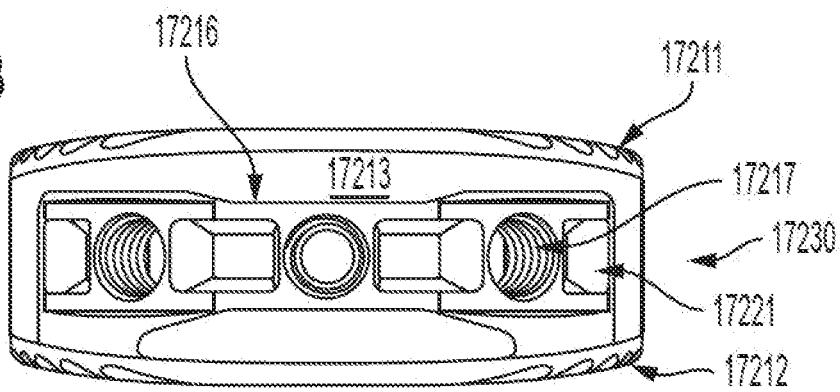
FIG. 93 is a rear view of the third implant showing the optional rear tool engagement area.
Figure 94:
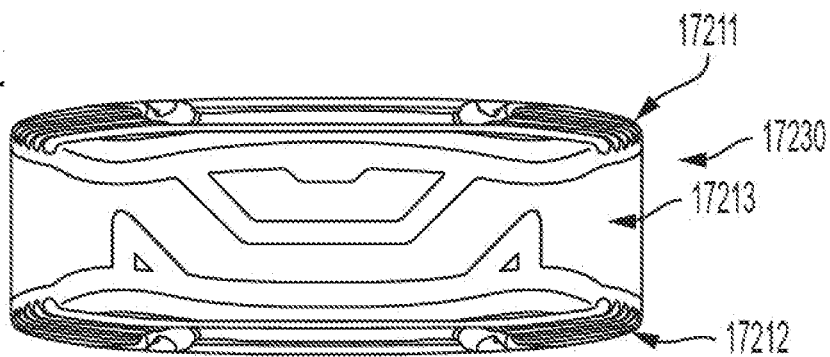
FIG. 94 is a front view of the third implant showing the position of the endplates relative to one another.
Figure 95:
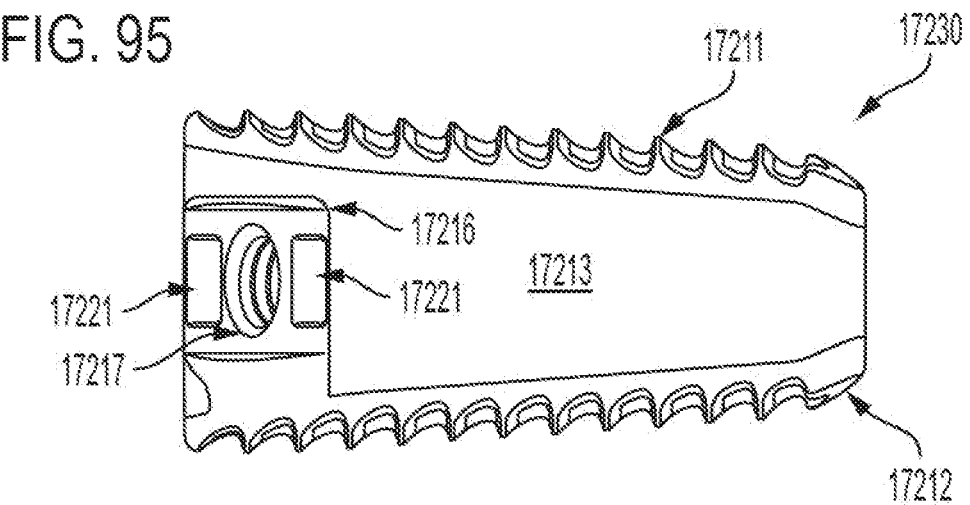
FIG. 95 is a side view of the third implant also showing the position of the endplates relative to one another.
Figure 96:
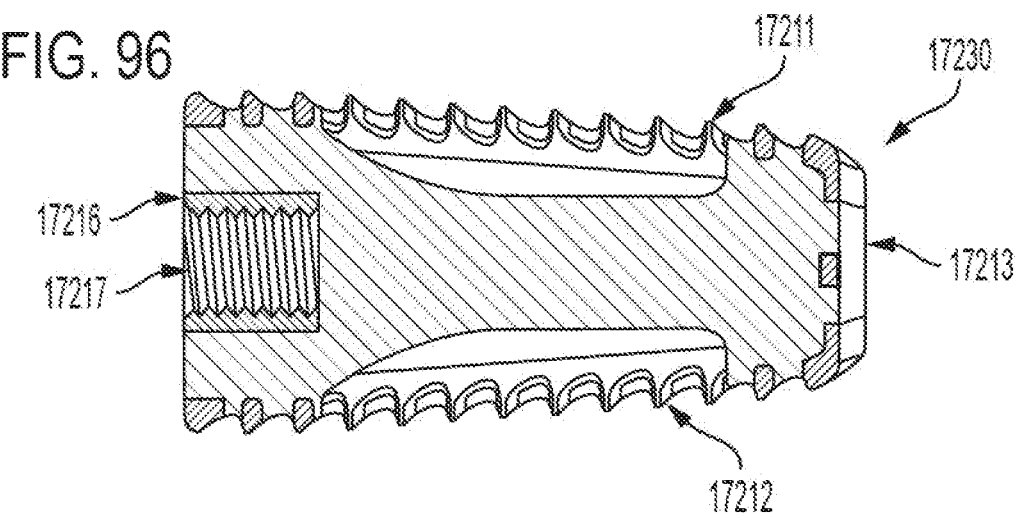
FIG. 96 is a side sectioned view of the third implant, sectioned through line EE in FIG. 92.
Figure 97:
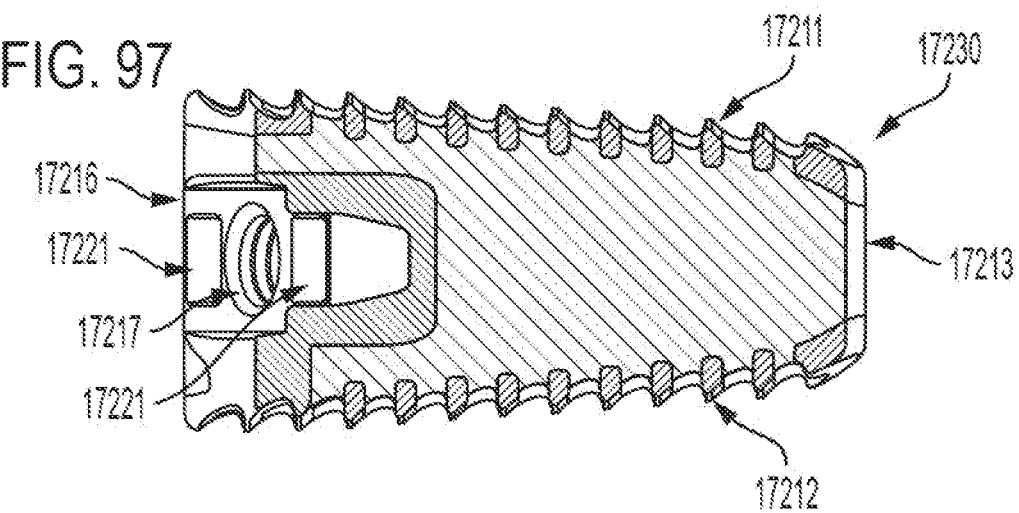
FIG. 97 is an alternative side sectioned view of the third implant, sectioned through line FF in FIG. 92.

In FIG. 90 is an isometric view of the third implant 17230, showing the independent configuration of the endplates 17211 & 17212 relative to the body 17213. In FIG. 91 is an exploded isometric view of the third implant 17230, showing the endplates 17211 & 17212 separated from the body 17213, showing the lack of a direct and rigid connection between the endplates 17211 & 17212 in this embodiment. There may be direct connections between the endplates 17211 & 17212 to adjust the construct properties as long as the endplates 17211 & 17212 are capable of some movement relative to one another. In FIG. 92 is a top view of the third implant 17230 showing an exemplary endplate configuration and identifying lines EE and FF. In FIG. 93 is a rear view of the third implant 17230 showing the optional rear tool engagement area. In FIG. 94 is a front view of the second ALIF implant 17230 showing the position of the endplates relative to one another. In FIG. 95 is a side view of the second ALIF implant 17230, also showing the position of the endplates relative to one another. In FIG. 96 is a side sectioned view of the second ALIF implant 17230, sectioned through line EE in FIG. 90 and in FIG. 97 is an alternative side sectioned view of the second ALIF implant 17230, sectioned through line FF in FIG. 92. The side sectioned views show that the endplates 17211 & 17212 do not directly contact one another throughout the device in this example.

The upper endplate 17211 and lower endplate 17212 are independent to one another with respect to their ability to move independently of one another. In some embodiments, the upper endplate 17211 and lower endplate 17212 are on opposite sides of the body 17213 so that the endplates 17211 & 17212 can move independently of one another and where the amount of independent movement can be determined largely by the stiffness of the body 17213. While a body is disclosed as a structure that can provide independence between endplates, other structures noted previously may provide a similar independence.

The body 17213 preferably provides mechanical spacing between the adjacent bony structures or vertebrae and provides adequate rigidity between them to allow for bone ingrowth. The use of a body 17213 with a lower elastic modulus than the endplates 17211 & 17212 can allow the new bone growth to be stressed while ingrowth occurs, resulting in a stronger fused bone. The relatively higher modulus of elasticity of the endplates 17211 & 17212 distributes the load across the surface of the body 17213 and reduces the occurrence of the vertebral endplates from indenting the upper or lower surface of the body 17213. In some examples, the endplates 17211 & 17212 use optional raised ridges or teeth 17220 to mechanically anchor the endplates 17211 & 17212 to the bony structures or the endplates of the adjacent vertebrae. The ridges 17220 can extend from the endplates 17211 & 17212 to the surface of the body 17213 that extends to the superior and inferior surface of the device. In addition to distributing the load across the body 17213 and anchoring the implant 17230 relative to the bony structures or adjacent vertebrae, the endplates 17211 & 17212 can allow for bone attachment or ingrowth, providing stability between the device and the bony structures or the end plates of the adjacent vertebrae.

The implant 17230 also provides optional lumen 17214 as vertical bone fusion windows for radiolucency or bone fusion. The fusion windows can be used by clinicians to insert one or more compounds that promote bone growth or to assess fusion through the lumen 17214 during the healing process. Some compounds that would be appropriate for use in the fusion or viewing windows 17214 and 17215 are autograft, allograft synthetic graft, or a combination.

The lower endplate 17212 of the implant 17230 can include a tool engagement area 17216 to allow surgical tools to be fastened to the device 17230 during a surgical procedure. In some examples, the tool engagement area 17216 contains one or more threaded openings 17217 that are configured to accept a threaded rod to facilitate placement of the device 17230. On either side of each threaded opening 17217 can be a void 17221 designed to accommodate stabilizers on the threaded rod, if used. While the threaded openings 17217 can provide an adequate amount of leverage to locate the device 17230, the addition of stabilizers on an installation instrument that contact the device 17230 in the voids 17221 can increase the ability of a surgeon to rotate the device during insertion. The tool engagement area 17216 can be connected to an endplate 17211 & 17212 and/or to the body 17213.

In some embodiments, the upper and lower endplates 17211 & 17212 are comprised of a material or lattice with a volumetric density between and including 60% and 100%. Embodiments of the device include examples where the endplates 17211 & 17212 are comprised of a material or lattice with a volumetric density between and including 80% and 100%, 60% to 90%, 70% and 90%, 60% and 64% and less than 60%. In some embodiments, the body 17213 is comprised of a lattice with a volumetric density between and including 5% to 50%. Embodiments of the device include examples where the body 17213 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium or an alloy thereof.

In some embodiments, the upper and lower endplates 17211 & 17212 are comprised of a material or lattice with an elastic modulus between and including 300 MPa to 130 GPa. Embodiments of the device include examples where the upper and lower endplates are comprised of a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 17213 is comprised of a lattice with an elastic modulus between and including 10 MPa to 12 GPa.

Embodiments of the device include examples where the body 17213 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 17213 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In some embodiments, the third implant 17230 is an ALIF implant. In some embodiments, the third implant 17230 is an interbody fusion implant. In some embodiments, the third implant 17230 is a cervical stand-alone implant. In some embodiments, the third implant 17230 is an ankle fusion spacer implant. In some embodiments, the third implant 17230 is a bone fusion implant. In some embodiments, the third implant 17230 is configured for tissue attachment, tissue including but not limited to bony structures and connective tissue. In some embodiments, the third implant 17230 is configured to allow tissue in-growth, tissue including but not limited to bony structures and connective tissue.

In FIGS. 98 to 104 is a fourth implant 18310 with an independent endplate structure. The fourth implant 18310 can be inserted between bony structures or the endplates of two adjacent vertebrae, providing mechanical spacing between them and mechanical stability to promote bone growth, allowing them to fuse together over time. The fourth implant 18310 can be comprised substantially of three components—an upper endplate 18311, a lower endplate 18312 and a body 18313. The upper and lower endplates 18311 & 18312 can be comprised of a biocompatible material with a higher elastic modulus in the superior to inferior direction than the body 18313. The body 18313 can be comprised of a biocompatible material with a lower elastic modulus in the superior to inferior direction than the upper and lower endplates 18311 & 18312.

Figure 100:
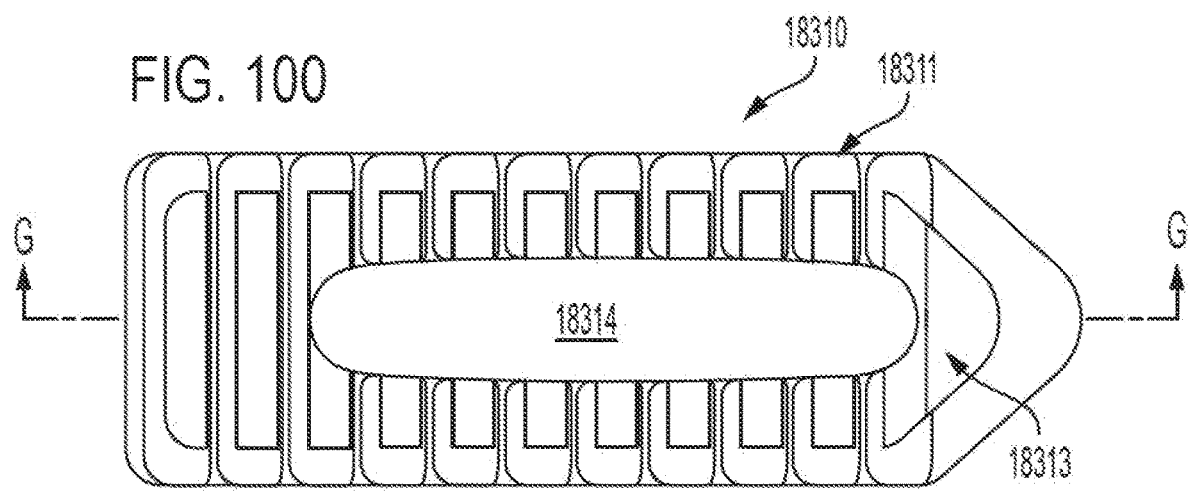
FIG. 100 is a top view of the fourth implant showing a possible configuration of an endplate top surface and the location of a later presented section view.
Figure 101:
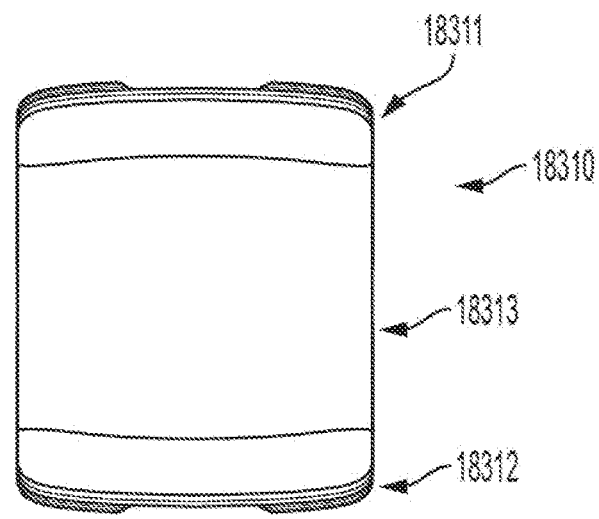
FIG. 101 is a rear view of the fourth implant configured without a rear tool engagement area.
Figure 102:
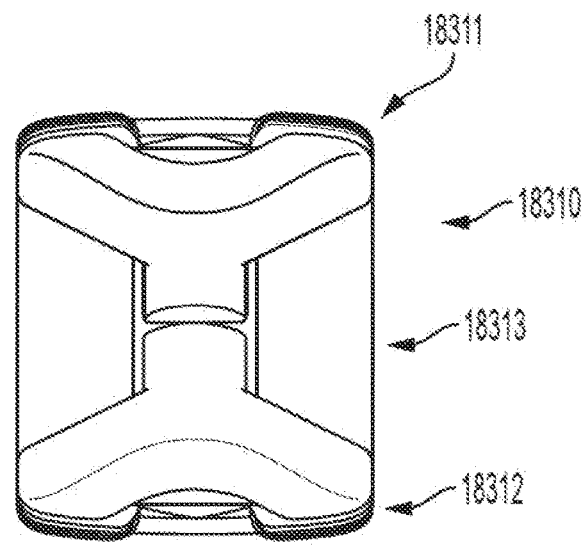
FIG. 102 is a front view of the fourth implant showing the position of the endplates relative to one another.
Figure 103:
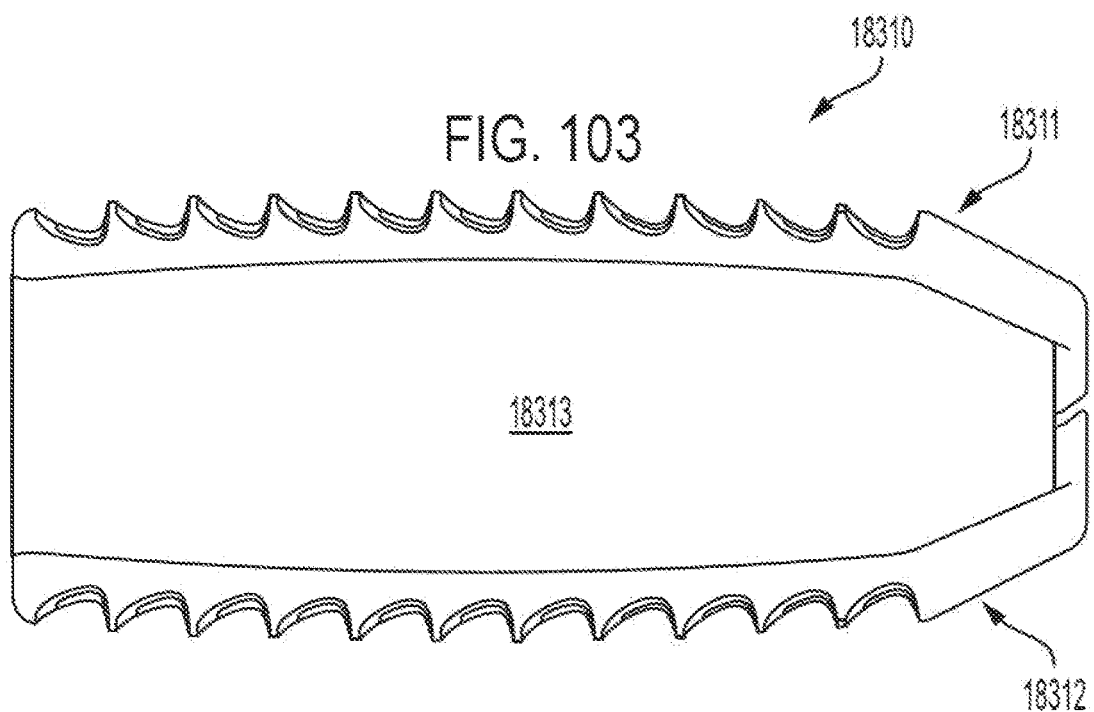
FIG. 103 is a side view of the fourth implant also showing the position of the endplates relative to one another.
Figure 104:
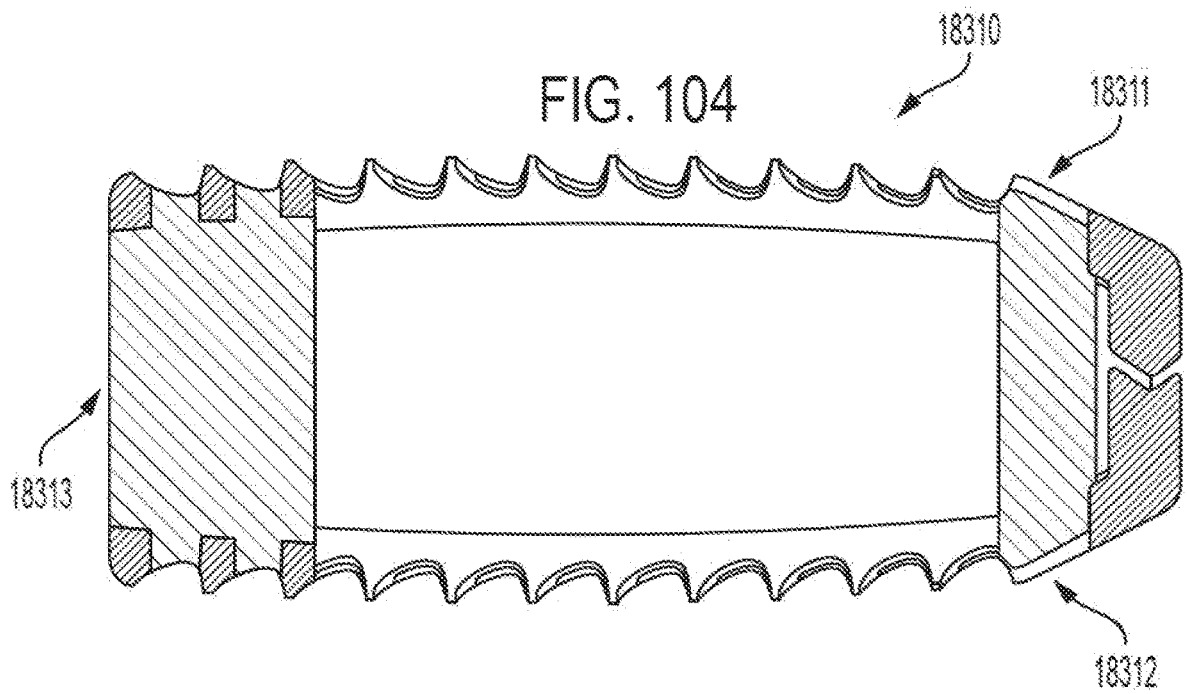
FIG. 104 is a side sectioned view of the fourth implant, sectioned through line GG in FIG. 100.

In FIG. 98 is an isometric view of the fourth implant 18310, showing the independent configuration of the endplates 18311 & 18312 relative to the body 18313. In FIG. 99 is an exploded isometric view of the fourth implant 18310, showing the endplates 18311 & 18312 separated from the body 18313 and showing the lack of a direct and rigid connection between the endplates 18311 & 18312 in this embodiment. There may be direct connections between the endplates 18311 & 18312 to adjust the construct properties as long as the endplates 18311 & 18312 are capable of movement independent of one another. In FIG. 100 is a top view of the fourth implant 18310 showing an exemplary endplate configuration and identifying line and GG. In FIG. 101 is a rear view of the fourth implant 18310 detailing an example without an optional rear tool engagement area. In FIG. 102 is a front view of the fourth implant 18310 showing the position of the endplates relative to one another. In FIG. 103 is a side view of the fourth implant 18310, also showing the position of the endplates relative to one another. In FIG. 104 is a side sectioned view of the fourth implant 18310, sectioned through line GG in FIG. 100, showing that the endplates 18311 & 18312 do not directly contact one another throughout the device in this example.

The upper endplate 18311 and lower endplate 18312 are independent to one another with respect to their ability to move independently of one another. In some embodiments, the upper endplate 18311 and lower endplate 18312 are on opposite sides of the body 18313 so that the endplates 18311 & 18312 can move independently of one another and where the amount of independent movement can be determined largely by the stiffness of the body 18313. While a body is disclosed as a structure that can provide independence between endplates, other structures noted previously may provide a similar independence.

The body 18313 preferably provides mechanical spacing between the adjacent bony structures or vertebrae and provides adequate rigidity between them to allow for bone ingrowth. The use of a body 18313 with a lower elastic modulus than the endplates 18311 & 18312 can allow the new bone growth to be stressed while ingrowth occurs, resulting in a stronger fused bone. The relatively higher modulus of elasticity of the endplates 18311 & 18312 distributes the load across the surface of the body 18313 and reduces the occurrence of the bony structures or vertebral endplates from indenting the upper or lower surface of the body 18313. In some examples, the endplates 18311 & 18312 use optional raised ridges or teeth 18320 to mechanically anchor the endplates 18311 & 18312 to the bony structures or the endplates of the adjacent vertebrae. The ridges 18320 can extend from the endplates 18311 & 18312 to the surface of the body 18313 that extends to the superior and inferior surface of the device. In addition to distributing the load across the body 18313 and anchoring the interbody fusion device 18330 relative to the adjacent bony structures or vertebrae, the endplates 18311 & 18312 can allow for bone attachment or ingrowth, providing stability between the implant and the bony structures or the endplates of the adjacent vertebrae.

The implant 18310 also provides optional lumen 18314 as a vertical bone fusion windows for radiolucency or bone fusion. The fusion window can be used by clinicians to insert one or more compounds that promote bone growth or to assess fusion through the lumen 18314 during the healing process. Some compounds that would be appropriate for use in the fusion or viewing windows 18314 are autograft, allograft synthetic graft, or a combination.

In some embodiments, the upper and lower endplates 18311 & 18312 are comprised of a material or lattice with a volumetric density between and including 60% and 100%. Embodiments of the device include examples where the endplates 18311 & 18312 are comprised of a material or lattice with a volumetric density between and including 80% and 100%, 60% and 90%, 70% and 90%, 60% and 64% and less than 60%. In some embodiments, the body 18313 is comprised of a lattice with a volumetric density between and including 5% to 50%. Embodiments of the device include examples where the body 18313 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium or an alloy thereof.

In some embodiments, the upper and lower endplates 18311 & 18312 are comprised of a material or lattice with an elastic modulus between and including 300 MPa to 130 GPa. Embodiments of the device include examples where the upper and lower endplates are comprised of a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 18313 is comprised of a lattice with an elastic modulus between and including 10 MPa to 12 GPa. Embodiments of the device include examples where the body 18313 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 18313 is comprised of a lattice with an elastic modulus that is substantially similar to the bulk elastic modulus of the adjacent b one. In some examples, the lattice is comprised of a metallic scaffold. In others, the lattice is comprised of a scaffold comprised of titanium or an alloy thereof.

In some embodiments, the fourth implant 18310 is a PLIF implant. In some embodiments, the fourth implant 18310 is a TLIF implant. In some embodiments, the fourth implant 18310 is a PLIF/TLIF implant. In some embodiments, the fourth implant 18310 is an interbody fusion implant. In some embodiments, the fourth implant 18310 is a bone fusion implant. In some embodiments, the fourth implant 18310 is configured for tissue attachment, tissue including but not limited to bony structures and connective tissue. In some embodiments, the fourth implant 18310 is configured to allow tissue ingrowth, tissue including but not limited to bony structures and connective tissue.

In FIGS. 105 to 111 is a fifth implant 19410 with an independent endplate structure. The fifth implant 19410 can be inserted between bony structures or the endplates of two adjacent vertebrae, providing mechanical spacing between them and mechanical stability to promote bone growth, allowing them to fuse together over time. The fifth implant 19410 can be comprised substantially of three components—an upper endplate 19411, a lower endplate 19412 and a body 19413. The upper and lower endplates 19411 & 19412 can be comprised of a biocompatible material with a higher elastic modulus in the superior to inferior direction than the body 19413. The body 19413 can be comprised of a biocompatible material with a lower elastic modulus in the superior to inferior direction than the upper and lower endplates 19411 & 19412.

Figure 107:
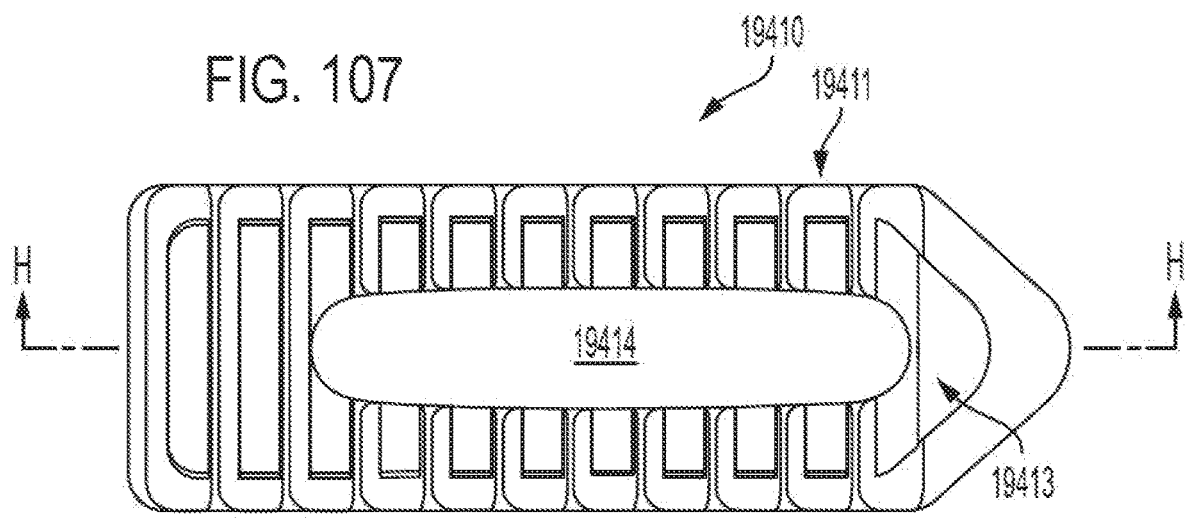
FIG. 107 is a top view of the fifth implant showing a possible configuration of an endplate top surface and the location of a later presented section view.
Figure 108:
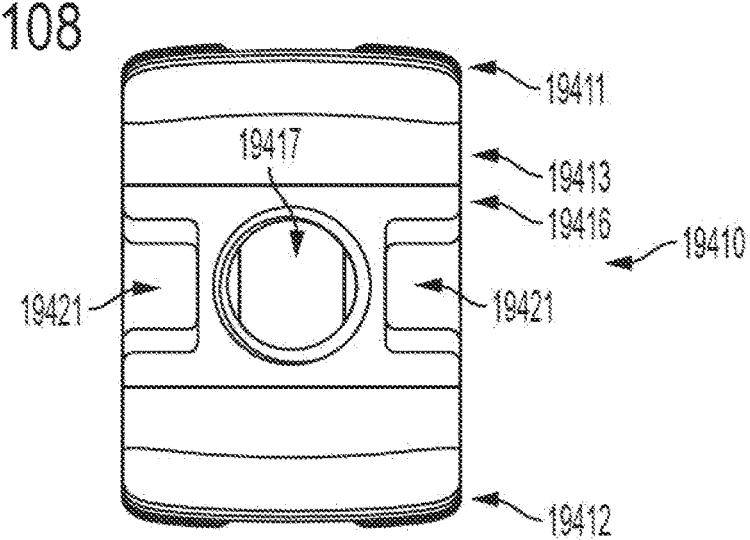
FIG. 108 is a rear view of the fifth implant with an optional rear tool engagement area.
Figure 109:
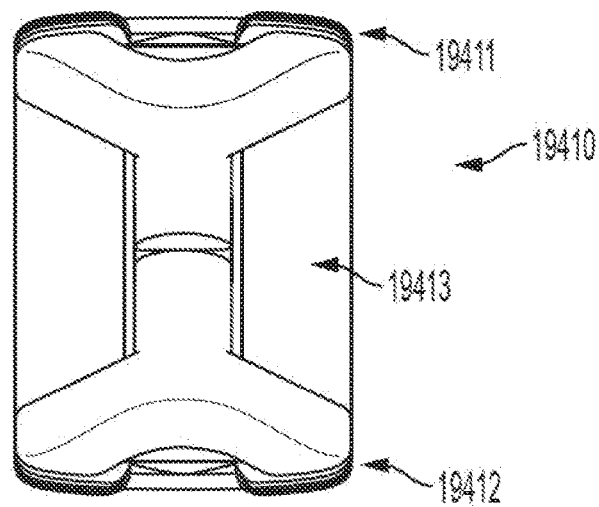
FIG. 109 is a front view of the fifth implant showing the position of the endplates relative to one another.

In FIG. 105 is an isometric view of the fifth implant 19410, showing the independent configuration of the endplates 19411 & 19412 relative to the body 18313. In FIG. 106 is an exploded isometric view of the fifth implant 19410, showing the endplates 19411 & 19412 separated from the body 19413 and showing the lack of a direct and rigid connection between the endplates 19411 & 19412 in this embodiment. There may be direct connections between the endplates 19411 & 19412 to adjust the construct properties as long as the endplates 19411 & 19412 are capable of some movement relative to one another. In FIG. 107 is a top view of the fifth implant 19410 showing an exemplary endplate configuration and identifying line and HH. In FIG. 108 is a rear view of the fifth implant 19410 showing the optional rear tool engagement area. In FIG. 109 is a front view of the fifth implant 19410 showing the position of the endplates relative to one another. In FIG. 110 is a side view of the fifth implant 19410, also showing the position of the endplates relative to one another. In FIG. 111 is a side sectioned view of the fifth implant 19410, sectioned through line HH in FIG. 107, showing that the endplates 19411 & 19412 do not directly contact one another throughout the device in this example.

The upper endplate 19411 and lower endplate 19412 are independent to one another with respect to their ability to move independently of one another. In some embodiments, the upper endplate 19411 and lower endplate 19412 are on opposite sides of the body 19413 so that the endplates 19411 & 19412 can move independently of one another and where the amount of independent movement can be determined largely by the stiffness of the body 19413. While a body is disclosed as a structure that can provide independence between endplates, other structures noted previously may provide a similar independence.

The body 19413 preferably provides mechanical spacing between the adjacent bony structures or vertebrae and provides adequate rigidity between them to allow for bone ingrowth. The use of a body 16113 with a lower elastic modulus than the endplates 19411 & 19412 can allow the new bone growth to be stressed while ingrowth occurs, resulting in a stronger fused bone. The relatively higher modulus of elasticity of the endplates 19411 & 19412 distributes the load across the surface of the body 19413 and reduces the occurrence of the bony structures or vertebral endplates from indenting the upper or lower surface of the body 19413. In some examples, the endplates 19411 & 19412 use optional raised ridges or teeth 19420 to mechanically anchor the endplates 19411 & 19412 to the bony structures or endplates of the adjacent vertebrae. The ridges 19420 can extend from the endplates 19411 & 19412 to the surface of the body 19413 that extends to the superior and inferior surface of the device. In addition to distributing the load across the body 19413 and anchoring the interbody fusion device 16130 relative to the adjacent bony structures or vertebrae, the endplates 19411 & 19412 can allow for bone attachment or ingrowth, providing stability between the implant and the bony structures or the endplates of the adjacent vertebrae.

The fifth implant 19410 also provides optional lumen 19414 as a vertical bone fusion windows for radiolucency or bone fusion. The fusion windows can be used by clinicians to insert one or more compounds that promote bone growth or to assess fusion through the lumen 19414 during the healing process. Some compounds that would be appropriate for use in the fusion or viewing windows 19414 and 19415 are autograft, allograft synthetic graft, or a combination.

The lower endplate 19412 of the fifth implant 19410 can include a tool engagement area 19416 to allow surgical tools to be fastened to the device 19430 during a surgical procedure. In some examples, the tool engagement area 19416 contains one or more threaded openings 19417 that are configured to accept a threaded rod to facilitate placement of the device 19410. On either side of each threaded opening 19417 can be a void 19421 designed to accommodate stabilizers on the threaded rod, if used. While the threaded openings 19417 can provide an adequate amount of leverage to locate the device 19410, the addition of stabilizers on an installation instrument that contact the device 19410 in the voids 19421 can increase the ability of a surgeon to rotate the device during insertion. The rigid section 19416 can be connected to an endplate 19411 & 19412 and/or to the body 19413.

In some embodiments, the upper and lower endplates 19411 & 19412 are comprised of a material or lattice with a volumetric density between and including 60% and 100%. Embodiments of the device include examples where the endplates 19411 & 19412 are comprised of a material or lattice with a volumetric density between and including 80% and 100%, 60% to 90%, 70% and 90%, 60% and 64% and less than 60%. In some embodiments, the body 19413 is comprised of a lattice with a volumetric density between and including 5% to 50%. Embodiments of the device include examples where the body 19413 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium or an alloy thereof.

In some embodiments, the upper and lower endplates 19411 & 19412 are comprised of a material or lattice with an elastic modulus between and including 300 MPa to 130 GPa. Embodiments of the device include examples where the upper and lower endplates are comprised of a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 19413 is comprised of a lattice with an elastic modulus between and including 10 MPa to 12 GPa. Embodiments of the device include examples where the body 19413 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 19413 is comprised of a lattice with an elastic modulus that is substantially similar to the bulk elastic modulus of the adjacent bone. In some examples, the lattice is comprised of a metallic scaffold. In others, the lattice is comprised of a scaffold comprised of titanium or an alloy thereof.

In some embodiments, the fifth implant 19410 is a PLIF implant. In some embodiments, the fifth implant 19410 is a TLIF implant. In some embodiments, the fifth implant 19410 is a PLIF/TLIF implant. In some embodiments, the fifth implant 19410 is an interbody fusion implant. In some embodiments, the fifth implant 19410 is a bone fusion implant. In some embodiments, the fifth implant 19410 is configured for tissue attachment, tissue including but not limited to bony structures and connective tissue. In some embodiments, the fifth implant 19410 is configured to allow tissue in-growth, tissue including but not limited to bony structures and connective tissue.

In FIGS. 112 to 116 is a sixth implant 20540 with an independent endplate structure. The sixth implant 20540 can be inserted between bony structures or the endplates of two vertebrae, providing mechanical spacing between them and mechanical stability to promote bone growth, allowing the vertebrae to fuse together over time. The implant 20540 can be comprised substantially of three components—an upper endplate 20511, a lower endplate 20512 and a body 20513. The upper and lower endplates 20511 & 20512 can be comprised of a biocompatible material with a higher elastic modulus than the body 20513. The body 20513 can be comprised of a biocompatible material with a lower elastic modulus than the upper and lower endplates 20511 & 20512.

Figure 112:
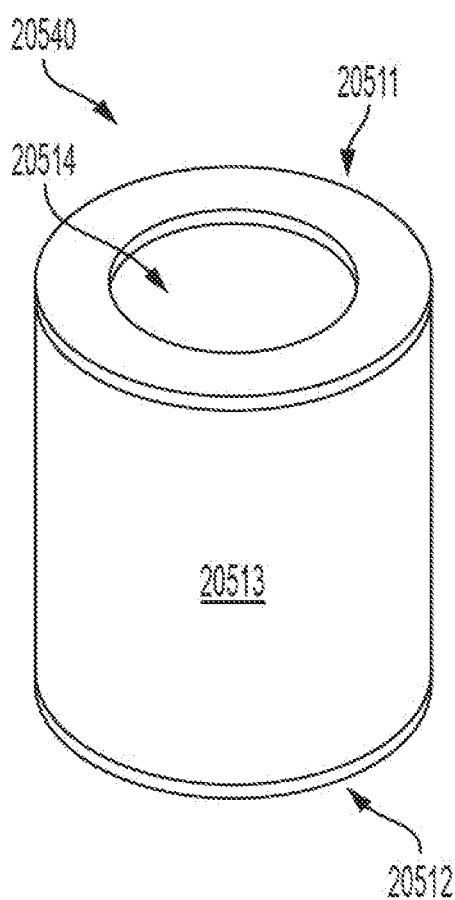
FIG. 112 is an isometric view of a sixth implant showing the inventive configuration of the endplates relative to the body on the exterior of the device.
Figure 113:
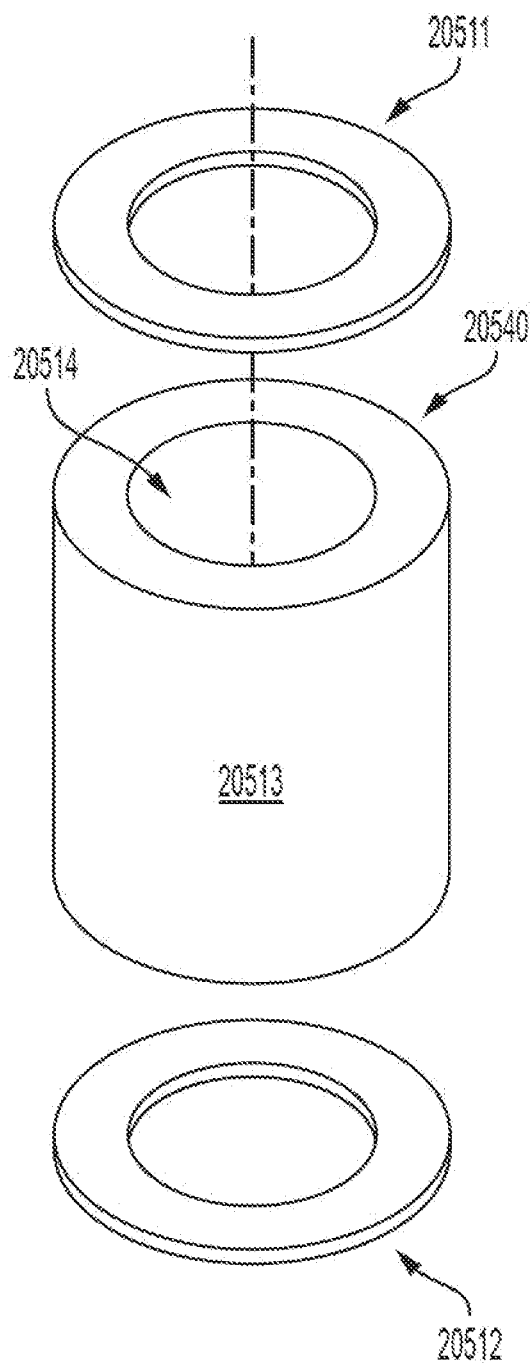
FIG. 113 is an exploded isometric view of the sixth implant showing the endplates separated from the body.
Figure 114:
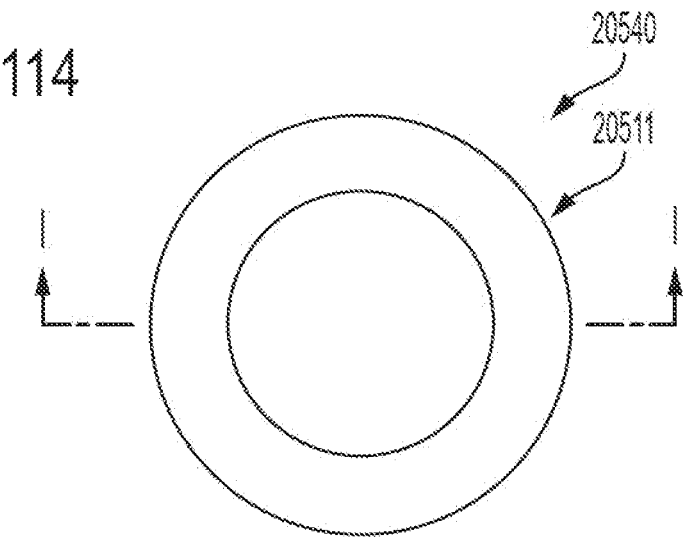
FIG. 114 is a top view of the sixth implant showing a possible configuration of an endplate top surface and the location of a later presented section view.
Figure 115:
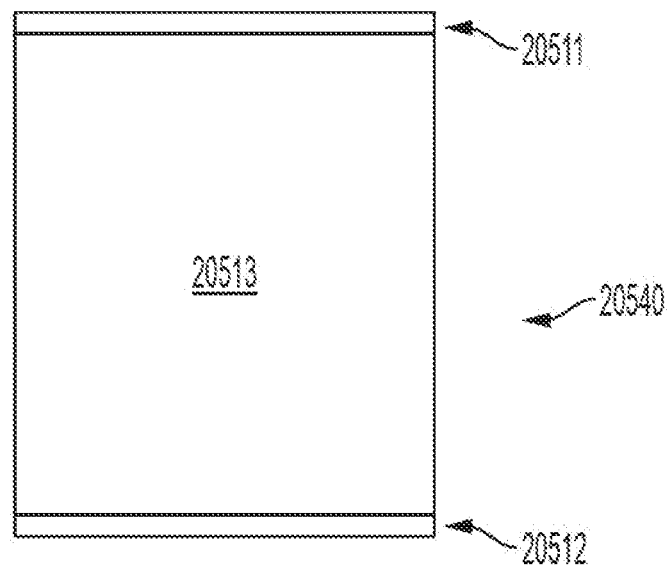
FIG. 115 is a rear view of the sixth implant configured without a rear tool engagement area.
Figure 116:
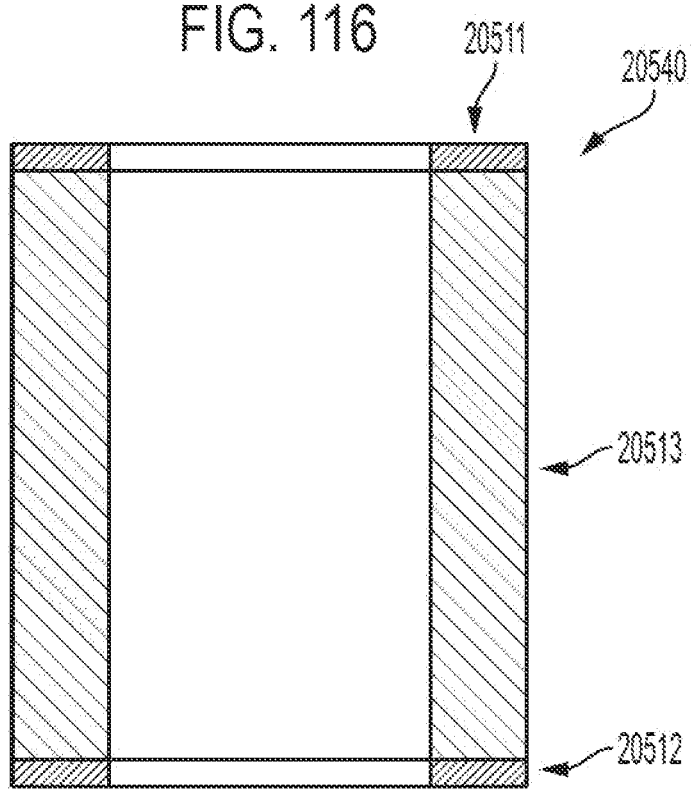
FIG. 116 is a side sectioned view of the sixth implant, sectioned through line II in FIG. 114.

In FIG. 112 is an isometric view of the sixth implant 20540, showing the independent configuration of the endplates 20511 & 20512 relative to the body 20513. In FIG. 113 is an exploded isometric view of the implant 20540, showing the endplates 20511 & 20512 separated from the body 20513 and showing the lack of a direct and rigid connection between the endplates 20511 & 20512 in this embodiment. There may be direct connections between the endplates 20511 & 20512 to adjust the construct properties as long as the endplates 20511 & 20512 are capable of some movement relative to one another. In FIG. 114 is a top view of the implant 20540 showing an exemplary endplate configuration and identifying line II. In FIG. 115 is a rear view of the implant 20540 showing the position of the endplates relative to one another. In FIG. 116 is a side sectioned view of the implant 20540, sectioned through line II in FIG. 114 showing that the endplates 20511 & 20512 do not directly contact one another throughout the device in this example.

The upper endplate 20511 and lower endplate 20512 are independent to one another with respect to their ability to move independently of one another. In some embodiments, the upper endplate 20511 and lower endplate 20512 are on opposite sides of the body 20513 so that the endplates 20511 & 20512 can move independently of one another and where the amount of independent movement can be determined largely by the stiffness of the body 20513. While a body is disclosed as a structure that can provide independence between endplates, other structures noted previously may provide a similar independence.

The body 20513 preferably provides mechanical spacing of the implant site and provides adequate rigidity to allow for bone ingrowth. The use of a body 20513 with a lower elastic modulus than the endplates 20511 & 20512 can allow the new bone growth to be stressed while ingrowth occurs, resulting in a stronger fused bone. The relatively higher modulus of elasticity of the endplates 20511 & 20512 distributes the load across the surface of the body 20513 and prevents the indentation of the upper or lower surface of the body 20513. In some examples, the endplates 20511 & 20512 use optional raised ridges or teeth to mechanically anchor the endplates 20511 & 20512 and prevent expulsion. The endplates 20511 & 20512 can allow for bone attachment or ingrowth, providing stability between the implant and the patient's bone.

The implant 20540 also provides optional lumen 20514 as a vertical bone fusion window for radiolucency or bone fusion. The fusion window can be used by clinicians to insert one or more compounds that promote bone growth or to assess fusion through the lumen 20514 during the healing process. Some compounds that would be appropriate for use in the fusion or viewing windows 20514 and 20515 are autograft, allograft, synthetic graft, or a combination.

In some embodiments, the upper and lower endplates 20511 & 20512 are comprised of a material or lattice with a volumetric density between and including 60% and 100%. Embodiments of the device include examples where the endplates 20511 & 20512 are comprised of a material or lattice with a volumetric density between and including 80% and 100%, 60% and 90%, 70% and 90%, 60% and 64% and less than 60%. In some embodiments, the body 20513 is comprised of a lattice with a volumetric density between and including 5% to 50%. Embodiments of the device include examples where the body 20513 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium or an alloy thereof.

In some embodiments, the upper and lower endplates 20511 & 20512 are comprised of a material or lattice with an elastic modulus between and including 300 MPa to 130 GPa. Embodiments of the device include examples where the upper and lower endplates are comprised of a material or lattice with an elastic modulus between and including 300

MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 20513 is comprised of a lattice with an elastic modulus between and including 10 MPa to 12 GPa. Embodiments of the device include examples where the body 20513 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 20513 is comprised of a lattice with an elastic modulus that is substantially similar to the elastic modulus of the adjacent bone. In some examples, the lattice is comprised of a metallic scaffold. In others, the lattice is comprised of a scaffold comprised of titanium or an alloy thereof.

In some embodiments, the sixth implant 20540 is a vertebral body replacement or corpectomy (hereinafter "VBR") implant. In some embodiments, the sixth implant 20540 is an ALIF implant. In some embodiments, the sixth implant 20540 is a cervical stand-alone implant. In some embodiments, the sixth implant 20540 is an ankle fusion spacer implant. In some embodiments, the sixth implant 20540 is a bone fusion implant. In some embodiments, the sixth implant 20540 is configured for tissue attachment, tissue including but not limited to bony structures and connective tissue. In some embodiments, the sixth implant 20540 is configured to allow tissue in-growth, tissue including but not limited to bony structures and connective tissue.

In FIGS. 117 to 123 is a seventh implant 21650 with an independent endplate structure. The seventh implant 21650 can be inserted in or between bones, segments of bone or within an area carved out of a single bone to provide mechanical spacing and mechanical stability to promote bone growth. The implant 21650 can be comprised substantially of three components—an upper endplate 21611, a lower endplate 21612 and a body 21613. The upper and lower endplates 21611 & 21612 can be comprised of a biocompatible material with a higher elastic modulus than the body 21613. The body 21613 can be comprised of a biocompatible material with a lower elastic modulus than the upper and lower endplates 21611 & 21612.

Figure 119:
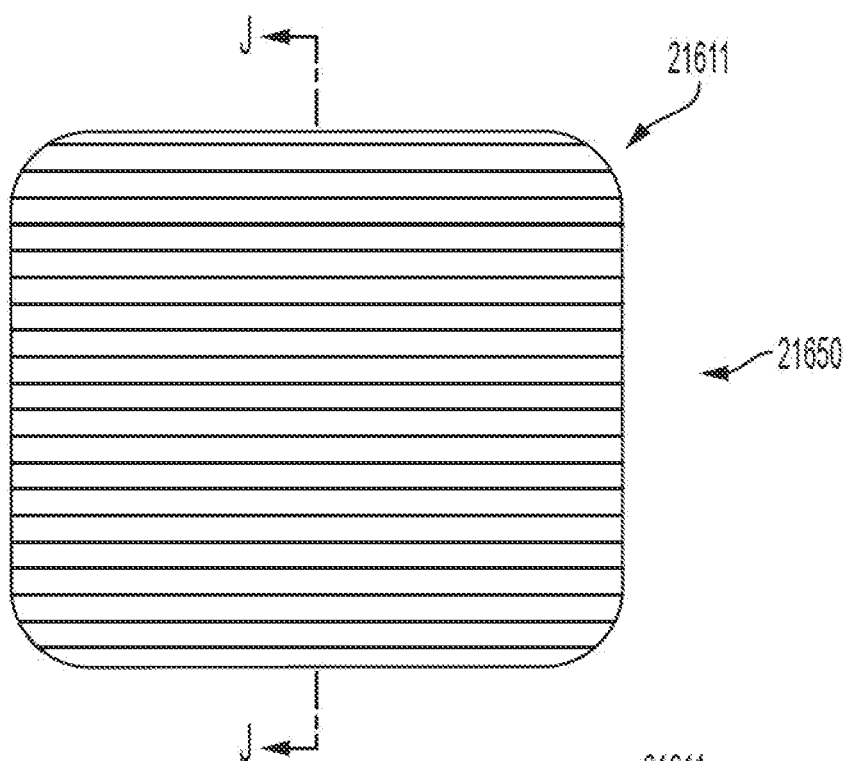
FIG. 119 is a top view of the seventh implant showing a possible configuration of an endplate top surface and the location of a later presented section view.
Figure 120:
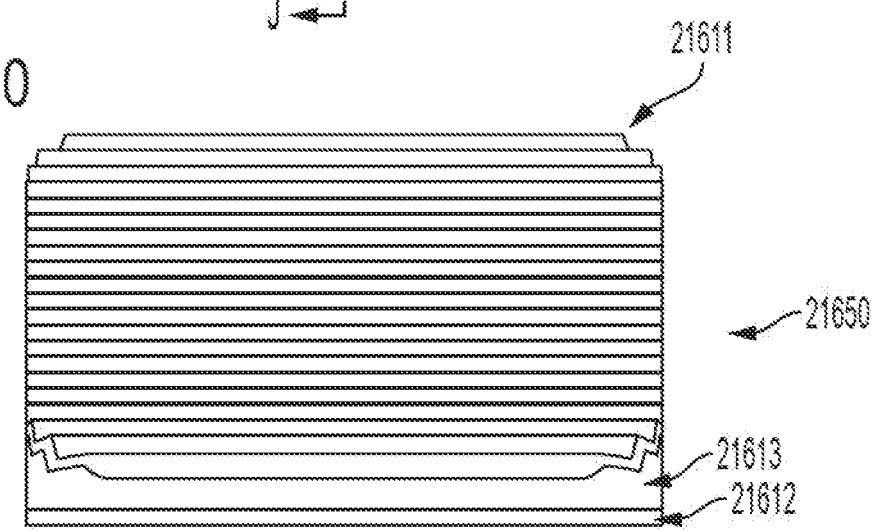
Figure 121:
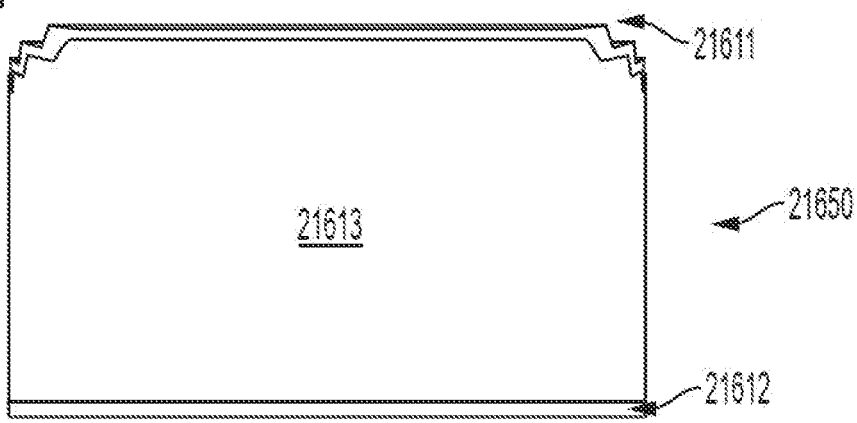
Figure 122:
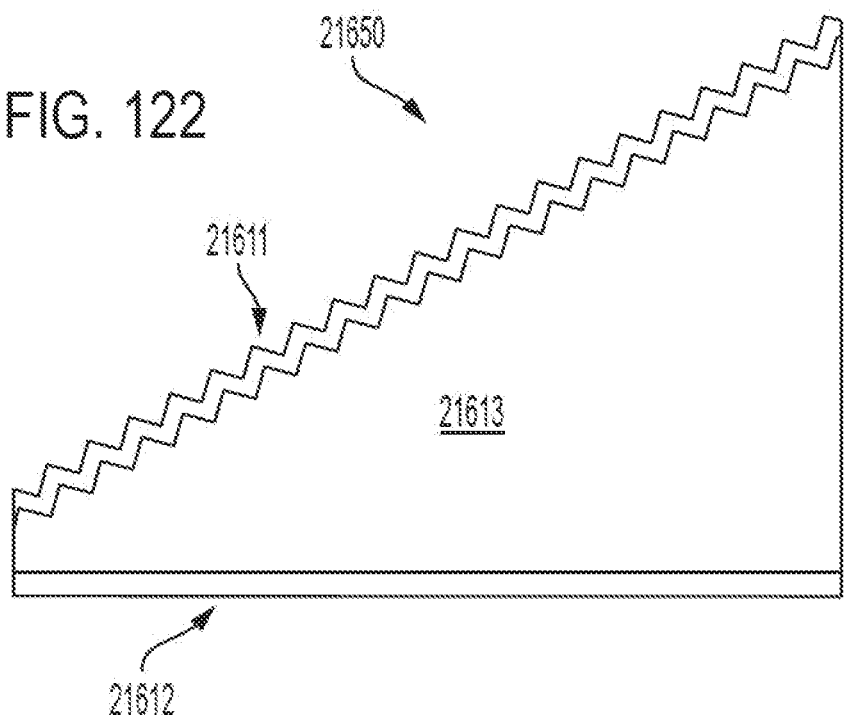
Figure 123:
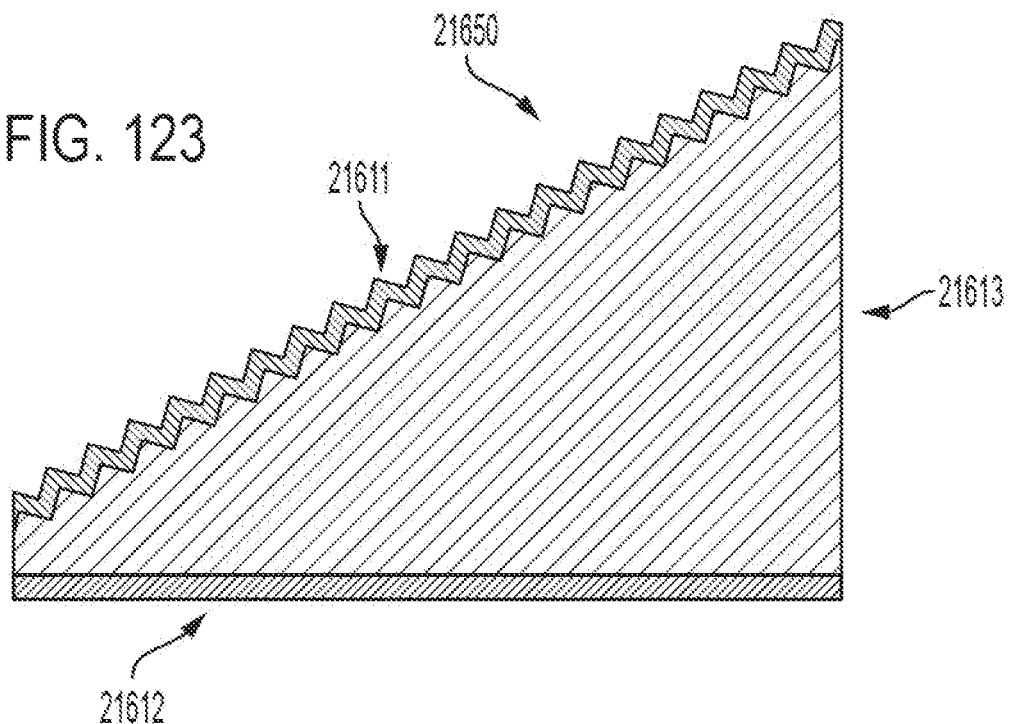

In FIG. 117 is an isometric view of the implant 21650, showing the independent configuration of the endplates 21611 & 12612 relative to the body 21613. In FIG. 118 is an exploded isometric view of the implant 21650, showing the endplates 21611 & 21612 separated from the body 21613 and showing the lack of a direct and rigid connection between the endplates 21611 & 21612 in this embodiment. There may be direct connections between the endplates 21611 & 21612 to adjust the construct properties as long as the endplates 21611 & 21612 are capable of some movement relative to one another. In FIG. 119 is a top view of the implant 21650 showing an exemplary endplate configuration and identifying line JJ. In FIG. 120 is a rear view of the implant 21650. In FIG. 121 is a front view of the implant 21650 showing the position of the endplates relative to one another. In FIG. 122 is a side view of the implant 21650, also showing the position of the endplates relative to one another. In FIG. 123 is a side sectioned view of the implant 21650, sectioned through line JJ in FIG. 119 and showing that the endplates 21611 & 21612 do not directly contact one another throughout the device in this example.

The upper endplate 21611 and lower endplate 21612 are independent to one another with respect to their ability to move independently of one another. In some embodiments, the upper endplate 21611 and lower endplate 21612 are on opposite sides of the body 21613 so that the endplates 21611 & 21612 can move independently of one another and where the amount of independent movement can be determined largely by the stiffness of the body 21613. While a body is disclosed as a structure that can provide independence between endplates, other structures noted previously may provide a similar independence.

The body 21613 preferably provides mechanical spacing of the implant site and provides adequate rigidity to allow for bone ingrowth. The use of a body 21613 with a lower elastic modulus than the endplates 21611 & 21612 can allow the new bone growth to be stressed while ingrowth occurs, resulting in a stronger fused bone. The relatively higher modulus of elasticity of the endplates 21611 & 21612 distributes the load across the surface of the body 21613 and prevents the indentation of the upper or lower surface of the body 21613. In some examples, the endplates 21611 & 21612 use optional raised ridges or teeth to mechanically anchor the endplates 21611 & 21612 and prevent expulsion. The endplates 21611 & 21612 can allow for bone attachment or ingrowth, providing stability between the implant and the patient's bone.

In some embodiments, the upper and lower endplates 21611 & 21612 are comprised of a material or lattice with a volumetric density between and including 60% and 100%. Embodiments of the device include examples where the endplates 21611 & 21612 are comprised of a material or lattice with a volumetric density between and including 80% and 100%, 60% to 90%, 70% and 90%, 60% and 64% and less than 60%. In some embodiments, the body 21613 is comprised of a lattice with a volumetric density between and including 5% to 50%. Embodiments of the device include examples where the body 21613 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium or an alloy thereof.

In some embodiments, the upper and lower endplates 21611 & 21612 are comprised of a material or lattice with an elastic modulus between and including 300 MPa to 130 GPa. Embodiments of the device include examples where the upper and lower endplates are comprised of a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 21613 is comprised of a lattice with an elastic modulus between and including 10 MPa to 12 GPa. Embodiments of the device include examples where the body 21613 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 21613 is comprised of a lattice with an elastic modulus that is substantially similar to the bulk elastic modulus of the adjacent bone. The body 21613 may also have an elastic modulus gradient matching the slope to maintain constant stiffness across the length. In some examples, the lattice is comprised of a metallic scaffold. In others, the lattice is comprised of a scaffold comprised of titanium or an alloy thereof.

In some embodiments, the seventh implant 21650 is an osteotomy wedge. In some embodiments, the seventh implant 21650 is a bone fusion implant. In some embodiments, the seventh implant 21650 is configured for tissue attachment, tissue including but not limited to bony structures and connective tissue. In some embodiments, the seventh implant 21650 is configured to allow tissue ingrowth, tissue including but not limited to bony structures and connective tissue.

In FIGS. 124 to 130 is an eighth implant 22760 with an independent endplate structure. The eighth implant 22760 can be inserted in or between bones, segments of bone or within an area carved out of a single bone to provide mechanical spacing and mechanical stability to promote bone growth. The implant 22760 can be comprised substantially of three components—an upper endplate 22711, a lower endplate 22712 and a body 22713. The upper and lower endplates 22711 & 22712 can be comprised of a biocompatible material with a higher elastic modulus than the body 22713. The body 22713 can be comprised of a biocompatible material with a lower elastic modulus than the upper and lower endplates 22711 & 22712.

Figure 124:
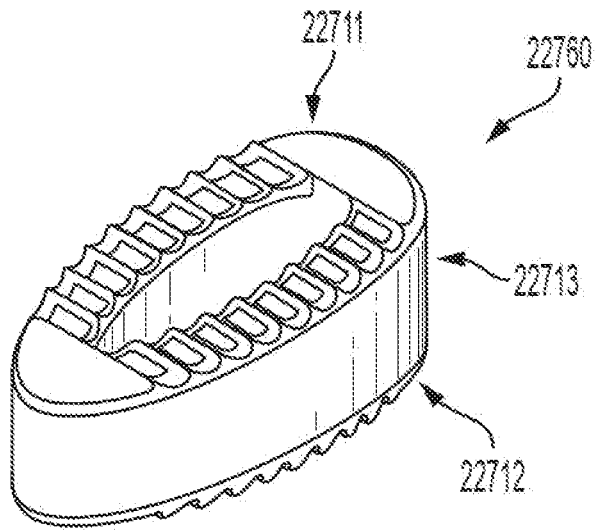
Figure 125:
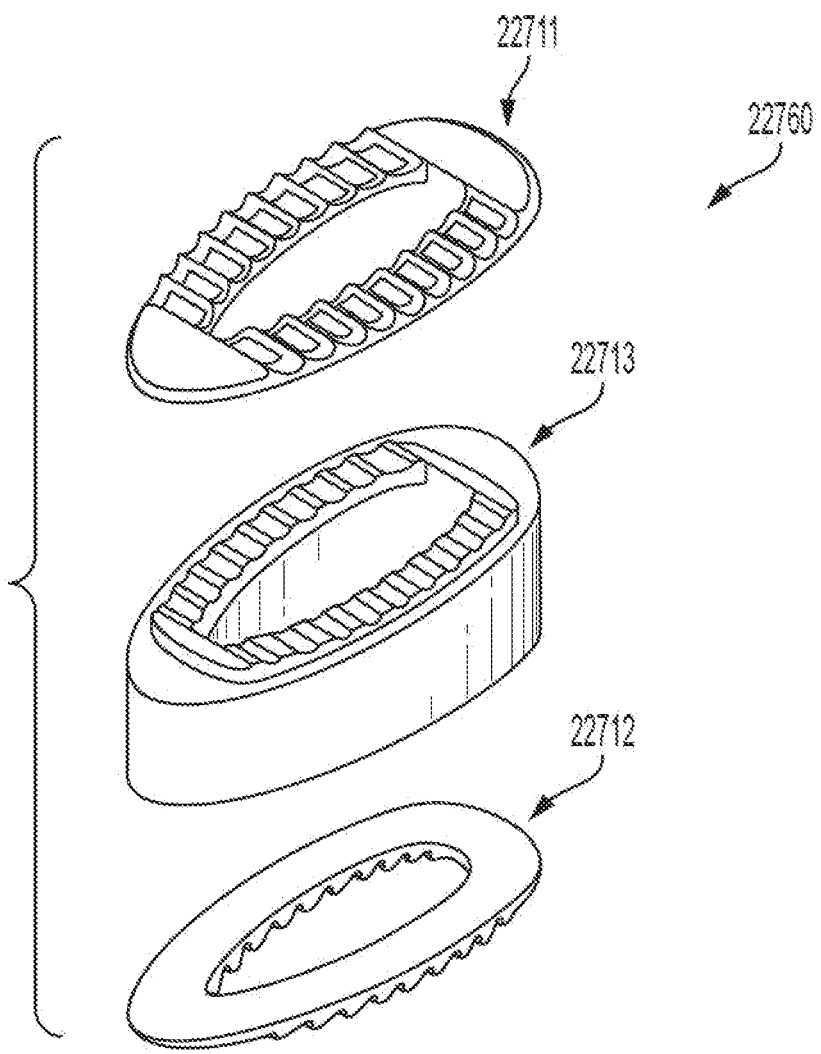
Figure 126:
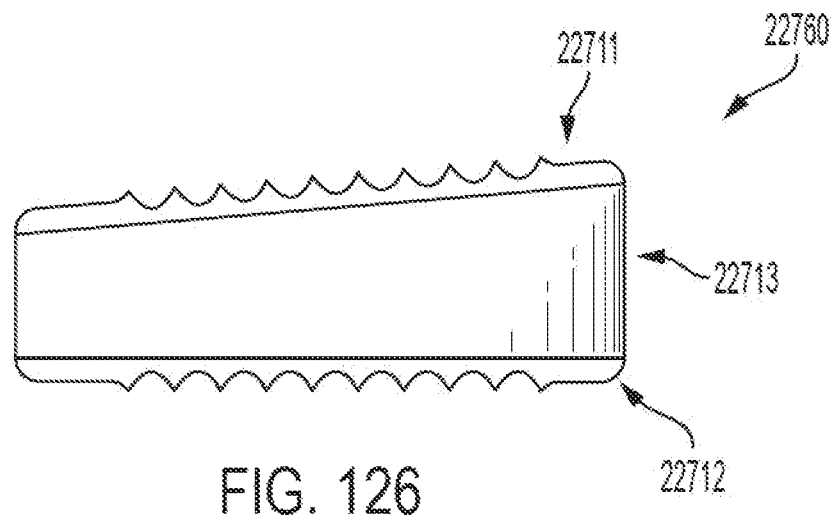
Figure 127:
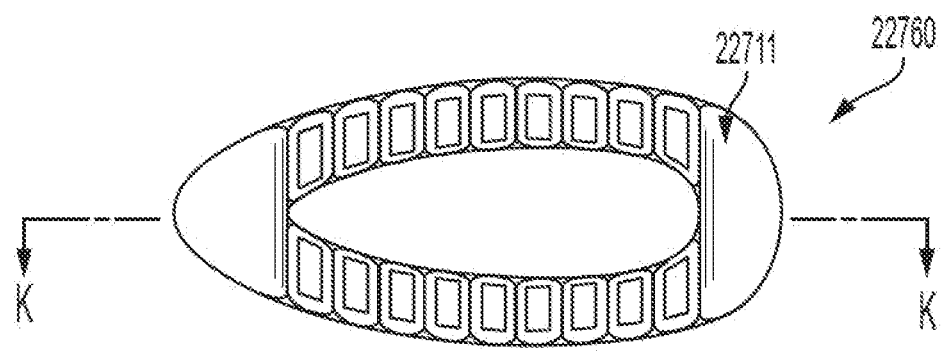
Figure 128:
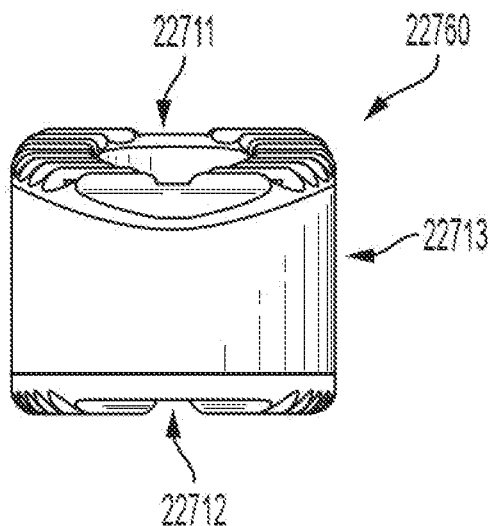
Figure 129:
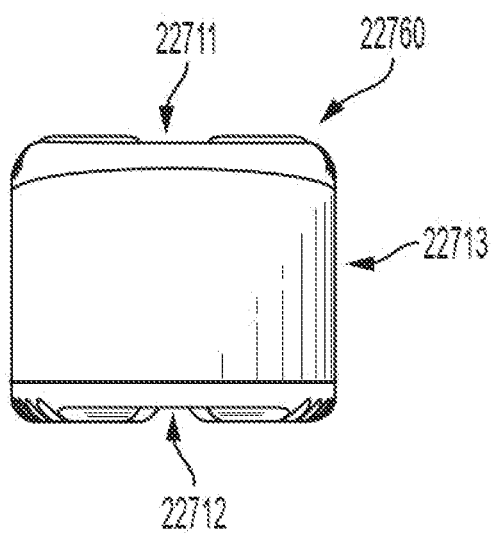
Figure 130:
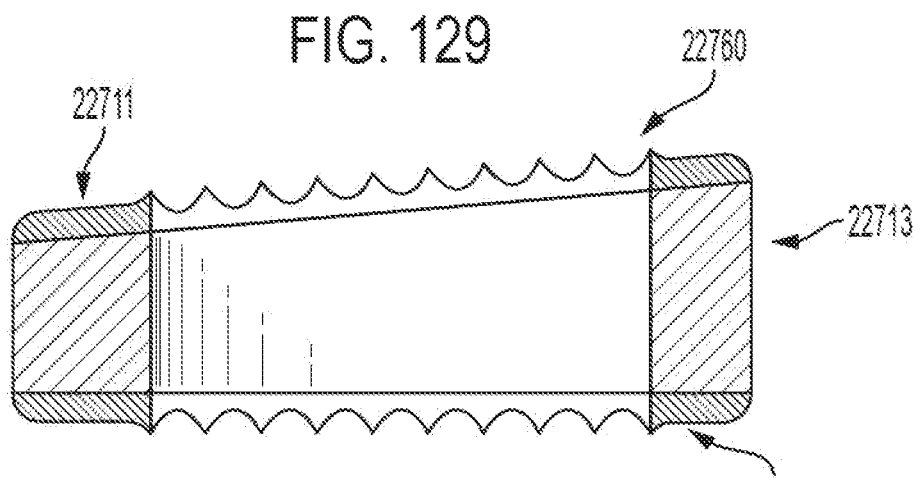

In FIG. 124 is a perspective view of the implant 22760, showing the independent configuration of the endplates 22711 & 22712 relative to the body 22713. In FIG. 125 is an exploded perspective view of the implant 22760, showing the endplates 22711 & 22712 separated from the body 22713 and showing the lack of a direct and rigid connection between the endplates 22711 & 22712 in this embodiment. There may be direct connections between the endplates 22711 & 22712 to adjust the construct properties as long as the endplates 22711 & 22712 are capable of some movement relative to one another. In FIG. 126 is a side view of the implant 22760, also showing the position of the endplates relative to one another. In FIG. 127 is a top view of the implant 22760 showing an exemplary endplate configuration and identifying line KK. In FIG. 128 is a front view and in FIG. 129 is a rear view of the implant 22760. In FIG. 130 is a side sectioned view of the implant 22760, sectioned through line KK in FIG. 127 and showing that the endplates 22711 & 22712 do not directly contact one another throughout the device in this example.

The upper endplate 22711 and lower endplate 22712 are independent to one another with respect to their ability to move independently of one another. In some embodiments, the upper endplate 22711 and lower endplate 22712 are on opposite sides of the body 22713 so that the endplates 22711 & 22712 can move independently of one another and where the amount of independent movement can be determined largely by the stiffness of the body 22713. While a body is disclosed as a structure that can provide independence between endplates, other structures noted previously may provide a similar independence.

The body 22713 preferably provides mechanical spacing of the implant site and provides adequate rigidity to allow for bone ingrowth. The use of a body 22713 with a lower elastic modulus than the endplates 22711 & 22712 can allow the new bone growth to be stressed while ingrowth occurs, resulting in a stronger fused bone. The relatively higher modulus of elasticity of the endplates 22711 & 22712 distributes the load across the surface of the body 22713 and prevents the indentation of the upper or lower surface of the body 22713. In some examples, the endplates 22711 & 22712 use optional raised ridges or teeth to mechanically anchor the endplates 22711 & 22712 and prevent expulsion. The endplates 22711 & 22712 can allow for bone attachment or ingrowth, providing stability between the implant and the patient's bone.

In some embodiments, the upper and lower endplates 22711 & 22712 are comprised of a material or lattice with a volumetric density between and including 60% and 100%. Embodiments of the device include examples where the endplates 22711 & 22712 are comprised of a lattice with a volumetric density between and including 80% and 100%, 60% and 90%, 70% and 90%, 60% and 64% and less than 60%. In some embodiments, the body 22713 is comprised of a lattice with a volumetric density between and including 5% to 50%. Embodiments of the device include examples where the body 22713 is comprised of a lattice with a volumetric density between and including 5% to 10%, 10% to 18%, 18% to 25%, 25% to 38% and 35% to 50%. In some examples, the lattice is comprised of a metallic scaffold. In others, the lattice is comprised of a scaffold comprised of titanium or an alloy thereof.

In some embodiments, the upper and lower endplates 22711 & 22712 are comprised of a material or lattice with an elastic modulus between and including 300 MPa to 130 GPa. Embodiments of the device include examples where the upper and lower endplates are comprised of a material or lattice with an elastic modulus between and including 300 MPa to 5 GPa, 1 GPa to 5 GPa, 5 GPa to 10 GPa, 10 GPa to 15 GPa., 15 GPa to 21 GPa, 21 GPa to 130 GPa and 300 MPa to 130 GPa. In some embodiments, the body 22713 is comprised of a lattice with an elastic modulus between and including 10 MPa to 12 GPa. Embodiments of the device include examples where the body 22713 is comprised of a scaffold with an elastic modulus between and including 10 MPa to 300 MPa, 300 MPa to 2 GPa, 300 MPa to 4 GPa, 1 GPa to 5 GPa, 2 GPa to 4 GPa, 3 GPa to 9 GPa, 8 GPa to 12 GPa and 300 MPa to 12 GPa. In another example, the body 22713 is comprised of a lattice with an elastic modulus that is substantially similar to the bulk elastic modulus of the adjacent bone. The body 22713 may also have an elastic modulus gradient matching the slope to maintain constant stiffness across the length. In some examples, the lattice is comprised of a metallic scaffold. In others, the lattice is comprised of a scaffold comprised of titanium or an alloy thereof.

In some embodiments, the eighth implant 22760 is a PLIF implant. In some embodiments, the eighth implant 22760 is a TLIF implant. In some embodiments, the eighth implant 22760 is a PLIF/TLIF implant. In some embodiments, the eighth implant 22760 is an ALIF implant. In some embodiments, the eighth implant 22760 is a VBR implant. In some embodiments, the eighth implant 22760 is a cervical stand-alone implant. In some embodiments, the eighth implant 22760 is an interbody fusion implant. In some embodiments, the eighth implant 22760 is an osteotomy wedge. In some implants, the eighth implant 22760 is an ankle fusion spacer implant. In some embodiments, the eighth implant 22760 is a bone fusion implant. In some embodiments, the eighth implant 22760 is configured for tissue attachment, tissue including but not limited to bony structures and connective tissue. In some embodiments, the eighth implant 22760 is configured to allow tissue in-growth, tissue including but not limited to bony structures and connective tissue.

In some embodiments of the implants with independent endplates disclosed herein, a first endplate is mechanically connected to a second endplate substantially only via a body, where the body is disposed at least partially between the first and second endplates. In some embodiments, substantially only via the body refers to a connection where the body has an elastic modulus that is at least 50 percent of a construct elastic modulus. In some embodiments, substantially only via the body refers to a connection where the body has an elastic modulus that is at least 90 percent of a construct elastic modulus. In some embodiments, the implant is configured to fuse multiple levels of the spine. In some embodiments, the implant is configured to fuse adjacent levels of the spine. In some embodiments, the implant is configured to fuse non-adjacent levels of the spine. In some embodiments, an endplate on the implant is configured to contact a bony structure. In some embodiments, an endplate on the implant is configured to contact tissue. In some embodiments, two endplates on the implant are configured to contact bony structures. In some embodiments, one endplate on the implant is configured to contact a bony structure and another endplate is configured to contact tissue. In some embodiments, two endplates on the implant are configured to contact tissue. In some embodiments, tissue is a connective tissue.

For the exemplary embodiments disclosed above and for other implants, certain ranges of elastic moduli for the body and endplates appear to optimize bone growth in implants of a given construct elastic modulus range and comprised of a lattice structure. Table 1 represents the ideal ranges of elastic moduli for the body and endplates in implants of a given construct elastic modulus range. Table 1 is calculated for a first endplate height of 2.5 mm, a body height of 2.0 mm and a second endplate height of 2.5 mm. Table 2 represents the preferential ranges of elastic moduli for the body and endplates in implants with a first endplate height of 1.5 mm, a body height of 4.0 mm, a second endplate height of 1.5 mm and within a given construct elastic modulus range. Table 3 represents the preferential ranges of elastic moduli for the body and endplates in implants with a first endplate height of 2.5 mm, a body height of 2.0 mm, a second endplate height of 2.5 mm and within a given construct elastic modulus range. Table 4 represents the most preferential ranges of elastic moduli for the body and endplates in PLIF/TLIF type implants with a first endplate height of 2.5 mm, a body height of 2.0 mm, a second endplate height of 2.5 mm and within a given construct elastic modulus range. Table 5 represents the most preferential ranges of elastic moduli for the body and end plates in ALIF type implants with a first end plate height of 2.5 mm, a body height of 6.0 mm, a second endplate height of 2.5 mm and within a given construct elastic modulus range.

The values given for the body and endplate elastic moduli for a given range of construct elastic moduli provide the ideal relationship between the stiffness of the endplates to the body to optimize bone growth. It is theorized that the increased loading of new bone growth stimulates bone growth and results in stronger bone growth. The use of the inventive implant structure and values allow for the use of a lower elastic modulus body protected by higher elastic modulus endplates to allow for a large volume of bone loading. The relationships given in Tables 1 to 5 can be applied to multiple types of implants of various footprint areas and heights. The tables and equations disclosed herein are intended to provide heights and elastic moduli for an implant at an actual stiffness. Since the tables and equations are based on an actual or as-tested stiffness value, they may be adjusted to include an adjustment factor for a method of manufacture. For instance, if a specific additive process is known to produce an implant with an actual stiffness that is 90% of the calculated value, the tables and equations can include an adjustment to compensate for this difference.

The method disclosed herein uses elastic modulus to approximate the bending stiffness of the endplates, however, their bending stiffness may be changed using equivalent methods. For examples, instead of reducing the volumetric density of an endplate, cutouts can be provided to reduce the integrity of the endplate. The use of partial cutouts on the outer surface of an endplate can serve to reduce its bending stiffness and provide anti-expulsion properties for the implant. The area of the endplates can also be reduced to reduce their bending stiffness. Where the footprint area of an implant is the area of the implant when viewed from above, less the area of any lumen, the endplate area can be between and including 10% to 100% of the footprint area. In general, the use of an endplate with an area less than the footprint would require the elastic modulus of the endplate to be increased.

The construct elastic modulus of an implant is related to the stiffness of an implant in the following equation:

$$K_{UBL} = A * E_{UBL} / L_{UBL}$$

Where:
$K_{UBL}$=Construct stiffness in the vertical direction (N/m), where the vertical direction is the direction from one endplate to another endplate
A=Average footprint area of the construct less the area of the lumen, if any ($m^2$)
$E_{UBL}$=Modulus of elasticity of construct (GPa)
$L_{UBL}$=Height of the construct (m)

Because the stiffness of an implant is dependent on the average construct footprint area, construct elastic modulus and the construct height, any one of these may be adjusted to change the stiffness. The method disclosed herein optimizes the composition of the construct elastic modulus between that of the endplates and body, but because of the relationship between the stiffness and average construct footprint, the optimal ranges may be adjusted by changing the average construct footprint.

The modulus of elasticity of an implant is dependent on the height of the implant, the height and modulus of elasticity of the body, and the height and modulus of elasticity of the endplates. In an implant with one body and two endplates, the construct modulus of elasticity is generally represented by the following equation:

$$E_{UBL} = L_{UBL} / (L_U/E_U + L_L/E_L + L_B/E_B)$$

Where:
$E_{UBL}$=Modulus of elasticity of construct (GPa)
$L_{UBL}$=Height of the construct (m)
$L_U$=Height of a first endplate (m)
$E_U$=Modulus of elasticity of a first endplate (GPa)
$L_L$=Height of a second endplate (m)
$E_L$=Modulus of elasticity of a second endplate (GPa)
$L_B$=Height of the body (m)
$E_B$=Modulus of elasticity of the body (GPa)

The stiffness, footprint area and height of a construct may be predetermined values, potentially related to patient anatomy or standard sizes, so that the height of each endplate, modulus of elasticity of the endplates, the height of the body, and the modulus of elasticity of the body must be calculated. Since the body is generally much taller than the height of the endplates, the body's elastic modulus is the main driver in determining the construct's elastic modulus. With the body's elastic modulus as the main driver in construct elastic modulus, the body's elastic modulus is often near that of the construct. It has been found that varying the endplate elastic moduli relative to that of the body, within certain ranges, optimizes the stiffness of the endplates relative to that of the body within a range of given construct values.

As apparent in the equations provided above, the stiffness of a material is a function of its elastic modulus, height and area. The height and area of an implant are generally given, in that they are specified based on a patient's need (i.e. size of implant location). In some cases, the construct elastic modulus or stiffness can be specified as well, resulting in a need to determine an appropriate elastic modulus and height for the body and endplates. In some cases, if the endplates and/or the body do not have the same footprint area as the construct, the area of each may also need to the be selected.

For each range of construct elastic moduli, a range of elastic moduli are given for the body and endplates because a range of values can be appropriate by changing the elastic modulus of each layer. For instance, if the elastic modulus of the body is reduced with all other variables remaining the same, the elastic modulus of the endplates would need to be increased to retain the same construct elastic modulus. Increasing the height of a layer with a homogenous elastic modulus generally increases that layer's impact on construct modulus. Therefore, it is possible to reduce the thickness of the endplate, while increasing its elastic modulus to maintain a level construct modulus. The opposite is also possible so that the height of the body may be increased and its elastic modulus reduced to maintain a level construct modulus.

The invention claimed is:

1. An implant comprising:
a first independent endplate comprising an upper surface and a lower surface configured to contact a first segment of tissue upon implantation;
a second independent endplate spaced apart from the first independent endplate, the second independent endplate comprising a lower surface and an upper surface configured to contact a second segment of tissue upon implantation; and
a biocompatible three-dimensionally printed body comprising a metallic lattice structure and disposed between the upper surface of the first independent endplate and the lower surface of the second independent endplate such that at least one portion of the first independent endplate is mechanically connected to the second independent endplate only via the body;
wherein the biocompatible three-dimensionally printed body comprises at least one pore having a diameter of 600 μm.

2. The implant of claim 1, wherein an elastic modulus of the body is lower than an elastic modulus of the first independent endplate and an elastic modulus of the second independent endplate.

3. The implant of claim 2, wherein the first independent endplate and the second independent end plate comprise a porosity configured to promote bone growth.

4. The implant of claim 3, wherein the lower surface of the first independent endplate comprises a first plurality of ridges configured to mechanically anchor the implant to the first segment of tissue.

5. The implant of claim 4, wherein the first plurality of ridges extend from the lower surface of the first independent endplate to an adjacent surface of the body.

6. The implant of claim 3, wherein the upper surface of the second independent endplate comprises a second plurality of ridge configured to mechanically anchor the implant to the second segment of tissue.

7. The implant of claim 6, wherein the second plurality of ridge extends from the upper surface of the second independent endplate to an adjacent surface of the body.

8. The implant of claim 3, wherein the body comprises a lumen configured to receive a compound for promoting healing at an implantation site of the implant.

9. The implant of claim 8, wherein the lumen comprises an oval-shaped structure.

10. The implant of claim 3, wherein the body comprises a lumen configured to increase radiolucency of the implant.

11. The implant of claim 3, wherein the first independent endplate comprises a tool engagement area configured to receive a surgical tool during implantation.

12. The implant of claim 3, wherein the metallic lattice structure comprises a scaffold configured to support bone growth and the elastic modulus of the body is configured to allow new bone growth to be loaded with physiological forces.

13. The implant of claim 3, wherein the three-dimensionally printed body comprises at least 50% of a construct elastic modulus in a direction between the first endplate and the second endplate.

14. The implant of claim 13, wherein the three-dimensionally printed body comprises a surface texture configured to allow for increased bone attachment.

15. The implant of claim 3, wherein the implant is an interbody bone fusion implant.

16. The implant of claim 3, wherein the implant comprises a single piece three-dimensional printed structure.

17. The implant of claim 3, wherein the metallic lattice structure comprises a plurality of unit cells.

18. The implant of claim 17, wherein each of the unit cells comprises a diamond shaped structure.

19. The implant of claim 1, wherein the metallic lattice structure comprises titanium.

20. The implant of claim 19, wherein the metallic lattice structure comprises an anisotropic lattice structure.

21. The implant of claim 1, wherein at least one of the first independent endplate and the second independent endplate comprises a second lattice structure.

22. The implant of claim 1, wherein the implant comprises a lumbar implant.

23. The implant of claim 22, wherein the lumbar implant comprises one of: a Posterior implant, a Transverse implant, an Anterior implant, a Lateral implant.

24. An implant comprising:
a first independent endplate comprising an upper surface and a lower surface configured to contact a first segment of tissue upon implantation;
a second independent endplate spaced apart from the first independent endplate, the second independent endplate comprising a lower surface and an upper surface configured to contact a second segment of tissue upon implantation; and
a biocompatible three-dimensionally printed body comprising a metallic lattice structure and disposed between the upper surface of the first independent endplate and the lower surface of the second independent endplate such that at least one portion of the first independent endplate is mechanically connected to the second independent endplate only via the body;
wherein an elastic modulus of the body is lower than an elastic modulus of the first independent endplate and an elastic modulus of the second independent endplate;
wherein the first independent endplate and the second independent end plate comprise a porosity configured to promote bone growth; and
wherein the first independent endplate comprises a tool engagement area configured to receive a surgical tool during implantation and the tool engagement area comprises a threaded opening configured to receive a device for facilitating placement of the implant.

25. The implant of claim 24, wherein the device comprises a threaded rod.

26. The implant of claim 25, wherein the tool engagement area and the first independent endplate comprise a single piece of material.

27. The implant of claim 26, wherein the tool engagement area is removably coupled to the first independent endplate.

28. An implant comprising:
- a first independent endplate comprising an upper surface and a lower surface configured to contact a first segment of tissue upon implantation;
- a second independent endplate spaced apart from the first independent endplate, the second independent endplate comprising a lower surface and an upper surface configured to contact a second segment of tissue upon implantation; and
- a biocompatible three-dimensionally printed body comprising a metallic lattice structure and disposed between the upper surface of the first independent endplate and the lower surface of the second independent endplate such that at least one portion of the first independent endplate is mechanically connected to the second independent endplate only via the body;
- wherein an elastic modulus of the body is lower than an elastic modulus of the first independent endplate and an elastic modulus of the second independent endplate;
- wherein the first independent endplate and the second independent end plate comprise a porosity configured to promote bone growth;
- wherein the metallic lattice structure comprises a scaffold configured to support bone growth and the elastic modulus of the body is configured to allow new bone growth to be loaded with physiological forces and the metallic lattice structure comprises 30% volumetric density filled by primary material and 70% void volume.

29. An implant comprising:
- a first independent endplate comprising an upper surface and a lower surface configured to contact a first segment of tissue upon implantation;
- a second independent endplate spaced apart from the first independent endplate, the second independent endplate comprising a lower surface and an upper surface configured to contact a second segment of tissue upon implantation; and
- a biocompatible three-dimensionally printed body comprising a metallic lattice structure and disposed between the upper surface of the first independent endplate and the lower surface of the second independent endplate such that at least one portion of the first independent endplate is mechanically connected to the second independent endplate only via the body;
- wherein an elastic modulus of the body is lower than an elastic modulus of the first independent endplate and an elastic modulus of the second independent endplate;
- wherein the first independent endplate and the second independent end plate comprise a porosity configured to promote bone growth; and
- wherein the lattice structure comprises a plurality of unit cells forming a repeating rhombic dodecahedron (RDD) structural scaffold.

30. The implant of claim 29, wherein the first independent endplate comprises a tool engagement area configured to receive a surgical tool during implantation.

* * * * *